United States Patent [19]

Maibaum et al.

[11] Patent Number: 5,641,778
[45] Date of Patent: Jun. 24, 1997

[54] AROMATICALLY SUBSTITUTED ω-AMINO-ALKANOIC ACID AMIDES AND ALKANOIC ACID DIAMIDES

[75] Inventors: Jürgen Klaus Maibaum, Weil-Haltingen, Germany; Pascal Rigollier, Mulhouse, France; Peter Herold, Arlesheim, Switzerland; Nissim Claude Cohen, Village-Neuf, France; Richard Göschke, Bottmingen; Stefan Stutz, Basel, both of Switzerland

[73] Assignee: Ciba-Geigy Corporation, Tarrytown, N.Y.

[21] Appl. No.: 568,332

[22] Filed: Dec. 6, 1995

[30] Foreign Application Priority Data

Dec. 8, 1994 [CH] Switzerland ............... 3724/94

[51] Int. Cl.$^6$ ............... A61K 31/165; A61K 31/535; C07C 237/22; C07D 295/145
[52] U.S. Cl. ............... 514/237.8; 514/617; 544/58.1; 544/86; 544/131; 544/165; 544/386; 544/400; 546/225; 546/227; 546/233; 546/316; 546/323; 548/253; 548/492; 548/568; 554/37
[58] Field of Search ............... 544/165; 548/492; 554/37; 514/237.8

[56] References Cited

U.S. PATENT DOCUMENTS 4,613,676 9/1986 Fuhrer et al.
4,898,877 2/1990 Meyer et al.

FOREIGN PATENT DOCUMENTS 212903 3/1987 European Pat. Off.
0678503 10/1995 European Pat. Off.

OTHER PUBLICATIONS

Plummer, Mark et al. Biorganic & Medicinal Chemistry Letters, vol. 3, No. 10 pp. 2119–2124, 1993.
Hanessdan, Stephen et al. Biorganic & Medicinal Chemistry Letters, vol. 4, No. 14, pp. 1697–1702, 1994.
Bradbury, Robert et al. Tetrahedron Letters, vol. 30, No. 29 pp. 3845–3848, 1989.
Prasad et al. Tetrahedron Letters, vol. 31, No. 13, pp. 1803–1806, 1990.
Hadrami et al. Tetrahedron Letters, vol. 32, No. 32, pp. 3985–3988, 1991.
Bradbury, Robert et al. J. Med. Chem. vol. 33, pp. 2335–2342, 1990.
Fray, Andrew et al. J. Org. Chem. vol. 51, pp. 4828–4833, 1986.

*Primary Examiner*—Robert W. Ramsuer
*Attorney, Agent, or Firm*—Marla J. Mathias

[57] ABSTRACT

Compounds of formula I

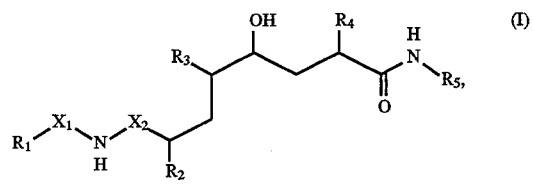

wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is an aliphatic or heterocycloaliphatic-aliphatic radical or free or aliphatically, araliphatically or heteroaraliphatically etherified hydroxy and the other is hydrogen, an aliphatic radical or free or esterified or amidated carboxy, $R_C$ is hydrogen, an aliphatic radical, free or aliphatically, araliphatically, heteroaraliphatically or heteroarylaliphatically etherified hydroxy or an unsubstituted or heteroaliphatically substituted amino group, and $R_D$ is an aliphatic, araliphatic or heteroaliphatic radical, one of the radicals $X_1$ and $X_2$ is carbonyl and the other is methylene, $R_2$ is an aliphatic radical, $R_3$ is unsubstituted or aliphatically substituted amino, $R_4$ is an aliphatic or araliphatic radical, and $R_5$ is an aliphatic or cycloaliphatic-aliphatic radical or an optionally hydrogenated and/or oxo-substituted heteroaryl radical or an optionally hydrogenated and/or oxo-substituted heteroaryl or heteroaliphatyl radical bonded via a carbon atom, and the salts thereof, have renin-inhibiting properties and can be used as antihypertensive active ingredients of medicaments.

9 Claims, No Drawings

AROMATICALLY SUBSTITUTED ω-AMINO-ALKANOIC ACID AMIDES AND ALKANOIC ACID DIAMIDES

The invention relates to compounds of formula I

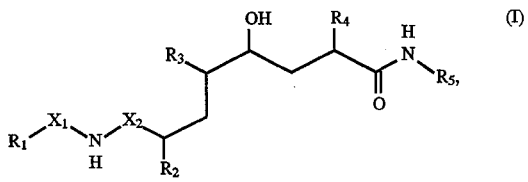

wherein $R_1$ is a 2-$R_A$-3-$R_B$-phenyl radical, a 2-$R_A$-4-$R_C$-phenyl radical, a 2-$R_A$-pyridin-3-yl radical a 3-$R_A$-pyridin-2-yl radical or a 1-$R_D$-indol-3-yl radical, wherein one of the radicals $R_A$ and $R_B$ is an aliphatic or heterecycloaliphatic-aliphatic radical or free or aliphatically, araliphatically or heteroaraliphatically etherified hydroxy and the other is hydrogen, an aliphatic radical or free or esterified or amidated carboxy, $R_C$ is hydrogen, an aliphatic radical, free or aliphatically, araliphatically, heterearaliphatically or heterearylaliphatically etherified hydroxy or an unsubstituted or heteroaliphatically substituted amino group, and $R_D$ is an aliphatic, araliphatic or heteroaliphatic radical, one of the radicals $X_1$ and $X_2$ is carbonyl and the other is methylene, $R_2$ is an aliphatic radical, $R_3$ is unsubstituted or aliphatically substituted amino, $R_4$ is an aliphatic or araliphatic radical, and $R_5$ is an aliphatic or cycloaliphatic-aliphatic radical or an optionally hydrogenated and/or oxo-substituted heteroaryl radical or an optionally hydrogenated and/or oxo-substituted heteroaryl or heteroaliphatyl radical bonded via a carbon atom, and to the salts thereof, to processes for the preparation of the compounds according to the invention, to pharmaceutical compositions comprising those compounds and to the use thereof as active ingredients of medicaments.

Hereinbefore, the general terms are preferably defined as follows:

Aliphatic radicals are, for example, lower alkyl, hydroxy-lower alkyl, lower alkanoyloxy-lower alkyl, lower alkoxy-lower alkyl, lower alkoxy-lower alkoxy-lower alkyl, lower alkoxy-lower alkoxy-lower alkyl, a free or amidated carboxy or carboxy-lower alkyl group, free or esterified or amidated dicarboxy-lower alkyl, free or esterified or amidated carboxy-(hydroxy)-lower alkyl, lower alkanesulfonyl-lower alkyl or unsubstituted or N-mono- or N,N-di-lower alkylated sulfamoyl-lower alkyl.

Free or aliphatically, araliphatically, heterocycloaliphatically-aliphatically or heteroarylaliphatically etherified hydroxy is, for example, hydroxy, lower alkoxy, hydroxy-lower alkoxy, lower alkanoyloxy-lower alkoxy, lower alkoxy-lower alkoxy, lower alkoxy-lower alkoxy-lower alkoxy, polyhalo-lower alkoxy or cyano-lower alkoxy; an amino-lower alkoxy radical that is unsubstituted or N-lower alkanoylated or N-mono- or N,N-di-lower alkylated or N,N-disubstituted by lower alkylene, hydroxy-, lower alkoxy- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene, or by optionally S-oxidised thia-lower alkylene; or is unsubstituted or substituted phenyl- or pyridyl-lower alkoxy, or free or amidated carboxy or carboxy-lower alkoxy or tetrazolyl-lower alkoxy.

Heteroaliphatic radicals are, for example, amino-lower alkyl radicals that are unsubstituted or N-lower alkanoylated or N-mono- or N,N-di-lower alkylated or N,N-disubstituted by lower alkylene, hydroxy-, lower alkoxy- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; or N-mono- or N,N-di-lower alkylated thiocarbamoyl-lower alkyl radicals. Araliphatic or heteroaliphatic radicals are, for example, unsubstituted or substituted phenyl- or pyridyl-lower alkyl groups.

Cycloaliphatic-aliphatic radicals are, for example, cycloalkyl-lower alkyl or free or esterified or amidated carboxycycloalkyl-lower alkyl.

Unsubstituted or aliphatically substituted amino is, for example, unsubstituted or N-lower alkanoylated or N-mono- or N,N-di-lower alkylated amino.

Unsubstituted or heteroaliphatically substituted amino is, for example, amino that is unsubstituted or N-lower alkanoylated or N-mono- or N,N-di-lower alkylated or N,N-di-substituted by lower alkylene, hydroxy-, lower alkoxy-, lower alkoxycarbonyl- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene.

Free or esterified or amidated carboxy is, for example, free or aliphatically or araliphatically etherified carboxy or aliphatically substituted carbamoyl.

Suitable substituents of phenyl, phenyl-lower alkoxy, pyridyl-lower alkyl, pyridyl-lower alkoxy and optionally hydrogenated and/or oxo-substituted heteroaryl are, for example, lower alkyl, lower alkoxy, hydroxy, nitro, amino, lower alkylamino, di-lower alkylamino, halogen and trifluoromethyl, it being possible for up to 3, especially 1 or 2, of those substituents to be present, which may be identical or different.

Amino that is unsubstituted or N-lower alkanoylated or N-mono- or N,N-di-lower alkylated or N,N-disubstituted by lower alkylene, hydroxy-, lower alkoxy-, lower alkoxycarbonyl- or lower alkoxy-lower alkoxy-lower alkylene, by unsubstituted or N-lower alkylated, N-lower alkanoylated or lower alkoxycarbonyl- or lower alkoxy-lower alkyl-N'-substituted aza-lower alkylene, by oxa-lower alkylene or by optionally S-oxidised thia-lower alkylene is, for example, amino, lower alkanoylamino, lower alkylamino, di-lower alkylamino, an unsubstituted or hydroxy-, lower alkoxy- or lower alkoxy-lower alkyl-substituted piperidino or pyrrolidino group, such as piperidino, hydroxypiperidino, lower alkoxypiperidino, lower alkoxy-lower alkoxypiperidino, lower alkoxycarbonylpiperidino, pyrrolidino, hydroxypyrrolidino, lower alkoxypyrrolidino, lower alkoxy-lower alkoxypyrrolidino, unsubstituted or N'-lower alkylated, N'-lower alkanoylated or lower alkoxycarbonyl- or lower alkoxy-lower alkyl- N'-substituted piperazino, such as piperazino, N'-lower alkylpiperazino, N'-lower alkanoylpiperazino, N'-lower alkoxycarbonylpiperazino or N'-lower alkoxy-lower alkylpiperazino, unsubstituted or lower alkylated morpholino, such as morpholino or lower alkylmorpholino, or optionally S-oxidised thiomorpholino, such as thiomorpholino, S-oxythiomorpholino or S,S-dioxythiomorpholino.

Amino-lower alkyl that is unsubstituted or N-lower alkanoylated or N-mono- or N,N-di-lower alkylated or N,N- disubstituted by lower alkylene, hydroxy-, lower alkoxy-, lower alkoxycarbonyl- or lower alkoxy-lower alkoxy-lower alkylene, by unsubstituted or N-lower alkylated, N-lower alkanoylated or lower alkoxycarbonyl- or lower alkoxy-lower alkyl-N'-substituted aza-lower alkylene; by oxa-lower alkylene or by optionally S-oxidised thia-lower alkylene is, for example, amino-lower alkyl, lower alkanoylamino-lower alkyl, lower alkylamino-lower alkyl, di-lower alkylamino-lower alkyl, unsubstituted or hydroxy-, lower alkoxy- or lower alkoxy-lower alkyl-substituted piperidino- or pyrrolidino-lower alkyl, such as piperidino-lower alkyl, hydroxypiperidino-lower alkyl, lower alkoxypiperidino-lower alkyl, lower alkoxy-lower alkoxypiperidino-lower alkyl, lower alkoxycarbonylpiperidino-lower alkyl, pyrrolidino-lower alkyl, hydroxypyrrolidino-lower alkyl, lower alkoxypyrrolidino-lower alkyl, lower alkoxy-lower alkoxypyrrolidino-lower alkyl, unsubstituted or N'-lower alkylated, N'-lower alkanoylated or lower alkoxycarbonyl- or lower alkoxy-lower alkyl-N'-substituted piperazino-lower alkyl, such as piperazino-lower alkyl, N'-lower alkylpiperazino-lower alkyl, N'-lower alkanoylpiperazino-lower alkyl, N'-lower alkoxycarbonylpiperazino-lower alkyl or N'-lower alkoxy-lower alkylpiperazino-lower alkyl, unsubstituted or lower alkylated morpholino-lower alkyl, such as morpholino-lower alkyl or lower alkylmorpholino-lower alkyl, or optionally S-oxidised thiomorpholino-lower alkyl, such as thiomorpholino-lower alkyl, S-oxythiomorpholino-lower alkyl or S,S-dioxythiomorpholino-lower alkyl.

Amino-lower alkoxy that is unsubstituted or N-lower alkanoylated or N-mono- or N,N-di-lower alkylated, N, N-disubstituted by lower alkylene, hydroxy-, lower alkoxy- or lower alkoxy-lower alkoxy-lower alkylene, by unsubstituted or N-lower alkylated, N-lower alkanoylated or lower alkoxycarbonyl- or lower alkoxy-lower alkyl-N'-substituted aza-lower alkylene, by oxa-lower alkylene or by optionally S-oxidised thia-lower alkylene is, for example, amino-lower alkoxy, lower alkanoylamino-lower alkoxy, lower alkylamino-lower alkoxy, di-lower alkylamino-lower alkoxy, unsubstituted or hydroxy-, lower alkoxy- or lower alkoxy-lower alkyl-substituted piperidino- or pyrrolidino-lower alkoxy, such as piperidino-lower alkoxy, hydroxypiperidino-lower alkoxy, lower alkoxypiperidino-lower alkoxy, lower alkoxy-lower alkoxypiperidino-lower alkoxy, pyrrolidino-lower alkoxy, hydroxypyrrolidino-lower alkoxy, lower alkoxypyrrolidino-lower alkoxy, lower alkoxy-lower alkoxypyrrolidino-lower alkoxy, unsubstituted or N'-lower alkylated, N'-lower alkanoylated or lower alkoxycarbonyl- or lower alkoxy-lower alkyl-N'-substituted piperazino-lower alkoxy, such as piperazino-lower alkoxy, N'-lower alkylpiperazino-lower alkoxy, N'-lower alkanoylpiperazino-lower alkoxy, N'-lower alkoxycarbonylpiperazino-lower alkoxy or N'-lower alkoxy-lower alkylpiperazino-lower alkoxy, unsubstituted or lower alkylated morpholino-lower alkoxy, such as morpholino-lower alkoxy or lower alkylmorpholino-lower alkoxy, or optionally S-oxidised thiomorpholino-lower alkoxy, such as thiomorpholino-lower alkoxy, S-oxythiomorpholino-lower alkoxy or S,S-dioxythiomorpholino-lower alkoxy.

Optionally S-oxidised lower alkylthio-lower alkoxy is, for example, lower alkylthio-lower alkoxy, lower alkanesulfinyl-lower alkoxy or lower alkanesulfonyl-lower alkoxy.

Free or amidated carboxy is, for example, carboxy, carbamoyl, lower alkyl carbamoyl, di-lower alkylcarbamoyl, unsubstituted or hydroxy-, lower alkoxy- or lower alkoxy-lower alkyl-substituted piperidino- or pyrrolidino-carbonyl, such as piperidinocarbonyl, hydroxy piperidinocarbonyl, lower alkoxypiperidinocarbonyl, lower alkoxy-lower alkoxypiperidino carbonyl, pyrrolidinocarbonyl, hydroxypyrrolidinocarbonyl, lower alkoxypyrrolidinocarbonyl, lower alkoxy-lower alkoxypyrrolidinocarbonyl, unsubstituted or N'-lower alkylated, N'-lower alkanoylated or lower alkoxycarbonyl- or lower alkoxy-lower alkyl-N'-substituted piperazinocarbonyl, such as piperazinocarbonyl, N'-lower alkylpiperazinocarbonyl, N'-lower alkanoylpiperazinocarbonyl, N'-lower alkoxycarbonylpiperazinocarbonyl or N'-lower alkoxy-lower alkylpiperazinocarbonyl, unsubstituted or lower alkylated morpholinocarbonyl, such as morpholinocarbonyl or lower alkylmorpholinocarbonyl, or optionally S-oxidised thiomorpholinocarbonyl, such as thiomorpholinocarbonyl, S-oxythiothiomorpholinocarbonyl or S,S-dioxythiomorpholinocarbonyl.

Free or esterified carboxy is, for example, carboxy or lower alkoxycarbonyl.

Free or amidated carboxy-lower alkoxy is, for example, carboxy-lower alkoxy, carbamoyl-lower alkoxy, lower alkylcarbamoyl-lower alkoxy, di-lower alkylcarbamoyl-lower alkoxy, unsubstituted or hydroxy-, lower alkoxy- or lower alkoxy-lower alkyl-substituted piperidino- or pyrrolidino-carbonyl-lower alkoxy, such as piperidinocarbonyl-lower alkoxy, hydroxypiperidinocarbonyl-lower alkoxy, lower alkoxypiperidinocarbonyl-lower alkoxy, lower alkoxy-lower alkoxypiperidinocarbonyl-lower alkoxy, pyrrolidinocarbonyl-lower alkoxy, hydroxy pyrrolidinocarbonyl-lower alkoxy, lower alkoxypyrrolidinocarbonyl-lower alkoxy, lower alkoxy-lower alkoxypyrrolidinocarbonyl-lower alkoxy, unsubstituted or N'-lower alkylated, N'-lower alkanoylated or lower alkoxycarbonyl- or lower alkoxy-lower alkyl-N'-substituted piperazinocarbonyl-lower alkoxy, such as piperazinocarbonyl-lower alkoxy, N'-lower alkylpiperazinocarbonyl-lower alkoxy, N'-lower alkanoylpiperazinocarbonyl-lower alkoxy, N'-lower alkoxycarbonylpiperazinocarbonyl or N'-lower alkoxy-lower alkylpiperazinocarbonyl-lower alkoxy, unsubstituted or lower alkylated morpholinocarbonyl-lower alkoxy, such as morpholinocarbonyl-lower alkoxy or lower alkylmorpholinocarbonyl-lower alkoxy, or optionally S-oxidised thiomorpholinocarbonyl-lower alkoxy, such as thiomorpholinocarbonyl-lower alkoxy, S-oxythiomorpholinocarbonyl or S,S-dioxythiomorpholinocarbonyl-lower alkoxy.

Free or amidated carboxy-lower alkyl is, for example, carboxy-lower alkyl, carbamoyl-lower alkyl, lower alkylcarbamoyl-lower alkyl, di-lower alkylcarbamoyl-lower alkyl, unsubstituted or hydroxy-, lower alkoxy- or lower alkoxy-lower alkyl-substituted piperidino- or pyrrolidinocarbonyl-lower alkyl, such as piperidinocarbonyl-lower alkyl, hydroxypiperidinocarbonyl-lower alkyl, lower alkoxypiperidinocarbonyl-lower alkyl, lower alkoxy-lower alkoxy piperidinocarbonyl-lower alkyl, pyrrolidinocarbonyl-lower alkyl, hydroxypyrrolidinocarbonyl-lower alkyl, lower alkoxypyrrolidinocarbonyl-lower alkyl, lower alkoxy-lower alkoxypyrrolidinocarbonyl-lower alkyl, unsubstituted or N'-lower alkylated, N'-lower alkanoylated or lower alkoxycarbonyl- or lower alkoxy-lower alkyl-N'-substituted piperazinocarbonyl-lower alkyl, such as piperazinocarbonyl-lower alkyl, N'-lower alkylpiperazinocarbonyl-lower alkyl, N'-lower alkanoylpiperazinocarbonyl-lower alkyl, N'-lower alkoxycarbonylpiperazinocarbonyl or N'-lower alkoxy-lower alkylpiperazinocarbonyl-lower alkyl, unsubstituted or lower alkylated morpholinocarbonyl-lower alkyl, such as morpholinocarbonyl-lower alkyl or lower alkylmorpholinocarbonyl-lower alkyl, or optionally S-oxidised thiomorpholinocarbonyl-lower alkyl, such as thiomorpholinocarbonyl-lower alkyl, S-oxythiomorpholinocarbonyl-lower alkyl or S,S-dioxythiomorpholinocarbonyl-lower alkyl.

Free or esterified carboxy-lower alkyl is, for example, carboxy-lower alkyl or lower alkoxycarbonyl-lower alkyl.

Unsubstituted or N-lower alkanoylated or N-mono- or N,N-di-lower alkylated amino is, for example, amino, lower alkanoylamino, lower alkylamino or di-lower alkylamino.

Free or esterified or amidated dicarboxy-lower alkyl is, for example, dicarboxy-lower alkyl, lower alkoxycarbonyl (carboxy)-lower alkyl, di-lower alkoxycarbonyl-lower alkyl, dicarbamoyl-lower lower alkyl, carbamoyl(carboxy)-lower alkyl, di(lower alkylcarbamoyl)-lower alkyl or di(di-lower alkylcarbamoyl)-lower alkyl.

Free or esterified or amidated carboxy(hydroxy)-lower alkyl is for example, carboxy(hydroxy)-lower alkyl, lower alkoxycarbonyl(hydroxy)-lower alkyl, carbamoyl(hydroxy)-lower alkyl, lower alkylcarbamoyl(hydroxy)-lower alkyl or di-lower alkycarbamoyl(hydroxy)-lower alkyl.

Free or esterified or amidated carboxycycloalkyl-lower alkyl is, for example, carboxycycloalkyl-lower alkyl, lower alkoxycarbonylcycloalkyl-lower alkyl, carbamoylcycloalkyl-lower alkyl, lower alkylcarbamoylcycloalkyl-lower alkyl or di-lower alkylcarbamoylcycloalkyl-lower alkyl.

Unsubstituted or N-mono- or N,N-di-lower alkylated thiocarbamoyl-lower alkyl is, for example, thiocarbamoyl-lower alkyl, N-lower alkylthiocarbamoyl-lower alkyl or N,N-di-lower alkylthiocarbamoyl-lower alkyl.

Unsubstituted or N-mono- or N,N-di-lower alkylated sulfamoyl-lower alkyl is, for example, sulfamoyl-lower alkyl, lower alkylsulfamoyl-lower alkyl or di-lower alkylsulfamoyl-lower alkyl.

Optionally hydrogenated and/or oxo-substituted heteroaryl radicals are, for example, optionally partially hydrogenated and/or benzofused 5-membered aza-, diaza-, triaza-, oxadiaza- or tetraaza-aryl or 6-membered aza- or diaza-aryl radicals, such as unsubstituted or oxo-substituted pyrrolidinyl, e.g. pyrrolidinyl or oxopyrrolidinyl, imidazolyl, e.g. imidazol-4-yl, benzimidazolyl, e.g. benzimidazol-2-yl, oxadiazolyl, e.g. 1,2,4-oxadiazol-5-yl, pyridyl, e.g. pyridin-2-yl, oxopiperidinyl, dioxopipeddinyl, oxothiazolyl, oxo-oxazolinyl or quinolinyl, e.g. quinolin-2-yl, or unsubstituted or N-lower alkanoylated piperidyl, such as 1-lower alkanoylpiperidinyl.

Lower alkyl substituted by an optionally hydrogenated and/or oxo-substituted heteroaryl radical that is bonded via a carbon atom contains as optionally hydrogenated heteroaryl radical, for example, an optionally partially hydrogenated and/or benzofused 5-membered aza-, diaza-, triaza-, oxadiaza- or tetraaza-aryl radical or 6-membered aza- or diaza-aryl radical and is, for example, unsubstituted or oxo-substituted pyrrolidinyl-lower alkyl, e.g. pyrrolidinyl-lower alkyl or oxopyrrolidinyl-lower alkyl, imidazolyl-lower alkyl, benzimidazolyl-lower alkyl, oxadiazolyl-lower alkyl, pyridyl-lower alkyl, oxopiperidinyl-lower alkyl, dioxopiperidinyl-lower alkyl, oxothiazolyl-lower alkyl, oxo-oxazonlinyl-lower alkyl or quinolinyl-lower piperidyl-lower alkyl, oxothiazolyl-lower alkyl, oxo-oxazolinyl-lower alkyl or quinolinyl-lower alkyl, also morpholinocarbonyl-lower alkyl or unsubstituted or N-lower alkanoylated piperidyl-lower alkyl, such as 1-lower alkanoyl piperidinyl-lower alkyl.

Amino-lower alkoxy is, for example, amino-$C_1$–$C_7$alkoxy, such as 2-aminoethoxy, 3-aminopropyloxy, 4-aminobutyloxy or 5-aminopentyloxy.

Amino-lower alkyl is, for example, amino-$C_1$–$C_4$alkyl, such as 2-aminoethyl, 3-aminopropyl or 4-aminobutyl.

Benzimidazolyl-lower alkyl is, for example, benzimidazolyl-$C_1$–$C_4$alkyl, such as benzimidazolylmethyl, 2-benzimidazolylethyl, 3-benzimidazolylpropyl or 4-benzimidazolyl butyl.

Carbamoyl(carboxy)-lower alkyl is, for example, carbamoyl(carboxy)-$C_1$–$C_7$alkyl, especially carbamoyl(carboxy)-$C_2$–$C_7$alkyl, such as 2-carbamoyl-1-carboxyethyl, 1-carbamoyl-2-carboxyethyl, 3-carbamoyl-2-carboxypropyl or 2-carbamoyl-3-carboxypropyl.

Carbamoyl(hydroxy)-lower alkyl is, for example, carbamoyl-$C_1$–$C_4$(hydroxy)alkyl, such as 1-carbamoyl-2-hydroxyethyl.

Carbamoylcycloalkyl-lower alkyl has, for example, from 3 to 8, especially from 5 to 7, ring members and is, for example, carbamoylcyclopentyl-, carbamoylcyclohexyl- or carbamoylcycloheptyl-methyl.

Carbamoyl-lower alkoxy is, for example, carbamoyl-$C_1$–$C_7$alkoxy, such as carbamoylmethoxy, 2-carbamoylethoxy, 3-carbamoylpropyloxy, 2-(3-carbamoyl)propyloxy, 2-carbamoylpropyloxy, 3-(1-carbamoyl)propyloxy, 2-(2-carbamoyl)propyloxy, 2-(carbamoyl-2-methyl)propyloxy, 4-carbamoylbutyloxy, 1-carbamoylbutyloxy, 1-(1-carbamoyl-2-methyl)butyloxy, 3-(4-carbamoyl-2-methyl)butyloxy, especially 3-carbamoylpropyloxy or 2-carbamoyl-2-methyl-ethoxy.

Carbamoyl-lower alkyl is, for example, carbamoyl-$C_1$–$C_7$alkyl, such as carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-(carbamoyl-2-methyl)propyl, 4-carbamoylbutyl, 1-carbamoylbutyl, 1-(1-carbamoyl-2-methyl)butyl, 3-(4-carbamoyl-2-methyl)butyl, especially 3-carbamoylpropyl or 2-carbamoyl-2-methyl-ethyl.

Carboxycycloalkyl-lower alkyl has, for example, from 3 to 8, especially from 5 to 7, ring members and is, for example, carboxycyclopentyl-, carboxycyclohexyl- or carboxycycloheptyl-methyl.

Carboxy(hydroxy)-lower alkyl is, for example, carboxy-$C_1$–$C_7$(hydroxy)alkyl, such as 1-carboxy-2-hydroxyethyl.

Carboxy-lower alkoxy is, for example, carboxy-$C_1$–$C_4$alkoxy, such as carboxymethoxy, 2-carboxyethoxy, 2- or 3-carboxypropyloxy, 2-carboxy-2-methyl-propyloxy, 2-carboxy-2-ethyl-butyl or 4-carboxybutyloxy, especially carboxymethoxy.

Carboxy-lower alkyl is, for example, carboxy-$C_1$–$C_4$alkyl, such as carboxymethyl, 2-carboxy-ethyl, 2- or 3-carboxpropyl, 2-carboxy-2-methyl-propyl, 2-carboxy-2-ethyl-butyl or 4-carboxybutyl, especially carboxymethyl.

Quinolinyl-lower alkyl is, for example, quinolinyl-$C_1$–$C_4$alkyl, such as quinolinylmethyl, 2-quinolinylethyl or 3-quinolinylpropyl, especially quinolinylmethyl.

Cyano-lower alkoxy is, for example, cyano-$C_1$–$C_4$alkoxy, such as cyanomethoxy, 2-cyanoethoxy, 2- or 3-cyanopropyloxy, 2-cyano-2-methyl-propyloxy, 2-cyano-2-ethyl-butyloxy or 4-cyanobutyloxy, especially cyanomethoxy.

Cyano-lower alkyl is, for example, cyano-$C_1$–$C_4$alkyl, such as cyanomethyl, 2-cyanoethyl, 2- or 3-cyanopropyl, 2-cyano-2-methyl-propyl, 2-cyano-2-ethyl-butyl or 4-cyanobutyl, especially cyanomethyl.

Cycloalkyl-lower alkyl has, for example, from 3 to 8, especially from 5 to 7, ring members and is, for example, cyclopentyl, cyclohexyl or cycloheptyl, also cyclopropyl, cyclobutyl or cyclooctyl.

Di(di-lower alkylcarbamoyl)-lower alkyl is, for example, di-(di-$C_1$-$C_4$alkylcarbamoyl)-$C_1$-$C_4$alkyl, such as 1,2-di(di-$C_1$-$C_4$alkylcarbamoyl)ethyl or 1,3-di(di-$C_1$-$C_4$alkylcarbamoyl)propyl, wherein $C_1$-$C_4$alkyl is, for example, methyl, ethyl or propyl.

Di(lower alkylcarbamoyl)-lower alkyl is, for example, di($C_1$-$C_4$alkylcarbamoyl)-$C_1$-$C_4$alkyl, such as 1,2-di($C_1$-$C_4$alkylcarbamoyl)ethyl or 1,3-di($C_1$-$C_4$alkylcarbamoyl)propyl, wherein $C_1$-$C_4$alkyl is, for example, methyl, ethyl or propyl.

Dicarbamoyl-lower alkyl is, for example, dicarbamoyl-$C_1$-$C_4$alkyl, such as 1,2-dicarbamoyl-ethyl or 1,3-dicarbamoylpropyl.

Dicarboxy-lower alkyl is, for example, dicarboxy-$C_1$-$C_4$alkyl, such as 1,2-dicarboxyethyl or 1,3-dicarboxypropyl.

Di-lower alkyl-Di-lower alkylamino-lower alkoxy is, for example, N,N-di-$C_1$-$C_4$alkylamino-$C_1$-$C_4$alk as 2-dimethylaminoethoxy, 3-dimethylaminopropyloxy, 4-dimethylaminobutyloxy, 2-diethylaminoethyoxy, 2-(N-methyl-N-ethyl-amino)ethoxy or 2-(N-butyl-N-methyl-amino)ethoxy, especially 3-dimethylaminopropyloxy.

Di-lower alkylamino-lower alkyl is, for example, N,N-di-$C_1$-$C_4$alkylamino-$C_1$-$C_4$alkyl, such as 2-dimethylaminoethyl, 3-dimethylaminopropyl, 4-dimethylaminobutyl, 2-diethylaminoethyl, 2-(N-methyl-N-ethyl-amino)ethyl or 2-(N-butyl-N-methyl-amino)ethyl, especially dimethylaminomethyl.

Di-lower alkoxycarbonyl-lower alkyl is, for example, di-lower alkoxycarbonyl-$C_1$-$C_4$alkyl, such as 1,2-dimethoxycarbonylethyl, 1,3-dimethoxycarbonylpropyl, 1,2-dimethoxycarbonylethyl or 1,3-diethoxycarbonylpropyl.

Di-lower alkylamino is, for example, di-$C_1$-$C_4$alkylamino, such as dimethylamino, N-methyl-N-ethylamino, diethylamino, N-methyl-N-propylamino or N-butyl-N-methyl-amino.

Di-lower alkylamino-lower alkoxy is, for example, N,N-di-$C_1$-$C_4$alkylamino-$C_1$-$C_4$alkoxy, such as 2-dimethylaminoethoxy, 3-dimethylaminopropyloxy, 2-dimethylaminopropyloxy, 2-(dimethylamino-2-methyl) propyloxy or 2-(1-dimethylamino-3-methyl)butyloxy, especially 3-dimethylaminopropyloxy.

Di-lower alkylcarbamoyl is, for example, di-$C_1$-$C_4$alkylcarbamoyl, such as dimethylcarbamoyl, N-methyl-N-ethylcarbamoyl, diethylcarbamoyl, N-methyl-N-propylcarbamoyl or N-butyl-N-methyl-carbamoyl.

Di-lower alkylcarbamoyl(hydroxy)-lower alkyl is, for example, di-$C_1$-$C_4$alkylcarbamoyl-$C_1$-$C_7$(hydroxy)alkyl, such as 1-dimethylcarbamoyl- or 1-diethylcarbamoyl-2-hydroxy-ethyl.

Di-lower alkylcarbamoylcycloalkyl-lower alkyl has, for example, from 3 to 8, especially from 5 to 7, ring members and is, for example, di-$C_1$-$C_4$alkylcarbamoyl-$C_5$-$C_7$cycloalkyl-$C_1$-$C_4$alkyl, such as dimethylcarbamoylcyclopentyl-, dimethylcarbamoylcyclohexyl- or dimethylcarbamoylcycloheptyl-methyl.

Di-lower alkylcarbamoyl-lower alkoxy is, for example, N, N-di-$C_1$-$C_4$alkylcarbamoyl-$C_1$-$C_4$alkoxy, such as 2-dimethylcarbamoylethoxy, 3-dimethylcarbamoylpropyloxy, 2-dimethylcarbamoylpropyloxy, 2-(dimethylcarbamoyl-2-methyl)propyloxy or 2-(1-dimethylcarbamoyl-3-methyl) butyloxy, especially 2-dimethylcarbamoylethoxy.

Di-lower alkylcarbamoyl-lower alkyl is, for example, N,N-di-$C_1$-$C_4$alkylcarbamoyl-$C_1$-$C_4$alkyl, such as 2-dimethylcarbamoylethyl, 3-dimethylcarbamoylpropyl, 2-dimethylcarbamoyl propyl, 2-(dimethylcarbamoyl-2-methyl)propyl or 2-(1-dimethylcarbamoyl-3-methyl)butyl, especially 2-dimethylcarbamoylethyl.

Di-lower alkylsulfamoyl-lower alkyl is, for example, N,N-di-$C_1$-$C_4$alkylsulfamoyl-$C_1$-$C_4$alkyl, N,N-dimethylsulfamoyl-$C_1$-$C_4$alkyl, such as N,N-dimethylsulfamoylmethyl, (N,N-dimethylcarbamoyl)ethyl, 3-(N,N-dimethylcarbamoyl)propyl or 4-(N,N-dimethylcarbamoyl)butyl, especially N,N-dimethylcarbamoylmethyl.

Dioxopiperidinyl-lower alkyl is, for example, dioxopiperidino-$C_1$-$C_4$alkyl, such as 2,6-dioxopiperidin-1-ylmethyl, such as 2-(2,6-dioxopiperidin-1-yl)ethyl or 2,6-dioxopiperidin-4-yl-methyl.

S,S-Dioxothiomorpholinocarbonyl-lower alkoxy is, for example, S,S-dioxothiomorpholinocarbonyl-$C_1$-$C_4$alkoxy, such as S,S-dioxothiomorpholinocarbonylmethoxy,2-(S,S-dioxo)thiomorpholinocarbonylethoxy, 3-(S,S-dioxo) thiomorpholinocarbonylpropyloxy or 1- or 2-[4-(S,S-dioxo) thiomorpholinocarbonyl]butyloxy.

S,S-Dioxothiomorpholinocarbonyl-lower alkyl is, for example, S,S-dioxothiomorpholinocarbonyl-$C_1$-$C_4$alkyl, such as S,S-dioxothiomorpholinocarbonylmethyl, 2-(S,S-dioxo)thiomorpholinocarbonylethyl, 3-(S,S-dioxo) thiomorpholinocarbonylpropyl or 1- or 2-[4-(S,S-dioxo) thiomorpholinocarbonyl]butyl.

S,S-Dioxothiomorpholino-lower alkoxy is, for example, S,S-dioxothiomorpholino-$C_1$-$C_4$alkoxy, such as S,S-dioxothiomorpholinomethoxy, 2-(S,S-dioxo) thiomorpholinoethoxy, 3-(S,S-dioxo) thiomorpholinopropyloxy or 1- or 2-[4-(S,S-dioxo) thiomorpholino]butyloxy.

S,S-Dioxothiomorpholino-lower alkyl is, for example, S,S-dioxothiomorpholino-$C_1$-$C_4$alkyl, such as S,S-dioxothiomorpholinomethyl, 2-(S,S-dioxo) thiomorpholinoethyl, 3-(S,S-dioxo)thiomorpholinopropyl or 1- or 2-[4-(S,S-dioxo)thiomorpholino]butyl.

Hydroxy-lower alkoxy is, for example, hydroxy-$C_2$-$C_7$alkoxy, especially hydroxy-$C_2$-$C_4$alkoxy, such as 2-hydroxyethoxy, 3-hydroxypropyloxy or 4-hydroxybutyloxy.

Hydroxy-lower alkoxy-lower alkyl is, for example, hydroxy-$C_1$-$C_4$alkoxy-$C_1$-$C_4$alkyl, such as 2-hydroxyethoxymethyl, 2-(2-hydroxyethoxy)ethyl, 3-(3-hydroxypropyloxy)propyl or 4-(2-hydroxybutyloxy)butyl, especially 2-(3-hydroxypropyloxy)ethyl or 2-(4-hydroxybutyloxy)ethyl.

Hydroxy-lower alkyl is, for example, hydroxy-$C_2$-$C_7$alkyl, especially hydroxy-$C_2$-$C_4$alkyl, such as 2-hydroxyethyl, 3-hydroxypropyl or 4-hydroxybutyl.

Hydroxy-lower alkylene, together with the carbon atom that binds its free valencies, is, for example, 3-hydroxypyrrolidino or 3- or 4-hydroxypiperidino.

Hydroxypiperidinocarbonyl is, for example, 3- or 4-hydroxypiperidinocarbonyl.

Hydroxypiperidinocarbonyl-lower alkoxy is, for example, hydroxypiperidinocarbonyl-$C_1$-$C_4$alkoxy, such as 3- or 4-hydroxypiperidinocarbonylmethoxy.

Hydroxypiperidinocarbonyl-lower alkyl is, for example, hydroxypiperidinocarbonyl-$C_1$-$C_4$alkyl, such as 3- or 4-hydroxypiperidinocarbonylmethyl.

Hydroxypiperidino-lower alkoxy is, for example, 3- or 4-hydroxypiperidino-$C_1$–$C_4$alkoxy, such as 3- or 4-hydroxypiperidino-4-ylmethoxy, 2-(3- or 4-hydroxypiperidino)ethoxy, 3-(3- or 4-hydroxypiperidino) propyloxy or 4-(3- or 4-hydroxypiperidino)butyloxy.

Hydroxypiperidino-lower alkyl is, for example, 3- or 4-hydroxypiperidino-$C_1$–$C_4$alkyl, such as 3- or 4-hydroxypiperidino-4-ylmethyl, 2-(3- or 4-hydroxypiperidino)ethyl, 3-(3- or 4-hydroxypiperidino) propyl or 4-(3- or 4-hydroxypiperidino)butyl.

Hydroxypyrrolidinocarbonyl-lower alkoxy is, for example, hydroxypyrrolidinocarbonyl-$C_1$–$C_4$alkoxy, such as 3-hydroxypyrrolidinocarbonylmethoxy.

Hydroxypyrrolidinocarbonyl-lower alkyl is, for example, hydroxypyrrolidinocarbonyl-$C_1$–$C_4$ alkyl, such as 3-hydroxypyrrolidinocarbonylmethyl Hydroxypyrrolidino-lower alkoxy is, for example, 3-hydroxypyrrolidino-$C_1$–$C_4$alkoxy, such as 3-hydroxypiperidinopyrrolidinomethoxy.

Hydroxypyrrolidino-lower alkyl is, for example, 3- or 4-hydroxypyrrolidino-$C_1$–$C_4$alkyl, such as 3-hydroxypyrrolidinomethyl.

Imidazolyl-lower alkyl is, for example, imidazolyl-$C_1$–$C_4$alkyl, such as imidazolylmethyl, 2-imidazolylethyl, 3-imidazolylpropyl or 4-imidazolylbutyl.

Morpholinocarbonyl-lower alkoxy is, for example, morpholinocarbonyl-$C_1$–$C_4$alkoxy, such as morpholinocarbonylmethoxy, 2-morpholinocarbonylethoxy, 3-morpholinocarbonylpropyloxy or 4-morpholinocarbonylbutyloxy.

Morpholinocarbonyl-lower alkyl is, for example, morpholinocarbonyl-$C_1$–$C_4$alkyl, such as morpholinocarbonylmethyl, 2-morpholinocarbonylethyl, 3-morpholinocarbonylpropyl or 4-morpholinocarbonylbutyl, especially 2-morpholinocarbonylethyl.

Morpholino-lower alkoxy is, for example, morpholino-$C_1$–$C_4$alkoxy, such as morpholinomethoxy, 2-morpholinoethoxy, 3-morpholinopropyloxy or 4-morpholinobutyloxy, especially 2-morpholinoethoxy or 3-morpholinopropyloxy.

Morpholino-lower alkyl is, for example, morpholino-$C_1$–$C_4$alkyl, such as morpholinomethyl, 2-morpholinocarbonylethyl, 3-morpholinopropyl methyl, 2-morpholinobutyloxy, especially morpholinomethyl, 2-morpholinoethyl or 3-morpholinopropyl.

Morpholino-lower alkylcarbamoyl-lower alkoxy is, for example, N-(morpholino-$C_1$–$C_4$alkylcarbamoyl)-$C_4$–$C_4$alkoxy, such as especially 2-morpholinoethoxycarbamoylmethoxy.

Lower alkanoylamino-lower alkyl is, for example, N-$C_1$–$C_4$alkanoylamino-$C_1$–$C_4$alkyl, such as 2-acetoxyaminoethyl.

Lower alkanoylamino is, for example, N-$C_1$–$C_7$alkanoylamino, such as formylamino, acetylamino or pivaloylamino.

Lower alkanoylamino-lower alkoxy preferably carries the lower alkanoylamino group in a position higher than the co-position and is, for example, N-$C_1$–$C_7$alkanoylamino-$C_1$–$C_4$alkoxy, such as 2-formylaminoethoxy, 2-acetylaminoethoxy or 2-pivaloylaminoethoxy, especially 2-acetylaminoethoxy.

Lower alkanoyloxy-lower alkoxy preferably carries the lower alkanoyloxy group in a position higher than the α-position and is, for example, $C_1$–$C_7$alkanoyloxy-$C_1$–$C_4$alkoxy, such as 4-acetyloxybutyloxy.

Lower alkanoyloxy-lower alkyl preferably carries the lower alkanoyloxy group in a position higher than the α-position and is, for example, $C_1$–$C_7$alkanoyloxy-$C_1$–$C_4$alkyl, such as 4-acetoxybutyl.

Lower alkanoylpiperazinocarbonyl is, for example, N-$C_2$–$C_7$alkanoylpiperazinocarbonyl, such as 4-acetylpiperazinocarbonyl.

Lower alkanoylpiperazinocarbonyl-lower alkoxy is, for example, N'-$C_2$–$C_7$alkanoylpiperazinocarbonyl-$C_1$–$C_4$alkoxy, such as 4-acetylpiperazinocarbonylmethoxy.

Lower alkanoylpiperazinocarbonyl-lower alkyl is, for example, N'-$C_2$–$C_7$alkanoylpiperazinocarbonyl-$C_1$–$C_4$alkyl, such as especially N'-acetylpiperazinomethyl.

Lower alkanoylpiperazino-lower alkoxy is, for example, N'-$C_2$–$C_7$alkanoylpiperazino-$C_1$–$C_4$-alkoxy, such as 4-acetylpiperazinomethoxy.

Lower alkanoylpiperazino-lower alkyl is, for example, N'-$C_2$–$C_7$alkanoylpiperazino-$C_1$–$C_4$alkyl, such as 4-acetylpiperazinomethyl.

Lower alkanoylpiperidinyl is, for example, N'-$C_2$–$C_7$alkanoylpiperidin-4-yl, such as 1-acetylpiperidin-4-ylmethyl. Lower alkanoylpiperidinyl-lower alkyl is, for example N'-$C_2$–$C_7$alkxanoylpiperidin-4-yl-$C_1$–$C_4$-)alkyl, such as especially 2-(1-acetylpiperidin-4-yl)ethyl.

Lower alkanesulfinyl-lower alkoxy is, for example, $C_2$–$C_7$alkanesulfinyl-$C_1$–$C_4$alkoxy, such as methanesulfinylmethoxy or 3-methanesulfinyl-2-hydroxy-propyloxy.

Lower alkanesulfonyl-lower alkoxy is, for example, $C_1$–$C_7$alkanesulfonyl-$C_1$–$C_4$alkoxy, such as methanesulfonylmethoxy or 3-methanesulfonyl-2-hydroxy-propyloxy.

Lower alkanesulfonyl-lower alkyl is, for example, $C_1$–$C_7$alkanesulfonyl-$C_1$–$C_4$alkyl, such as ethanesulfonylmethyl, 2-ethanesulfonylethyl, 3-ethanesulfonylpropyl or 3-(1,1-dimethylethanesulfonyl) propyl.

Lower alkoxy is, for example, $C_1$–$C_7$alkoxy, preferably $C_1$–$C_4$alkoxy, such as methoxy, ethoxy, propyloxy, isopropyloxy, butyloxy, isobutyloxy, sec-butyloxy, tert-butyloxy, pentyloxy or a hexyloxy or heptyloxy group.

Lower alkoxycarbonyl is, for example, $C_2$–$C_4$alkoxycarbonyl, such as methoxycarbonyl or methoxycarbonyl, ethoxycarbonyl, propyloxycarbonyl, isopropyloxycarbonyl, butyloxycarbonyl, isobutyloxycarbonyl, sec-butyloxycarbonyl, tert-butyloxycarbonyl, pentyloxycarbonyl or a hexyloxycarbonyl or heptyloxycarbonyl group.

Lower alkoxycarbonyl(carboxy)-lower alkyl is, for example, $C_1$–$C_4$alkoxycarbonyl(carboxy)-$C_1$–$C_7$alkyl, especially $C_1$–$C_4$alkoxycarbonyl(carboxy)-$C_2$–$C_7$alkyl, such as 2-methoxycarbonyl-1-carboxyethyl, 1-methoxycarbonyl-2-carboxyethyl, 3-methoxycarbonyl-2-carboxy-propyl or 2-methoxycarbonyl-3-carboxy-propyl.

Lower alkoxycarbonyl(hydroxy)-lower alkyl is, for example, $C_1$–$C_4$alkoxycarbonyl-$C_1$–$C_7$-(hydroxy)alkyl, such as 1-methoxycarbonyl- or 1-ethoxycarbonyl-2-hydroxy-ethyl.

Lower alkoxycarbonylcycloalkyl-lower alkyl has, for example, from 3 to 8, especially from 5 to 7, ring members and is, for example, $C_1$–$C_4$alkoxycarbonylcyclopentyl-, $C_1$–$C_4$alkoxycarbonylcyclohexyl- or $C_1$–$C_4$alkoxycarbonylcycloheptyl-methyl.

Lower alkoxycarbonyl-lower alkyl is, for example, $C_1$–$C_4$alkoxycarbonyl-$C_1$–$C_4$alkyl, such as methoxycarbonyl- or ethoxycarbonyl-methoxy, 2-methoxycarbonyl- or 2-ethoxycarbonylethoxy, 3-methoxycarbonyl- or 3-ethoxycarbonyl-propyloxy or 4-ethoxycarbonylbutyloxy.

Lower alkoxycarbonylpiperazinocarbonyl is, for example, N'-$C_1$–$C_4$alkoxycarbonylpiperazinocarbonyl, such as 4-methoxycarbonylpiperazinocarbonyl.

Lower alkoxycarbonylpiperazino-lower alkoxy is, for example, N'-$C_1$-$C_4$alkoxycarbonylpiperazinocarbonyl-$C_1$-$C_4$alkoxy, such as 2-(4-methoxycarbonylpiperazinocarbonyl)ethoxy.

Lower alkoxycarbonylpiperazino-lower alkyl is, for example, N'-$C_1$-$C_4$alkoxycarbonylpiperazinocarbonyl-$C_1$-$C_4$alkyl, such as 2-(4-methoxycarbonylpiperazioncarbonyl)ethyl.

Lower alkoxycarbonylpiperidinyl-lower alkyl is, for example, N'-$C_1$-$C_4$alkoxycarbonylpiperazinocarbonyl-$C_1$-$C_4$alkyl, such as 2-(2-methoxycarbonylpiperazinocarbonyl)ethyl.

Lower alkoxy-lower alkenyloxy is, for example, $C_1$-$C_4$alkoxy-$C_2$-$C_4$alkenyloxy, such as 4-methoxybut-2-enyloxy.

Lower alkoxy-lower alkoxy is, for example, $C_1$-$C_4$alkoxy-$C_2$-$C_4$alkoxy, such as 2-methoxy-, 2-ethoxy- or 2-propyloxy-ethoxy, 3-methoxy- or 3-ethoxy-propyloxy or 4-methoxybutyloxy, especially 2-methoxyethoxy, 3-methoxypropyloxy, 4-methoxybutyloxy, 5-methoxypentyloxy.

Lower alkoxy-lower alkoxy-lower alkoxy is, for example, $C_1$-$C_4$alkoxy-$C_1$-$C_4$alkoxy-$C_1$-$C_4$alkoxy, such as 2-methoxy-, 2-ethoxy- or 2-propyloxy-ethoxymethoxy, 2-(2-methoxy-, 2-ethoxy- or 2-propyloxy-ethoxy)ethoxy, 3-(3-methoxy- or 3-ethoxy-propyloxy)propyloxy or 4-(2-methoxybutyloxy)butyloxy, especially 2-(methoxymethoxy)ethoxy or 2-(2-methoxyethoxy)ethoxy.

Lower alkoxy-lower alkoxy-lower alkyl is, for example, $C_1$-$C_4$alkoxy-$C_1$-$C_4$alkoxy-$C_1$-$C_4$alkyl, such as 2-methoxy-, 2-ethoxy- or 2-propyloxy-ethoxymethyl, 2-(2-methoxy-, 2-ethoxy- or 2-propyloxy-ethoxy)ethyl, 3-(3-methoxy- or 3-ethoxy-propyloxy)propyl or 4-(2-methoxybutyloxy)butyl, especially 2-(3-methoxypropyloxy)ethyl or 2-(4-methoxybutyloxy)ethyl.

Lower alkoxy-lower alkoxy-lower alkylene, together with the carbon atom that binds its free valencies, is, for example, $C_1$-$C_4$alkoxy-$C_1$-$C_4$alkoxy-$C_1$-$C_4$alkylene, such as 3-(3-methoxypropyloxy)pyrrolidino, 3-(3-methoxypropyloxy)piperidino or 4-(3-methoxypropyloxy)piperidino.

Lower alkoxy-lower alkoxypiperidinocarbonyl is, for example, $C_1$-$C_4$alkoxy-$C_1$-$C_4$alkoxypiperidinocarbonyl, such as 3-(3-methoxypropyloxy)- or 4-(3-methoxypropyloxy)-piperidinocarbonyl.

Lower alkoxy-lower alkoxypiperidinocarbonyl-lower alkoxy is, for example, $C_1$-$C_4$alkoxy-$C_1$-$C_4$alkoxypiperidinocarbonyl-$C_1$-$C_4$alkoxy, such as 3-(3-methoxypropyloxy)- or 4-(3-methoxypropyl)-piperidinocarbonylmethoxy.

Lower alkoxy-lower alkoxypiperidinocarbonyl-lower alkyl is, for example, $C_1$-$C_4$alkoxy-$C_1$-$C_4$alkoxy-piperidinocarbonyl-$C_1$-$C_4$alkyl, such as 3-(3-methoxypropyloxy)- or 4-(3-methoxypropyloxy)-piperidinocarbonylmethyl.

Lower alkoxy-lower alkoxypiperidino-lower alkoxy is, for example, 3- or 4-$C_1$-$C_4$alkoxy-$C_1$-$C_4$alkoxy-piperidino-$C_1$-$C_4$alkoxy, such as 3-(3-methoxypropyloxy)- or 4-(3-methoxypropyloxy)piperidinomethoxy, 2-[3-(3-methoxypropyloxy)- or 2-[4-methoxypropyloxy)-piperidino]ethoxy, 3-(3- or 4-hydroxypiperidino)propyloxy or 4-(3- or 4-hydroxypiperidino)butyloxy.

Lower alkoxy-lower alkoxypiperidino-lower alkyl is, for example, 3- or 4-$C_1$-$C_4$alkoxy-$C_1$-$C_4$alkoxy-piperidino-$C_1$-$C_4$alkyl, such as 3-(3-methoxypropyloxy)- or 4-(3-methoxypropyloxy)piperidino-4-ylmethyl, 2-(3- or 4-hydroxypiperidino)ethyl, 3-(3- or 4-hydroxypiperidino)propyl or 4-(3- or 4-hydroxypiperidino)butyl.

Lower alkoxy-lower alkoxypyrrolidinocarbonyl-lower alkoxy is, for example, $C_1$-$C_4$alkoxy-$C_1$-$C_4$alkoxy-pyrrolidinocarbonyl- or hydroxypyrrolidinocarbonyl-$C_1$-$C_4$alkoxy, such as 3-(3-methoxypropyloxy) pyrrolidinocarbonylmethoxy.

Lower alkoxy-lower alkoxypyrrolidinocarbonyl-lower alkyl is, for example, $C_1$-$C_4$alkoxy-pyrrolidinocarbonyl)- or hydroxypyrrolidinocarbonyl-$C_1$-$C_4$alkyl, such as 3-(3-methoxypropyloxy)pyrrolidinocarbonylmethyl.

Lower alkoxy-lower alkoxypyrrolidino-lower alkoxy is, for example, 3- or 4-$C_1$-$C_4$alkoxy-$C_1$-$C_4$alkoxy-pyrrolidino-$C_1$-$C_4$alkoxy, such as 3-(3-methoxypropyloxy) pyrrolidin-1-ylmethoxy.

Lower alkoxy-lower alkoxypyrrolidino-lower alkyl is, for example, 3- or 4-$C_1$-$C_4$alkoxy-$C_1$-$C_4$alkoxy-pyrrolidino-$C_1$-$C_4$alkyl, such as 3-(3-methoxypropyloxy)pyrrolidin-1-ylmethyl.

Lower alkoxy-lower alkyl is, for example, $C_1$-$C_4$alkoxy-$C_1$-$C_4$alkyl, such as ethoxymethyl, propyloxymethyl, butyloxymethyl, 2-methoxy-, 2-ethoxy- or 2-propyloxy-ethyl, 3-methoxy- or 3-ethoxy-propyl or 4-methoxybutyl, especially 3-methoxypropyl or 4-methoxybutyl, especially propyloxymethoxy.

Lower alkoxy-lower alkylene, together with the carbon atom that binds its free valencies, is, for example, $C_1$-$C_4$alkoxy-$C_1$-$C_4$alkylene, such as 3-methoxypyrrolidino, 3-methoxypiperidino or 4-methoxypiperidino.

Lower alkoxy-lower alkylpiperazinocarbonyl is, for example, N'-$C_1$-$C_4$alkoxy-$C_1$-$C_4$alkoxypiperazinocarbonyl, such as N'-(3-methoxypropyl)piperazinocarbonyl, N'-(4-methoxybutyl)piperazinocarbonyl or N'-(3-ethoxypropyl)piperazinocarbonyl.

Lower alkoxy-lower alkylpiperazinocarbonyl-lower alkoxy is, for example, N'-$C_1$-$C_4$alkoxy-$C_1$-$C_4$alkylpiperazinocarbonyl-$C_1$-$C_4$alkoxy, such as N'-(3-methoxypropyl)piperazinocarbonylmethoxy, 2-[N'-(3-methoxypropyl)piperazinocarbonyl]ethoxy, 3-[N'-(3-methoxypropyl)piperazinocarbonyl]propyloxy or 4-[N'-(3-methoxypropyl)piperazinocarbonyl]butyloxy.

Lower alkoxy-lower alkylpiperazinocarbonyl-lower alkyl is, for example, N'-$C_1$-$C_4$alkoxy-$C_1$-$C_4$alkylpiperazinocarbonyl-$C_1$-$C_4$alkyl, such as N'-(3-methoxypropyl)piperazinocarbonylmethyl, 2-[N'-(3-methoxypropyl)piperazinocarbonyl]ethyl, 3-[N'-(3-methoxypropyl)piperazinocarbonyl]propyl or 4-[N'-(3-methoxypropyl)piperazinocarbonyl]butyl.

Lower alkylpiperazino-lower alkoxy is, for example, N'-$C_1$-$C_4$alkylpiperazino-$C_1$-$C_4$alkoxy, such as N'-(3-methoxypropyl)piperazinomethoxy, 2-[N'-(3-methoxypropyl)piperazino]ethoxy, 3-[N'-(3-methoxypropyl)piperazino]propyloxy or 4-[N'-(3-methoxypropyl)piperazino]butyloxy.

Lower alkoxy-lower alkylpiperazino-lower alkyl is, for example, N'-$C_1$-$C_4$alkoxy-$C_1$-$C_4$alkylpiperazino-$C_1$-$C_4$alkyl, such as N'-(3-methoxypropyl)piperazinomethyl, 2-[N'-(3-methoxypropyl)piperazino]ethyl, 3-[N'-(3-methoxypropyl)piperazino]propyl or 4-[N'-(3-methoxypropyl)piperazino]butyl.

Lower alkoxypiperidinocarbonyl is, for example, $C_1$-$C_4$alkoxypiperidinocarbonyl, such as 3- or 4-methoxypiperidinocarbonyl, 3- or 4-ethoxypiperidinocarbonyl, 3- or 4-propyloxypiperidinocarbonyl or 3- or 4-butyloxypiperidinocarbonyl.

Lower alkoxypiperidinocarbonyl-lower alkoxy is, for example, $C_1$-$C_4$alkoxypiperidinocarbonyl-$C_1$-$C_4$alkoxy such as 3- or 4-methoxypiperidinocarbonylmethoxy, 2-(3- or 4-methoxypiperidinocarbonyl)ethoxy, 3-(3- or 4-methoxypiperidinocarbonyl)propyloxy or 4-(3- or 4-methoxypiperidinocarbonyl)butyloxy.

Lower alkoxypiperidinocarbonyl-lower alkyl is, for example, $C_1-C_4$alkoxypiperidinocarbonyl-$C_1-C_4$alkyl, such as 3- or 4-methoxypiperidinocarbonylmethyl, 2-(3- or 4-methoxypiperidinocarbonyl)ethyl, 3-(3- or 4-methoxypiperidinocarbonyl)propyl or 4-methoxypiperidinocarbonyl)butyl.

Lower alkoxypiperidino-lower alkoxy is, for example, $C_1-C_4$alkoxypiperidino-$C_1-C_4$alkoxy, such as 2-(3- or 4-methoxypiperidino)piperidinoethoxy, 3-(3- or 4-metholxypiperidino)piperidinopropyloxy or 4-(3- or 4-methoxypiperidino)piperidinobutyloxy.

Lower alkoxypiperidino-lower alkyl is, for example, $C_1-C_4$alkoxypiperidino-$C_1-C_4$alkyl, such as 3- or 4-methoxypiperidinomethyl, 2-(3- or 4-methoxypiperidino) piperidinoethyl, 3-(3- or 4-methoxypiperidino) piperidinopropyl or 4-(3- or 4-methoxypiperidino) piperidinobutyl.

Lower alkoxypyrrolidinocarbonyl-lower alkoxy is, for example, $C_1-C_4$alkoxy-pyrrolidinocarbonyl-$C_1-C_4$alkoxy, such as 3-methoxypyrrolidinocarbonylmethoxy, 2-(3-methoxypyrrolidinocarbonyl)ethoxy, 3-(3-methoxypyrrolidinocarbonyl)propyloxy or 4-(3-methoxypyrrolidinocarbonyl)butyloxy.

Lower alkoxypyrrolidinocarbonyl-lower alkyl is, for example, $C_1-C_4$alkoxy-pyrrolidinocarbonyl-$C_1-C_4$alkyl, such as 3-methoxypyrrolidinocarbonylmethyl, 2-(3-methoxypyrrolidinocarbonyl)ethyl, 3-(3-methoxypyrrolidinocarbonyl)propyl or 4-(3-methoxypyrrolidinocarbonyl)butyl.

Lower alkoxypyrrolidino-lower alkoxy is, for example, $C_1-C_4$alkoxy-pyrrolidino-$C_1-C_4$alkoxy, such as 3-methoxypyrrolidinomethoxy, 2-(3-methoxypyrrolidino) ethoxy, 3-(3-methoxypyrrolidino)propyloxy or 4-(3-methoxypyrrolidino)butyloxy.

Lower alkoxypyrrolidino-lower alkyl is, for example, $C_1-C_4$alkoxy-pyrrolidino-$C_1-C_4$alkyl, such as 3-methoxypyrrolidinomethyl, 2-(3-methoxypyrrolidino) ethyl, 3-(3-methoxypyrrolidino)propyl or 4-(3-methoxypyrrolidino)butyl.

Lower alkanoylamino-lower alkoxy is, for example, N-$C_1-C_4$alkanoylamino-$C_1-C_4$alkoxy, such as 2-acetyloxyaminoethoxy.

Lower alkyl may be straight-chained or branched and/or bridged and is, for example, corresponding $C_1-C_7$alkyl, such as methyl, ethyl, propyl, isopropyl, butyl, isobutyl, sec-butyl, tert-butyl, or a pentyl, hexyl or heptyl group.

Lower alkylamino is, for example, $C_1-C_4$alkylamino, such as methylamino, ethylamino, propylamino, butylamino, isobutylamino, sec-butylamino or tert-butylamino.

Lower alkylamino-lower alkoxy is, for example, $C_1-C_4$alkylamino-$C_1-C_4$alkoxy, such as propylaminomethoxy, 2-methylamino-, 2-ethylamino-, 2-propylamino- or 2-butylaminoethoxy, 3-ethylamino- or 3-propylamino-propyloxy or 4-methylaminobutoxy.

Lower alkylamino-lower alkoxy is, for example, $C_1-C_4$alkylamino-$C_1-C_4$alkoxy, such as propylaminomethoxy, 2-methylamino-, 2-ethylamino-, 2-propylamino- or 2-butylaminoethoxy, 3-ethylamino- or 3-propylamino-propyloxy or 4-methylaminobutoxy.

Lower alkylcarbamoyl is, for example, $C_1-C_4$alkylcarbamoyl, such as methylcarbamoyl, ethylcarbamoyl, propylcarbamoyl, butylcarbamoyl, isobutylcarbamoyl, sec-butylcarbamoyl or tertbutylcarbamoyl, especially methylcarbamoyl.

Lower alkylcarbamoyl(hydroxy)-lower alkyl is, for example, $C_1-C_4$alkylcarbamoyl-$C_1-C_4$alkylcarbamoyl-$C_1-C_7$(hydroxy)alkyl, such as 1-methylcarbamoyl- or 1-ethylcarbamoyl-2-hydroxy-ethyl.

Lower alkylcarbamoylcycloalkyl-lower alkyl has, for example, from 3 to 8, especially from 5 to 7, ring members and is, for example, $C_1-C_4$alkylcarbamoyl-$C_5-C_7$cycloalkyl-$C_1-C_4$alkyl, such as methylcarbamoylcyclopentyl-, methylcarbamoylcyclohexyl- or methylcarbamoylcycloheptyl-methyl.

Lower alkylcarbamoyl-lower alkoxy is, for example, N-$C_1-C_4$alkylcarbamoyl-$C_1-C_4$alkoxy, such as 2-propylcarbamoylethoxy, 3-ethylcarbamoylpropyloxy, 2-ethylcarbamoylpropyloxy, 2-(methylcarbamoyl-2-methyl) propyloxy, 2-(1-methylcarbamoyl-3-methyl)butyloxy or especially butylcarbamoylmethoxy.

Lower alkylcarbamoyl-lower alkyl is, for example, N-$C_1-C_4$alkylcarbamoyl-$C_1-C_4$alkyl, such as 2-methylcarbamoylethyl, 3-methylcarbamoylpropyl, 2-methylcarbamoylpropyl, 2-(methylcarbamoyl-2-methyl) propylor 2-(1-methylcarbamoyl-3-methyl)butyl, especially 2-methylcarbamoylethyl.

Lower alkylcarbamoyl-lower alkyl is, for example, N-$C_1-C_7$alkylcarbamoyl-$C_1-C_4$alkyl, such as methyl- or dimethyl-carbamoyl-$C_1-C_4$alkyl, e.g. methylcarbamoylmethyl, 2-methylcarbamoylethyl, 3-methylcarbamoylpropyl or especially 2-methylcarbamoyl-2-methyl-propyl.

Lower alkylene, together with the carbon atom that binds its free valencies, is, for example, pyrrolidino or piperidino.

Lower alkylmorpholinocarbonyl is, for example, 4-($C_1-C_4$alkyl)morpholinocarbonyl, such as 4-methylmorpholinocarbonyl, 4-ethylmorpholinocarbonyl, 4-propylmorpholinocarbonyl or 4-butylmorpholinocarbonyl.

Lower alkylmorpholinocarbonyl-lower alkoxy is, for example, $C_1-C_4$alkylmorpholinocarbonyl-$C_1-C_4$alkoxy, such as methylmorpholinocarbonylmethoxy, 2-methylmorpholinocarbonylethoxy, 3-methylmorpholinocarbonylpropyloxy or 4-methylmorpholinocarbonylbutyloxy.

Lower alkylmorpholinocarbonyl-lower alkyl is, for example, $C_1-C_4$alkylmorpholinocarabonyl-$C_1-C_4$alkyl, such as methylmorpholinocarbonylmethyl, 2-methylmorpholinocarbonylethyl, 3-methylmorpholinocarbonylpropyl or 4-methylmorpholinocarbonylbutyl, especially 2-methylmorpholinocarbonylethyl.

Lower alkylmorpholino-lower alkoxy is, for example, $C_1-C_4$alkylmorpholino-$C_1-C_4$alkoxy, such as methylmorpholinomethoxy, 2-methylmorpholinoethoxy, 3-methylmorpholinopropyloxy or 4-methylmorpholinobutyloxy, especially 2-methylmorpholinoethoxy or 3-methylmorpholinopropyloxy.

Lower alkylmorpholino-lower alkyl is, for example, $C_1-C_4$alkylmorpholino-$C_1-C_4$alkyl, such as methylmorpholinomethyl, 2-methylmorpholinocarbonylethyl, 3-methylmorpholinopropyl or 4-methylmorpholinobutyl.

Lower alkylpiperazinocarbonyl is, for example, N'-$C_1-C_4$alkylpiperazinocarbonyl, such as N'-methylpiperazinocarbonyl, N'-ethylpiperazinocarbonyl, N'-propylpiperazinocarbonyl or N'-butylpiperazinocarbonyl.

Lower alkylpiperazinocarbonyl-lower alkoxy is, for example, N'-$C_1$-$C_4$alkylpiperazinocarbonyl-$C_1$-$C_4$alkoxy, such as N'-methylpiperazinocarbonylmethoxy, 2-(N'-methylpiperazinocarbonyl)ethoxy, 3-(N'-methylpiperazinocarbonyl)propyloxy or 4-(N'-methylpiperazinocarbonyl)butyloxy.

Lower alkylpiperazinocarbonyl-lower alkyl is, for example, N'-$C_1$-$C_4$alkylpiperazinocarbonyl-$C_1$-$C_4$alkyl, such as N'-methylpiperazinocarbonylmethyl, 2-(N'-methylpiperazinocarabonyl)ethyl, 3-(N'-methylpiperazinocarbonyl)propyl or 4-(N'-methylpiperazinocarbonyl)butyl, especially N'-methylpiperazinocarbonylmethyl.

Lower alkylpiperazino-lower alkoxy is, for example, N'-$C_1$-$C_4$alkylpiperazino-$C_1$-$C_4$alkoxy, such as N'-methylpiperazinomethoxy, 2-(N'-methylpiperazino)ethoxy, 3-(N'-methylpiperazino)propyloxy or 4-(N'-methylpiperazino)butyloxy.

Lower alkylpiperazino-lower alkyl is, for example, N'-$C_1$-$C_4$alkylpiperazino-$C_1$-$C_4$alkyl, such as N'-methylpiperazinomethyl, 2-(N'-methylpiperazino)ethyl, 3-(N'-methylpiperazino)propyl or 4-(N'-methylpiperazino)butyl, especially N'-methylpiperazinomethyl.

Lower alkylsulfamoyl-lower alkyl is, for example, N-$C_1$-$C_7$alkylsulfamoyl-$C_1$-$C_4$alkyl, such as N-methyl-, N-ethyl-, N-propyl- or N-butyl-sulfamoyl-$C_1$-$C_4$alkyl, such as N-methyl-, N-ethyl-, N-propyl- or N-butyl-sulfamoylmethyl, 2-(N-methylsulfamoyl)ethyl, 2-(N-butylsulfamoyl)ethyl, 3-(N-methylsulfamoyl)propyl, 3-(N-butylsulfamoyl)propyl, or 4-(N-methylsulfamoyl)butyl, 4-(N-butylsulfamoyl)butyl or 4-(N,N-dimethylsulfamoyl) butyl, especially N-methyl-, N-butyl- or N, N-dimethylsulfamoylmethyl.

Lower alkylthio-lower alkoxy is, for example, N-$C_1$-$C_4$alkylthio-$C_1$-$C_4$alkoxy, such as methylthio-$C_1$-$C_4$alkoxy, e.g. methylthiomethoxy, 2-methylthioethyoxy or 3-methylthiopropyloxy.

Oxadiazolyl-lower alkyl is, for example, 1,2,4-oxadiazol-5-yl-$C_1$-$C_4$alkyl, such as 1,2,4-oxadiazol-5-ylmethyl.

Oxo-oxazolinyl-lower alkyl is, for example, oxo-oxazolinyl-$C_1$-$C_4$alkyl, such as 5-oxo-oxazolin-3-ylmethyl.

Oxopiperidinyl-lower alkyl is, for example, oxopiperidinyl-$C_1$-$C_4$alkyl, such as 2-oxopiperidin-1-ylmethyl or 2-oxopiperidin-4-ylmethyl.

Oxopyrrolidinyl-lower alkyl is, for example, oxopyrrolidinyl-$C_1$-$C_4$alkyl, such as 2-oxopyrrolidin-1-ylmethy 2-oxo-pyrrolidin-4-ylmethyl or 2-oxo-pyrrolidin-5-ylmethyl.

Oxothiazolyl-lower alkyl is, for example, oxothiazolyl-$C_1$-$C_4$alkyl, such as 2-oxothiazol-4-ylmethyl or 2-oxothiazol-5-ylmethyl.

S-Oxothiomorpholinocarbonyl-lower alkoxy is, for example, S-oxothiomorpholinocarbonyl-$C_1$-$C_4$alkoxy, such as S-oxothiomorpholinocarbonylmethoxy, 2-(S-oxo) thiomorpholinocarbonylethoxy, 3-(S-oxo) thiomorpholinocarbonylpropyloxy or 1- or 2-[4-(S-oxo) thiomorpholinocarbonyl]butyloxy.

S-Oxothiomorpholino-lower alkyl is, for example, S-oxothiomorpholino-$C_1$-$C_4$alkyl, such as S-oxothiomorpholinomethyl, 2-(S-oxo)thiomorpholinoethyl, 3-(S-oxo)thiomorpholinopropyl or 1- or 2-[4-(S-oxo)thiomorpholino]butyl.

Phenyl-lower alkoxy is, for example, phenyl-$C_1$-$C_4$alkoxy, such as benzyloxy, 2-phenylethoxy, 3-phenylpropyloxy or 4-phenylbutyloxy.

Phenyl-lower alkyl is, for example, $C_1$-$C_4$alkylmorpholino-$C_1$-$C_4$alkyl, such as methylmorpholinomethyl, 2-methylmorpholinocarbonylethyl, 3-methylmorpholinopropyl or 4-methylmorpholinobutyl.

Piperazinocarbonyl-lower alkoxy is, for example, piperazinocarbonyl-$C_1$-$C_4$alkoxy, such as piperazinocarbonylmethoxy, 2-piperazinocarbonylethoxy, 3-piperazinocarbonylpropyloxy or 4-piperazinocarbonylbutyloxy.

Piperazinocarbonyl-lower alkyl is, for example, piperazinocarbonyl-$C_1$-$C_4$alkyl, such as piperazinocarbonylmethyl, 2-piperazinocarbonylethyl, 3-piperazinocarbonylpropyl or 4-piperazinocarbonylbutyl, especially piperazinocarbonylmethyl.

Piperidinocarbonyl-lower alkoxy is, for example, piperidinocarbonyl-$C_1$-$C_4$alkoxy, such as piperidinocarbonylmethoxy, 2-piperidinocarbonylethoxy, 3-piperidinocarbonylpropyloxy or 4-piperidinocarbonylbutyloxy.

Piperidinocarbonyl-lower alkyl is, for example, piperidinocarbonyl-$C_1$-$C_4$alkyl, such as piperidinocarbonylmethyl, 2-piperidinocarabonylethyl, 3-piperidinocarbonylpropyl or 4-piperidinocarbonylbutyl.

Piperidino-lower alkoxy is, for example, piperidino-$C_1$-$C_4$alkoxy, such as 2-piperidinoethoxy, 3-piperidinopropyloxy or 4-piperidinobutyloxy, especially 2-piperidinoethoxy.

Piperidino-lower alkyl is, for example, piperidino-$C_1$-$C_4$alkyl, such as piperidinomethyl, 2-piperidinoethyl, 3-piperidinopropyl or 4-piperidinobutyl, especially piperidinomethyl.

Polyhalo-lower alkoxy is, for example, di-, tri- or tetra-halo-$C_1$-$C_4$alkoxy, such as trifluoromethoxy.

Pyridyl-lower alkoxy is, for example, pyridyl-$C_1$-$C_4$alkoxy, such as pyridylmethoxy, 2-pyridylethoxy, 3-pyridylpropyloxy or 4-pyridylbutyloxy.

Pyridyl-lower alkyl is, for example, pyridyl-$C_1$-$C_4$alkyl, such as pyridylmethyl, 2-pyridylethyl, 3-pyridylpropyl or 4-pyridylbutyl, especially pyridylmethyl.

Pyrrolidinocarbonyl-lower alkoxy is, for example, pyrrolidinocarbonyl-$C_1$-$C_4$alkoxy, such as pyrrolidinocarbonylmethoxy, 2-pyrrolidinocarbonylethoxy, 3-pyrrolidinocarbonylpropyloxy or 4-pyrrolidinocarbonylbutyloxy.

Pyrrolidinocarbonyl-lower alkyl is, for example, pyrrolidinocarbonyl-$C_1$-$C_4$alkyl, such as pyrrolidinocarbonylmethyl, 2-pyrrolidinocarbonylethyl, 3-pyrrolidinocarbonylpropyl or 4-pyrrolidinocarbonylbutyl.

Pyrrolidino-lower alkyl is, for example, pyrrolidino-$C_1$-$C_4$alkyl, such as pyrrolidinomethyl, 2-pyrrolidinoethyl, 3-pyrrolidinopropyl or 4-pyrrolidinobutyl, especially pyrrolidinomethyl.

Pyrrolidinyl-lower alkyl is, for example, pyrrolidinyl-$C_1$-$C_4$alkyl, such as pyrrolidin-2-ylmethyl, pyrrolidin-3-ylmethyl, 2-pyrrolidin-2-ylethyl, 2-pyrrolidin-3-ylethyl, 3-pyrrolidin-2-ylpropyl or 4-pyrrolidin-2-ylbutyl.

Sulfamoyl-lower alkyl is, for example, sulfamoyl-$C_1$-$C_4$alkyl, such as sulfamoyl-$C_1$-$C_4$alkyl, such as sulfamoylmethyl, 2-sulfamoylethyl, 3-sulfamoylpropyl or 4-sulfamoylbutyl.

Tetrazolyl-lower alkoxy is, for example, tetrazolyl-$C_1$-$C_4$alkoxy, such as tetrazol-5-ylmethoxy, 2-(tetrazol-5-yl)ethoxy, 3-(tetrazol-5-yl)propyloxy or 4-(tetrazol-4-yl) butyloxy, especially tetrazol-5-yl methoxy.

Thiocarbamoyl-lower alkyl is, for example, thiocarbamoyl-$C_1$-$C_4$alkyl, such as thiocarbamoylmethyl, 2-thiocarbamoylethyl, 3-thiocarbamoylpropyl or 4-thiocarbamoylbutyl.

Thiomorpholinocarbonyl-lower alkyl is, for example, thiomorpholinocarbonyl-$C_1$–$C_4$alkyl, such as thiomorpholinocarbonylmethyl, 2-thiomorpholinocarbonylethyl, 3-thiomorpholinocarbonylpropyl or 1- or 2-(4-thiomorpholinocarbonyl)butyl.

Thiomorpholino-lower alkoxy is, for example, thiomorpholino-$C_1$–$C_1$–$C_4$alkoxy, such as thiomorpholinomethoxy, 2-thiomorpholinomethoxy, 3-thiomorpholinopropyloxy or 1- or 2-(4-thiomorpholino)butyloxy.

Thiomorpholino-lower alkyl is, for example, thiomorpholino-$C_1$–$C_4$alkyl, such as thiomorpholinomethyl, 2-thiomorpholinoethyl, 3-thiomorpholinopropyl or 1- or 2-(4-thiomorpholino)butyl, especially 2-thiomorpholinoethyl.

Depending on whether asymmetric carbon atoms are present, the compounds of the invention can be present as mixtures of isomers, especially as racemates, or in the form of pure isomers, especially optical antipodes.

Salts of compounds having salt-forming groups are especially acid addition salts, salts with bases or, where several salt-forming groups are present, can also be mixed salts or internal salts.

Salts are especially the pharmaceutically acceptable or non-toxic salts of compounds of formula I.

Such salts are formed, for example, by compounds of formula I having an acid group, for example a carboxy group or a sulfo group, and are, for example, salts thereof with suitable bases, such as non-toxic metal salts derived from metals of groups Ia, Ib, IIa and IIb of the Periodic Table of the Elements, for example alkali metal salts, especially lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkylamines, or with quaternary ammonium bases, for example with methyl-, ethyl-, diethyl- or triethyl-amine, mono-, bis- or tris-(2-hydroxy-lower alkyl)-amines, such as ethanol-, diethanol- or triethanol-amine, tris (hydroxymethyl)methylamine or 2-hydroxy-tertbutylamine, N,N-di-lower alkyl-N-(hydroxy-lower alkyl)-amines, such as N,N-dimethyl-N-(2-hydroxyethyl)-amine, or N-methyl-D-glucamine, or quaternary ammonium hydroxides, such as tetrabutylammonium hydroxide. The compounds of formula I having a basic group, for example an amino group, can form acid addition salts, for example with suitable inorganic acids, for example hydrohalic acids, such as hydrochloric acid or hydrobromic acid, or sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic, sulfo or phosphonic acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, such as the α-amino acids mentioned hereinbefore, and with methanesulfonic acid, ethanesulfonic acid, 2-hydroxyethanesulfonic acid, ethane-1,2-disulfonic acid, benzenesulfonic acid, 4-methylbenzenenesulfonic acid, naphthalene-2-sulfonic acid, 2- or 3-phosphoglycerate, glucose-6-phosphate, or N-cyclohexylsulfamic acid (forming cyclamates) or with other acidic organic compounds, such as ascorbic acid. Compounds of formula I having acid and basic groups can also form internal salts.

For isolation and purification purposes it is also possible to use pharmaceutically unacceptable salts.

The compounds of the present invention have enzyme-inhibiting properties. In particular, they inhibit the action of the natural enzyme renin. The latter passes from the kidneys into the blood where it effects the cleavage of angiotensinogen, releasing the decapeptide angiotensin I which is then cleaved in the lungs, the kidneys and other organs to form the octapeptide angiotensinogen II. The octapeptide increases blood pressure both directly by arterial vasoconstriction and indirectly by liberating from the adrenal glands the sodium-ion-retaining hormone aldosterone, accompanied by an increase in extracellular fluid volume. That increase can be attributed to the action of angiotensin II. Inhibitors of the enzymatic activity of renin bring about a reduction in the formation of angiotensin I. As a result a smaller amount of angiotensin II is produced. The reduced concentration of that active peptide hormone is the direct cause of the hypotensive effect of renin inhibitors.

The action of renin inhibitors is demonstrated inter alia experimentally by means of in vitro tests, the reduction in the formation of angiotensin I being measured in various systems (human plasma, purified human renin together with synthetic or natural renin substrate). Inter alia the following in vitro test is used: an extract of human renin from the kidney (0.5 mGU [milli-Goldblatt units]/ml) is incubated for one hour at 37° C. and pH 7.2 in 1-molar aqueous 2-N-(tris-hydroxymethylmethyl)amino-ethanesulfonic acid buffer solution with 23 µg/ml of synthetic renin substrate, the tetradecapeptide H-Asp-Arg-Val-Tyr-Ile-His-ProPhe-His-Leu-Leu-Val-Tyr-Ser-OH. The amount of angiotensin I formed is determined by radioimmunoassay. Each of the inhibitors according to the invention is added to the incubation mixture in various concentrations. The $IC_{50}$ is defined as the concentration of a particular inhibitor that reduces the formation of angiotensin I by 50%. In the in vitro systems the compounds of the present invention exhibit inhibiting activities at minimum concentrations of from approximately $10^{-6}$ to approximately $10^{-10}$ mol/l.

In animals deficient in salt, renin inhibitors bring about a reduction in blood pressure. Human renin differs from the renin of other species. In order to test inhibitors of human renin, primates (marmosets, Callithrix jacchus) are used, because human renin and primate renin are substantially homologous in the enzymatically active region. Inter alia the following in vivo test is used: the test compounds are tested on normotensive marmosets of both sexes having a body weight of approximately 350 g that are conscious, allowed to move freely and in their normal cages. The blood pressure and heart rate are measured via a catheter in the descending aorta and recorded radiometrically. The endogenous release of renin is stimulated by the combination of a 1-week low-salt diet and a single intramuscular injection of furosemide (5-(aminosulfonyl)-4-chloro-2-[(2-furanylmethyl) amino]benzoic acid) (5 mg/kg). 16 hours after the injection of furosemide the test compounds are administered either directly into the femoral artery using an injection cannula or, in the form of a suspension or solution, via an oesophageal tube into the stomach, and their action on the blood pressure and heart rate are evaluated. In the in vivo test described, the compounds of the present invention have hypotensive action at doses of from approximately 0.003 to approximately 0.3 mg/kg i.v. and at doses of from approximately 0.31 to approximately 10 mg/kg p.o.

The compounds of the present invention also have the property of regulating, especially reducing, intra-ocular pressure.

The extent of the reduction in intra-ocular pressure after administration of a pharmaceutical active ingredient of formula I according to the present invention can be determined, for example, in animals, especially rabbits or monkeys. Two typical experimental procedures that illustrate the present invention, but are not intended to limit it in any way, are described hereinafter.

The in vivo test on a rabbit of the "Fauve de Bourgogne" type to determine the intra-ocular-pressure-reducing activity of topically applied compositions can be designed, for example, as follows. The intra-ocular pressure (IOP) is measured using an aplanation tonometer both before the experiment and at regular intervals of time. After a local anaesthetic has been administered, the suitably formulated test compound is applied topically in a precisely defined concentration (e.g. 0.000001–5% by weight) to one eye of the animal in question. The contralateral eye is treated, for example, with physiological saline. The measured values thus obtained are evaluated statistically.

The in vivo tests on monkeys of the species *Macaca Fasciculads* to determine the intra-ocular-pressure-reducing activity of topically applied compositions can be carried out, for example, as follows. The suitably formulated test compound is applied in a precisely defined concentration (e.g. 0.000001–5% by weight) to one eye of each monkey. The other eye of the monkey is treated correspondingly, for example with physiological saline. Before the start of the test, the animals are anaesthetised with intramuscular injections of, for example, ketamine. At regular intervals of time, the intra-ocular pressure (IOP) is measured. The test is carded out and evaluated in accordance with the rules of "good laboratory practice" (GLP).

The compounds of the present invention can be used in the treatment of hypertension, congestive heart failure, cardiac hypertrophy, cardiac fibrosis, cardiomyopathy post-infarction, complications resulting from diabetes, such as nephrophathy, vasculopathy and neuropathy, diseases of the coronary vessels, restenosis following angioplasty, raised intra-ocular pressure, glaucoma, abnormal vascular growth, hyperaldosteronism, anxiety states and cognitive disorders.

The groups of compounds mentioned below are not to be regarded as exclusive; rather, as appropriate, for example in order to replace general definitions with more specific definitions, parts of those groups of compounds can be interchanged or exchanged for the definitions given above, or omitted.

The invention relates especially to compounds of formula I wherein $R_1$ is a 2-$R_A$-3-$R_B$-phenyl radical, a 2-$R_A$-4$R_C$-phenyl radical, a 2-$R_A$-pyridin-3-yl radical, a one of the radicals $R_A$ and $R_B$ is lower alkyl, hydroxy-lower alkyl, lower alkanoyloxy-lower alkyl, lower alkoxy-lower alkyl, lower alkoxy-lower alkoxy-lower alkyl; an amino-lower alkyl or amino-lower alkoxy radical that is unsubstituted or N-lower alkanoylated or N-mono- or N,N-di-lower alkylated or N,N-disubstituted by lower alkylene, hydroxy-, lower alkoxy- or lower alkoxy-lower alkoxy-lower alkylene, by unsubstituted or N'-lower alkanoylated, lower alkoxy-carbonyl- or lower alkoxy-lower alkyl-N'-substituted or N'-lower alkylated aza-lower alkylene, by oxa-lower alkylene or by optionally S-oxidised thia-lower alkylene; hydroxy, lower alkoxy, hydroxy-lower alkoxy, lower alkanoyloxy-lower alkoxy, lower alkoxy-lower alkoxy, lower alkoxy-lower alkoxy-lower alkoxy, polyhalo-lower alkoxy, cyano-lower alkoxy, unsubstituted or substituted phenyl- or pyridyl-lower alkoxy, lower alkoxy-lower alkenyloxy, optionally S-oxidised lower alkylthio-lower alkoxy, or amino-lower alkoxy that is unsubstituted or N-lower alkanoylated or N-mono- or N,N-di-lower alkylated or N,N-disubstituted by lower alkylene, hydroxy-, lower alkoxy- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; and the other is hydrogen, lower alkyl, carbamoyl, hydroxy, lower alkoxy or polyhalo-lower alkoxy, $R_C$ is hydrogen, lower alkyl, hydroxy, lower alkoxy, hydroxy-lower alkoxy, lower alkoxy-lower alkoxy, morpholino-lower alkylcarbamoyl-lower alkoxy, lower alkoxy-lower alkoxy-lower alkyl; an amino, amino-lower alkyl or amino-lower alkoxy group that is unsubstituted or N-lower alkanoylated or N-mono- or N,N-di-lower alkylated or N,N-disubstituted by lower alkylene, hydroxy-, lower alkoxy-, lower alkoxycarbonyl- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; or a free or amidated carboxy- or carboxy-lower alkoxy group or tetrazolyl-lower alkoxy, and $R_D$ is lower alkyl, hydroxy-lower alkyl, lower alkoxy-lower alkyl, lower alkoxy-lower alkoxy-lower alkyl, hydroxy-lower alkoxy-lower alkyl, a free or amidated carboxy or carboxy-lower alkyl group, cyano-lower alkyl, or an unsubstituted or substituted phenyl- or pyridyl-lower alkyl group, one of the radicals $X_1$ and $X_2$ is carbonyl and the other is methylene, $R_2$ is lower alkyl, $R_3$ is unsubstituted or N-lower alkanoylated or N-mono- or N,N-di-lower alkylated amino, $R_4$ is lower alkyl or phenyl-lower alkyl, and $R_5$ is lower alkyl, cycloalkyl-lower alkyl, hydroxy-lower alkyl, lower alkoxy-lower alkyl, lower alkanoyloxy-lower alkyl; amino-lower alkyl that is unsubstituted or N-lower alkanoylated or N-mono- or N,N-di-lower alkylated or N,N-disubstituted by lower alkylene, hydroxy-, lower alkoxy-, lower alkoxy-lower alkyl- or lower alkanoyloxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; free or esterified or amidated carboxy-lower alkyl, cyano-lower alkyl, free or esterified or amidated dicarboxy-lower alkyl, free or esterified or amidated carboxy (hydroxy)-lower alkyl, free or esterified or amidated carboxycycloalkyl-lower alkyl, lower alkanesulfonyl-lower alkyl, unsubstituted or N-mono- or N,N-di-lower alkylated thio-lower carbamoyl-lower alkyl, unsubstituted or N-mono- or N, N-di-lower alkylated sulfamoyl-lower alkyl or an optionally hydrogenated and/or oxo-substituted heteroaryl radical or lower alkyl substituted by an optionally hydrogenated and/or oxo-substituted heteroaryl radical that is bonded via a carbon atom,
and to the salts thereof.

The invention relates especially to compounds of formula I wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ a $R_B$ is lower alkyl, hydroxy-lower alkyl, lower alkanoyloxy-lower alkyl, lower alkoxy-lower alkyl, lower alkoxy-lower alkoxy-lower alkyl, amino-lower alkyl, lower alkanoylamino-lower alkyl, lower alkylamino-lower alkyl, di-lower alkylamino-lower alkyl; piperidino- or pyrrolidino-lower alkyl that is unsubstituted or substituted by hydroxy, lower alkoxy or by lower alkoxy-lower alkyl; piperazino-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholino-lower alkyl, optionally S-oxidised thiomorpholino-lower alkyl, amino-lower alkoxy, lower alkanoylamino-lower alkoxy, lower alkylamino-lower alkoxy, di-lower alkylamino-lower alkoxy; piperidino- or pyrrolidino-lower alkoxy that is unsubstituted or substituted by hydroxy, lower alkoxy or by lower alkoxy-lower alkyl; piperazino-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholino-lower alkoxy, optionally S-oxidised thiomorpholino-lower alkoxy, hydroxy, lower alkoxy, hydroxy-lower alkoxy, lower alkanoyloxy-lower alkoxy, lower alkoxy-lower alkoxy, lower alkoxy-lower alkoxy-lower alkoxy, polyhalo-lower alkoxy, cyano-lower alkoxy; phenyl- or pyridyl-lower alkoxy that is unsubstituted or substituted by lower alkyl, lower alkoxy, hydroxy, nitro, amino, lower alkylamino, di-lower alkylamino, halogen and/or by trifluoromethyl; lower alkoxy-lower alkenyloxy, lower alkylthio-lower alkoxy, lower alkanoylamino-lower alkoxy, lower alkanesulfonyl-lower alkoxy, amino-lower alkoxy, lower alkanoylamino-lower alkoxy, lower alkylamino-lower alkoxy, di-lower alkylamino-lower alkoxy; piperidino- or pyrrolidino-lower alkoxy that is unsubstituted or substituted by hydroxy, lower alkoxy or by lower alkoxy-lower alkyl; piperazino-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholino-lower alkoxy or optionally S-oxidised thiomorpholino-lower alkoxy, and the other is hydrogen, carbamoyl, hydroxy, lower alkoxy or polyhalo-lower alkoxy, $R_C$ is hydrogen, lower alkyl, lower alkoxy-lower alkoxy-lower alkyl, amino-lower alkyl, lower alkanoylamino-lower alkyl, lower alkylamino-lower alkyl, di-lower alkylamino-lower alkyl; piperidino- or pyrrolidino-lower alkyl that is unsubstituted or substituted by hydroxy, lower alkoxy or by lower alkoxy-lower alkyl; piperazino-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholino-lower alkyl, optionally S-oxidised thiomorpholino-lower alkyl, di-lower alkylamino; a piperidino or pyrrolidino group that is unsubstituted or substituted by hydroxy, lower alkoxy or by lower alkoxy-lower alkyl; piperazino that is unsubstituted or N'-lower alkylated, N'-lower alkanoylated or N'-substituted by lower alkoxycarbonyl or by lower alkoxy-lower alkyl; unsubstituted or lower alkylated morpholino, optionally S-oxidised thiomorpholino, hydroxy, lower alkoxy, hydroxy-lower alkoxy, lower alkoxy-lower alkoxy, morpholino-lower alkylcarbamoyl-lower alkoxy, amino-lower alkoxy, lower alkanoylamino-lower alkoxy, lower alkylamino-lower alkoxy, di-lower alkylamino-lower alkoxy; piperidino- or pyrrolidino-lower alkoxy that is unsubstituted or substituted by hydroxy, lower alkoxy or by lower alkoxy-lower alkyl; piperazino-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholino-lower alkoxy, optionally S-oxidised thiomorpholino-lower alkoxy, carboxy-lower alkoxy, carbamoyl-lower alkoxy, lower alkylcarbamoyl-lower alkoxy, di-lower alkylcarbamoyl-lower alkoxy; piperidino- or pyrrolidino-carbonyl-lower alkoxy that is unsubstituted or substituted by hydroxy, lower alkoxy or by lower alkoxy-lower alkyl; piperazinocarbonyl-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholinocarbonyl-lower alkoxy, optionally S-oxidised thiomorpholinocarbonyl-lower alkoxy, tetrazolyl-lower alkoxy, carboxy, carbamoyl, lower alkylcarbamoyl or di-lower alkylcarbamoyl, and $R_D$ is lower alkyl, hydroxy-lower alkyl, lower alkoxy-lower alkyl, lower alkoxy-lower alkoxy-lower alkyl, hydroxy-lower alkoxy-lower alkyl, carboxy-lower alkyl, lower alkoxycarbonyl-lower alkyl, carbamoyl-lower alkyl, lower alkylcarbamoyl-lower alkyl, di-lower alkylcarbamoyl-lower alkyl; piperidino- or pyrrolidino-carbonyl-lower alkyl that is unsubstituted or substituted by hydroxy, lower alkoxy or by lower alkoxy-lower alkyl; piperazinocarbonyl-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholinocarbonyl-lower alkyl, optionally S-oxidised thiomorpholinocarbonyl-lower alkyl, carboxy-lower alkyl, lower alkoxycarbonyl-lower alkyl or a phenyl- or pyridyl-lower alkyl group that is unsubstituted or substituted by lower alkyl, lower alkoxy, hydroxy, nitro, amino, lower alkylamino, di-lower alkylamino, halogen and/or by trifluoromethyl, one of the radicals $X_1$ and $X_2$ is carbonyl and the other is methylene, $R_2$ is lower alkyl, $R_3$ is amino, lower alkanoylamino, lower alkylamino or di-lower alkylamino, $R_4$ is lower alkyl or phenyl-lower alkyl and $R_5$ is lower alkyl, cycloalkyl-lower alkyl, hydroxy-lower alkyl, lower alkoxy-lower alkyl, lower alkanoyloxy-lower alkyl; piperidino- or pyrrolidino-carbonyl-lower alkyl that is unsubstituted or substituted by hydroxy, lower alkoxy or by lower alkoxy-lower alkyl; piperazinocarbonyl-lower alkyl that is unsubstituted or N'-lower alkylated, N'-lower alkanoylated or N'-substituted by lower alkoxycarbonyl or by lower amorpholinocarbonyl-lower alkylated or lower alkylated morpholinocarbonyl-lower alkyl, optionally S-oxidised thiomorpholinocarbonyl-lower alkyl, carboxy-lower alkyl, lower alkoxycarbonyl-lower alkyl, carbamoyl-lower alkyl, lower alkylcarbamoyl-lower alkyl, di-lower alkylcarbamoyl-lower alkyl; piperidino- or pyrrolidino-carbonyl-lower alkyl that is unsubstituted or substituted by hydroxy, lower alkoxy or by lower alkoxy-lower alkyl; piperazinocarbonyl-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholinocarbonyl-lower alkyl, optionally S-oxidised thiomorpholinocarbonyl-lower alkyl, cyano-lower alkyl, dicarboxy-lower alkyl, lower alkoxycarbonyl(carboxy)-lower alkyl, di-lower alkoxycarbonyl-lower alkyl, dicarbamoyl-lower alkyl, carbamoyl(carboxy)-lower alkyl, di-(lower alkylcarbamoyl)-lower alkyl, di-(di-lower alkylcarbamoyl)-lower alkyl, carboxy(hydroxy)-lower alkyl, lower alkoxycarbonyl(hydroxy)-lower alkyl, carbamoyl(hydroxy)-lower alkyl, lower alkylcarbamoyl(hydroxy)-lower alkyl or di-lower alkylcarbamoyl(hydroxy)-lower alkyl, carboxycycloalkyl-lower alkyl, lower alkoxycarbonylcycloalkyl-lower alkyl, carbamoylcycloalkyl-lower alkyl, lower alkylcarbamoylcycloalkyl-lower alkyl, di-lower alkylcarbamoylcycloalkyl-lower alkyl, lower alkanesulfonyl-lower alkyl, thiocarbamoyl-lower alkyl, N-lower alkylthiocarbamoyl-low alkyl, N-lower alkylthiocarbamoyl-lower alkyl or N,N-di-lower alkylthiocarbamoyl-lower alkyl, sulfamoyl-lower alkyl, lower alkylsulfamoyl-lower alkyl or di-lower alkylsulfamoyl-lower alkyl, unsubstituted or oxo-substituted pyrrolidinyl, imidazolyl, benzimidazolyl, oxadiazolyl, pyridyl, oxopiperidinyl, dioxopiperidinyl, oxothiazolyl, oxo-oxazolinyl or quinolinyl, unsubstituted or oxo-substituted pyrrolidinyl-lower alkyl, imidazolyl-lower alkyl, benzimidazolyl-lower alkyl, oxadiazolyl-lower alkyl, pyridyl-lower alkyl, oxopiperidinyl-lower alkyl, dioxopiperidinyl-lower alkyl, oxothiazolyl-lower alkyl, oxo-oxazolinyl-lower alkyl or quinolinyl-lower alkyl, morpholinocarbonyl-lower alkyl or unsubstituted or N-lower alkanoylated piperidyl-lower alkyl or unsubstituted or N-lower alkanoylated piperidyl, and the salts thereof.

The invention relates especially to compounds of formula I wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is $C_1$–$C_4$alkyl, hydroxy-$C_1$–$C_4$alkyl, $C_1$–$C_4$alkanoyloxy-$C_1$–$C_4$alkyl, $C_1$–$C_4$alkoxy-$C_1$–$C_4$alkyl, $C_1$–$C_4$alkoxy-$C_1$–$C_4$alkoxy-$C_1$–$C_4$alkyl, amino-$C_1$–$C_4$alkyl, $C_1$–$C_4$alkanoylamino-$C_1$–$C_4$alkyl, $C_1$–$C_4$alkylamino-$C_1$–$C_4$alkyl, di-$C_1$–$C_4$alkylamino-$C_1$–$C_4$alkyl, piperidino-$C_1$–$C_4$-alkyl, hydroxypiperidino-$C_1$–$C_4$alkyl, $C_1$–$C_4$alkoxypiperidino-$C_1$–$C_4$alkyl, $C_1$–$C_4$alkoxy-$C_1$–$C_4$-alkoxypiperidino-$C_1$–$C_4$alkyl, $C_1$–$C_4$alkoxycarbonylpiperidino-$C_1$–$C_4$alkyl, pyrrolidino-$C_1$–$C_4$alkyl, hydroxypyrrolidino-$C_1$–$C_4$alkyl, $C_1$–$C_4$alkoxypyrrolidino-$C_1$–$C_4$alkyl, $C_1$–$C_4$-alkoxy-$C_1$–$C_4$alkoxypyrrolidino-$C_1$–$C_4$alkyl, piperazino-$C_1$–$C_4$alkyl, N'-$C_1$–$C_4$alkylpiperazino-$C_1$–$C_4$alkyl, N'-$C_1$–$C_4$alkanoylpiperazino-$C_1$–$C_4$alkyl, N'-$C_1$–$C_4$alkoxycarbonylpiperazino-$C_1$–$C_4$alkyl, N'-$C_1$–$C_4$alkoxy-$C_1$–$C_4$alkylpiperazino-$C_1$–$C_4$alkyl, morpholino-$C_1$–$C_4$alkyl, $C_1$–$C_4$alkylmorpholino-$C_1$–$C_4$alkyl, thiomorpholino-$C_1$–$C_4$alkyl, S-oxythiomorpholino-$C_1$–$C_4$alkyl, S,S-dioxythiomorpholino-$C_1$–$C_4$alkyl, $C_1$–$C_7$alkoxy, such as propyloxy, amino-$C_1$–$C_7$alkoxy, $C_1$–$C_4$alkanoylamino-$C_1$–$C_4$alkoxy, $C_1$–$C_4$alkylamino-$C_1$–$C_4$alkoxy, di-$C_1$–$C_4$alkylamino-$C_1$–$C_4$alkoxy, piperidino-$C_1$–$C_4$alkoxy, hydroxypiperidino-$C_1$–$C_4$alkoxy, $C_1$–$C_4$alkoxypiperidino-$C_1$–$C_4$alkoxy, $C_1$–$C_4$alkoxy-$C_1$–$C_4$alkoxypiperidino-$C_1$–$C_4$alkoxy, pyrrolidino-$C_1$–$C_4$alkoxy, hydroxypyrrolidino-$C_1$–$C_4$alkoxy, $C_1$–$C_4$alkoxypyrrolidino-$C_1$–$C_4$alkoxy, $C_1$–$C_4$alkoxy-$C_1$–$C_4$alkoxypyrrolidino-$C_1$–$C_4$alkoxy, piperazino-$C_1$–$C_4$alkoxy, N'-$C_1$–$C_4$alkylpiperazino-$C_1$–$C_4$alkoxy, N'-$C_1$–$C_4$alkanoylpiperazino-$C_1$–$C_4$-$C_4$alkoxy, N'-$C_1$–$C_4$alkoxycarbonylpiperazino-$C_1$–$C_4$alkoxy, N'-$C_1$–$C_4$alkoxy-$C_1$–$C_4$alkylpiperazino-$C_1$–$C_4$alkoxy, morpholino-$C_1$–$C_4$alkoxy or $C_1$–$C_4$alkylmorpholino-$C_1$–$C_4$alkoxy, thiomorpholino-$C_1$–$C_4$alkoxy, S-oxythiomorpholino-$C_1$–$C_4$alkoxy, S,S-dioxythiomorpholino-$C_1$–$C_4$alkoxy, hydroxy, hydroxy-$C_1$–$C_4$alkoxy, $C_1$–$C_4$alkanoyloxy-$C_1$–$C_4$alkoxy, $C_1$–$C_4$alkoxy-$C_1$–$C_4$alkoxy, $C_1$–$C_4$alkoxy-$C_1$–$C_4$alkoxy-$C_1$–$C_4$alkoxy, polyhalo-$C_1$–$C_4$alkoxy, cyano-$C_1$–$C_4$alkoxy, carbamoyl-$C_1$–$C_4$alkoxy, such as 2-carbamoylethoxy; phenyl- or pyridyl-$C_1$–$C_4$alkoxy that is unsubstituted or substituted by $C_1$–$C_4$alkyl, $C_1$–$C_4C_4$alkoxy, hydroxy, nitro, amino, $C_1$–$C_4$alkylamino, di-$C_1$–$C_4$alkylamino, halogen and/or by trifluoromethyl; $C_1$–$C_4$alkoxy-$C_1$–$C_4$alkenyloxy, $C_1$–$C_4$alkylthio-$C_1$–$C_4$alkoxy, $C_1$–$C_4$alkanesulfinyl-$C_1$–$C_4$alkoxy, $C_1$–$C_4$alkanesulfonyl-$C_1$–$C_4$alkoxy, amino-$C_1$–$C_7$alkoxy, $C_1$–$C_4$alkanoylamino-$C_1$–$C_4$alkoxy, $C_1$–$C_4$alkylamino-$C_1$–$C_4$alkoxy, di-$C_1$–$C_4$alkylamino-$C_1$–$C_4$alkoxy, piperidino-$C_1$–$C_4$alkoxy, hydroxypiperidino-$C_1$–$C_4$alkoxy, $C_1$–$C_4$alkoxypiperidino-$C_1$–$C_4$alkoxy, $C_1$–$C_4$alkoxy-$C_1$–$C_4$alkoxypiperidino-$C_1$–$C_4$alkoxy, pyrrolidino-$C_1$–$C_4$alkoxy, hydroxypyrrolidino-$C_1$–$C_4$alkoxy, $C_1$–$C_4$alkoxypyrrolidino-$C_1$–$C_4$alkoxy, $C_1$–$C_4$alkoxy-$C_1$–$_4$alkoxypyrrolidino-$C_1$–$C_4$alkoxy, piperazino-$C_1$–$C_4$alkoxy, N'-$C_1$–$C_4$alkylpiperazino-$C_1$–$C_4$alkoxy, N'-$C_1$–$C_4$alkanoylpiperazino-$C_1$–$C_4$alkoxy, N'-$C_1$–$C_4$alkoxycarbonylpiperazino-$C_1$–$C_4$-alkoxy, N'-$C_1$–$C_4$alkoxy-$C_1$–$C_4$alkylpiperazino-$C_1$–$C_4$alkoxy, morpholino-$C_1$–$C_4$alkoxy or $C_1$–$C_4$alkylmorpholino-$C_1$–$C_4$alkoxy or thiomorpholino-$C_1$–$C_4$alkoxy, and the other is hydrogen, carbamoyl, $C_1$–$C_4$alkyl, hydroxy, $C_1$–$C_4$alkoxy or trihalo-$C_1$–$C_4$alkoxy, $R_C$ is hydrogen, hydroxy, di-$C_2$–$C_4$alkylamino, piperidino, pyrrolidino, morpholino, thiomorpholino, S-oxythiomorpholino, S,S-dioxythiomorpholino, $C_1$–$C_4$alkoxy, hydroxy-$C_1$–$C_4$alkoxy, $C_1$–$C_4$alkoxy-$C_1$–$C_4$alkoxy, morpholino-$C_1$–$C_4$alkylcarbamoyl-$C_1$–$C_4$alkoxy, $C_1$–$C_4$alkoxy-$C_1$–$C_4$alkoxy-$C_1$–$C_4$alkyl, amino-$C_1$–$C_4$alkyl, $C_1$–$C_4$alkyl, $C_1$–$C_4$alkylamino-$C_1$–$C_4$alkyl, di-$C_1$–$C_4$alkylamino-$C_1$–$C_4$alkyl; piperidino- or pyrrolidino-$C_1$–$C_4$alkyl that is unsubstituted or substituted by hydroxy, $C_1$–$C_4$alkoxy or by $C_1$–$C_4$alkoxy-$C_1$–$C_4$alkyl; amino-$C_1$–$C_4$alkyl, $C_1$–$C_4$alkanoylamino-$C_1$–$C_4$alkyl, $C_1$–$C_4$alkylamino-$C_1$–$C_4$alkylamino-$C_1$–$C_4$alkyl, di-$C_1$–$C_4$alkylamino-$C_1$–$C_4$alkyl, piperidino-$C_1$–$C_4$alkyl, hydroxypiperidino-$C_1$-$C_4$alkyl,
$C_1$-$C_4$alkoxypiperidino-$C_1$-$C_4$alkyl, $C_1$-$C_4$alkoxy-$C_1$-$C_4$alkoxypiperidino-$C_1$-$C_4$alkyl,
$C_1$-$C_4$alkoxycarbonylpiperidino-$C_1$-$C_4$alkyl,
pyrrolidino-$C_1$-$C_4$alkyl, hydroxypyrrolidino-$C_1$-$C_4$alkyl, $C_1$-$C_4$alkoxypyrrolidino-$C_1$-$C_4$alkyl,
$C_1$-$C_4$alkoxypyrrolidino-$C_1$-$C_4$alkyl, piperazino-$C_1$-$C_4$alkyl, N'-$C_1$-$C_4$alkanoylpiperazino-$C_1$-$C_4$alkyl,
N'-$C_1$-$C_4$alkanoylpiperazino-$C_1$-$C_4$alkyl,
N'-$C_1$-$C_4$alkoxycarbonylpiperazino-$C_1$-$C_4$alkyl,
N'-$C_1$-$C_4$alkoxy-$C_1$-$C_4$alkylpiperazino-$C_1$-$C_4$alkyl,
morpholino-$C_1$-$C_4$alkyl, $C_1$-$C_4$alkylmorpholino-$C_1$-$C_4$alkyl, thiomorpholino-$C_1$-$C_4$alkyl,
S-oxythiomorpholino-$C_1$-$C_4$alkyl, S,S-dioxythiomorpholino-$C_1$-$C_4$alkyl, amino-$C_1$-$C_7$alkoxy, $C_1$-$C_4$alkanoylamino-$C_1$-$C_4$alkoxy,
$C_1$-$C_4$alkylamino-$C_1$-$C_4$alkoxy, di-$C_1$-$C_4$alkylamino-$C_1$-$C_4$ alkoxy, piperidino-$C_1$-$C_4$alkoxy,
hydroxypiperidino-$C_1$-$C_4$alkoxy,
$C_1$-$C_4$alkoxypiperdino-$C_1$-$C_4$alkoxy, $C_1$-$C_4$alkoxy-$C_1$-$C_4$alkoxypiperidino-$C_1$-$C_4$alkoxy, pyrrolidino-$C_1$-$C_4$alkoxy, hydroxypyrrolidino-$C_1$-$C_4$alkoxy,
$C_1$-$C_4$alkoxypyrrolidino-$C_1$-$C_4$alkoxy, $C_1$-$C_4$alkoxy-$C_1$-$C_4$alkoxypyrrolidino-$C_1$-$C_4$alkoxy, piperazino-$C_1$-$C_4$alkoxy, N'-$C_1$-$C_4$alkylpiperazino-$C_1$-$C_4$alkoxy,
N'-$C_1$-$C_4$alkanoylpiperazino-$C_{1-C4}$alkoxy,
N'-$C_1$-$C_4$alkoxycarbonylpiperazino-$C_1$-$C_4$alkoxy,
N'-$C_1$-$C_4$alkoxy-$C_1$-$C_4$alkylpiperazino-$C_1$-$C_4$alkoxy,
morpholino-$C_1$-$C_4$alkoxy or $C_1$-$C_4$alkylmorpholino-$C_1$-$C_4$alkoxy, thiomorpholino-$C_1$-$C_4$alkoxy,
S-oxythiomorpholino-$Cl_1$-$C_4$alkoxy, S,S-dioxythiomorpholino-$C_1$-$C_4$alkoxy, carboxy-$C_1$-$C_4$alkoxy, carbamoyl-$C_1$-$C_4$alkoxy,
$C_1$-$C_4$alkylcarbamoyl-$C_1$-$C_4$alkoxy,
di-$C_1$-$C_4$alkylcarbamoyl-$C_1$-$C_4$alkoxy,
di-$C_1$-$C_4$alkoxy, such as 3-dimethylaminopropyloxy,
piperidinocarbonyl-$C_1$-$C_4$alkoxy,
hydroxypiperidinocarbonyl-$C_1$-$C_4$alkoxy,
$C_1$-$C_4$alkoxypiperidinocarbonyl-$C_1$-$C_4$alkoxy,
$C_1$-$C_4$alkoxy-$C_1$-$C_4$alkoxypiperidinocarbonyl-$C_1$-$C_4$alkoxy, pyrrolidinocarbonyl-$C_1$-$C_4$alkoxy,
hydroxypyrrolidinocarbonyl-$C_1$-$C_4$alkoxy,
$C_1$-$C_4$alkoxypyrrolidinocarbonyl-$C_1$-$C_4$ alkoxy,
$C_1$-$C_4$alkoxy-$C_1$-$C_4$alkoxypyrrolidinocarbonyl-$C_1$-$C_4$alkoxy, piperazinocarbonyl-$C_1$-$C_4$alkoxy,
N'-$C_1$-$C_4$alkylpiperazinocarbonyl-$C_1$-$C_4$alkoxy,
N'-$C_1$-$C_4$alkoxycarabonylpiperazinocarbonyl or
N'-$C_1$-$C_4$alkoxy-$C_1$-$C_4$alkylpiperazinocarbonyl-$C_1$-$C_4$alkoxy, morpholinocarbonyl-$C_1$-$C_4$alkoxy,
$C_1$-$C_1$alkylmorpholinocarbonyl-$C_1$-$C_1$alkoxy,
thiomorpholinocarbonyl-$C_1$-$C_4$alkoxy, S-oxythiomorpholinocarbonyl, S,S-dioxythiomorpholinocarbonyl-$C_1$-$C_4$alkoxy,
tetrazolyl-$C_1$-$C_1$alkoxy, carboxy, carbamoyl or
$C_1$-$C_4$alkylcarbamoyl, such as methylcarbamoyl, and $R_D$ is $C_1$-$C_4$alkyl, hydroxy-$C_1$-$C_4$alkyl, $C_1$-$C_4$alkoxy-$C_1$-$C_4$alkyl, $C_4$alkoxy-$C_1$-$C_4$alkoxy-$C_1$-$C_4$-alkyl,
hydroxy-$C_1$-$C_4$alkoxy-$C_{1-C4}$alkyl, carboxy-$C_1$-$C_4$alkyl, $C_1$-$C_4$alkoxycarbonyl-$C_1$-$C_4$alkyl,
carbamoyl-$C_1$-$C_4$alkyl, $C_1$-$C_4$alkylcarbamoyl-$C_1$-$C_4$alkyl, di-$C_1$-$C_4$alkylcarbamoyl-$C_1$-$C_4$alkyl,
piperidino-$C_1$-$C_4$alkyl, hydroxypiperidino-$C_1$-$C_4$alkyl, $C_1$-$C_4$alkoxypiperidino-$C_1$-$C_4$alkyl,
$C_1$-$C_4$alkoxy-$C_1$-$C_4$alkoxypiperidino-$C_1$-$C_4$alkyl,
$C_1$-$C_4$alkoxycarbonylpiperidino-$C_1$-$C_4$alkyl,
pyrrolidino-$C_1$-$C_4$alkyl, hydroxypyrrolidino-$C_1$-$C_4$alkyl, $C_1$-$C_4$alkoxypyrrolidino-$C_1$-$C_4$alkyl,
$C_1$-$C_4$alkoxy-$C_1$-$C_4$alkoxypyrrolidino-$C_1$-$C_4$alkyl,
piperazino-$C_1$-$C_4$alkyl, N'-$C_1$-$C_4$alkylpiperazino-$C_1$-$C_4$alkyl, N'-$C_1$-$C_4$alkanoylpiperazino-$C_1$-$C_4$alkyl,
N'-$C_1$-$C_4$alkoxycarbonylpiperazino- $C_1$-$C_4$alkyl,
N'-$C_1$-$C_4$alkoxy-$C_1$-$C_4$alkylpiperzino-$C_1$-$C_4$alkyl,
morpholino-$C_1$-$C_4$alkyl, $C_1$-$C_4$alkylmorpholino-$C_1$-$C_4$alkyl, thiomorpholino-$C_1$-$C_4$alkyl,
S-oxythiomorpholino-$C_1$-$C_4$alkyl, S,S-dioxythiomorpholino-$C_1$-$C_4$alkyl, carboxy-$C_1$-$C_4$alkyl, $C_1$-$C_4$alkoxycarbonyl-$C_1$-$C_4$alkyl, or is
phenyl-$C_1$-$C_4$alkyl or pyridyl-$C_1$-$C_4$alkyl that is
unsubstituted or substituted by $C_1$-$C_4$alkyl,
$C_1$-$C_4$alkoxy, hydroxy, nitro, amino,
$C_1$-$C_4$alkylamino, di-$C_1$-$C_4$alkylamino, halogen and/or by trifluoromethyl, one of the radicals $X_1$ and $X_2$ is carbonyl and the other is methylene, $R_2$ is $C_1$-$C_4$alkyl, $R_3$ is amino, $C_1$-$C_4$alkanoylamino, $C_1$-$C_4$alkylamino or di-$C_1$-$C_4$alkylamino, $R_4$ is $C_1$-$C_4$alkyl or phenyl-$C_1$-$C_4$alkyl, and $R_5$ is $C_1$-$C_4$alkyl, cycloalkyl-$C_1$-$C_4$alkyl, hydroxy-$C_1$-$C_4$alkyl, $C_1$-$C_4$alkoxy-$C_1$-$C_4$alkyl,
$C_1$-$C_4$alkanoyloxy-$C_1$-$C_4$alkyl, piperidino-$C_1$-$C_4$alkyl, hydroxypiperidino-$C_1$-$C_4$alkyl,
$C_4$alkoxypiperidino-$C_1$-$C_4$alkyl, $C_1$-$C_4$alkoxy-$C_1$-$C_4$alkoxypiperidino-$C_1$-$C_4$alkyl,
$C_1$-$C_4$alkoxycarbonylpiperidino-$C_1$-$C_4$alkyl,
pyrrolidino-$C_1$-$C_4$alkyl, hydroxypyrrolidino-$C_1$-$C_4$alkyl, $C_1$-$C_4$alkoxypyrrolidino-$C_1$-$C_4$alkyl,
$C_1$-$C_4$alkoxy-$C_1$-$C_4$alkoxypyrrolidino-$C_1$-$C_4$alkyl,
piperazino-$C_1$-$C_4$alkyl, N'-$C_1$-$C_4$alkylpiperazino-$C_1$-$C_4$alkyl, N'-$C_1$-$C_4$alkanoylpiperazino-$C_1$-$C_4$alkyl,
N'-$C_1$-$C_4$alkoxycarbonylpiperazino-$C_1$-$C_4$alkyl,
N'-$C_1$-$C_4$alkoxy-$C_1$-$C_4$alkylpiperazino-$C_1$-$C_4$alkyl,
morpholino-$C_1$-$C_4$alkyl, $C_1$-$C_4$alkylmorpholino-$C_1$-$C_4$alkyl, thiomorpholino-$C_1$-$C_1$-alkyl,
S-oxythiomorpholino-$C_1$-$C_4$alkyl, S,S-dioxythiomorpholino-$C_2$-$C_4$alkyl, carboxy-$C_1$-$C_4$alkyl, $C_1$-$C_4$alkoxycarbonyl-$C_1$-$C_4$alkyl,
carbamoyl-$C_1$-$C_4$alkyl, $C_1$-$C_4$alkylcarbamoyl-$C_1$-$C_4$alkyl, di-$C_1$-$C_4$alkylcarbamoyl-$C_1$-$C_4$alkyl,
piperidinocarbonyl-$C_1$-$C_4$alkyl,
hydroxypiperidinocarbonyl-$C_1$-$C_4$alkyl,
$C_1$-$C_4$alkoxypiperidinocarbonyl-$C_1$-$C_4$alkyl,
$C_1$-$C_4$alkyl, $C_1$-$C_4$alkoxy-$C_1$-$C_4$alkoxypiperidinocarbonyl-$C_1$-$C_4$alkyl,
pyrrolindinocarbonyl-$C_1$-$C_4$alkyl,
hydrolxypyrrolidinocarbonyl-$C_1$-$C_4$alkyl,
$C_1$-$C_4$alkoxypyrrolidinocarbonyl-$C_1$-$C_4$alkyl,
$C_1$-$C_4$alkoxy-$C_1$-$C_4$alkoxypyrrolidinocarbonyl-$C_1$-$C_4$alkyl, piperazinocarbonyl-$C_1$-$C_4$alkyl,
N'-$C_1$-$C_4$alkylpiperazinocarbonyl-$C_1$-$C_4$alkyl,
N'-$C_1$-$C_4$alkanoylpiperazinocarbonyl-$C_1$-$C_4$alkyl,
N'-$C_1$-$C_4$alkoxycarbonylpiperazinocarbonyl,
N'-$C_1$-$C_4$alkoxy-$C_1$-$C_4$alkylpiperazinocarbonyl-$C_1$-$C_4$alkyl, morpholinocarbonyl-$C_1$-$C_4$alkyl,
$C_1$-$C_4$alkylmorpholinocarbonyl-$C_1$-$C_4$alkyl,
thiomorpholinocarbonyl-$C_1$-$C_4$alkyl,
S-oxythiomorpholinocarbonyl-$C_1$-$C_4$alkyl, S,S-dioxythiomorpholinocarbonyl-$C_1$-$C_4$alkyl, carbamoyl-$C_1$-$C_4$alkyl, $C_1$-$C_4$alkylcarbamoyl-$C_1$-$C_4$alkyl,
di-$C_1$-$C_4$alkylcarbamoyl-$C_1$-$C_4$alkyl, cyano-$C_1$-$C_4$alkyl, dicarboxy-$C_1$-$C_4$alkyl,
$C_1$-$C_4$alkoxycarbonyl(carboxy)-$C_1$-$C_4$alkyl,
di-$C_1$-$C_4$alkoxycarbonyl-$C_1$-$C_4$alkyl, dicarbamoyl- $C_1$–$C_4$alkyl, carbamoyl(carboxy) (carboxy)-$C_1$–$C_4$alkyl, di-($C_1$–$C_4$alkylcarbamoyl)-$C_1$–$C_4$alkyl, di-(di-$C_1$–$C_4$alkylcarbamoyl)-$C_1$–$C_4$alkyl, carbamoyl (hydroxy)-$C_1$–$C_4$alkyl, $C_1$–$C_4$alkylcarbamoyl (hydroxy)-$C_1$–$C_4$alkyl or di-$C_1$–$C_4$alkylcarbamoyl (hydroxy)-$C_1$–$C_4$alkyl, carboxycycloalkyl-$C_1$–$C_4$alkyl, $C_1$–$C_4$alkoxycarbonylcycloalkyl-$C_1$–$C_4$alkyl, carbamoylcycloalkyl-$C_1$–$C_4$alkyl, $C_1$–$C_4$alkylcarbamoylcycloalkyl-$C_1$–$C_4$alkyl, di-$C_1$–$C_4$alkylcarbamoylcycloalkyl-$C_1$–$C_4$alkyl, amoylcycloalkyl-$C_1$–$C_4$alkyl, $C_1$–$C_4$alkanesulfonyl-$C_1$–$C_4$alkyl, thiocarbamoyl-$C_1$–$C_4$alkyl, N-$C_1$–$C_4$alkylthiocarbamoyl-$C_1$–$C_4$alkyl or N,N-di-$C_1$–$C_4$alkylthiocarbamoyl-$C_1$–$C_4$alkyl, sulfamoyl-$C_1$–$C_4$alkyl, $C_1$–$C_4$alkylsulfamoyl-$C_1$–$C_4$alkyl or di-$C_1$–$C_4$alkylsulfamoyl-$C_1$–$C_4$alkyl, unsubstituted or oxo-substituted pyrrolidinyl, imidazolyl, benzimidazolyl, oxadiazolyl, pyridyl, oxopiperidinyl, dioxopiperidinyl, oxothiazolyl, oxo-oxazolinyl or quinolinyl, unsubstituted or oxo-substituted pyrrolidinyl-$C_1$–$C_4$alkyl, imidazolyl-$C_1$–$C_4$alkyl, benzimidazolyl-$C_1$–$C_4$alkyl, oxadiazolyl-$C_1$–$C_4$alkyl, pyridyl-$C_1$–$C_4$alkyl, oxopiperidinyl-$C_1$–$C_4$alkyl, dioxopiperidinyl-$C_1$–$C_4$alkyl, oxothiazolyl-$C_1$–$C_4$alkyl, oxo-oxazolinyl-$C_1$–$C_4$alkyl or quinolinyl-$C_1$–$C_4$alkyl, morpholinocarbonyl-$C_1$–$C_4$alkyl or unsubstituted or N-$C_1$–$C_4$alkanoylated piperidyl-$C_1$–$C_4$alkyl or unsubstituted or N-$C_1$–$C_4$alkanoylated piperidyl, and the salts thereof.

The invention relates especially to compounds of formula I wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is $C_1$–$C_4$alkyl, $C_1$–$C_4$alkoxy-$C_1$–$C_4$alkyl, such as propyloxymethyl, di-$C_1$–$C_4$alkylamino-$C_1$–$C_4$alkyl, such as dimethylaminomethyl, piperidino-$C_1$–$C_4$alkyl, such as piperidinomethyl, $C_1$–$C_4$alkanoylpiperidinyl-$C_1$–$C_4$alkyl, such as 2-methoxycarbonylpiperidin-4-yl) ethyl, pyrrolidino-$C_1$–$C_4$alkyl, such as pyrrolidinomethyl, piperazino-C,-$C_1$–alkyl, N'-$C_1$–$C_4$alkylpiperazino-$C_1$–$C_4$alkyl, such as N'-methylpiperazinomethyl, N'-$C_1$–$C_4$alkanoylpiperazino-$C_1$–$C_4$alkyl, such as N'-acetylpiperazinomethyl, morpholino-$C_1$–$C_4$alkyl, such as morpholinomethyl, 2-morpholinoethyl or 3-morpholinopropyl, $C_1$–$C_4$alkylmorpholino-$C_1$–$C_4$alkyl, thiomorpholino-$C_1$–$C_4$alkyl, such as 2-thiomorpholinoethyl, amino-$C_1$–$C_7$alkoxy, such as 2-aminoethoxy, 3-aminopropyloxy, $C_1$–$C_4$alkanoylamino-$C_1$–$C_4$alkoxy, such as 2-acetylaminoethoxy, di-$C_1$–$C_4$-alkylamino-$C_1$–$C_4$-alkoxy, such as 3-dimethylaminopropyloxy, piperidino-$C_1$–$C_4$alkoxy, such as 2-piperidinoethoxy, morpholino-$C_1$–$C_4$alkoxy, such as 2-morpholinoethoxy or 3-morpholinopropyloxy, hydroxy, $C_1$–$C_7$alkoxy, such as propyloxy, $C_1$–$C_4$alkoxy-$C_1$–$C_4$alkoxy, such as 2-methoxyethoxy, 3-methoxypropyloxy, 4-methoxybutyloxy or 5-methoxypentyloxy, $C_1$–$C_4$alkoxy-$C_1$–$C_4$alkoxy, such as 2-(methoxymethoxy)ethoxy or 2-(2-methoxyethoxy) ethoxy, $C_1C_4$alkoxy-$C_1$–$C_4$alkenyloxy, such as 4-methoxy-but-2-enyloxy, amino-$C_2$–$C_1$–$C_7$alkoxy, such as 2-aminoethoxy or 3-aminopropyloxy, $C_1$–$C_4$alkanoylamino-$C_1$–$C_4$alkoxy, such as 2-acetylaminoethoxy, di-$C_1$–$C_4$alkylamino-$C_1$–$C_4$alkoxy, such as 3-dimethylaminopropyloxy, piperidino-$C_1$–$C_4$alkoxy, such as 2-piperidinoethoxy, morpholino-$C_1$–$C_4$alkoxy, such as 2-morpholinoethoxy or 3-morpholinopropyloxy, carbamoyl, carbamoyl-$C_1$–$C_4$alkoxy, such as 2-carbamoylethoxy, and the other is hydrogen, $C_1$–$C_4$alkyl, such as methyl, hydroxy, or $C_1$–$C_4$alkoxy, such as methoxy.

$R_C$ is hydrogen, hydroxy, $C_1$–$C_4$alkoxy, such as methoxy, $C_1$–$C_4$alkoxy, such as 2-methoxyethoxy, 3-methoxypropyloxy, 4-methoxybutyloxy or 5-metholxypentyloxy, morpholino-$C_1$–$C_4$alkylcarbamoyl-$C_1$–$C_4$alkoxy, such as 2-morpholinoethylcarbamoylmethoxy, di-$C_1$–$C_4$alkylamino-$C_1$–$C_4$alkyl, such as dimethylaminomethyl, piperidino-$C_1$–$C_4$alkyl, such as piperidinomethyl, $C_1$–$C_4$alkoxycarbonylpiperidino-$C_1$–$C_4$alkyl, such as 2-(1-methoxycarbonylpiperidin-4-yl)ethyl, pyrrolidino-$C_1$–$C_4$alkyl, such as pyrrolidinomethyl, piperazinocarbonyl-$C_1$–$C_4$alkyl, N'-$C_1$–$C_4$alkylpiperazinocarbonyl-$C_1$–$C_4$alkyl, such as N'-acetylpiperazinocarbonyl-$C_1$–$C_4$alkyl, such as N'-acetylpiperazinocarbonylmethyl, morpholino, morpholino-$C_1$–$C_4$alkyl, such as morpholinomethyl, 2-morpholinoethyl or 3-morpholinopropyl, thiomorpholino-$C_1$–$C_4$alkyl, such as 2-thiomorpholinoethyl, $C_1$–$C_4$alkoxy, such as methoxy, amino-$C_1$–$C_7$alkoxy, such as 2-aminoethoxy or 3-aminopropyloxy, $C_1$–$C_4$$C_4$alkanoylamino-$C_1$–$C_4$alkoxy, such as 2-acetylaminoethoxy, di-$C_1$–$C_4$alkylamino-$C_1$–$C_4$alkoxy, such as 3-dimethylaminopropyloxy, piperidino-$C_1$–$C_4$alkoxy, such as 2-piperidinoethoxy, morpholino-$C_1$–$C_4$alkoxy, such as 2-morpholinoethoxy or 3-morpholinopropyloxy, morpholino-$C_1$–$C_4$alkylcarbamoyl-$C_1$–$C_4$alkoxy, such as 2-morpholinoethylcarbamoylmethoxy, carboxy, carbamoyl, $C_1$–$C_4$alkylcarbamoyl, such as methylcarbamoyl, carboxy-$C_1$–$C_4$alkoxy, such as carboxymethoxy, carbamoyl-$C_1$–$C_4$alkoxy, such as 2-carbamoylethoxy, $C_1$–$C_4$alkylcarbamoyl-$C_1$–$C_4$alkoxy, such as butylcarbamoylmethoxy, di-$C_1$–$C_4$alkylamino-$C_1$–$C_4$alkoxy, such as a 3-dimethylaminopropyloxy, or tetrazolyl-$C_1$–$C_4$alkoxy, such as tetrazol-5-ylmethoxy, and $R_D$ is $C_1$–$C_4$alkyl, such as methyl, $C_1$–$C_4$alkoxy-$C_1$–$C_4$alkyl, such as propyloxymethyl, carbamoyl-$C_1$–$C_4$alkyl, such as 3-carbamoylpropyl or 2-carbamoyl-2-methyl-ethyl, $C_1$–$C_4$alkylcarbamoyl-$C_1$–$C_4$alkyl, such as 2-methylcarbamoyl-2-methyl-propyl, di-$C_1$–$C_4$alkylcarbamoyl-$C_1$–$C_4$alkyl, such as 2-dimethylcarbamoylethyl, piperidino-$C_1$–$C_4$alkyl, such as pyrrolidinomethyl, or $C_1$–$C_4$alkoxycarbonylpiperidino-$C_1$–$C_4$alkyl, such as 2-(1-methoxycarbonylpiperidin-4-yl)ethyl, one of the radicals $X_1$ and $X_2$ is carbonyl and the other is methylene, $R_2$ is $C_1$–$C_4$alkyl, such as methyl or isopropyl, $R_3$ is amino or $C_1$–$C_4$alkanoylamino, such as acetylamino, $R_4$ is $C_1$–$C_4$alkyl, such as methyl or isopropyl, and $R_5$ is $C_1$–$C_4$alkyl, such as butyl, $C_1$–$C_4$alkoxy-$C_1$–$C_4$alkyl, such as propyloxymethyl, $C_1$–$C_4$alkoxycarbonylpiperidino-$C_1$–$C_4$alkyl, such as 2-(1-methoxycarbonylpiperidin-4-yl)ethyl, pyrrolidino-$C_1$–$C_4$alkyl, such as pyrrolidinomethyl, N'-$C_1$-$C_4$alkylpiperazino-$C_1$-$C_4$alkyl, such as N'-methylpiperazinomethyl, N'-$C_1$-$C_4$alkoxycarbonylpiperazino-$C_1$-$C_4$alkyl, such as N'-methoxycarbonylpiperazinomethyl, or N'-$C_1$-$C_7$alkanoylpiperazino-$C_1$-$C_4$alkyl, such as N'-acetylpiperazinomethyl, morpholino-$C_1$-$C_4$alkyl, such as 2-morpholinoethyl or 3-morpholinopropyl, thiomorpholino-$C_1$-$C_4$alkyl, such as 2-thiomorpholinoethyl, morpholinocarbonyl-$C_1$-$C_4$alkyl, such as 2-morpholinocarbonylethyl, carbamoyl-$C_1$-$C_4$alkyl, such as 3-carbamoylpropyl or 2-carbamoyl-2-methyl-ethyl, $C_1$-$C_4$ alkylcarbamoyl-$C_1$-$C_4$alkyl, such as 2-methylcarbamoyl-2-methyl-ethyl, di-$C_1$-$C_4$alkylcarbamoyl-$C_1$-$C_4$alkyl, such as 2-dimethylcarbamoylethyl, piperidinocarbonyl-$C_1$-$C_4$alkyl, such as piperidinocarbonylmethyl, piperazinocarbonyl-$C_1$-$C_4$alkyl, N'-$C_1$-$C_4$alkylpiperazinocarbonyl-$C_1$-$C_4$alkyl, N'-$C_1$-$C_4$alkanoylpiperazinocarbonyl-$C_1$-$C_4$alkyl, such as N'-acetylpiperazinocarbonylmethyl, N'-$C_1$-$C_4$alkylpiperazinocarbonyl-$C_1$-$C_4$alkyl, such as N'-methylpiperazinocarbonylmethyl, or morpholinocarbonyl-$C_1$-$C_4$alkyl, such as 2-morpholinocarbonylethyl, and the salts thereof.

The invention relates above all to compounds of formula I, especially of formula Ia

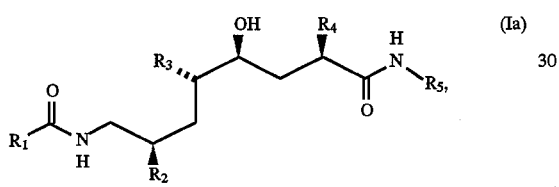

wherein $R_1$ is a 2-$R_A$-4-$R_C$-phenyl radical, a 2-$R_A$-pyridin-3-yl radical or a 3-$R_A$-pyridin-2-yl radical, wherein $R_A$, is $C_1$-$C_4$alkoxy-$C_1$-$C_4$alkyl, such as propyloxymethyl, morpholino-$C_1$-$C_4$alkyl, such as 2-morpholinoethyl or 3-morpholinopropyl, $C_1$-$C_7$alkanoylpiperazino-$C_1$-$C_4$alkyl, such as N'-acetylpiperazinomethyl, $C_1$-$C_7$alkoxy, such as propyloxy, $C_1$-$C_4$alkoxy-$C_1$-$C_4$alkoxy, such as 2-methoxyethoxy, 3-methoxypropyloxy, 4-methoxybutyloxy or 5-methoxypentyloxy, $C_1$-$C_4$alkoxy-$C_1$-$C_4$alkenyloxy, such as 4-methoxy-but-2-enyloxy, $C_1$-$C_4$alkoxy-$C_1$$C_4$alkoxy, such as 2-(methoxymethoxy)ethoxy or 2-(2-methoxyethoxy)ethoxy, amino-$C_1$-$C_4$alkoxy, such as 2-aminoethoxy or 3-aminopropyloxy, di-$C_1$-$C_4$alkylamino-$C_1$-$C_4$alkoxy, such as 3-dimethylaminopropyloxy, carbamoyl-$C_1$-$C_4$alkoxy, such as 2-carbamoylethoxy, or carbamoyl, and $R_C$ is hydrogen, di-$C_1$-$C_4$alkylamino-$C_1$-$C_4$alkyl, such as dimethylaminomethyl, piperidino-$C_1$-$C_4$alkyl, such as piperidinomethyl, pyrrolidino-$C_1$-$C_4$alkyl, such as pyrrolidinomethyl, morpholino-$C_1$-$C_4$alkyl, such as morpholinomethyl, $C_1$-$C_7$alkanoylpiperazino-$C_1$-$C_4$alkyl, such as N'-acetylpiperazinomethyl, or $C_1$-$C_4$alkylpiperazino-$C_1$-$C_4$alkyl, such as N'-methylpiperazinomethyl, morpholino, $C_1$-$C_4$alkoxy, such as methoxy, morpholino-$C_1$-$C_4$alkoxy, such as 2-morpholinoethoxy or 3-morpholinopropyloxy, morpholino-$C_1$-$C_4$alkylcarbamoyl-$C_1$-$C_4$alkoxy, such as 2-morpholinoethylcarbamoylmethoxy, piperidino-$C_1$-$C_4$alkoxy, such as 2-piperidinoethoxy, carboxy, carbamoyl, $C_1$-$C_4$alkylcarbamoyl, such as methylcarbamoyl, carboxy-$C_1$-$C_4$alkoxy, such as carboxymethoxy, di-$C_1$-$C_4$alkylamino-$C_1$-$C_4$alkoxy, such as 3-dimethylaminopropyloxy, $C_1$-$C_7$alkylcarbamoyl-$C_1$-$C_4$alkoxy, such as butylcarbamoylmethoxy, or tetrazolyl-$C_1$-$C_4$alkoxy, such as tetrazol-5-ylmethoxy, $X_1$ is carbonyl and $X_2$ is methylene, $R_2$ and $R_4$ are each independently of the other $C_1$-$C_4$alkyl, such as methyl or isopropyl, $R_3$ is amino and $R_5$ is $C_1$-$C_4$alkyl, such as butyl, morpholino-$C_1$-$C_4$alkyl, such as 2-morpholinoethyl or 3-morpholinopropyl, thiomorpholino-$C_1$-$C_4$alkyl, such as 2-thiomorpholinoethyl, morpholinocarbonyl-$C_1$-$C_4$alkyl, such as 2-morpholinocarbonylethyl, carbamoyl-$C_1$-$C_4$alkyl, such as 3-carbamoylpropyl or 2-carbamoyl-2-methyl-ethyl, $C_1$-$C_4$alkylcarbamoyl-$C_1$-$C_4$alkyl, such as 2-methylcarbamoyl-2-methyl-ethyl, di-$C_1$-$C_4$alkylcarbamoyl-$C_1$-$C_4$alkyl, such as 2-dimethylcarbamoylethyl, N'-$C_1$-$C_4$alkylpiperazino-$C_1$-$C_4$alkyl, such as N'-methylpiperazinomethyl, N'-$C_1$-$C_4$alkoxycarbonylpiperazino-$C_1$-$C_4$alkyl, such as N'-methoxycarbonylpiperazinomethyl, or N'-$C_1$-$C_7$alkanoylpiperazino-$C_1$-$C_4$alkyl, such as N'-acetylpiperazinomethyl, and the salts thereof, especially the pharmaceutically acceptable salts thereof.

The invention relates specifically to the compounds of formula I mentioned in the Examples and to the salts thereof, especially the pharmaceutically acceptable salts thereof.

The process according to the invention for the preparation of compounds of formula I is as follows:

a) a compound of formula II

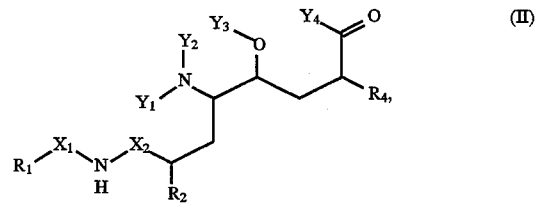

wherein $Y_1$ is lower alkyl, lower alkanoyl or an amino-protecting group, $Y_2$ is hydrogen or together with $Y_3$ is a bivalent protecting group, $Y_3$ is hydrogen, a hydroxy-protecting group or together with $Y_2$ is a bivalent protecting group or together with $Y_4$ is a direct bond, $Y_4$ is free or reactively etherified or esterified hydroxy or together with $Y_3$ is a direct bond and $R_1$, $R_2$, $R_3$, $R_4$, $R_5$, $X_2$ and $X_2$ are as defined for formula I, is reacted with an amine of formula III

wherein $R_5$ is as defined for formula I, with the formation of an amide bond and any protecting groups present are removed, or b) compounds of formulae IV and V

-continued

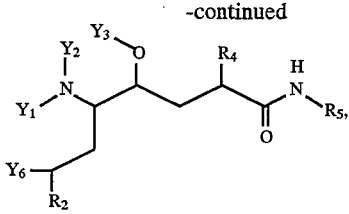

wherein $Y_1$ is lower alkyl, lower alkanoyl or an amino-protecting group, $Y_2$ is hydrogen or together with $Y_3$ is a bivalent protecting group, $Y_3$ is hydrogen, a hydroxy-protecting group or together with $Y_2$ is a bivalent protecting group, one of the radicals $Y_5$ and $Y_6$ is an aminomethyl group and the other is a free or functionally modified carboxy group and $R_1$, $R_2$, $R_3$, $R_4$ and $R_5$ are as defined for formula I, are condensed with one another and any protecting groups present are removed, or c) for the preparation of compounds of formula I wherein $R_3$ is amino, in a compound of formula VI

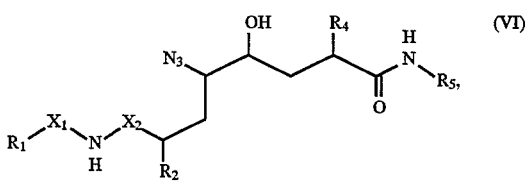

wherein $R_1$, $R_2$, $R_4$, $R_5$, $X_1$ and $X_2$ are as defined for formula I and $Y_3$ is hydrogen or a hydroxy-protecting group, the azido group is reduced to amino and condensed and any protecting groups present are removed, and in each case, if desired, a compound of formula I having at least one salt-forming group obtainable by one of the above-mentioned processes is converted into its salt, or an obtainable salt is converted into the free compound or into a different salt and/or mixtures of isomers that may be obtainable are separated and/or a compound of formula I according to the invention is converted into a different compound of formula I according to the invention. Functional groups in starting materials the reaction of which is to be avoided, especially carboxy, amino and hydroxy groups, can be protected by suitable protecting groups (conventional protecting groups) which are customarily used in the synthesis of peptide compounds, and also in the synthesis of cephalosporins and penicillins as well as nucleic acid derivatives and sugars. Those protecting groups may already be present in the precursors and are intended to protect the functional groups in question against undesired secondary reactions, such as acylation, etherification, esterification, oxidation, solvolysis, etc. In certain cases the protecting groups can additionally cause the reactions to proceed selectively, for example stereoselectively. It is characteristic of protecting groups that they can be removed easily, i.e. without undesired secondary reactions taking place, for example by solvolysis, reduction, photolysis, and also enzymatically, for example under physiological conditions. Protecting groups may also be present in the end products, however. Compounds of formula I having protected functional groups may have greater metabolic stability or pharmacodynamic properties that are better in some other way than the corresponding compounds having free functional groups.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, New York 1981, in "The Peptides", Volume 3 (E. Gross and J. Meienhofer, eds.), Academic Press, London and New York 1981, in "Methoden der organischen Chemie", Houben-Weyl, 4th edition, Volume 15/1, Georg Thieme Velag, Stuttgart 1974, in H.-D. Jakubke and H. Jescheit, "Aminosäuren, Peptide, Proteine" ("Amino acids, peptides, proteins"), Velag Chemie, Weinheim, Deerfield Beach and Basle 1982, and in Jochen Lehmann, "Chemie der Kohlenhydrate: Monosacchadn und Derivatel" ("The Chemistry of carbohydrates: monossacharin and derivatives"), Georg Thieme Verlag, Stuttgart 1974.

Amino-protecting groups $Y_1$ are, for example, acyl groups other than lower alkanoyl, also arylmethyl, lower alkylthio, 2-acyl-lower alk-1-enyl or silyl. The group $Y_1$—N ($Y_2$)— can also be in the form of an azido group.

Acyl groups other than lower alkanoyl are, for example, halo-lower alkanoyl, for example 2-haloacetyl, such as 2-chloro-, 2-bromo-, 2-iodo-, 2,2,2-trifluoro- or 2,2,2-trichloro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in 1- or 2-position, for example tertiary lower alkoxycarbonyl, such as tert-butyloxycarbonyl, arylmethoxycarbonyl having one or two aryl radicals which are phenyl that is unsubstituted or mono- or poly-substituted, for example, by lower alkyl, for example tertiary lower alkyl, such as tertiary butyl, lower alkoxy, such as methoxy, hydroxy, halogen, such as chlorine, and/or by nitro, for example benzyloxycarbonyl, unsubstituted or substituted benzyloxycarbonyl, such as 4-nitrobenzyloxycarbonyl, diphenylmethoxycarbonyl, fluorenylmethoxycarbonyl or substituted diphenylmethoxycarbonyl, such as di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, 2-(tri-substituted silyl)alkoxycarbonyl, for example 2-tri-lower alkylsily-lower alkoxycarbonyl, for example 2-trimethylsilylethoxycarabonyl or 2-(di-n-butyl-methyl-silyl)-ethoxycarbonyl, or triarylsilyl-lower alkoxycarbonyl, for example 2-triphenylsilylethoxycarbonyl.

In a 2-acyl-lower alk-1-enyl radical that can be used as an amino-protecting group, acyl is, for example, the corresponding radical of a lower alkanecarboxylic acid, of a benzoic acid that is unsubstituted or substituted, for example, by lower alkyl, such as methyl or tertiary butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or lower alkoxycarbonyl-prop-1-en-2-yl, for example 1-ethoxycarbonyl-prop-1-en-2-yl.

A silylamino group is, for example, a tri-lower alkylsilylamino group, for example trimethyl-silylamino. The silicon atom of the silylamino group can also be substituted by only two lower alkyl groups, for example methyl groups, and by the amino group or carboxy group of a second molecule of formula I. Compounds having such protecting groups can be prepared, for example, using dimethylchlorosilane as silylating agent.

An amino group can also be protected by conversion into the protonated form; suitable corresponding anions are especially those of strong inorganic acids, such as sulfuric acid, phosphoric acid or hydrohalic acids, for example the chlorine or bromine anion, or of organic sulfonic acids, such as p-toluenesulfonic acid.

Preferred amino-protecting groups $Y_1$ are acyl radicals of carbonic acid semiesters, such as lower alkoxycarbonyl, especially tert-butyloxycarbonyl or fluorenylmethoxycarbonyl, unsubstituted or lower alkyl-, lower alkoxy-, nitro- and/or halo-substituted α-phenyl- or α,α-diphenyl-lower alkoxycarbonyl, such as benzyloxycarbonyl, p-nitrobenzyloxycarbonyl or diphenylmethoxycarbonyl, or 2-halo-lower alkoxycarbonyl, e.g. 2,2,2-trichloroethoxycarbonyl, yl, also trityl.

Hydroxy-protecting groups $Y_3$ are, for example, acyl groups, for example lower alkanoyl that is substituted by halogen, such as chlorine, for example 2,2-dichloroacetyl, or especially acyl radicals of a carbonic acid semiester mentioned for protected amino groups. A preferred hydroxy-protecting group is, for example, 2,2,2-trichloroethoxycarbonyl, 4-nitrobenzyloxycarbonyl, diphenylmethoxycarbonyl or trityl. A further suitable hydroxy-protecting group $Y_3$ is tri-lower alkylsilyl, for example trimethylsilyl, triisopropylsilyl or dimethyl-tertbutylsilyl, a readily removable esterifying group, for example an alkyl group, such as tertiary lower alkyl, for example tertiary butyl, an oxa- or a thia-aliphatic or -cycloaliphatic, especially 2-oxa- or 2-thia-aliphatic or -cycloaliphatic, hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thiacycloalkyl having from 5 to 7 ring atoms, for example 2-tetrahydrofuryl or 2-tetrahydropyranyl, or a corresponding thia analogue, and also 1-phenyl-lower alkyl, for example benzyl, diphenylmethyl or trityl, wherein the phenyl radicals can be substituted, for example, by halogen, for example chlorine, lower alkoxy, for example methoxy, and/or by nitro.

Bivalent protecting groups formed by $Y_2$ and $Y_3$ together are, for example, methylene groups substituted by one or two alkyl radicals or by an alkylene radical and are accordingly unsubstituted or substituted alkylidene, such as lower alkylidene, for example isopropylidenene, cycloalkylidene, for example cyclohexylidene, also carbonyl or benzylidene.

Process variant a): If $Y_4$ in starting materials of formula II is reactively etherified or esterified hydroxy, the terminal group —(=O)—$Y_4$, is a reactively functionally modified carboxylic acid function and is, for example, in the form of an activated ester or anhydride. The reactive acid derivatives can also be formed in situ.

Such activated esters of compounds of formula II are especially internal esters, for example γ-lactones, also esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N, N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted thiophenols, inter alia by the anhydride or carbodiimide method; activated thiol esters method), or especially amino or amido esters (obtainable, for example, by treatment of the corresponding acid with an N-hydroxyamino or N-hydroxyimido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4one, for example by the anhydride or carbodiimide method; activated N-hydroxy esters method).

The condensation of internal esters, especially γ-lactones, i.e. compounds of formula II wherein $Y_3$ and $Y_4$ together form a direct bond, is advantageously carried out in the presence of a basic condensation agent, preferably 2-hydroxypyridine at elevated temperature. This process variant is especially excellently suitable for the reaction with sterically hindered amines.

Anhydrides of acids of formula II may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiesters, for example carbonic acid lower alkyl semiesters (obtainable, for example, by treatment of the corresponding acid with chloroformic acid lower alkyl esters or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Several methods can be used to prepare the starting materials of formula II. For example, a compound of formula IIa

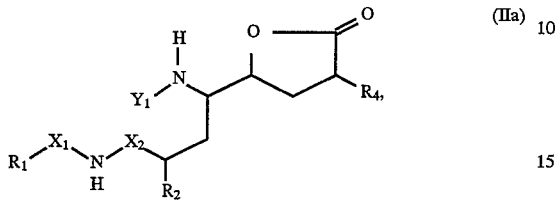
(IIa)

wherein $X_1$ is methylene, $X_2$ is carbonyl and $Y_1$ is an amino-protecting group, especially tertbutyloxycarbonyl, is obtained, for example, by reacting E-1,4-dibromobut-2-ene first with a compound of formula VII

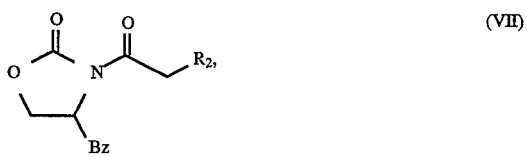
(VII)

and then with a compound of formula VIII

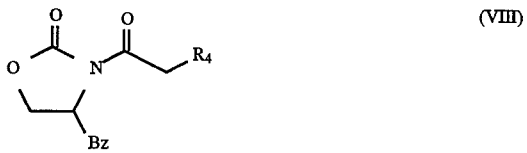
(VIII)

to form the corresponding compound of formula IX

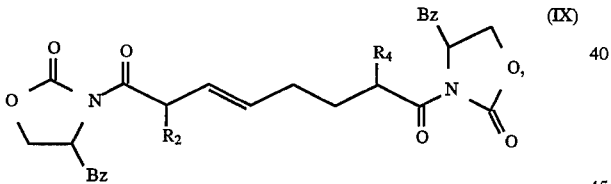
(IX)

converting that compound, for example by treatment with a customary halogenating agent, such as elemental halogen, especially bromine or iodine, or preferably with an N-halo-succinimide, especially N-bromosuccinimide in 1,2-dimethoxyethane (DME), into the corresponding compound of formula X

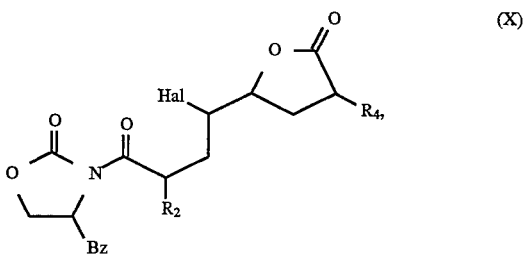
(X)

wherein Hal is halogen, separating the desired isomer in respect of $R_2$ and $R_4$ and in that isomer replacing the halogen atom by azido, for example by treatment with tetrabenzyl ammonium azide in toluene, and in the resulting compound of formula XI

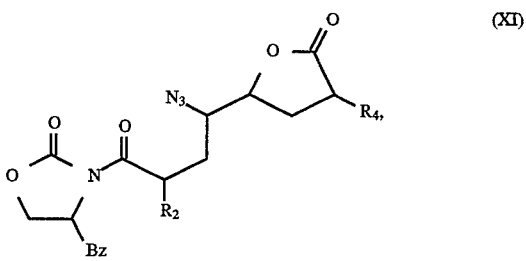
(XI)

wherein $R_2$ and $R_4$ are as defined above and Bz is benzyl, hydrolysing the 4-benzyl-2-oxo-oxazolidin-1-ylcarbonyl group selectively to carboxy, reclosing, using a acid catalyst, a lactone ring which may have been opened; in the resulting compound of formula XII

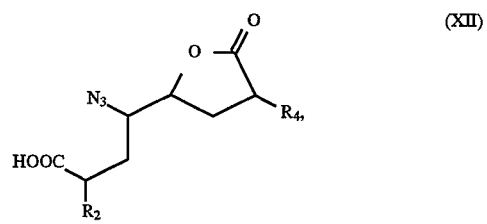
(XII)

reducing the azido group to amino in customary manner, for example using hydrogen on palladium on carbon, temporarily protecting the amino group formed with an amino-protecting group $Y_4$, for example tert-butyloxycarbonyl, for example by reaction with di-tertbutyl dicarbonate, and condensing the resulting compound of formula XIII

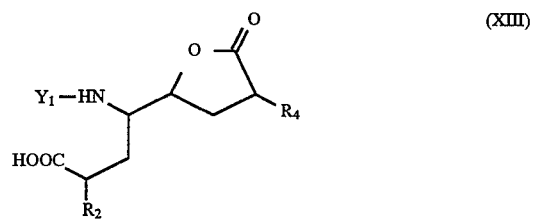
(XIII)

in customary manner, for example as described below under Process variant c), with a compound of formula IV

$R_1$—$Y_5$ (IV)

wherein $Y_5$ is aminomethyl.

Intermediates of formula IIa, wherein $X_1$ is carbonyl, $X_2$ is methylene and $Y_1$ is an amino-protecting group, for example tert-butyloxycarbonyl, can be obtained from compounds of formula XII obtainable as described above, by first reducing the carboxy group to hydroxymethyl, for example by reaction with a chloroformic acid ester and subsequent treatment with sodium borohydride, and then reducing the azido group to amino, for example using hydrogen in the presence of palladium on carbon, protecting the amino group formed with an amino-protecting group $Y_4$, for example with tert-butyloxycarbonyl, for example by reaction with di-tert-butyl dicarbonate, and in the resulting compound of formula XIV

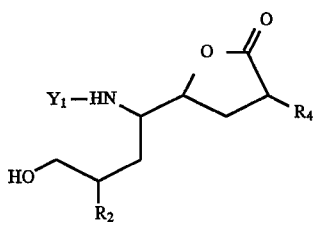

replacing the terminal hydroxy group by azido in customary manner, for example by treatment first with methanesulfonyl chloride and then with sodium azide; in the resulting compound of formula XV

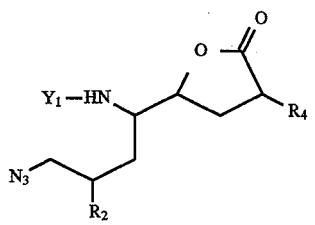

the azido group is reduced to amino in customary manner, for example as described above, and then substituted by the desired radical $R_1$ by reaction with a carboxylic acid of formula IV wherein $Y_5$ is carboxy. Starting materials of formula IIb

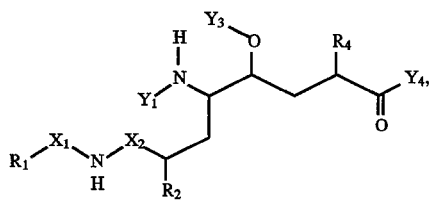

wherein $Y_1$ is an amino-protecting group, especially tert-butyloxycarbonyl, $Y_3$ is a hydroxy-protecting group, such as tri-lower alkylsilyl, $Y_4$ is hydroxy, $X_1$ is carbonyl and $X_2$ is methylene, can be prepared from azides of formula XV, for example by treatment with an alkali metal hydroxide, such as lithium hydroxide, subsequent reaction with tert-butyl-(dimethyl)silyl chloride, followed by customary reduction of the azido group to amino and, finally, reaction with a compound of formula IV

wherein $Y_5$ is free or reactively functionally modified carboxy.

Process variant b): Free or functionally modified carboxy $Y_5$ and $Y_6$, in starting materials of formulae IV and V, respectively, is, for example, free carboxy or carboxy present in the form of an ester or an anhydride. The reactive acid derivatives can also be formed in situ.

Esters of acids of formulae IV and V wherein $Y_5$ and $Y_6$, respectively, are carboxy are, for example, the aliphatic, araliphatic or aromatic esters thereof, such as a lower alkyl ester or a phenyl-lower alkyl ester that is unsubstituted or substituted in the phenyl moiety, for example by lower alkyl, lower alkoxy, halogen and/or by nitro, or a phenyl ester that is unsubstituted or substituted, for example, by lower alkyl, lower alkoxy, halogen and/or by nitro. Also suitable are activated esters. Suitable activated esters are especially esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitrosubstituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-norbornene-2,3-dicarboxylic acid imide, 1-hydroxybenzotriazole or 3-hydroxy-3,4-dihydro-1,2,3-benzotriazin-4-one, for example by the anhydride or carbodiimide method; activated N-hydroxy esters method).

Anhydrides of acids of formulae IV and V wherein $Y_5$ and $Y_6$, respectively, are carboxy may be symmetric or preferably mixed anhydrides of those acids, for example anhydrides with inorganic acids, such as acid halides, especially acid chlorides (obtainable, for example, by treatment of the corresponding acid with thionyl chloride, phosphorus pentachloride or oxalyl chloride; acid chloride method), azides (obtainable, for example, from a corresponding acid ester via the corresponding hydrazide and treatment thereof with nitrous acid; azide method), anhydrides with carbonic acid semiesters, for example carbonic acid lower alkyl semiesters (obtainable, for example, by treatment of the corresponding acid with chloroformic acid lower alkyl esters or with a 1-lower alkoxycarbonyl-2-lower alkoxy-1,2-dihydroquinoline; 1-$R_D$-indol-3yl radical, mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate) or with phosphorous acid derivatives, or anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as a lower alkane- or aryl-, for example methane- or p-toluenesulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

The condensation of compounds of formulae IV and V can be carried out in a manner known per se, for example as described in standard works, such as Houben-Weyl, "Methoden der organischen Chemie", 4th edition, Volume 15/11 (1974), Volume IX (1955), Volume E 11 (1985), Georg Thieme Verlag, Stuttgart, "The Peptides" (E. Gross and J. Meienhofer, eds.), Volumes 1 and 2, Academic Press, London and New York, 1979/1980, or M. Bodansky, "Principles of Peptide Synthesis", Springer-Verlag, Berlin 1984.

The condensation of a free carboxylic acid with the corresponding amine can be carried out preferably in the presence of one of the customary condensation agents. Customary condensation agents are, for example, carbodiimides, for example diethyl-, dipropyl-, N-ethyl-N'-(3-dimethylaminopropyl)-carbodiimide or especially dicyclohexylcarbodiimide, also suitable carbonyl compounds, for example carbonyldiimidazole, 1,2-oxazolium compounds, for example 2-ethyl-5-phenyl-1,2-oxazolium-3'-sulfonate and 2-tert-butyl-5-methylisoxazolium perchlorate, or a suitable acylamino compound, for example 2-ethoxy-1-ethoxycarbonyl-1,2-dihydroquinoline, also activated phosphoric acid derivatives, for example diphenylphosphoryl azide, diethylphosphoryl cyanide, phenyl-N-phenylphosphoroamidochloridate, bis(2-oxo-3-oxazolidinyl)phosphinic acid chloride or 1-benzotdazolyloxytris (dimethylamino)phosphoniumhexafluorophosphate.

If desired, an organic base is added, for example a tri-lower alkylamine having bulky radicals, for example ethyldiisopropylamine, and/or a heterocyclic base, for example pyridine, N-methylmorpholine or preferably 4-dimethylaminopyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent may additionally be used as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (usually together with a sulfate).

Carboxylic acid chlorides, for example the chlorocarbonic acid derivatives derived from the acid of formula II, are condensed with the corresponding amines preferably in the presence of an organic amine, for example the above-mentioned tri-lower alkylamines or heterocyclic bases, where appropriate in the presence of a hydrogen sulfate.

The condensation is preferably carried out in an inert, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately $-40°$ C. to approximately $+100°$ C., preferably from approximately $-10°$ C. to approximately $+50°$ C., and in the case where arylsulfonyl esters are used also at approximately $+100°$ C. to $+200°$ C., and if necessary under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone can also be added where appropriate.

The condensation can also be carried out in accordance with the technique known as solid-phase synthesis which originates from R. Merrifield and is described, for example, in Angew. Chem. 97, 801–812 (1985), Naturwissenschaften 71,252–258 (1984) or in R. A. Houghten, Proc. Natl. Acad. Sci. U.S.A. 82, 5131–5135 (1985).

In a preferred variant of that process, which is suitable especially for the preparation of compounds of formula I wherein $X_1$ is carbonyl, $X_2$ is methylene and $R_1$ is, for example, a 1-$R_D$-indol-3-yl radical, the starting material used is a carboxylic acid of formula IV which is reacted with the amine component of formula V in the presence of a cyanophosphonic acid diester, for example cyanophosphonic acid diethyl ester, or a benzotriazolyloxy-tris(di-lower alkylamino)phosphonium salt, for example 1-benzotriazolyloxy-tris(dimethylamino)phosphonium-hexafluoro-phosphate or -chloride, and a tertiary organic amine, such as a tri-lower alkylamine, for example trimethylamine, and in a polar solvent, for example a nitrile, such as acetonitrile, an amide, such as dimethylformamide, N,N-dimethylacetamide, N-methylpyrrolidone or hexamethylphosphoric acid triamide, a urea, for example N,N'-dimethyl-N, N'-propylenylurea, lower alkoxy-lower alkanol, for example diethylene glycol monomethyl ether, in dimethyl sulfoxide or in a mixture of the mentioned solvents or in a mixture of one or more of the mentioned solvents with water, at temperatures of from $-30°$ C. to $100°$ C., preferably from $20°$ C. to $80°$ C., the comments made above applying in respect of the protecting groups.

Starting materials of formula IV are known or can be prepared analogously to the method of formation of known compounds of formula IV.

Starting materials of formula V wherein $Y_6$ is amino, $Y_1$ is, for example, tert-butyloxycarbonyl and $Y_2$ and $Y_3$ together are, for example, isopropylidene, can be prepared, for example, in accordance with methods known per se, by condensing a compound of formula XVI

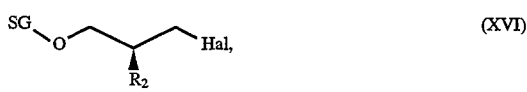

wherein SG is a hydroxy-protecting group, such as α-phenyl-lower alkyl, especially benzyl, Hal is halogen and $R_2$ is as defined, with a compound of formula XVII (XVII)

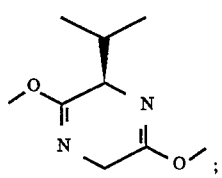

first hydrolysing the resulting compound of formula XVIII

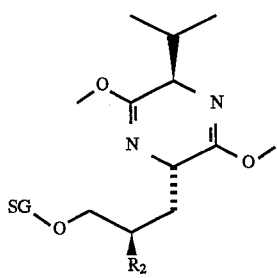

(XVIII)

in customary manner, for example in the presence of dilute hydrochloric acid, and then reacting the product with di-tert-butyl dicarbonate, reacting the resulting compound of formula XIX

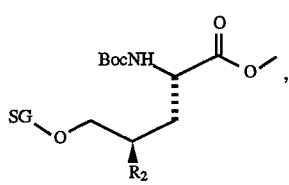

(XIX)

wherein Boc is tert-butyloxycarbonyl, in succession with dibutylaluminium hydride, with an N-$R_5$-methacrylamide, butyllithium and triisopropyloxytitanium chloride and, after separation of the resulting stereoisomeric mixture, with hydrogen in the presence of [Ru $_2Cl_4$-(S)-(BINAP)$_2$]NEt$_3$ and with dimethoxypropene and with p-toluenesulfonic acid, and in the resulting compound of formula XX

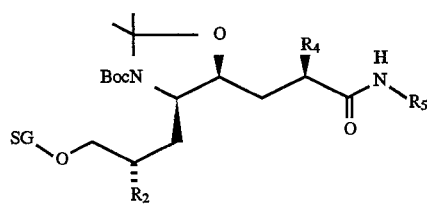

(XX)

converting the protected hydroxy group SG—O— into amino in customary manner, for example by hydrogenolytic debenzylation, for example with hydrogen in the presence of palladium on carbon, reaction with a sulfonyl halide, such as methanesulfonyl chloride, further reaction with an alkali metal azide, such as sodium azide, and hydrogenation again, for example with hydrogen in the presence of palladium on carbon.

Process variant c): (Reduction of the azido group):

In starting materials of formula VI, functional groups that are not intended to participate in the reaction are protected by one of the protecting groups mentioned under Process a).

Reducing agents suitable for the reduction of the azido group are those which under the reaction conditions of the process reduce an optionally functionalised hydroxy group or azido group selectively or more rapidly than the amide groups present in compounds of formula I.

The reduction is preferably carried out with hydrogen in the presence of suitable heavy metal catalysts, for example Raney nickel or platinum or palladium catalysts, for example platinum or palladium on active carbon.

Intermediates of formula VI can be prepared, for example, by reacting E-1,4-dibromobut-2-ene first with a compound of formula VII

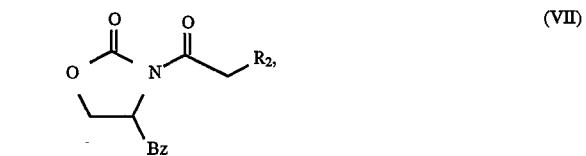

(VII)

and then with a compound of formula VIII

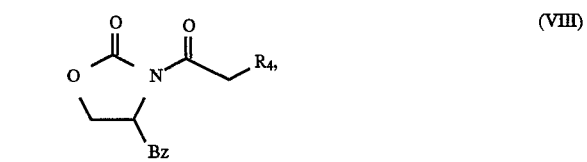

(VIII)

to form the corresponding compound of formula IX

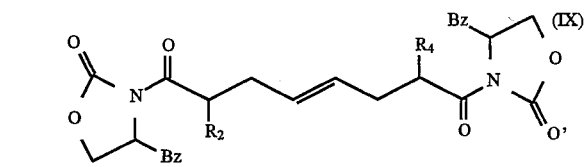

(IX)

converting that compound, for example by treatment with a customary halogenating agent, such as elemental halogen, especially bromine or iodine, or preferably with an N-halosuccinimide, especially N-bromosuccinimide in 1,2-dimethoxyethane (DME), into the corresponding compound of formula X

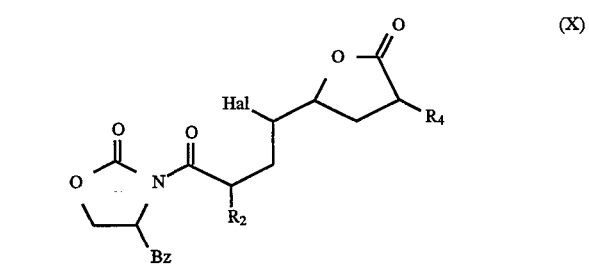

(X)

wherein Hal is halogen; separating the desired isomer in respect of $R_2$ and $R_4$ and in that isomer replacing the halogen atom by azido, for example by treatment with tetra benzylammonium azide in toluene, and in the resulting compound of formula XI

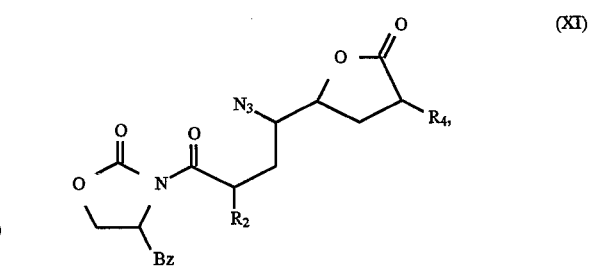

(XI)

wherein $R_2$ and $R_4$ are as defined above and Bz is benzyl, hydrolysing the 4-benzyl-2-oxo-oxazolidin-1-ylcarbonyl group selectively to carboxy; reclosing, using an acid catalyst, a lactone ring which may have been opened; condensing the resulting compound of formula XII

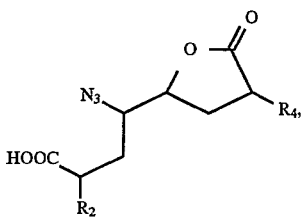

(XII)

or a reactive functional carboxy derivative thereof, with a compound of formula IV $R_1-Y_5$ (IV), wherein $Y_5$ is aminomethyl, and condensing the resulting compound of formula XXII

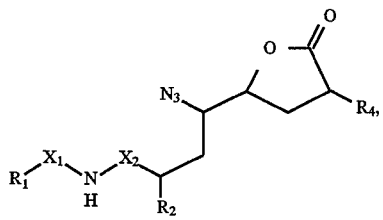

(XXI)

wherein $X_1$ is methylene and $X_2$ is carbonyl, in customary manner, for example as described under Process variant a), with an amine of formula III $H_2N-R_5$ (III)

wherein $R_5$ is as defined for formula I,

Intermediates of formula VI wherein $X_1$ is carbonyl and $X_2$ is methylene can be prepared, for example, by converting the carboxy group into aminomethyl, especially in a manner analogous to that described for the preparation of compounds of formula IIb, at the stage of the compound of formula XII.

The removal of protecting groups that are not constituents of the desired end product of formula I, for example carboxy-, amino-, hydroxy- and/or mercapto-protecting groups, which may be carried out subsequent to the process variants described above, is effected in a manner known per se, for example by means of solvolysis, especially hydrolysis, alcoholysis or acidolysis, or by means of reduction, especially hydrogenolysis or chemical reduction, as well as photolysis, as appropriate stepwise or simultaneously, it being possible also to use enzymatic methods. The removal of the protecting groups is described, for example, in the standard works mentioned hereinabove in the section relating to protecting groups.

For example, protected carboxy, for example tertiary lower alkoxycarbonyl, lower alkoxycarbonyl substituted in the 2-position by a trisubstituted silyl group or in the 1-position by lower alkoxy or by lower alkylthio, or unsubstituted or substituted diphenylmethoxycarbonyl, can be converted into free carboxy by treatment with a suitable acid, such as formic acid or trifluoroacetic acid, where appropriate with the addition of a nucleophilic compound, such as phenol or anisole. Unsubstituted or substituted benzyloxycarbonyl can be cleaved, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can be converted into free carboxy also by reduction, for example by treatment with an alkali metal dithionite, such as sodium dithionite, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can be cleaved also by treatment with a nucleophilic, preferably salt-forming, reagent, such as sodium thiophenolate or sodium iodide. 2-(Tri-substituted silyl)-lower alkoxycarbonyl, such as 2-tri-lower alkylsilyl-lower alkoxycarbonyl, can be converted into free carboxy also by treatment with a salt of hydrofluoric acid that yields the fluoride anion, such as an alkali metal fluoride, for example sodium or potassium fluoride, where appropriate in the presence of a macrocyclic polyether ("crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases.

A protected amino group is freed in a manner known per se and, according to the nature of the protecting groups, in various ways, preferably by solvolysis or reduction. 2-Halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can be cleaved also by treatment with a nucleophitic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-(tri-substituted silyl)-lower alkoxycarbonylamino, such as 2-tri-lower alkylsilyl-lower alkoxycarbonylamino, can be cleaved by treatment with a suitable acid, for example formic or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water; and an amino group protected in the form of silylamino can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate of thiourea, and subsequent solvolysis, such as alcoholysis or hydrolysis, of the resulting condensation product. An amino group protected by 2-(trisubstituted silyl)-lower alkoxycarbonyl, such as 2-tri-lower alkylsilyl-lower alkoxycarbonyl, can be converted into the free amino group also by treatment with a salt of hydrofluoric acid that yields fluoride anions, as indicated above in connection with the freeing of a correspondingly protected carboxy group. Likewise, silyl, such as trimethylsilyl, bonded directly to a hetero atom, such as nitrogen, can be removed using fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, by reduction using mercapto compounds, such as dithiothreitol or mercaptoethanol, or by treatment with zinc in the presence of an acid, such as acetic acid. The catalytic hydrogenation is preferably carried out in an inert solvent, such as a halogenated hydrocarbon, for example methylene chloride, or in water or in a mixture of water and an organic solvent, such as an alcohol or dioxane, at approximately from 20° to 25° C., or with cooling or heating.

A hydroxy or mercapto group protected by a suitable acyl group, by a tri-lower alkylsilyl group or by unsubstituted or substituted 1-phenyl-lower alkyl is freed analogously to a correspondingly protected amino group. A hydroxy or mercapto group protected by 2,2-dichloroacetyl is freed, for example, by basic hydrolysis, and a hydroxy or mercapto group protected by tertiary lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Mercapto protected by pyridyldiphenylmethyl can be freed, for example, using mercury(II) salts at pH 2–6 or by zinc/acetic acid or by electrolytic reduction; acetamidomethyl and isobutyrylamidomethyl can be removed, for example, by reaction with mercury(II) salts at pH 2–6; 2-chloroacetamido methyl can be removed, for example, using 1-piperidinothiocarboxamide; and S-ethylthio, S-tertbutylthio and S-sulfo can be cleaved, for example, by thiolysis with thiophenol, thio glycolic acid, sodium thiophenolate or 1,4-dithiothreitol. Two hydroxy groups or an adjacent amino and hydroxy group which are protected together by means of a bivalent protecting group, preferably, for example, by a methylene group mono- or di-substituted by alkyl, such as lower alkylidene, for example isopropyldene, cycloalkyldene, for example cyclohexyldene, or benzyldene, can be freed by acid solvolysis, especially in the presence of a mineral acid or a strong organic acid. 2-Halo-lower alkoxycarbonyl is also removed using the above-mentioned reducing agents, for example a reducing metal, such as zinc, reducing metal salts, such as chromium(II)salts, or using sulfur compounds, for example sodium dithionite or preferably sodium sulfide and carbon disulfide.

When several protected functional groups are present, if desired the protecting groups may be so selected that more than one such group can be removed simultaneously, for example by acidolysis, such as by treatment with trifluoroacetic acid, or with hydrogen and a hydrogenation catalyst, such as a palladium on carbon catalyst. Conversely, the groups may also be so selected that they are not all removed simultaneously, but rather they are removed in a desired sequence or only some of them are removed.

In each of the processes mentioned above, the starting compounds may also be used in the form of salts, provided that the reaction conditions allow it.

The invention relates also to those forms of the process in which a compound obtainable as intermediate at any stage is used as starting material and the remaining steps are carried out or the process is interrupted at any stage or a starting material is formed under the reaction conditions or is used in the form of a reactive derivative or salt, or a compound obtainable in accordance with the process of the invention is formed under the process conditions and further processed in situ. It is preferable to use those starting materials which result in the compounds described above as being very preferred or very especially preferred.

The invention relates also to novel starting materials, which have been developed specifically for the preparation of the compounds according to the invention, especially the group of starting materials resulting in the compounds of formula I described at the beginning as being preferred, to processes for their preparation and to their use as intermediates.

Compounds of formula I obtainable in accordance with the process can be converted into different compounds of formula I in customary manner.

For example, in a compound of formula I obtainable in accordance with the process, a carboxy group in free or reactive form may be esterified or amidated or an esterified or amidated carboxy group may be converted into a free carboxy group.

For the esterification or amidation of a carboxy group in a compound of formula I, if desired the free acid can be used or the free acid can be converted into one of the abovementioned reactive derivatives and reacted with an alcohol, with ammonia, or with a primary or secondary amine, or, in the case of esterification, the free acid or a reactive salt, for example the caesium salt, can be reacted with a reactive derivative of an alcohol. For example, the caesium salt of a carboxylic acid can be reacted with a halide or sulfonic acid ester corresponding to the alcohol. The esterification of the carboxy group can also be carried out with other customary alkylating agents, for example with diazomethane, Meerwein salts or 1-substituted 3-aryltriazenes.

For the conversion of an esterified or amidated carboxy group into the free carboxy group it is possible to use one of the methods described above for the removal of carboxyprotecting groups or, if desired, alkaline hydrolysis in accordance with the reaction conditions mentioned in Organikum, 17th edition, VEB Deutscher Verlag der Wissenschaften, Berlin 1988.

In a compound of formula I obtainable in accordance with the process, an esterified carboxy group can be converted into an unsubstituted or substituted carboxamide group by aminolysis with ammonia or with a primary or secondary amine, optionally in the presence of a suitable condensation agent or catalyst. The aminolysis can be carried out in accordance with the reaction conditions mentioned for such reactions in Organikum, 15th edition, VEB Deutscher Verlag der Wissenschaften, Berlin (East) 1976.

A free amino group present in a compound of formula I obtainable in accordance with the process can be acylated or alkylated, for example to introduce a radical $R_6$ other than hydrogen. The acylation and the alkylation can be carried out in accordance with one of the methods mentioned for protecting groups or according to one of the procedures mentioned in Organikum, 17th edition, VEB Deutscher Verlag der Wissenschaften, Berlin (East) 1988.

Furthermore, a free hydroxy group present in a compound of formula I obtainable in accordance with the process, for example as a constituent of the radical $R_5$, can be acylated. The acylation can be carried out with acylating reagents in accordance with one of the methods mentioned for protecting groups or according to one of the procedures mentioned in Organikum, 17th edition, VEB Deutscher Verlag der Wissenschaften, Berlin (East) 1988.

In a compound of formula I obtainable in accordance with the process it is also possible to obtain from a sulfide the corresponding sulfoxide or sulfone, that is to say to oxidise a thio group to a sulfinyl or sulfonyl group or a sulfinyl group to sulfonyl, and also to oxidise thiomorpholino to S-oxy- or S,S-dioxy-thiomorpholino.

The oxidation to the sulfone can be carried out with most of the customary oxidising agents. It is especially preferable to use oxidising agents that oxidise the thio group or the sulfide sulfur selectively in the presence of other functional groups, for example amino or hydroxy groups, of the compound of formula I in question, for example aromatic or aliphatic peroxycarboxylic acids, for example peroxybenzoic acid, monoperphthalic acid, m-chloroperbenzoic acid, peracetic acid, performic acid or trifluoroperacetic acid. The oxidation with peroxycarboxylic acids is carried out in the customary solvents suitable for that purpose, for example chlorinated hydrocarbons, for example methylene chloride or chloroform, ethers, such as diethyl ether, esters, such as ethyl acetate or the like, at temperatures of from −78° C. to room temperature, for example from −20° C. to +10° C., preferably about 0° C. The peroxycarboxylic acid can also be formed in situ, for example with hydrogen peroxide in acetic acid or formic acid that optionally contains acetic anhydride, for example with 30% or 90% hydrogen peroxide in acetic acid/acetic anhydride. Other peroxo compounds are also suitable, for example potassium peroxomonosulfate in lower alkanol/water mixtures, for example methanol/water or ethanol/water, or in aqueous acetic acid at temperatures of from −70° C. to +30° C., for example from −20° C. to room temperature, also sodium metaperiodate in methanol or methanol/water mixtures at temperatures of from 0° C. to 50° C., for example about room temperature. If stoichiometric amounts of the mentioned oxidising agents are used it is also possible to obtain the corresponding sulfoxides.

If desired, it is possible by reduction of a sulfonyl group or a sulfone radical in an obtainable compound of formula I to obtain the corresponding thio compound or the corresponding sulfide, for example with diisobutylaluminium hydride in ether or tetrahydrofuran.

In compounds of formula I it is also possible to reduce a free or esterified carboxy group to hydroxymethyl in customary manner, for example using a di-light metal hydride, such as lithium aluminium hydride or sodium boranate, in an inert solvent, such as an ether, for example in tetrahydrofuran.

In compounds of formula I it is also possible to replace hydroxy $R_A$, $R_B$ and/or $R_C$ by one of the etherified hydroxy groups mentioned under formula I by reacting the corresponding compound of formula I wherein $R_A$, $R_B$ and/or $R_C$ is hydroxy in customary manner, for example in the presence of a basic condensation agent, with a compound of the formula(e) $R_A$—Y, $R_B$—Y and/or $R_C$—Y wherein one of the radicals $R_A$ and $R_B$ is an aliphatic, araliphatic or heteroaraliphatic radical, for example an amino-lower alkoxy radical that is unsubstituted or N-lower alkanoylated or N-mono- or N,N-di-lower alkylated or N,N-disubstituted by lower alkylene, hydroxy-, lower alkoxy- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; lower alkoxy, hydroxy-lower alkoxy, lower alkanoyloxy-lower alkoxy, lower alkoxy-lower alkoxy, lower alkoxy-lower alkoxy-lower alkoxy, polyhalo-lower alkoxy, cyano-lower alkoxy, unsubstituted or substituted phenyl- or pyridyl-lower alkoxy, lower alkoxy-lower alkenyloxy, optionally S-oxidised lower alkylthio-lower alkoxy, or amino-lower alkoxy that is unsubstituted or N-lower alkanoylated or N-mono- or N,N-di-lower alkylated or N,N-disubstituted by lower alkylene, hydroxy-, lower alkoxy- or lower alkoxy-lower alkoxy-lower alkylene, by unsubstituted or N'-lower alkanoylated, lower alkoxycarbonyl- or lower alkoxy-lower alkyl-N'substituted or N'-lower alkylated aza-lower alkylene; by oxa-lower alkylene or by optionally S-oxidised thia-lower alkylene; and the other is hydrogen, lower alkyl, carbamoyl, hydroxy, lower alkoxy or polyhalo-lower alkoxy, $R_C$ is an aliphatic, araliphatic, heteroaraliphatic or heteroarylaliphatic radical, for example hydroxy, lower alkoxy, hydroxy-lower alkoxy, lower alkoxy-lower alkoxy, morpholino-lower alkylcarbamoyl-lower alkoxy; an amino-lower alkoxy group that is unsubstituted or N-lower alkanoylated or N-mono- or N,N-di-lower alkylated or N,N-disubstituted by lower alkylene, hydroxy-, lower alkoxy-, lower alkoxycarbonyl- or lower alkoxy-lower alkoxy-lower alkylene, by unsubstituted or N'-lower alkanoylated or lower alkoxycarbonyl- or lower alkoxy-lower alkyl-N'-substituted or N'-lower alkylated aza-lower alkylene, by oxa-lower alkylene or by optionally S-oxidised thia-lower alkylene; or a free or amidated carboxy or carboxy-lower alkoxy group or tetrazolyl-lower alkoxy, and Y is reactive esterified hydroxy, especially hydroxy esterified by a mineral acid, by sulfuric acid or by an organic sulfonic acid, such as halogen, preferably chlorine, bromine or iodine, a group of the formula —O—SO$_2$—O—R$_A$, —O—SO$_2$—O—R$_B$ or —O—SO$_2$—R$_A$ or lower alkanesulfonyloxy or unsubstituted or substituted benzenesulfonyloxy, especially methane-, ethane-, benzene-, p-toluene- or p-bromobenzene-sulfonyl.

The reaction is, as mentioned, preferably carried out in the presence of a basic condensation agent, such as an alkali metal carbonate, for example potassium carbonate, in an inert solvent, such as a lower alkanol, such as methanol, ethanol, butanol, tert-butanol or especially amyl alcohol, advantageously at elevated temperature, for example in a temperature range of approximately from 40° C. to 140° C., if necessary with removal of the resulting water of reaction by distillation, for example by azeotropic distillation.

It is also possible for salts of compounds of formula I obtainable in accordance with the process to be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

Stereoisomeric mixtures, that is to say mixtures of diastereoisomers and/or enantiomers, such as, for example, racemic mixtures, can be separated into the corresponding isomers in a manner known per se by suitable separating processes. For example, mixtures of diastereoisomers can be separated into the individual diastereoisomers by fractional crystallisation, chromatography, solvent partition etc. Racemates can be separated from one another, after conversion of the optical antipodes into diastereoisomers, for example by reaction with optically active compounds, for example optically active acids or bases, by chromatography on column materials charged with optically active compounds or by enzymatic methods, for example by selective reaction of only one of the two enantiomers. This separation can be carried out either at the stage of one of the starting materials or with the compounds of formula I themselves.

In a compound of formula I the configuration at individual chirality centres can be selectively reversed. For example, the configuration of asymmetric carbon atoms that carry nucleophilic substituents, such as amino or hydroxy, can be reversed by second order nucleophilic substitution, optionally after conversion of the bonded nucleophilic substituent into a suitable nucleofugal leaving group and reaction with a reagent introducing the original substituent, or the configuration at carbon atoms having hydroxy groups can be reversed by oxidation and reduction, analogously to the procedure in European Patent Application EP-A-0 236 734.

Also advantageous is the reactive functional modification of the hydroxy group and the subsequent replacement thereof by hydroxy with the configuration being reversed. For that purpose, the amino and hydroxy groups shown in formula I are bridged by a bivalent group, especially carbonyl, there being obtained a compound of formula XXII

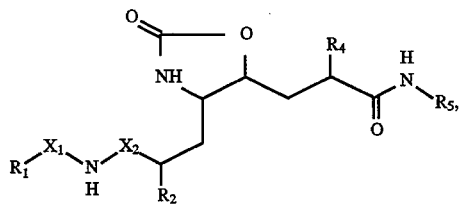

(XXII)

which can be cleaved again by treatment with thionyl chloride with the configuration being reversed.

The invention relates also to pharmaceutical compositions comprising compounds of formula I.

The pharmacologically acceptable compounds of the present invention may be used, for example, in the preparation of pharmaceutical compositions that comprise an effective amount of the active ingredient together or in admixture with a significant amount of inorganic or organic, solid or liquid, pharmaceutically acceptable carriers.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, for example mannitol, for such solutions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of anti-oxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmirate, "Labrafil M 2375" (polyoxyethylene glycerol trioleate, Gattefossé, Paris), "Miglyol 812" (triglyceride of saturated fatty acids with a chain length of $C_8$ to $C_{12}$, Chemische Werke Witten/Ruhr, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. They can also be incorporated into plastics carriers that allow the active ingredients to diffuse or be released in measured amounts.

Suitable carriers are especially filters, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules of gelatin and also soft, sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it likewise being possible for stabilisers and/or antibacterial agents to be added. Dyes or pigments may be added to the tablets or dragée coatings and to the capsule casings, for example for identification purposes or to indicate different doses of active ingredient.

The invention relates also to the use of compounds of formula I in the treatment of disorders responsive to the inhibition of renin, such as those mentioned at the beginning, especially hypertension and/or glaucoma.

The doses to be administered to warm-blooded animals, for example human beings, of, for example, approximately 70 kg body weight, especially the doses effective in the inhibition of the enzyme renin, in lowering blood pressure and/or in improving the symptoms of glaucoma, are from approximately 3 mg to approximately 3 g, preferably from approximately 10 mg to approximately 1 g, for example approximately from 20 mg to 200 mg, per person per day, divided preferably into 1 to 4 single doses which may, for example, be of the same size. Usually, children receive about half of the adult dose. The dose necessary for each individual can be monitored, for example by measuring the serum concentration of the active ingredient, and adjusted to an optimum level.

The following Examples serve to illustrate the invention; temperatures are given in degrees Celsius, pressures in mbar.

The following Examples serve to illustrate the invention; temperatures are given in degrees Celsius and pressures are given in mbar.

TLC eluant systems:

| | |
|---|---|
| A | hexane-ethyl acetate (9:1) |
| B | hexane-ethyl acetate (4:1) |
| C | hexane-ethyl acetate (3:1) |
| D | hexane-ethyl acetate (2:1) |
| E | hexane-ethyl acetate (1:1) |
| F | hexane-ethyl acetate (1:2) |
| G | hexane-ethyl acetate-glacial acetic acid (50:50:1) |
| H | ethyl acetate-methanol-conc. ammonia (98:1:1) |
| I | ethyl acetate-methanol-conc. ammonia (90:10:1) |
| J | ethyl acetate-methanol-conc. ammonia (80:15:5) |
| K | ethyl acetate-methanol-conc. ammonia (40:45:5) |
| L | dichloromethane-methanol (90:10) |
| M | dichloromethane-methanol (92:8) |
| N | dichloromethane-methanol (95:5) |
| O | dichloromethane-methanol (96:4) |
| P | dichloromethane-methanol (97:3) |
| Q | dichloromethane-methanol (98:2) |
| R | dichloromethane-methanol (99:1) |
| S | dichloromethane-methanol-conc. ammonia (99:1:1) |
| T | dichloromethane-methanol-conc. ammonia (98:2:1) |
| U | dichloromethane-methanol-conc. ammonia (96:4:1) |
| V | dichloromethane-methanol-conc. ammonia (97:3:1) |
| W | dichloromethane-methanol-conc. ammonia (90:10:1) |
| X | dichloromethane-methanol-acetic acid (90:10:1) |
| Y | dichloromethane-methanol-acetic acid (95:5:1) |

HPLC eluent gradients on C18-Nucleosil® (5 μM), column length 25 cm: 20% acetonitrile/80% water/0.1% trifluoroacetic acid to 100% acetonitrile/0% water/0.1% trifluoroacetic acid for 20 minutes, then 100% acetonitrile/0.1% trifluoroacetic acid for 8 minutes.

The abbreviation "$R_f(A)$" means, for example, that the $R_f$ value is determined in solvent system A. The ratio of solvents to one another is always given in parts by volume.

For the designation of the eluant systems, the same abbreviations are used in the case of flash chromatography and medium-pressure chromatography.

The short names and abbreviations used have the following meanings:

| | |
|---|---|
| bar | pressure in bar |
| C18-Nucleosil® | trade name for HPLC reverse phase column material charged with octadecyl radicals |
| FAB-MS | fast atom bombardment mass spectroscopy |
| HRMS(FAB) | high resolution fast atom bombardment mass spectroscopy |
| TLC | thin-layer chromatography |
| FC | flash column chromatography |
| HPLC | high-performance liquid chromatography |
| Hyflo® | trade name for filter aids (Fluka, Buchs, Switzerland) |
| min | minute(s) |
| b.p. | boiling point at the pressure given in torr |
| ml | milliliters |
| $R_f$ | ratio of the migration of a substance to the distance of the eluant front from the starting point in TLC |
| $R_t$ | retention time of a substance in HPLC |
| m.p. | melting point |

EXAMPLE 1

A mixture of 2-(3-methoxypropoxy)-benzoic acid (0.105 g), bis(2-oxo-3-oxazolidinyl)phosphinic acid chloride (0.127 g) and triethylamine (0.140 ml) in dichloromethane (2 ml) is stirred at room temperature for one hour. Then a solution of (2R,4'S,5'S,2"S)-3-[4'-(2"-aminomethyl-3"-methylbutyl)-3'-(tert-butoxycarbonul)-2',2'-dimethyl-1,3-oxazolidin-5'-yl]-2-methylpropionic acid N-(butyl)amide (0.111 g) in dichloromethane (2 ml) and 4-dimethylaminopyridine (0.024 g) are added, and the reaction mixture is stirred overnight. After removal of the solvent by evaporation, saturated sodium hydrogen carbonate solution (30 ml) is added to the residue and extraction is then carried out with ethyl acetate (3×30 ml). The organic phases are dried over magnesium sulfate, concentrated by evaporation and purified by FC (20 g of silica gel, eluant F). (2S,4'S,5'S,2"R)-N-{2-[5'-(2"-Butylcarbamoylpropyl)-3'-(tert-butoxycarbonyl)-2',2'-dimethyl-1,3-oxazolidin-4'-ylmethyl]-3-methylbutyl}-2-(3-methoxypropoxy)-benzamide (0.112 g) is obtained in the form of a colourless oil: $R_f$ (F)=0.28. HPLC $R_t$=21.0 min.

The (2R,4'S,5'S,2"S)-3-[4'-(2"-aminomethyl-3"-methybutyl)-3'-(tert-butoxycarbonyl)-2',2'-dimethyl-1,3-oxazolidin-5'-yl]-2-methylpropionic acid N-(butyl)amide used as starting material is prepared as follows:

a) (2R,4'S,5'S,2"S)-3-[4'-(2"-Aminomethyl-3"-methylbutyl)-3'-(tert-butoxycarbonyl)-2',2°-dimethyl-1,3-oxazolidin-5'-yl]-2-methylpropionic acid N-(butyl)amide: (2R,4'S,5'S,2"S)-3-[4-(2"-Azidomethyl-3"-methylbutyl)-3'-(tert-butoxycarbonyl)-2',2'-dimethyl-1,3-oxazolidin-5'-yl]-2-methylpropionic acid N-(butyl)amide (0.435 g) dissolved in ethyl acetate (25 ml) is hydrogenated for 2 hours at room temperature and under normal pressure in the presence of 10% Pd/C (0.100 g). Filtration over Hyflo® and removal of the solvent yield 0.41 g of the crude title compound in the form of a pale-yellow oil: $R_f$ (dichloromethane-methanol-conc. ammonia 350:50:1)=0.19. HPLC $R_t$=13.6 min. MS(FAB) m/e 442 (M$^+$+1).

b) (2R,4'S,5'S,2"S)-3-[4'-(2"-Azidomethyl-3"-methylbutyl)-3'-(tert-butoxycarbonyl)-2',2'-dimethyl-1,3-oxazolidin-5'-yl]-2-methylpropionic acid N-(butyl)amide: A mixture of (2S,4'S,5'S,2"R)-methanesulfonic acid 2-[5'-(2"-butylcarbamoylpropyl)-3'-(tert-butoxycarbonyl)-2',2'-dimethyl-1,3-oxazolidin-4'-ylmethyl]-3-methylbutyl ester (0.52 g) and sodium azide (0.65 g) in 1,3-dimethyl-3,4,5,6-tetrahydro-2(1H)-pydmidinone (5 ml) is stirred at 50° C. for 5 hours. The cooled reaction mixture is poured onto water (100 ml) and extracted with diethyl ether (3×100 ml). The organic phases are washed with water (2×100 ml) and brine (100 ml), dried over magnesium sulfate and concentrated by evaporation. FC (35 g of silica gel, eluant D) of the evaporation residue yields the title compound (0.438 g) in the form of a pale-yellow oil: $R_f$ (E)=0.49. HPLC $R_t$=21.0 min. MS(FAB) m/e 468 (M$^+$+1).

c) (2S,4'S,5'S,2"R)-Methanesulfonic acid 2-[5'-(2"-butylcarbamoylpropyl)-3'-(tert-butoxycarbonyl)-2',2'-dimethyl-1,3-oxazolidin-4'-ylmethyl]-3-methylbutyl ester: To a stirred solution of (2R,4'S,5'S,2"S)-3-[4'-(2"-hydroxymethyl-3"-methyl-butyl)-3'-(tert-butoxycarbonyl)-2',2'-dimethyl-1,3-oxazolidin-5'-yl]-2-methylpropionic acid N-(butyl)amide (0.442 g) in dichloromethane (15 ml) there are added at 0° C. first triethylamine (0.418 ml) and then methanesulfonic acid chloride (0.117 ml). The reaction mixture is stirred at 0° C. for one hour and then the solvent is concentrated to half. FC (25 g of silica gel, eluant E) yields the title compound (0.51 g) in the form of a colourless oil: $R_f$ (E)=0.27. HPLC $R_t$=18.5 min. MS(FAB) m/e 521 (M$^+$+1).

d) (2R,4'S,5'S,2"S)-3-[4'-(2"-Hydroxymethyl-3"-methyl-butyl)-3'-(tert-butoxycarbonyl)-2',2'-dimethyl-1,3-oxazolidin-5'-yl]-2-methylpropionic acid N-(butyl)amide: (2R,4'S,5'S,2"S)-3-[4'-(2"-Benzyloxymethyl-3"-methyl-butyl)-3'-(tert-butoxycarbonyl)-2',2'-dimethyl-1,3-oxazolidin-5'-yl]-2-methylpropionic acid N-(butyl)amide (2.20 g), dissolved in tetrahydrofuran (60 ml), is hydrogenated for 0.5 hour at room temperature and under normal pressure in the presence of 10% Pd/C Degussa E 101N (0.220 g). Filtration over Hyflo® and removal of the solvent yield the title compound (1.79 g) in the form of a colourless oil: $R_f$ (E)=0.23. HPLC $R_t$=18.3 min. MS(FAB) m/e 443 (M$^+$+1).

e) (2R,4'S,5'S,2"S)-3-[4'-(2"-Benzyloxymethyl-3"-methyl-butyl)-3'-(tert-butoxycarbonyl)-2',2'-dimethyl-1,3-oxazolidin-5'-yl]-2-methylpropionic acid N-(butyl)amide: 2',2'-Dimethoxypropane (5 ml) and p-toluenesulfonic acid (0.01 g) are added in succession, with stirring, to a solution of (2RS,4S,5S,7S)-7-benzyloxymethyl-5-(tert-butoxycarbonyl)amino-4-hydroxy-2,8-dimethyl-nonanoic acid N(butyl)amide (3.0 g) in dichloremethane (30 ml), and the reaction mixture is then left to stand for 20 hours. The solvent is concentrated and the crude product, which consists of the two (2S,4'S,5'S,2"S)- and (2R,4'S,5'S,2"S)-diastereoisomers in the ratio 2:8 (HPLC $R_t$=23.3/23.5 min), is chromatographed (FC on 160 g of silica gel, eluant C). The stereoisomerically pure title compound (2.22 g) is obtained in the form of a colourless oil: $R_f$ (E)=0.47. HPLC $R_t$=23.5 min.

f) (2RS,4S,5S,7S)-7-Benzyloxymethyl-5-(tert-butoxycarbonyl)amino-4-hydroxy-2,8-dimethyl-nonanoic acid N-(butyl)amide: A solution of (2S,3S,5S)-2-[3-(tert-butoxycarbonyl)amino-5-(benzyloxymethyl)-2-hydroxy-6-methylheptyl]-N-(butyl)acrylamide (A) (3.0 g) in anhydrous methanol (25 ml) is hydrogenated for 22 hours at room temperature and under a pressure of 25 bar in the presence of [Ru$_2$Cl$_4$[(S)-BINAP]$_2$]NEt$_3$ (39.5 mg). The reaction mixture is concentrated by evaporation and then purified by FC (100 g of silica gel, eluant E). The title compound (3.0 g) is obtained in the form of a pale-yellow oil: $R_f$(E)=0.15. HPLC $R_t$=19.4 min.

g) (2S,3S,5S)-2-[3-(tert-Butoxycarbonyl)amino-5-(benzyloxymethyl)-2-hydroxy-6-methylheptyl]-N-(butyl)acrylamide (A) and (2R,3S,5S)-2-[3-(tert-butoxycarbonyl) amino-5-(benzyloxymethyl)-2-hydroxy-6-methylheptyl]-N-(butyl)acrylamide (B): A 1.6M n-butyllithium solution in hexane (73.3 ml) is added at −75° C. over a period of 15 minutes, with stirring, to a solution of methacrylic acid N-(butyl)amide (7.92 g) in tetrahydrofuran (125 ml). When the addition is complete, the reaction mixture is stirred at 0° C. for 30 minutes and is cooled to −75° C., and a 1M chlorotitanium triisopropoxide solution in hexane (89.3 ml) is added dropwise over a period of 40 minutes. The mixture is stirred at −75° C. for a further 15 minutes and then a solution of (2S,4S)-2-(tert-butoxycarbonyl)amino-4-(benzyloxymethyl)-5-methyl-hexanal (9.10 g) in tetrahydrofuran (90 ml) is added dropwise at the same temperature over a period of 15 minutes. The reaction mixture is stirred at −75° C. for a further 75 minutes, and saturated ammonium chloride solution (150 ml) is then added at −20° C. The aqueous phase is extracted with diethyl ether (3×600 ml), and the combined organic phases are washed in succession with water (600 ml) and saturated sodium chloride solution (600 ml), dried over magnesium sulfate and concentrated by evaporation. The crude product is chromatographed on 1.3 kg of silica gel (eluant C) with separation of the mixture of diastereoisomers. Title compound A (3.01 g) is obtained in the form of a pale-yellow oil: $R_f$ (D)=0.22. HPLC $R_t$=20.1 min. In addition, title compound B (5.70 g) is obtained in the form of a pale-yellow oil: $R_f$(D)=0.17. HPLC $R_t$=19.87 min.

h) (2S,4S)-2-(tert-Butoxycarbonyl)amino-4-(benzyloxymethyl)-5-methyl-hexanal: A 1.2M diisobutyla-luminium hydride solution in toluene (51 ml) is slowly added at −75° C., with stirring, to a solution of (2S,4S)-2-(tert-butoxycarbonyl)amino-4-(benzyloxymethyl)-5- methyl-hexanoic acid methyl ester (9.70 g) in toluene (100 ml). The reaction mixture is stirred at the same temperature for a further 45 minutes, and then methanol (20 ml) is added carefully. The resulting mixture is poured onto 1N hydrochloric acid/ice (500 ml) and is extracted with ethyl acetate (3×500 ml). The organic phases are washed in succession with water (2×500 ml) and saturated sodium chloride solution (500 ml), are clarified by filtration over Hyflo® and are dried over magnesium sulfate. The solvent is removed by evaporation and the residue is dried under a high vacuum. The crude title compound (8.91 g) is obtained in the form of a colourless oil: $R_f$(B)=0.25. HPLC $R_t$=19.2 min.

i) (2S,4S)-2-(tert-Butoxycarbonyl)amino-4-(benzyloxymethyl)-5-methyl-hexanoic acid methyl ester: Ethyl diisopropylamine (17.4 ml) and a solution of di-tert-butyl dicarbonate (18.8 g) in dichloromethane (0.1 liter) are added in succession at 0° C., with stirring, to a solution of (2S,4S)-2-amino-4-(benzyloxymethyl)-5-methyl-hexanoic acid methyl ester (21.9 g) in dichloromethane (0.5 liter). The reaction mixture is stirred for a further 16 hours at room temperature and is then concentrated by evaporation. FC (2.4 kg of silica gel, ethyl acetate-hexane 1:6) of the evaporation residue yields the title compound (27.0 g) in the form of a slightly yellowish oil: $R_f$(B)=0.32. HPLC $R_t$=27.2 min.

j) (2S,4S)-2-Amino-4-(benzyloxymethyl)-5-methyl-hexanoic acid methyl ester: A 1N hydrochloric acid solution (400 ml) is added at room temperature to a solution of (2S,2'S,5R)-2-[2'-(benzyloxymethyl)-3'-methylbutyl]-2,5-dihydro-5-isopropyl-3,6-dimethoxypyrazine (36.2 g) in acetonitrile (400 ml), and the mixture is stirred for 2 hours. The reaction mixture is then poured onto a mixture of saturated sodium hydrogen carbonate solution and ice (1 liter), and extraction washed out with dichloromethane (3×0.8 liter). The organic phases are washed with water (1 liter), dried over magnesium sulfate and concentrated by evaporation. The evaporation residue is purified by FC (2.4 kg of silica gel, dichloromethane-methanol-conc. ammonia 95:5:0.1). The title compound (21.9 g) is obtained in the form of a colourless oil: $R_f$ (dichloromethaneomethanol-conc. ammonia 700:50:1)=0.34. HPLC $R_t$=13.6 min.

k) (2S,2'S,5R)-2-[2'-(Benzyloxymethyl)-3'-methylbutyl]-2,5-dihydro-5-isopropyl-3,6-dimethoxypyrazine: A 1.6M n-butyllithium solution in hexane (100 ml) is added dropwise at −75° C. to a solution of (2R)-2,5-dihydro-2-isopropyl-3,6-dimethoxypyrazine (29.5 g) in absolute tetrahydrofuran (530 ml). The reaction mixture is then stirred at −75° C. for 30 minutes, and then a solution of 2(S)-(benzyloxymethyl)-3-methyl-butyl bromide (29 g) in tetrahydrofuran (130 ml) is added over a period of 20 minutes. The reaction solution is stirred at −75° C. for a further 2 hours and is then left to stand at −18° C. for 64 hours. The reaction mixture is concentrated by evaporation, water (500 ml) is added, and extraction is carried out with diethyl ether (3×500 ml). The organic phases are washed with saturated sodium chloride solution (500 ml), dried over magnesium sulfate and concentrated by evaporation. The evaporation residue is purified by FC (2.4 kg of silica gel, ethyl acetate-hexane 1:15), and the title compound (36.2 g) is obtained in the form of a yellowish oil: $R_f$(B)=0.58. HPLC $R_t$=25.8 min.

The 2-(3-methoxypropoxy)-benzoic acid used as starting material is prepared as follows:

a) 1N sodium hydroxide solution (11.1 ml) is added to a solution of 2-(3-methoxypropoxy)-benzoic acid ethyl ester (2.4 g) in ethanol (20 ml) and water (10 ml), and the reaction mixture is stirred at 50° C. for 7 hours. The mixture is concentrated and the acidified aqueous phase is extracted with dichloromethane (3×40 ml). The organic phase is washed with saturated sodium chloride solution, dried over magnesium sulfate and concentrated. 2-(3-Methoxypropoxy)-benzoic acid, $R_f$ (hexane-ethyl acetate-glacial acetic acid 1:2:0.1)=0.43, is obtained in the form of a yellowish oil.

b) 2-(3-Methoxypropoxy)-benzoic acid ethyl ester: Dried potassium carbonate powder (3.49 g) is added, with stirring, to a solution of salicylic acid ethyl ester (3.5 g) in anhydrous acetone (50 ml), and then a solution of 3-methoxypropyl bromide (4.83 g) in anhydrous acetone (15 ml) is quickly added dropwise at room temperature. The suspension is heated under reflux for 38 hours. After cooling, filtration is carried out, the filtrate is concentrated and the residue is purified by FC (200 g of silica gel, eluant A). The title compound, $R_f$ (hexane-ethyl acetate-glacial acetic acid 1:1:0.1)=0.39, is obtained in the form of a colouress oil.

EXAMPLE 2

In a manner analogous to that described in Example 1), the following compounds are prepared:

a) From 128 mg of (2R,4'S,5'S,2"S)-3-[4'-(2"-aminomethyl-3"-methylbutyl)-3'-(tert-butoxycarbonyl)-2', 2'-dimethyl-1,3-oxazolidin-5'-yl]-2-methylpropionic acid N-(butyl)amide and 139 mg of 3-methoxy-2-(3-methoxypropoxy)-benzoic acid, (2S,4'S,5'S,2"R)-N-{2-[5'-(2"-butylcarbamoylpropyl)-3'-(tert-butoxycarbonyl)-2',2'-dimethyl-1,3-oxazolidin-4'-ylmethyl]-3-methylbutyl}-3-methoxy-2-(3-methoxypropoxy)-benzamide, $R_f$ (L)=0.65; HPLC $R_t$=20.9 min; MS(FAB) m/e 664 (M⁺+1), in the form of a colourless oil.

b) From 128 mg of (2R,4'S,5'S,2"S)-3-[4'-(2"-aminomethyl-3"-methylbutyl)-3'-(tert-butoxycarbonyl)-2', 2'-dimethyl-1,3-oxazolidin-5'-yl]-2-methylpropionic acid N-(butyl)amide and 139 mg of 4-methoxy-2-(3-methoxypropoxy)-benzoic acid, (2S,4'S,5'S,2"R)-N-{2-[5=-(2"-butylcarbamoylpropyl)-3'-(tert-butoxycarbonyl)-2',2'-dimethyl-1,3-oxazolidin-4'-ylmethyl]-3-methylbutyl}-4-methoxy-2-(3-methoxypropoxy)-benzamide,$R_f$(N)=0.17; HPLC $R_t$=21.4 min; MS(FAB) m/e 664 (M⁺+1), in the form of a colourless oil.

c) From 111 mg of (2R,4'S,5'S,2"S)-3-[4'-(2"-aminomethyl-3"-methylbutyl)-3'-(tert-butoxycarbonyl)-2', 2'-dimethyl-1,3-oxazolidin-5'-yl]-2-methylpropionic acid N-(butyl)amide and 105 mg of 3-(3-methoxypropoxy)-benzoic acid, (2S,4'S,5'S,2"R)-N-{2-[5'-(2"butylcarbamoylpropyl)-3'-(tert-butoxycarbonyl)-2',2'-dimethyl-1,3-oxazolidin-4'-ylmethyl]-3-methylbutyl}-3-(3-methoxypropoxy)-benzamide, $R_f$ (N)=0.26; HPLC $R_t$=20.7 min; MS(FAB) m/e 634 (M⁺+1), in the form of a white foam.

The 3-(3-methoxypropoxy)-benzoic acid used as starting material is prepared as follows:

a) Alkaline hydrolysis of 3-(3-methoxypropoxy)-benzoic acid methyl ester in a manner analogous to that described in Example 1) yields the title compound, $R_f$ (hexane-ethyl acetate-glacial acetic acid 3:1:0.01)=0.18; m.p. 82°-84° C., in the form of a solid.

b) 3-(3-Methoxypropoxy)-benzoic acid methyl ester: Sodium hydride in the form of an 80% dispersion in oil (0.39 g) is added at 0° C., with stirring, to a solution of 3-hydroxybenzoic acid methyl ester (2.04 g) in tetrahydrofuran (50 ml). After stirring for 30 minutes, a solution of 3-methoxypropyl bromide (3.08 g) in tetrahydrofuran (15 ml) is added dropwise at 0° C. The mixture is heated slowly to 50° C. and the white suspension is stirred for a further 30 hours. The mixture is poured onto ice-water (40 ml) and the aqueous phase is extracted with dichloromethane (3×40 ml). The combined organic phases are washed with saturated sodium chloride solution, dried over magnesium sulfate and concentrated. Purification of the crude product by FC (100 g of silica gel, eluant A) yields the title compound, $R_f$ (C)=0.36, in the form of a yellowish oil.

The 4-methoxy-2-(3-methoxypropoxy)-benzoic acid and 3-methoxy-2-(3-methoxy propoxy)-benzoic acid used above as starting materials are prepared in a manner analogous to that described in Example 1).

EXAMPLE 3 p-Toluenesulfonic acid (2 mg) is added, with stirring, to a solution of (2S,4'S,5'S,2"R)-N-{2-[5'-(2"-butylcarbamoylpropyl)-3'-(tert-butoxycarbonyl)-2',2'-dimethyl-1,3-oxazolidin-4'-ylmethyl]-3-methylbutyl}-2-(3-methoxypropoxy)-benzamide (105 mg) in methanol (3 ml), and the mixture is stirred for a further 24 hours at room temperature. The solvent is removed by evaporation at room temperature and the residue is purified by FC (40 g of silica gel, eluant N). (2S,4S,5S,7R)-N-[4-(tert-Butoxycarbonyl)amino-7-butylcarbamoyl-5-hydroxy-2-isopropyl-octyl]-2-(3-methoxypropoxy)-benzamide (86 mg) is obtained in the form of a white foam: $R_f$ (F)=0.09. HPLC $R_t$=17.2 min.

EXAMPLE 4

In a manner analogous to that described in Example 3), the following compounds are prepared:

a) From 150 mg of (2S,4'S,5'S,2"R)-N-{2-[5'-(2'-butylcarbamoylpropyl)-3'-(tert-butoxycarbonyl)-2',2'-dimethyl-1,3-oxazolidin-4'-ylmethyl]-3-methylbutyl}-3-methoxy-2-(3-methoxypropoxy)-benzamide, (2S,4S,5S,7R)-N-[4-(tert-butoxycarbonyl)amino-7-butyl carbamoyl-5-hydroxy-2-isopropyl-octyl]-3-methoxy-2-(3-methoxypropoxy)-benzamide, $R_f$ (F)=0.05; HPLC $R_t$=17.2 min; MS(FAB) m/e 624 (M$^+$+1), in the form of a colourless oil.

b) From 172 mg of (2S,4'S,5'S,2"R)-N-{2-[5'-(2"-butylcarbamoylpropyl)-3'-(tert-butoxycarbonyl)-2',2'-dimethyl-1,3-oxazolidin-4'-ylmethyl]-3-methylbutyl}-4-methoxy-2-(3-methoxypropoxy)-benzamide, (2S,4S,5S,7R)-N-[4-(tert-butoxycarbonyl)amino-7-butylcarbamoyl-5-hydroxy-2-isopropyl-octyl]-4-methoxy-2-(3-methoxypropoxy)-benzamide, $R_f$ (N)=0.30; HPLC $R_t$=17.6 min; MS(FAB) m/e 624 (M$^+$+1), in the form of a colourless oil.

c) From 105 mg of (2S,4'S,5'S,2"R)-N-{2-[5'-(2"-butylcarbamoylpropyl)-3'-(tert-butoxycarbonyl)-2',2'-dimethyl-1,3-oxazolidin-4'-ylmethyl]-3-methylbutyl}-3-(3-methoxypropoxy)-benzamide, (2S,4S,5S,7R)-N-[4-(tert-butoxycarbonyl)amino-7-butylcarbamoyl-5-hydroxy-2-isopropyl-octyl]-3-(3-methoxypropoxy)-benzamide, $R_f$ (N)=0.18; HPLC $R_t$=17.0 min; MS(FAB) m/e 594 (M$^+$+1), in the form of a white foam.

EXAMPLE 5

(2S,4S,5S,7R)-N-[4-(tert-Butoxycarbonyl)amino-7-butylcarbamoyl-5-hydroxy-2-isopropyl-octyl]-2-(3-methoxypropoxy)-benzamide (82 mg) is dissolved at 0° C. in 3 ml of a 4N hydrochloric acid solution in dioxane, and the solution is stirred at 0° C. for 2 hours. The reaction mixture is lyophilised and (2S,4S,5S,7R)-N-(4-amino-7-butylcarbamoyl-5-hydroxy-2-isopropyl-octyl)-2-(3-methoxypropoxy)-benzamide hydrochloride is obtained in the form of a white foam: $R_f$ (L)=0.12. HPLC $R_t$=11.6 min. MS(FAB) m/e 494 (M$^+$+1).

EXAMPLE 6

In a manner analogous to that described in Example 5), the following compounds are prepared by de-Bocylation:

a) From 117 mg of (2S,4S,5S,7R)-N-[4-(tert-butoxycarbonyl)amino-7-butylcarbamoyl-5-hydroxy-2-isopropyl-octyl]-3-methoxy-2-(3-methoxypropoxy)-benzamide, (2S,4S,5S,7R)-N-(4-amino-7-butylcarbamoyl-5-hydroxy-2-isopropyl-octyl)-3-methoxy-2-(3-methoxypropoxy)-benzamide hydrochloride: $R_f$ (L)=0.15. HPLC $R_t$=11.7 min. MS(FAB) m/e 524 (M$^+$+1).

b) From 119 mg of (2S,4S,5S,7R)-N-[4-(tert-butoxycarbonyl)amino-7-butylcarbamoyl-5-hydroxy-2-isopropyl-octyl]-4-methoxy-2-(3-methoxypropoxy)-benzamide, (2S,4S,5S,7R)-N-(4-amino-7-butylcarbamoyl-5-hydroxy-2-isopropyl-octyl)-4-methoxy-2-(3-methoxypropoxy)-benzamide hydrochloride: $R_f$ (L)=0.13. HPLC $R_t$=12.3 min. MS(FAB) m/e 524 (M$^+$+1).

c) From 82 mg of (2S,4S,5S,7R)-N-[4-(tert-butoxycarbonyl)amino-7-butylcarbamoyl-5-hydroxy-2-isopropyl-octyl]-3-(3-methoxypropoxy)-benzamide, (2S,4S,5S,7R)-N-(4-amino-7-butylcarbamoyl-5-hydroxy-2-isopropyl-octyl)-3-(3-methoxypropoxy)-benzamide hydrochloride: $R_f$ (L)=0.20. HPLC $R_t$=11.4 min. MS(FAB) m/e 494 (M$^+$+1).

EXAMPLE 7

Triethylamine (0.034 ml) and formic acid 4-nitrophenyl ester (28 mg) are added at room temperature, with stirring, to a solution of (2S,4S,5S,7R)-N-(4-amino-7-butylcarbamoyl-5-hydroxy-2-isopropyl-octyl)-3-methoxy-2-(3-methoxypropoxy)-benzamide hydrochloride (Example 6a) (67 mg) in dichloromethane (4 ml). The resulting reaction solution is stirred for a further 30 minutes and is then concentrated by evaporation. The residue is purified by FC (18 g of silica gel; eluant E, then ethyl acetate-hexane-methanol 5:5:1). (2S,4S,5S,7R)-N-(7-Butylcarbamoyl-4-formylamino-5-hydroxy-2-isopropyl-octyl)-3-methoxy-2-(3-methoxypropoxy)-benzamide is obtained in the form of a white foam: $R_f$ (L)=0.58. HPLC $R_t$=13.2 min. MS(FAB) m/e 552 (M$^+$+1).

EXAMPLE 8

(2R,4'S,5'S,2"R)-3-[4'-(2"-Aminomethyl-3"-methylbutyl)-3'-(tert-butoxycarbonyl)-2',2'-dimethyl-1,3-oxazolidin-5'-yl]-2-methylpropionic acid N-(butyl)amide (100 mg) is reacted in dichloromethane in accordance with the process described in Example 1) with 1-benzyl-1H-indole-3-carboxylic acid (114 mg) in the presence of bis(2-oxo-3-oxazolidinyl)phosphinic acid chloride (115 mg), triethylamine (0.13 ml) and a catalytic amount of 4-dimethylaminopyridine. When the reaction is complete, the solvent is removed by evaporation and the residue is immediately purified by FC (30 g of silica gel, eluant W). (2R,4'S,5'S,2"R)-1-Benzyl-1H-indole-3-carboxylic acid N-{2-[5'-(2"-butylcarbamoylpropyl)-2',2'-dimethyl-1,3-oxazolidin-4'-ylmethyl]-3-methylbutyl}-amide, $R_f$ (L)= 0.61, is obtained in the form of a yellowish oil.

The (2R,4'S,5'S,2"R)-3-[4'-(2"-aminomethyl-3"-methylbutyl)-3'-(tert-butoxycarbonyl)-2',2'-dimethyl-1,3-oxazolidin-5'-yl]-2-methylpropionic acid N-(butyl)amide used as starting material is prepared as follows:

a) (2R,4'S,5'S,2"R)-3-[4'-(2"-Aminomethyl-3"-methylbutyl)-3'-(tert-butoxycarbonyl)-2',2°-dimethyl-1,3- oxazolidin-5'-yl]-2-methylpropionic acid N-(butyl)amide: The title compound is obtained in the form of a pale-yellow oil, $R_f$ (W)=0.32, from (2R,4'S,5'S,2"R)-3-[4'-(2"-azidomethyl-3"-methylbutyl)-3'-(tert-butoxycarbonyl)-2',2'-dimethyl-1,3-oxazolidin-5'-yl]-2-methylpropionic acid N-(butyl)amide (0.6 g) by hydrogenolysis analogously to Example 1a) and then purification by FC (100 g of silica gel, eluant V).

b) (2R,4'S,5'S,2"R)-3-[4'-(2"-Azidomethyl-3"-methylbutyl)-3'-(tert-butoxycarbonyl)-2',2'-dimethyl-1,3-oxazolidin-5'-yl]-2-methylpropionic acid N-(butyl)amide: Reaction of (2R,4S,5S,2'R)-methanesulfonic acid 2-[5'-(2"-butylcarbamoylpropyl)-3'-(tert-butoxycarbonyl)-2',2'-dimethyl-1,3-oxazolidin-4'-ylmethyl]-3-methylbutyl ester (1.30 g) with sodium azide (1.92 g) in a manner analogous to that described in Example 1b) and purification by FC (200 g of silica gel, eluant D) yield the title compound, $R_f$ (E)=0.61, in the form of a pale-yellow oil.

c) (2R,4'S,5'S,2"R)-Methanesulfonic acid 2-[5'-(2"-butylcarbamoylpropyl)-3'-(tert-butoxycarbonyl)-2',2'-dimethyl-1,3-oxazolidin-4'-ylmethyl]-3-methylbutyl ester: The title compound is obtained in a manner analogous to that described in Example 1c) in the form of a colourless oil (1.30 g), $R_f$ (E)=0.33, starting from (2R,4'S,5'S,2"R)-3-[4'-(2"-hydroxymethyl-3"-methylbutyl)-3'-(tert-butoxycarbonyl)-2',2'-dimethyl-1,3-oxazolidin-5'-yl]-2-methylpropionic acid N-(butyl)amide (1.1 0 g).

d) (2R,4'S,5'S,2"R)-3-[4'-(2"-Hydroxymethyl-3"-methylbutyl)-3'-(tert-butoxycarbonyl)-2',2'-dimethyl-1,3-oxazolidin-5'-yl]-2-methylpropionic acid N-(butyl)amide: The title compound is obtained in the form of a white solid (1.16 g), $R_f$(hexane-ethyl acetate 1:3)=0.44; m.p. 110°–112° C., from (2R,4'S,5'S,2"R)-3-[4'-(2"-benzyloxymethyl-3"-methylbutyl)-3'-(tert-butoxycarbonyl)-2',2'-dimethyl-1,3-oxazolidin-5'-yl]-2-methylpropionic acid N-(butyl)amide (1.64 g) by hydrogenation in a manner analogous to that described in Example 1d) and then purification by FC (50 g of silica gel, eluant gradient from E to ethyl acetate).

e) (2R,4'S,5'S,2"R)-3-[4'-(2"-Benzyloxymethyl-3"-methylbutyl)-3'-(tert-butoxycarbonyl)-2',2'-dimethyl-1,3-oxazolidin-5'-yl]-2-methylpropionic acid N-(butyl)amide: A mixture of (2RS,4S,5S,7R)-7-benzyloxymethyl-5-(tert-butoxycarbonyl)amino-4-hydroxy-2,8-dimethyl-nonanoic acid N-(butyl)amide (1.9 g) and para-toluenesulfonic acid hydrate (0.037 g) in 2',2'-dimethoxyprepane (35 ml) and dichloromethane (35 ml) is stirred at room temperature for one hour. Pyridine (16 µl) and hexane (35 ml) are then added, the solvent is concentrated in vacuo, and the oily residue is chromatographed on 100 g of silica gel (eluant gradient from hexane-ethyl acetate 6:1 to 4:1). Fractions containing pure (2R,4'S,5'S,2"R)-diastereoisomer are combined, while mixed fractions are chromatographed again under the same conditions. Combination of the corresponding fractions, concentration of the solvent and drying of the residue under a high vacuum yield the title compound (1.64 g; $R_f$ (E)=0.72; HPLC, $R_t$=22.8 min; MS(FAB) m/e 533 (M$^+$+1)) together with a 6:4 mixture of the two (2R,4'S,5'S, 2"R)- and (2R,4'S,5'S,2"S)-diastereoisomers (0.28 g; $R_f$ (E)=0.72/0.66; HPLC, $R_t$=22.8 and 23.0 min).

f) (2RS,4S,5S,7R)-7-Benzyloxymethyl-5-(tert-butoxycarbonyl)amino-4-hydroxy-2,8-dimethyl-nonanoic acid N-(butyl)amide: In a manner analogous to that described in Example 1f), hydrogenation of the stereoisomerically pure (2S,3S,5R)-2-[3-(tert-butoxycarbonyl) amino-5-(benzyloxymethyl)-2-hydroxy-6-methylheptyl]-N-(butyl)acrylamide (A) (2.5 g, 5.10 mmol) in the presence of catalytic amounts of [Ru $_2$Cl$_4$[(S)-BINAP]$_2$]NEt$_3$ (30 mg) yields the title compound in the form of a mixture of diastereoisomers (1.91 g) that cannot be separated on silica gel, the (2R,4S,5S,2'R)-isomer preferentially being formed: yellowish oil, $R_f$ (E)=0.25, MS(FAB) m/e 493 (M$^+$+1).

g) (2S,3S,5R)-2-[3-(tert-Butoxycarbonyl)amino-5-(benzyloxymethyl)-2-hydroxy-6-methylheptyl]-N-(butyl) acrylamide (A) and (2R,3S,5R)-2-[3-(tert-butoxycarbonyl) amino-5-(benzyloxymethyl)-2-hydroxy-6-methylheptyl]-N-(butyl)acrylamide (B): In a manner analogous to that described in Example 1g), there is obtained first, by reduction of (2S,4R)-2-(tert-butoxycarbonyl)amino-4-(benzyloxymethyl)-5-methyl-hexanoic acid methyl ester (8.0 g), dissolved in anhydrous toluene (120 ml), with a 1.2M diisobutylaluminium hydride solution in toluene (34.9 ml), (2S,4R)-2-(tert-butoxycarbonyl)amino-4-(benzyloxymethyl)-5-methyl-hexanal in the form of a pale-yellow oil ($R_f$ (N)=0.6). The crude aldehyde is reacted in a manner analogous to that described in Example 1g) without being purified further. The crude product (14.8 g) obtained after aqueous working-up is chromatographed over 1.0 kg of silica gel using an eluant gradient from B to E, with separation of the two (2S,3S,5R)- and (2R,3S,5R)-diastereoisomers. There are obtained title compound A (2.52 g, 24%) in the form of a light-yellow oil, $R_f$ (E)=0.55, HPLC $R_t$=19.8 min, MS(FAB) m/e 491 (M$^+$+1), and title compound B (3.76 g, 35%) in the form of a light-yellow oil, $R_f$ (E)=0.42, HPLC $R_t$=19.6 min. MS(FAB) m/e 491 (M$^+$+1).

h) (2S,4R)-2-(tert-Butoxycarbonyl)amino-4-(benzyloxymethyl)-5-methyl-hexanoic acid methyl ester: In a manner analogous to that described in Examples 1i and 1j), (2S,2'R,5R)-2-[2'-(benzyloxymethyl)-3'-methylbutyl]-2,5-dihydro-5-isopropyl-3,6-dimethoxypyrazine (15.7 g) is first hydrolysed in the presence of 1N hydrochloric acid solution (176 ml) and then the product ($R_f$ (W)=0.59) obtained after working-up and purification by FC (1.0 kg of silica gel, eluant V) is reacted with di-tert-butyl dicarbonate in the presence of Hünig base. Purification by FC (1.0 kg of silica gel, hexane-ethyl acetate 6:1) yields the title compound (13.4 g) in the form of a pale-yellow oil: $R_f$ (C)=0.43.

i) (2S,2'R,5R)-2-[2'-(Benzyloxymethyl)-3'-methylbutyl]-2,5-dihydro-5-isopropyl-3,6-dimethoxypyrazine: A solution of (2R)-2,5-dihydro-2-isopropyl-3,6-dimethoxypyrazine (13.0 g) in absolute tetrahydrofuran (230 ml) is reacted in a manner analogous to that described in Example 1k) first with a 1.6M n-butyllithium solution in hexane (44 ml) and then with 2(R)-(benzyloxymethyl)-3-methylbutyl bromide (12.8 g) in tetrahydrofuran (60 ml). After working up the reaction mixture, the oily crude product is purified by FC (1.0 kg of silica gel, ethyl acetate-hexane 1:20). There is obtained, in addition to the (2R,2'R,5R)-diastereoisomer (3.49 g; yellowish oil, $R_f$ (ethyl acetate-hexane 1:6)=0.50), the stereoisomerically pure title compound (12.9 g) in the form of a yellowish oil: $R_f$ (ethyl acetate-hexane 1:6)=0.62.

EXAMPLE 9

In a manner analogous to that described in Example 8), the following compounds are prepared:

a) From 100 mg of (2R,4'S,5'S,2"R)-3-[4'-(2"-aminomethyl-3"-methylbutyl)-3'-(tert-butoxycarbonyl)-2',2'-dimethyl-1,3-oxazolidin-5'-yl]-2-methylpropionic acid N-(butyl)amide and 99 mg of 1-(2-methoxyethyl)-1H-indole-3-carboxylic acid, (2R,4'S,5'S,2"R)-1-(2-methoxyethyl)-1H-indole-3-carboxylic acid N-{2-[5'-(2"-butylcarbamoylpropyl)-2',2'-dimethyl-1,3-oxazolidin-4'-ylmethyl]-3-methylbutyl}-amide, $R_f$ (L)=0.68, in the form of a yellowish oil.

b) From 46 mg of (2R,4'S,5'S,2"R)-3-[4'-(2"-aminomethyl-3"-methylbutyl)-3'-(tert-butoxycarbonyl)-2',2'-dimethyl-1,3-oxazolidin-5'-yl]-2-methylpropionic acid N-(butyl)amide and 53 mg of 1-pyridin-2-yl-1H-indole-3-carboxylic acid, (2S,4'S,5'S,2"R)-1-pyridin-2yl-1H-indole-3-carboxylic acid N-{2-[5'-(2"-butylcarbamoylpropyl)-2',2'-dimethyl-oxazolidin-4'-ylmethyl]-3-methylbutyl}-amide, $R_f$ (L)=0.81, in the form of a yellowish oil.

c) From 46 mg of (2R,4'S,5'S,2"R)-3-[4'-(2"-aminomethyl-3"-methylbutyl)-3'-(tert-butoxycarbonyl)-2',2'-dimethyl-1,3-oxazolidin-5'-yl]-2-methylpropionic acid N-(butyl)amide and 59 mg of 1-(2-methoxybenzyl)-1H-indole-3-carboxylic acid, (2R,4'S,5'S,2"R)-1-(2-methoxybenzyl)-1H-indole-3-carboxylic acid N-{2-[5'-(2"-butylcarbamoylpropyl)-2',2'-dimethyl-oxazolidin-4'-ylmethyl]-3-methylbutyl}-amide, $R_f$ (L)=0.73, in the form of a colourless oil.

The 1-(2-methoxyethyl)-1H-indole-3-carboxylic acid used as starting material is prepared as follows:

a) 1-(2-Methoxyethyl)-1H-indole-3-carboxylic acid: 1N sodium hydroxide solution (5.1 ml) is added to a solution of 1-(2-methoxyethyl)-1H-indole-3-carboxylic acid ethyl ester (1.26 g) in ethanol (10 ml) and water (5 ml), and the mixture is heated at 50° C. for one hour, with stirring. Further 1N sodium hydroxide solution (7.1 ml) is added, and stirring is continued for a further 5 hours at 80° C. The mixture is concentrated in a rotary evaporator with removal of the ethanol, the aqueous phase is acidified by the addition of 1M potassium hydrogen sulfate solution, and extraction is carried out with dichloromethane. The organic phase is washed with saturated sodium chloride solution, dried over sodium sulfate and concentrated. The title compound (0.96 g), $R_f$ (hexane-ethyl acetate-glacial acetic acid 67:33:1)=0.15, is obtained in the form of a yellowish solid.

b) 1-(2-Methoxyethyl)-1H-indole-3-carboxylic acid ethyl ester: Sodium hydride in the form of an 80% dispersion in oil (0.27 g) is added to a solution of 1H-indole-3-carboxylic acid ethyl ester (1.0 g) in N,N-dimethylformamide (25 ml), and the mixture is stirred at room temperature for 30 minutes. 3-Methoxyethyl iodide (1.5 g) is then added and the reaction mixture is stirred first for one hour at 50° C. and then overnight at 80° C. The mixture is poured into ice-water (50 ml), the aqueous phase is extracted with dichloromethane, and the combined organic phases are washed with saturated sodium chloride solution, dried over sodium sulfate and concentrated. The crude product is purified by FC (100 g of silica gel, eluant gradient from C to D). The title compound (1.26 g), $R_f$ (C, double track)=0.44, is obtained in the form of an oil.

EXAMPLE 10

In a manner analogous to that described in Example 3), the following compounds are prepared:

a) From 126 mg of (2R,4'S,5'S,2"R)-1-benzyl-1H-indole-3-carboxylic acid N-{2-[5'-(2"-butylcarbamoylpropyl)-2',2'-dimethyl-1,3-oxazolidin-4'-ylmethyl]-3-methylbutyl}-amide, (2R,4S,5S,7R)-1-benzyl-1H-indole-3-carboxylic acid N-[4-(tert-butoxycarbonyl)amino-7-butylcarbamoyl-5-hydroxy-2-isopropyl-octyl]-amide, $R_f$(L)=0.55, in the form of a white foam.

b) From 146 mg of (2R,4'S,5'S,2"R)-1-(2-methoxyethyl)-1H-indole-3-carboxylic acid N-{2-[5'-(2"-butylcarbamoylpropyl)-2',2'-dimethyl-1,3-oxazolidin-4'-ylmethyl]-3-methylbutyl}-amide, (2R,4S,5S,7R)-1-(2-methoxyethyl)-1H-indole-3-carboxylic acid N-[4-(tert-butoxycarbonyl)-amino-7-butylcarbamoyl-5-hydroxy-2-isopropyl-octyl]-amide, $R_f$ (L)=0.52, in the form of a colourless oil.

c) From 77 mg of (2R,4'S,5'S,2"R)-1-pyridin-2-yl-1H-indole-3-carboxylic acid N-{2-[5'-(2"-butylcarbamoylpropyl)-2',2'-dimethyl-1,3-oxazolidin-4'-ylmethyl]-3-methylbutyl}-amide, with purification by FC on 10 g of silica gel (eluant S), (2R,4S,5S,7R)-1-pyridin-2-yl-1H-indole-3-carboxylic acid N-[4-(tert-butoxycarbonyl)amino-7-butylcarbamoyl-5-hydroxy-2-isopropyl-octyl]-amide, $R_f$ (W)=0.54, in the form of a colourless foam.

d) From 67 mg of (2R,4'S,5'S,2"R)-1-(2-methoxybenzyl)-1H-indole-3-carboxylic acid N-{2-[5'-(2"-butylcarbamoylpropyl)-2',2'-dimethyl-1,3-oxazolidin-4'-ylmethyl]-3-methylbutyl}-amide, (2R,4S,5S,7R)-1-(2-methoxybenzyl)-1H-indole-3-carboxylic acid N-[4-(tert-butoxycarbonyl)amino-7-butylcarbamoyl-5-hydroxy-2-isopropyl-octyl]-amide, $R_f$ (L)=0.61, in the form of a colourless foam.

EXAMPLE 11

In a manner analogous to that described in Example 5), the following compounds are prepared by de-Bocylation:

a) From 93 mg of (2R,4S,5S,7R)-1-benzyl-1H-indole-3-carboxylic acid N-[4-(tert-butoxycarbonyl)amino-7-butylcarbamoyl-5-hydroxy-2-isopropyl-octyl]-amide, (2R,4S,5S,7R)-1-benzyl-1H-indole-3-carboxylic acid N-(4-amino-7-butylcarbamoyl-5-hydroxy-2-isopropyl-octyl)-amide hydrochloride: $R_f$ (W)=0.32. HPLC $R_t$=13.8 min. MS(FAB) m/e 535 (M$^+$+1).

b) From 89 mg of (2R,4S,5S,7R)-1-(2-methoxyethyl)-1H-indole-3-carboxylic acid N-[4-(tert-butoxycarbonyl)amino-7-butylcarbamoyl-5-hydroxy-2-isopropyl-octyl]-amide, (2R,4S,5S,7R)-1-(2-methoxyethyl)-1H-indole-3-carboxylic acid N-(4-amino-7-butylcarbamoyl-5-hydroxy-2-isopropyl-octyl)-amide hydrochloride: $R_f$ (W)=0.29. HPLC $R_t$=11.7 min. MS(FAB) m/e 503 (M$^+$+1).

c) From 60 mg of (2R,4S,5S,7R)-1-pyridin-2-yl-1H-indole-3-carboxylic acid N-[4-(tert-butoxycarbonyl)amino-7-butylcarbamoyl-5-hydroxy-2-isopropyl-octyl]-amide, (2R,4S,5S,7R)-1-pyridin-2-yl-1H-indole-3-carboxylic acid N-(4-amino-7-butylcarbamoyl-5-hydroxy-2-isopropyl-octyl)-amide hydrochloride: $R_f$ (W)=0.24. HPLC $R_t$=9.94 min. MS(FAB) m/e 536 (M$^+$+4).

d) From 50 mg of (2R,4S,5S,7R)-1-(2-methoxybenzyl)-1H-indole-3-carboxylic acid N-[4-(tert-butoxycarbonyl)amino-7-butylcarbamoyl-5-hydroxy-2-isopropyl-octyl]-amide, (2R,4S,5S,7R)-1H-indole-3-carboxylic acid N-(4-amino-7-butylcarbamoyl-5-hydroxy-2-isopropyl-octyl)-amide hydrochloride: $R_f$ (W)=0.32. HPLC $R_t$=14.0 min. MS(FAB) m/e 565 (M$^+$+1).

EXAMPLE 12

In a manner analogous to that described in Example 5), (2R,4S,5S,7R)-N-(4-amino-7-butylcarbamoyl-5-hydroxy-2-isopropyl-octyl)-2-(3-methoxypropoxy)-benzamide hydrochloride, $R_f$(W)=0.28, HPLC $R_t$=11.9 min, MS(FAB) m/e 494 (M$^+$+1), is obtained from (2R,4S,5S,7R)-N-[4-(tert-butoxycarbonyl)amino-7-butylcarbamoyl-5-hydroxy-2-isopropyl-octyl]-2-(3-methoxypropoxy)-benzamide (93 mg).

The (2R,4S,5S,7R)-N-[4-(tert-butoxycarbonyl)amino-7-butyl carbamoyl-5-hydroxy-2-isopropyl-octyl]-2-(3-methoxypropoxy)-benzamide used as starting material is prepared as follows:

a) In accordance with the process described in Example 3), (2R,4S,5S,7R)-N-[4-(tert-butoxycarbonyl)amino-7-butylcarbamoyl-5-hydroxy-2-isopropyl-octyl]-2-(3- methoxypropoxy)-benzamide, $R_f$ (N)=0.28, is obtained in the form of a colourless oil from 135 mg of (2R,4'S,5'S,2"R)-N-{2-[5'-(2"-butylcarbamoylpropyl)-3'-(tert-butoxycarbonyl)-2',2'-dimethyl-1,3-oxazolidin-4'-ylmethyl]-3-methylbutyl}-2-(3-methoxypropoxy)-benzamide.

b) (2R,4'S,5'S,2"R)-N-{2-[5'-(2"-Butylcarbamoylpropyl)-3'-(tert-butoxycarbonyl)-2',2'-dimethyl-1,3-oxazolidin-4'-ylmethyl]-3-methylbutyl}-2-(3-methoxypropoxy)-benzamide: In accordance with the process described in Example 1), the title compound, $R_f$(M)=0.57, is obtained in the form of a pale-yellow oil from 100 mg of (2R,4'S,5'S,2"R)-3-[4'-(2"-aminomethyl-3"-methylbutyl)-3'-(tert-butoxycarbonyl)-2',2'-dimethyl-1,3-oxazolidin-5'-yl]-2-methylpropionic acid N-(butyl)amide and 95 mg of 2-(3-methoxypropoxy)-benzoic acid.

EXAMPLE 13

Hydrogenolysis of (2R,4'S,5'S,2"R)-3-[4'-(3"-azido-2"-methylpropyl)-3'-(tert-butoxycarbonyl)-2',2'-dimethyl-1,3-oxazolidin-5'-yl]-2-methylpropionic acid N-(butyl)amide (0.67 g) in a manner analogous to that described in Example 1a) yields (2R,4'S,5'S,2"R)-3-[4'-(3"-amino-2"-methylpropyl)-3'-(tert-butoxycarbonyl)-2',2'-dimethyl-1,3-oxazolidin-5'-yl]-2-methylpropionic acid N-(butyl)amide in the form of a pale-yellow oil: $R_1$ (W)=0.33.

The (2R,4'S,5'S,2"R)-3-[4'-(3"-azido-2"-methylpropyl)-3'-(tert-butoxycarbonyl)-2',2'-dimethyl-1,3-oxazolidin-5'-yl]-2-methylpropionic acid N-(butyl)amide used as starting material is prepared as follows:

a) (2R,4'S,5'S,2"R)-3-[4'-(3"-Azido-2"-methylpropyl)-3'-(tert-butoxycarbonyl)-2',2'-dimethyl-1,3-oxazolidin-5'-yl]-2-methylpropionic acid N-(butyl)amide: The title compound (0.86 g), $R_f$ (E)=0.71, is obtained in the form of a pale-yellow oil from (2R,4'S,5'S,2"R)-3-[3'-(tert-butoxycarbonyl)-4'-(3"-hydroxy-2"-methylpropyl)-2',2'-dimethyl-1,3-oxazolidin-5'-yl]-2-methylpropionic acid N-(butyl)amide (0.85 g) in a manner analogous to that described in Examples 1c) and 1b) and after purification by FC (100 g of silica gel, ethyl acetate-hexane 3:1).

b) (2R,4'S,5'S,2"R)-3-[3'-(tert-Butoxycarbonyl)-4'-(3"-hydroxy-2"-methylpropyl)-2',2'-dimethyl-1,3-oxazolidin-5'-yl]-2-methylpropionic acid N-(butyl)amide: In a manner analogous to that described in Examples 1d), 1e) and 1f), the stereoisomerically pure title compound: colourless oil (1.46 g; purification of the crude alcohol by FC on 50 g of silica gel, eluant gradient from D to hexane-ethyl acetate 1:3), $R_f$ (hexane-ethyl acetate 1:3)=0.29, is obtained by (1) stereoselective hydrogenation of (2S,3S,5R)-2-[6-(benzyloxymethyl)-3-(tert-butoxycarbonyl)amino-2-hydroxy-5-methylhexyl]-N-(butyl)acrylamide (A) (3.17 g) in absolute methanol in the presence of [Ru$_2$Cl$_4$[(S)-BINAD]$_2$]NEt$_3$ (0.057 g), followed by (2) N,O-acetalisation by reaction with 2',2'-dimethoxypropane in the presence of para-toluenesulfonic acid and chromatographic separation of the resulting approximately 9:1 diastereoisomeric mixture of (2R,4'S,5'S,2"R)-3-[4'-(3"-benzyloxy-2"-methylpropyl)-3'-(tert-butoxycarbonyl)-2',2'-dimethyl-1,3-oxazolidin-5'-yl]-2-methylpropionic acid N-(butyl)amide ($R_f$ (E)=0.64) and (2S,4'S,5'S,2"R)-3-[4'-(3"-benzyloxy-2"-methylpropyl)-3'-(tert-butoxycarbonyl)-2',2'-dimethyl-1,3-oxazolidin-5'-yl]-2-methylpropionic acid N-(butyl)amide ($R_f$(E)=0.54) by FC on 100 g of silica gel (eluant gradient from hexane-ethyl acetate 5:1 to ethyl acetate), and then (3) hydrogenolysis of the resulting (2R,4'S,5'S,2"R)-3-[4'-(3"-benzyloxy-2"-methylpropyl)-3'-(tert-butoxycarbonyl)-2',2'-dimethyl-1,3-oxazolidin-5'-yl]-2-methylpropionic acid N-(butyl)amide on 10% palladium-on-carbon.

c) (2S,3S,5R)-2-[6-Benzyloxy-3-(tert-butoxycarbonyl)amino-2-hydroxy-5-methylhexyl]-N-(butyl)acrylamide (A) and (2R,3S,5R)-2-[6-benzyloxy-3-(tert-butoxycarbonyl)amino-2-hydroxy-5-methylhexyl]-N-(butyl)acrylamide (B): In a manner analogous to that described in Example 1h), there is obtained first, by reduction of (2S,4R)-5-benzyloxy-2-(tert-butoxycarbonyl)amino-4-methylpentanoic acid methyl ester (9.51 g) in the presence of a 1.2M diisobutylaluminium hydride solution in toluene, (2S,4R)-5-benzyloxy-2-(tert-butoxycarbonyl)amino-4-methylpentanal (8.2 g of crude product) in the form of a pale-yellow oil. The crude aldehyde is reacted in a manner analogous to that described in Example 1g) without being purified further. The crude product (17.1 g) so obtained comprises an approximately 1:1.45 mixture of the two diastereoisomers A and B. Purification by column chromatography with separation of the two stereoisomers on silica gel (0.6 kg, eluant gradient from C to E) yields title compound A (2.05 g) in the form of a waxy solid, $R_f$ (E)=0.43, MS(FAB) m/e 463 (M$^+$+1), and title compound B (3.01 g) in the form of a light-yellow oil, $R_f$ (E)=0.35, MS(FAB) m/e 463 (M$^+$+1).

d) (2S,4R)-5-Benzyloxy-2-(tert-butoxycarbonyl)amino-4-methylpentanoic acid methyl ester: In a manner analogous to that described in Examples 1i and 1j), (2S,2'R,5R)-2-(3'-benzyloxy-2'-methylpropyl)-2,5-dihydro-5-isopropyl-3,6-dimethoxypyrazine (18.4 g) is first hydrolysed in the presence of 1N hydrochloric acid solution (215 ml) and then reacted with di-tert-butyl dicarbonate in the presence of H ünig base. Purification by FC (0.9 kg of silica gel, eluant A) yields the title compound (16.0 g) in the form of a colourless oil: $R_f$(C)=0.54.

e) (2S,2R,5R)-2-(3—Benzyloxy-2-methylpropyl)-2,5-dihydro-5-isopropyl-3,6dimethoxypyrazine: A solution of (2R)-2,5-dihydro-2-isopropyl-3,6-dimethoxypyrazine (14.7 ml) in absolute tetrahydrofuran (230 ml) is reacted in a manner analogous to that described in Example 1k) first with a 1.6M n-butyllithium solution in hexane (47.4 ml) and then with 2(S)-3-benzyloxy-2-methylpropyl bromide (20.0 g) in tetrahydrofuran (115 ml). After working up the reaction mixture, the oily crude product is purified by FC (0.9 kg of silica gel, ethyl acetate-hexane 5:95). There is obtained in addition to the (2R,2'R,5R)-diastereoisomer (1.1 g; yellowish oil, $R_f$ (ethyl acetate-hexane 1:6)=0.27), the stereoisomerically pure title compound (18.4 g) in the form of a yellowish oil: $R_f$ (ethyl acetate-hexane 1:6)=0.33.

EXAMPLE 14

In a manner analogous to that described in Example 5), (2R,4S,5S,7R)-N-(4-amino-7-butylcarbamoyl-5-hydroxy-2-methyl-octyl)-2-(3-methoxypropoxy)-benzamide hydrochloride, $R_f$(W)=0.25, HPLC $R_t$=9.0 min, MS(FAB) m/e 466 (M$^+$+1), is obtained from (2R,4S,5S,7R)-N-[4-(tert-butoxycarbonyl)amino-7-butylcarbamoyl-5-hydroxyl-2-methyloctyl]-2-(3-methoxypropoxy)-benzamide (82 mg).

The (2R,4S,5S,7R)-N-[4-(tert-butoxycarbonyl)amino-7-butylcarbamoyl-5-hydroxy-2-methyloctyl]-2-(3-methoxypropoxy)-benzamide used as starting material is prepared as follows:

a) In accordance with the process described in Example 3), (2R,4S,5S,7R)-N-[4-(tert-butoxycarbonyl)amino-7-butylcarbamoyl-5-hydroxy-2-methyloctyl]-2-(3-methoxypropoxy)-benzamide, $R_f$ (L)=0.36, is obtained in the form of a yellowish oil from 134 mg of (2R,4'S,5'S,2"R)-N-{3-[5'-(2"-butylcarbamoylpropyl)-3'-(tert-butoxycarbonyl)-2',2'-dimethyl-1,3-oxazolidin-4'-yl]-2-methylpropyl}-2-(3-methoxypropoxy)-benzamide.

b) (2R,4'S,5'S,2"R)-N-{3-[5'-(2"-Butylcarbamoylpropyl)-3'-(tert-butoxycarbonyl)-2',2'-dimethyl-1,3-oxazolidin-4'-yl]-2-methylbutyl}-2-(3-methoxypropoxy)-benzamide: In accordance with the process described in Example 1), the title compound, $R_f$ (L)=0.43, is obtained in the form of a pale-yellow oil from 100 mg of (2R,4'S,5'S,2"R)-3-[4'-(3"-amino-2"-methylpropyl)-3'-(tert-butoxycarbonyl)-2',2'-dimethyl-1,3-oxazolidin-5'-yl]-2-methylpropionic acid N-(butyl)amide and 102 mg of 2-(3-methoxypropoxy)-benzoic acid.

EXAMPLE 15

A mixture of 2-(3-methoxypropoxy)-benzoic acid (1.7 g), bis(2-oxo-3-oxazolidinyl)phosphinic acid chloride (1.90 g) and triethylamine (2.81 ml) in dichloromethane (40 ml) is stirred at room temperature for 60 minutes. Then a solution of (3S,5S,1S',3'S)-5-[3'-aminomethyl-1'-(tert-butoxycarbonyl)amino-4'-methylpentyl]-3-isopropyl-dihydrofuran-2-one (1.80 g) in 40 ml of dichloromethane and 4-dimethylaminopyridine (380 mg) are added. The reaction mixture is stirred overnight. After the addition of dichloromethane (200 ml), the organic phase is washed in succession with dilute sodium hydroxide solution (pH 9), dilute aqueous hydrochloric acid and saturated sodium chloride solution, dried over magnesium sulfate and concentrated. FC on silica gel (eluant R) yields (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-methoxypropoxy)-benzamide in the form of a pale-yellow oil (2.70 g): $R_f$ (E)=0.30. MS(FAB) m/e 563 ($M^+$+1).

The (3S,5S,1S',3'S)-5-[3'-aminomethyl-1'-(tert-butoxycarbonyl)amino-4'-methylpentyl]-3-isopropyl-dihydrofuran-2-one used as starting material is prepared as follows:

a) (3S,5S,1'S,3'S)-5-[3'-Azidomethyl-1'-(tert-butoxycarbonyl)amino-4'-methylpentyl]-3-isopropyl-dihydrofuran-2-one (12.4 g), dissolved in ethyl acetate (500 ml), is hydrogenated for 3 hours at room temperature and under normal pressure in the presence of 10% Pd/C (2.5 g). Filtration over Hyflo® and removal of the solvent yield the title compound in the form of a white solid (11.3 g): $R_f$ (W)=0.34. M.p. 136°–138° C. (recrystallised from dichloromethane-hexane).

b) (3S,5S,1'S,3'S)-5-[3'-Azidomethyl-1'-(tert-butoxycarbonyl)amino-4'-methylpentyl]-3-isopropyl-dihydrofuran-2-one: A mixture of (2S,2'S,2"S,4"S)-methanesulfonic acid N-(tert-butoxycarbonyl)-2-[2'-amino-2'-(4"-isopropyl-5"-oxo-tetrahydrofuran-2"-yl)-ethyl]-3-methylbutyl ester (30.2 g) and sodium azide (22.5 g) in 1,3-dimethyl-3,4,5,6-tetrahydro-2(1H)-pyrimidinone (290 ml) is stirred overnight at 50° C. After cooling the reaction mixture, dichloromethane (650 ml) is added and the organic phase is washed with water at pH 8 (140 ml) and with saturated sodium chloride solution, dried over magnesium sulfate and concentrated. FC of the crude product on silica gel (2 kg, eluant B) yields the title compound in the form of a white solid (23.6 g): $R_f$ (C)=0.36. M.p. 78°–81° C. MS(FAB) m/e 383 ($M^+$+1).

c) (2S,2'S,2"S,4"S)-Methanesulfonic acid N-(tert-butoxycarbonyl)-2-[2'-amino-2'-(4"-isopropyl-5"-oxo-tetrahydrofuran-2"-yl)-ethyl]-3-methylbutyl ester: To a solution of (3S,5S,1'S,3'S)-N-(tert-butoxycarbonyl)-5-(1'-amino-3'-hydroxymethyl-4'-methylpentyl)-3-isopropyl-dihydrofuran-2-one (24.8 g) in dichloromethane (750 ml) there are added with stirring at −10° C. first triethylamine (14.5 ml) and then, over a period of 10 minutes, methanesulfonyl chloride (5.64 ml). After stirring for a further 30 minutes at −10° C., the reaction mixture is poured carefully onto ethyl acetate (1 liter). The organic phase is washed in succession with 0.5M aqueous $H_3PO_4$ solution, saturated sodium hydrogen carbonate solution and saturated sodium chloride solution, dried over magnesium sulfate and concentrated. The title compound is obtained in the form of a crude product (31.1 g, colourless oil), which slowly crystallises out when left to stand. $R_f$ (E)=0.63.

d) (3S,5S,1'S,3'S)-N-(tert-Butoxycarbonyl)-5-(1'-amino-3'-hydroxymethyl-4'-methylpentyl)-3-isopropyl-dihydrofuran-2-one: A solution of (3S,5S,1'S,3'S)-5-(1'-azido-3'-hydroxymethyl-4'-methylpentyl)-3-isopropyl-dihydrofuran-2-one (24.8 g) in ethyl acetate (250 ml) is hydrogenated for 24 hours at room temperature and under normal pressure in the presence of 10% Pd/C (8.68 g). Filtration is carried out over Hyflo®, followed by repeated washing with ethyl acetate and concentration. The resulting crude (3S,5S,1'S,3'S)-5-(1'-amino-3'-hydroxymethyl-4'-methylpentyl)-3-isopropyl-dihydrofuran-2-one (23.0 g; colourless oil, $R_f$ (W)=0.67) is dissolved in ethyl acetate (500 ml) and there are added thereto at 0°–5°, with stirring, first N-ethyldiisopropylamine (23.7 ml) and then, dropwise, a solution of di-tert-butyl dicarbonate (21.0 g) in ethyl acetate (100 ml). After warming to room temperature, stirring is continued overnight. The reaction mixture is concentrated and the oily residue is purified by FC (250 g of silica gel, eluant D). The title compound (24.9 g) is obtained in the form of a white solid: $R_f$(dichloromethane-methanol 1:1)= 0.64. M.p. 126°–128° C. (diethyl ether). MS(FAB) m/e 358 ($M^+$+1).

e) (3S,5S,1'S,3'S)-5-(1'-Azido-3'-hydroxymethyl-4'-methylpentyl)-3-isopropyl-dihydrofuran-2-one: Triethylamine (5.62 ml) and chloroformic acid methyl ester (2.59 ml) are added dropwise in succession, at −10° C., to a solution of (2S,2'S,2"S,4"S-[2'-azido-2'-(4"-isopropyl-5"-oxo-tetrahydrofuran-2"-yl)-ethyl]-3-methyl-butyric acid (8.0 g) in anhydrous tetrahydrofuran (180 ml). The white suspension is then stirred first at −10° C. for one hour and then at 0° for 2 hours. The mixture is diluted with ethyl acetate (100 ml) and the organic phase is washed in succession with ice-cold 0.5N hydrochloric acid, saturated sodium hydrogen carbonate solution and water, dried over sodium sulfate and concentrated. The pale-yellow oily residue is taken up in tetrahydrofuran (160 ml), and sodium borohydride (1.12 g) is added in portions at −20°, with stirring. Then methanol (1.5 ml) is added dropwise over a period of 10 minutes (slightly exothermic reaction). The slightly cloudy mixture is allowed to warm slowly to 0°–5° and is stirred overnight at that temperature, and then 1N hydrochloric acid (39 ml) is added dropwise and the aqueous phase is extracted with ethyl acetate (100 ml). The organic phase is washed until neutral with ice-cold 1N sodium carbonate solution (70 ml) and then with saturated sodium chloride solution, dried over magnesium sulfate and concentrated. Drying under a high vacuum yields the title compound in the form of a pale-yellow oil (7.18 g). Analytically pure product (pale-yellow oil) is obtained after flash chromatography on silica gel (eluant gradient hexane-ethyl acetate from 5:1 to 3:1): $R_f$(hexane-ethyl acetate 1:1)=0.50.

EXAMPLE 16

A mixture of 2-(4-methoxybutoxy)-benzoic acid (1.7 g), bis(2-oxo-3-oxazolidinyl)phosphinic acid chloride (1.90 g) and triethylamine (2.81 ml) in dichloromethane (40 ml) is stirred at room temperature for 60 minutes. Then a solution of (3S,5S,1S',3'S)-5-[3'-aminomethyl-1'-(tert-butoxycarbonyl)amino-4'-methylpentyl]-3-isopropyl-dihydrofuran-2-one (1.80 g) in dichloromethane (40 ml) and 4-dimethylaminopyridine (380 mg) are added, and the reaction mixture is stirred overnight. After the addition of dichloromethane (200 ml), the organic phase is washed in succession with dilute sodium hydroxide solution (pH 9), dilute aqueous hydrochloric acid and saturated sodium chloride solution, dried over magnesium sulfate and concentrated. FC on silica gel (eluant R) yields (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-benzamide in the form of a pale-yellow oil (2.70 g). $R_f$(E)=0.30. MS(FAB) m/e 563 (M$^+$+1).

The 2-(4-methoxybutoxy)-benzoic acid used as starting material is prepared as follows:

a) In a manner analogous to that described in Example 1), 2-(4-methoxybutoxy)-benzoic acid ethyl ester (4.35 g) is hydrolysed with 1N sodium hydroxide solution (17.3 ml) in a 2:1 mixture of ethanol and water (30 ml). When the reaction is complete, dichloromethane (30 ml) is added and the aqueous phase is acidified by the addition of a 1M potassium hydrogen sulfate solution and extracted with dichloromethane (3×40 ml). The organic phase is washed with saturated sodium chloride solution, dried over magnesium sulfate and concentrated. The title compound, $R_f$(E)=0.39, is obtained in the form of a colourless oil, which crystallises out when left to stand.

b) 2-(4-Methoxybutoxy)-benzoic acid ethyl ester: A solution of 4-methoxybutyl bromide (4.5 g) in acetonitrile (15 ml) is added dropwise under reflux to a mixture of salicylic acid ethyl ester (2.63 ml), powdered potassium carbonate (3.10 g) and potassium iodide (10 mg) in acetonitrile (50 ml), and the reaction mixture is then stirred overnight. After cooling, filtration is carried out, the filtrate is concentrated and the residue is added under a high vacuum. The title compound (4.4 g), $R_f$(C)=0.28, is obtained in the form of a pale-yellow oil.

EXAMPLE 17

In a manner analogous to that described in Example 15) and with subsequent purification by FC on silica gel (eluant C or D), unless otherwise described in greater detail below, the following compounds are prepared:

a) From 80 mg of (3S,5S,1'S,3'S)-5-[3'-aminomethyl-1'-(tert-butoxycarbonyl)amino-4'-methylpentyl]-3-isopropyl-dihydrofuran-2-one and 81 mg of 2-propoxybenzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-propoxy-benzamide, $R_f$ (E)=0.39, in the form of a yellowish oil.

b) From 100 mg of (3S,5S,1'S,3'S)-5-[3'-aminomethyl-1'-(tert-butoxycarbonyl)amino-4'-methylpentyl]-3-isopropyl-dihydrofuran-2-one and 110 mg of 2-(2-methoxyethoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(2-methoxyethoxy)-benzamide, $R_f$ (E)=0.28, in the form of a colourless oil.

c) From 100 mg of (3S,5S,1'S,3'S)-5-[3'-aminomethyl-1'-(tert-butoxycarbonyl)amino-4'-methylpentyl]-3-isopropyl-dihydrofuran-2-one and 102 mg of 2-(methoxymethoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(methoxymethoxy)-benzamide, $R_f$ (E)=0.40, in the form of a yellowish solid.

d) From 100 mg of (3S,5S,1'S,3'S)-5-[3'-aminomethyl-1'-(tert-butoxycarbonyl)amino-4'-methylpentyl]-3-isopropyl-dihydrofuran-2-one and 135 mg of 2-[2-(2-methoxyethoxy)-ethoxy]-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(2-methoxyethoxy)-ethoxy]-benzamide, $R_f$ (E)=0.20, in the form of a yellowish oil.

e) From 100 mg of (3S,5S,1'S,3'S)-5-[3'-aminomethyl-1'-(tert-butoxycarbonyl)amino-4'-methylpentyl]-3-isopropyl-dihydrofuran-2-one and 135 mg of 4-methoxy-2-(3-methoxypropoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-methoxy-2-(3-methoxypropoxy)-benzamide, $R_f$(L)=0.80, in the form of a yellowish oil.

f) From 100 mg of (3S,5S,1'S,3'S)-5-[3'-aminomethyl-1'-(tert-butoxycarbonyl)amino-4'-methylpentyl]-3-isopropyl-dihydrofuran-2-one and 135 mg of 4-methoxy-3-(3-methoxypropoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-methoxy-3-(3-methoxypropoxy)-benzamide, $R_f$(L)=0.71, in the form of a pale-yellow oil.

g) From 100 mg of (3S,5S,1'S,3'S)-5-[3'-aminomethyl-1'-(tert-butoxycarbonyl)amino-4'-methylpentyl]-3-isopropyl-dihydrofuran-2-one and 109 mg of 2-(propoxymethyl)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(propoxymethyl)-benzamide, $R_f$ (E)=0.46, in the form of a yellowish oil.

h) From 80 mg of (3S,5S,1S',3'S)-5-[3'-aminomethyl-1'-(tert-butoxycarbonyl)amino-4'-methylpentyl]-3-isopropyl-dihydrofuran-2-one and 101 mg of 2-[2-(methoxymethoxy)-ethoxy]-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(methoxymethoxy)-ethoxy]-benzamide, $R_f$ (E)=0.38, in the form of a pale-yellow oil.

i) From 50 mg of (3S,5S,1S',3'S)-5-[3'-aminomethyl-1'-(tert-butoxycarbonyl)amino-4'-methylpentyl]-3-isopropyl-dihydrofuran-2-one and 75 mg of 2-acetamido-benzoic acid (reaction at room temperature for 48 hours and then at 50° C. for 12 hours), with subsequent purification of the crude product by FC on 20 g of silica gel (eluant D), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-acetamido-benzamide, $R_f$ (E)=0.25, in the form of a yellowish oil.

j) From 120 mg of (3S,5S,1S',3'S)-5-[3'-aminomethyl-1'-(tert-butoxycarbonyl)amino-4'-methylpentyl]-3-isopropyl-dihydrofuran-2-one and 143 mg of 2-(3-methoxypropoxy)-nicotinic acid, with subsequent purification of the crude product by FC on 30 g of silica gel (eluant S), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-methoxypropoxy)-nicotinamide, $R_f$(W)=0.77, in the form of a yellow oil.

k) From 120 mg of (3S,5S,1S',3'S)-5-[3'-aminomethyl-1'-(tert-butoxycarbonyl)amino-4'-methylpentyl]-3-isopropyl-dihydrofuran-2-one and 151 mg of 3-(4-methoxybutoxy)-pyridine-2-carboxylic acid, with subsequent purification of the crude product by FC on 30 g of silica gel (eluant T), (2S,2'S,2'S,4"S)-N-{2-[2'-(tert-butoxycarbonyl)amino-2'-(4"-isopropyl-5"-oxo-tetrahydrofuran-2"-yl)-ethyl]-3- methylbutyl}-3-(4-methoxybutoxy)-pyridine-2-carboxylic acid amide, $R_f$ (W)=0.70, in the form of a yellow oil.

l) From 50 mg of (3S,5S,1'S,3'S)-5-[3'-aminomethyl-1'-(tert-butoxycarbonyl)amino-4'-pentyl]-3-isopropyl-dihydrofuran-2-one and 63 mg of 2-[2-(acetamido)-ethoxy]-benzoic acid, with subsequent purification of the crude product on 10 g of silica gel (eluant T), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(acetamido)-ethoxy]-benzamide, $R_f$ (W)=0.65, in the form of an oil.

m) From 100 mg of (3S,5S,1'S,3'S)-5-[3'-aminomethyl-1'-(tert-butoxycarbonyl)amino-4'-methylpentyl]-3-isopropyl-dihydrofuran-2-one and 125 mg of 2-(4-methoxybutyl-2-enoxy)-benzoic acid, with subsequent purification of the crude product on 10 g of silica gel (eluant S), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutyl-2-enoxy)-benzamide, $R_f$ (W)=0.79, in the form of an oil.

n) From 100 mg of (3S,5S,1'S,3'S)-5-[3'-aminomethyl-1'-(tert-butoxycarbonyl)amino-4'-methylpentyl]-3-isopropyl-dihydrofuran-2-one and 137 mg of 2-(4-methoxybutoxy)-4-methyl-benzoic acid, with subsequent purification of the crude product on 25 g of silica gel (eluant S), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-methyl-benzamide, $R_f$ (W)=0.81, in the form of a pale-yellow oil.

o) From 100 mg of (3S,5S,1'S,3'S)-5-[3'-aminomethyl-1'-(tert-butoxycarbonyl)amino-4'-methylpentyl]-3-isopropyl-dihydrofuran-2-one and 134 mg of 2-(5-methoxypentoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(5-methoxypentoxy)-benzamide, $R_f$ (L)=0.79, in the form of a pale-yellow oil.

Unless otherwise described in greater detail below, the benzoic acid derivatives used as starting materials are prepared from corresponding precursors in a manner analogous to that described in Examples 1), 2), 16) and 50) or are obtained in accordance with standard general procedures.

A) 2-[2-(2-(Methoxyethoxy)-ethoxy]-benzoic acid ethyl ester: 2-[2-Methoxyethoxy]-ethyl bromide (2.25 g) and a catalytic amount of potassium iodide (20 mg) are added at 85° C. to a suspension of salicylic acid ethyl ester (1.86 g) and potassium carbonate powder (1.85 g) in anhydrous N,N-dimethylformamide (50 ml). The mixture is stirred overnight at 85° C. and, after cooling, is filtered and concentrated. Purification by FC (100 g of silica gel, eluant C) yields a pale-yellow oil (2.89 g): $R_f$ (D)=0.29.

B) 2-Propoxymethyl-benzoic acid: The title compound is obtained in the form of a pale-yellow solid, $R_f$ (hexane-ethyl acetate-glacial acetic acid 50:50:1)=0.63; MS(EI) m/e 194 (M⁺), from 2-propoxymethyl-benzoic acid propyl ester, by alkaline hydrolysis.

The 2-propoxymethyl-benzoic acid propyl ester used as starting material is prepared as follows:

a) Sodium hydride in the form of an 80% dispersion in oil (0.38 g) is added at room temperature, with stirring, to a solution of potassium 2-(hydroxymethyl)-benzoate (3.0 g), prepared in accordance with the procedure described in J. Am. Chem. Soc. (1989), 111, 1465–1473, in anhydrous N,N-dimethylformamide (20 ml). After stirring for 30 minutes, propyliodide (8.05 g) is added dropwise, the mixture is heated to 80° C., and stirring is continued for 20 hours. After cooling to room temperature, the reaction mixture is poured onto ice-water (50 ml) and the aqueous phase is extracted with diethyl ether (3×40 ml). The organic phase is dried over magnesium sulfate and concentrated. Purification by FC (80 g of silica gel, eluant B) yields 2-propoxymethyl-benzoic acid propyl ester (0.69 g), $R_f$ (D)=0.30, in the form of a yellow oil.

C) 2-[2-(Methoxymethoxy)-ethoxy]-benzoic acid ethyl ester: 2-(2-Methoxymethoxy)-ethyl chloride (5.62 g), dissolved in acetone (30 ml), and potassium iodide (4.5 g) are added to a mixture of salicylic acid ethyl ester (4.43 ml) and potassium carbonate powder (4.99 g) in anhydrous acetone (50 ml) and anhydrous dimethyl sulfoxide (100 ml). The mixture is stirred at 70° C. for two days. After cooling, the suspension is filtered, the filtrate is concentrated, and the residue is purified by FC (400 g of silica gel, hexane-ethyl acetate 5:1). The title compound is obtained in the form of a yellowish oil (3.8 g), $R_f$ (C)=0.35, which contains small amounts of an unidentified secondary product.

D) 2-(4-Methoxybut-2-enoxy)-benzoic acid methyl ester: A 30% methanolic sodium methoxide solution (8.83 ml) is added dropwise at 60° C. over a period of 30 minutes to 2-(4-bromo-but-2-enoxy)-benzoic acid methyl ester (12.1 g) in absolute methanol (70 ml), and the mixture is stirred for 5 hours. Customary working-up and purification by FC (hexane-ethyl acetate 8:1) yield the title compound in the form of a pale-yellow oil (6.77 g): $R_f$ (C)=0.36.

The 2-(4-bromo-but-2-enoxy)-benzoic acid methyl ester used as starting material is prepared as follows: 1,4-Dibromobutene (28.1 g) is added to a mixture of salicylic acid methyl ester (20.0 g) and anhydrous potassium carbonate (27.3 g) in acetonitrile (350 ml). The mixture is stirred under reflux for 4 hours and is filtered, and the filtrate is concentrated. FC (400 g of silica gel, eluant C) yields the title compound, $R_f$ (C)=0.34, in the form of an oil.

E) 2-(4-Methoxybutoxy)-4-methyl-benzoic acid: Alkaline hydrolysis of 2-(4-methoxybutoxy)-4-methyl-benzoic acid methyl ester yields the title compound, $R_f$ (hexane-ethyl acetate-glacial acetic acid 50:50:1)=0.38, in the form of a pale-yellow oil.

The 2-(4-metholxybutoxy)-4-methyl-benzoic acid methyl ester used as starting material is prepared as follows: In a manner analogous to that described in Example 50f, the title compound, $R_f$ (C)=0.31, is obtained in the form of an oil from 2-(4-bromobutoxy)-4-methyl-benzoic acid methyl ester ($R_f$ (C)=0.47).

The 2-(3-methoxypropoxy)-nicotinic acid used above as starting material is prepared as follows:

a) Alkaline hydrolysis in a manner analogous to that described in Example 1) yields the title compound, $R_f$ (hexane-ethyl acetate-glacial acetic acid 50:25:3)=0.30, in the form of a yellow oil from 2-(3-methoxypropoxy)-nicotinic acid ethyl ester.

b) 2-(3-Methoxypropoxy)-nicotinic acid ethyl ester: 2-Hydroxy-nicotinic acid ethyl ester (1.67 g), 3-methoxypropyl bromide (2.3 g) and silver carbonate (1.38 g) in toluene (80 ml) are reacted in accordance with the procedure described by Labaudinière et al. (J. Med. Chem. 1992, 35, 4315–4324). Purification of the crude product by FC (dichloromethane-methanol-conc. ammonia 95:5:1) yields 1-(3-methoxypropoxy)-3-carbomethoxy-2(1H)-pyridinone (1.1 7 g), $R_f$ (dichloromethane-methanol-conc. ammonia 95:5:1)=0.59, in the form of a pale-yellow oil, as well as the title compound (0.93 g), $R_f$ (dichloromethane-methanol-conc. ammonia 95:5:1)=0.79, in the form of a yellowish oil.

The 3-(4-methoxybutoxy)-picolinic acid used above as starting material is prepared as follows:

a) Alkaline hydrolysis as described in Example 1) yields the title compound in the form of a solid from 3-(4-methoxybutoxy)-picolinic acid ethyl ester.

b) 3-(4-Methoxybutoxy)-picolinic acid ethyl ester: Analogously to the procedure of Labaudinière et al. (*J. Med. Chem.* 1992, 35, 4315–4324), the title compound (0.98 g), $R_f$ (hexane-ethyl acetate-glacial acetic acid 1:1:0.01)=0.21, is obtained in the form of a yellow oil from 3-hydroxy-picolinic acid ethyl ester (2.0 g) and 4-methoxybutyl bromide (2.99 g), with subsequent purification by FC (dichloromethane-methanol-conc. ammonia 95:5:1).

EXAMPLE 18

A solution of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-methoxypropoxy)-benzamide (60 mg) in n-butylamine (2 ml) is stirred at 50° C. for 40 hours. The mixture is concentrated and the oily residue is purified by FC (10 g of silica gel, eluant gradient from E to hexane-ethyl acetate 1:3). (2S,4S,5S,7S)-N-[4-(tert-Butoxycarbonyl)amino-7-butyl carbamoyl-5-hydroxy-2-isopropyl-8-methyl-nonyl]-2-(3-methoxypropoxy)-benzamide, $R_f$ (E) 0.07; HPLC $R_f$=18.4 min; MS(FAB) m/e 622 (M$^+$+1), is obtained in the form of a yellowish oil.

EXAMPLE 19

In a manner analogous to that described in Example 18), reaction of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-benzamide (71 mg) in n-butylamine (2 ml) at 50° C. for 48 hours and subsequent purification of the crude product by FC on 10 g of silica gel (eluant gradient from E to hexane-ethyl acetate 1:4) yield (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-benzamide, $R_f$ (E)=0.14, in the form of a foamy solid.

EXAMPLE 20

In a manner analogous to that described in Example 18), the following compounds are obtained by lactone opening with n-butylamine:

a) From 116 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-propoxy-benzamide, (2S,4S,5S,7S)-N-[4-(tert-butoxycarbonyl)amino-7-butylcarbamoyl-5-hydroxy-2-isopropyl-8-methyl-nonyl]-2-propoxy-benzamide, $R_f$(E)=0.19, in the form of an oil.

b) From 75 mg of (2S,2'S,2"S,4"S)-N-{2-[2'-(tert-butoxycarbonyl)amino-2'-(4"-isopropyl-5"-oxo-tetrahydrofuran-2"yl)-ethyl]-3-methylbutyl}-2-(2-methoxyethoxy)-benzamide, (2S,4S,5S,7S)-N-[4-(tert-butoxycarbonyl)amino-7-butylcarbamoyl-5-hydroxy-2-isopropyl-8-methyl-nonyl]-2-(2-methoxyethoxy)-benzamide, $R_f$ (E)=0.06, in the form of a foamy solid.

c) From 88 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(methoxymethoxy)-benzamide, (2S,4S,5S,7S)-N-[4-(tert-butoxycarbonyl)amino-7-butylcarbamoyl-5-hydroxy-2-isopropyl-8-methyl-nonyl]-2-(2-methoxymethoxy)-benzamide, $R_f$ (E)=0.09, in the form of a foamy solid.

d) From 50 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(2-methoxyethoxy)-ethoxy]-benzamide, (2S,4S,5S,7S)-N-[4-(tert-butoxycarbonyl)amino-7-butylcarbamoyl-5-hydroxy-2-isopropyl-8-methyl-nonyl]-2-[2-(2-methoxyethoxy)-ethoxy]-benzamide, $R_f$ (F)=0.11, in the form of an oil.

e) From 107 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-methoxyl2-(3-methoxypropoxy)-benzamide, with purification by FC on 25 g of silica gel (eluant gradient from R to P), (2S,4S,5S,7S)-N-[4-(tert-butoxycarbonyl)amino-7-butylcarbamoyl-5-hydroxy-2-isopropyl-8-methyl-nonyl]-4-methoxy-2-(3-methoxypropoxy)-benzamide, $R_f$ (L)=0.63, in the form of a yellow oil.

f) From 96 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-methoxy-3-(3-methoxypropoxy)-benzamide, with purification by FC as described in Example 20e), (2S,4S,5S,7S)-N-[4-(tert-butoxycarbonyl)amino-7-butylcarbamoyl-5-hydroxy-2-isopropyl-8-methyl-nonyl]-4-methoxy-3-(3-methoxypropoxy)-benzamide, $R_f$ (L)=0.53, in the form of a foamy solid.

g) From 70 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-propoxymethyl-benzamide, with purification by FC (25 g of silica gel, eluant R), (2S,4S,5S,7S)-N-[4-(tert-butoxycarbonyl)amino-7-butylcarbamoyl-5-hydroxy-2-isopropyl-8-methyl-nonyl]-2-propoxymethyl-benzamide, $R_f$ (L)=0.56, in the form of a foamy solid.

h) From 60 mg of (2S,2'S,2"S,4"S)-N-{2-[2'-(tert-butoxycarbonyl)amino-2'-(4"-isopropyl-5"-oxo-tetrahydrofuran-2'-yl)-ethyl]-3-methylbutyl}-2-[2-(methoxymethoxy)-ethoxy]-benzamide, (2S,4S,5S,7S)-N-[4-(tert-butoxycarbonyl)amino-7-butylcarbamoyl-5-hydroxy-2-isopropyl-8-methyl-nonyl]-2-[2-(methoxymethoxy)-ethoxy]-benzamide, $R_f$ (L)=0.56, in the form of a yellowish oil.

i) From 50 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-acetamido-benzamide, (2S,4S,5S,7S)-N-[4-(tert-butoxycarbonyl)amino-7-butylcarbamoyl-5-hydroxy-2-isopropyl-8-methyl-nonyl]-2-acetamido-benzamide, $R_f$ (L)=0.64, in the form of an oil.

j) From 60 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-methoxypropoxy)-nicotinamide, with purification of the crude product by FC on 25 g of silica gel (eluant gradient from O to P), (2S,4S,5S,7S)-N-[4-(tert-butoxycarbonyl)amino-7-butylcarbamoyl-5-hydroxy-2-isopropyl-8-methyl-nonyl]-2-(3-methoxypropoxy)-nicotinamide, $R_f$(L)=0.56, in the form of a colourless oil.

k) From 65 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-3-(4-methoxybutoxy)-pyridine-2-carboxylic acid amide, with purification of the crude product by FC on 25 g of silica gel (eluant V), (2S,4S,5S,7S)-N-[4-(tert-butoxycarbonyl) amino-7-butylcarbamoyl-5-hydroxy-2-isopropyl-8-methyl-nonyl]-3-(4-methoxybutoxy)-pyridine-2-carboxylic acid amide, $R_f$ (W)=0.56, in the form of a yellow oil.

l) From 75 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(acetamide)-ethoxy]-benzamide, with purification of the crude product by FC on 25 g of silica gel (eluant gradient from T to V), (2S,4S,5S,7S)-N-[4-(tert-butoxycarbonyl)amino-7-butylcarbamoyl-5-hydroxy-2-isopropyl-8-methyl-nonyl]-2-[2-(acetamido)-ethoxy]-benzamide, $R_f$ (W)=0.41, in the form of an oil.

m) From 75 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybut-2-enoxy)-benzamide, with purification of the crude product by FC on 25 g of silica gel (eluant gradient from S to V), (2S,4S,5S,7S)-N-[4-(tert-butoxycarbonyl)amino-7-butylcarbamoyl-5-hydroxy-2-isopropyl-8-methyl-nonyl]-2-(4-methoxybut-2-enoxy)-benzamide, $R_f$ (W)= 0.57, in the form of a solid.

n) From 75 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-methyl-benzamide, (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-methyl-benzamide, $R_f$ (W)=0.63, in the form of a solid.

EXAMPLE 21

A 4N hydrochloric acid solution in dioxane (2 ml) is added at 0° C. to (2S,4S,5S,7S)-N-[4-(tert-butoxycarbonyl)amino-7-butylcarbamoyl-5-hydroxy-2-isopropyl-8-methyl-nonyl]-2-(3-methoxypropoxy)-benzamide (50 mg). The reaction mixture is stirred at 0° C. for 2 hours (TLC monitoring) and then the solvent is immediately concentrated under a high vacuum with vigorous stirring until frozen and is subsequently removed by lyophilisation. After drying under a high vacuum, (2S,4S,5S,7S)-N-(4-amino-7-butylcarbamoyl-5-hydroxy-2-isopropyl-8-methyl-nonyl)-2-(3-methoxypropoxy)-benzamide hydrochloride is obtained in the form of a foamy solid: $R_f$ (W)=0.31. HPLC $R_t$=12.8 min. MS(FAB) m/e 522 (M$^+$+1).

EXAMPLE 22

In a manner analogous to that described in Example 21), reaction of (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-benzamide (61 mg) yields (2S,4S,5S,7S)-N-(4-amino-7-butylcarbamoyl-5-hydroxy-2-isopropyl-8-methyl-nonyl)-2-(4-methoxybutoxy)-benzamide hydrochloride: $R_f$(W)=0.29. HPLC $R_t$=13.3 min. MS(FAB) m/e 536 (M$^+$+1).

EXAMPLE 23

In a manner analogous to that described in Example 21), the following compounds are prepared by de-Bocylation:

a) From 100 mg of (2S,4S,5S,7S)-N-[4-(tert-butoxycarbonyl)amino-7-butylcarbamoyl-5-hydroxy-2-isopropyl-8-methyl-nonyl]-2-propoxy-benzamide, (2S,4S,5S,7S)-N-(4-amino-7-butylcarbamoyl-5-hydroxy-2-isopropyl-8-methyl-nonyl)-2-propoxy-benzamide hydrochloride: $R_f$ (W)=0.37. HPLC $R_t$=13.95 min. MS(FAB) m/e 492 (M$^+$+1).

b) From 60 mg of (2S,4S,5S,7S)-N-[4-(tert-butoxycarbonyl)amino-7-butylcarbamoyl-5-hydroxy-2-isopropyl-8-methyl-nonyl]-2-(2-methoxyethoxy)-benzamide, (2S,4S,5S,7S)-N-(4-amino-7-butylcarbamoyl-5-hydroxy-2-isopropyl-8-methyl-nonyl)-2-(2-methoxyethoxy)-benzamide hydrochloride: $R_f$ (W)=0.38. HPLC $R_t$=12.6 min. MS(FAB) m/e 508 (M$^+$+1).

c) From 38 mg of (2S,4S,5S,7S)-N-[4-(tert-butoxycarbonyl)amino-7-butylcarbamoyl-5-hydroxy-2-isopropyl-8-methyl-nonyl]-2-[2-(2-methoxyethoxy)-ethoxy]-benzamide, (2S,4S,5S,7S)-N-(4-amino-7-butylcarbamoyl-5-hydroxy-2-isopropyl-8-methyl-nonyl)-2-[2-(2-methoxyethoxy)-ethoxy]-benzamide hydrochloride: $R_f$(W)=0.19. HPLC $R_t$=12.4 min. MS(FAB) m/e 552 (M$^+$+1).

d) From 93 mg of (2S,4S,5S,7S)-N-[4-(tert-butoxycarbonyl)amino-7-butylcarbamoyl-5-hydroxy-2-isopropyl-8-methyl-nonyl]-4-methoxy-2-(3-methoxypropoxy)-benzamide, (2S,4S,5S,7S)-N-(4-amino-7-butylcarbamoyl-5-hydroxy-2-isopropyl-8-methyl-nonyl)-4-methoxy-2-(3-methoxypropoxy)-benzamide hydrochloride: $R_f$(W)=0.25. HPLC $R_t$=13.4 min. MS(FAB) m/e 552 (M$^+$+1).

e) From 76 mg of (2S,4S,5S,7S)-N-[4-(tert-butoxycarbonyl)amino-7-butylcarbamoyl-5-hydroxy-2-isopropyl-8-methyl-nonyl]-4-methoxy-3-(3-methoxypropoxy)-benzamide, (2S,4S,5S,7S)-N-(4-amino-7-butylcarbamoyl-5-hydroxy-2-isopropyl-8-methyl-nonyl)-4-methoxy-3-(3-methoxypropoxy)-benzamide hydrochloride: $R_f$(W)=0.28. HPLC $R_t$=12.1 min. MS(FAB) m/e 552 (M$^+$+1).

f) From 58 mg of (2S,4S,5S,7S)-N-[4-(tert-butoxycarbonyl)amino-7-butylcarbamoyl-5-hydroxy-2-isopropyl-8-methyl-nonyl]-2-propoxymethyl-benzamide, (2S,4S,5S,7S)-N-(4-amino-7-butylcarbamoyl-5-hydroxy-2-isopropyl-8-methyl-nonyl)-2-(propoxymethyl)-benzamide hydrochloride: $R_f$(W)=0.25. HPLC $R_t$=13.4 min. MS(FAB) m/e 506 (M$^+$+1).

g) From 40 mg of (2S,4S,5S,7S)-N-[4-(tert-butoxycarbonyl)amino-7-butylcarbamoyl-5-hydroxy-2-isopropyl-8-methyl-nonyl]-2-acetamido-benzamide, with purification of the crude product by FC on 10 g of silica gel (eluant M), (2S,4S,5S,7S)-N-(4-amino-7-butylcarbamoyl-5-hydroxy-2-isopropyl-8-methyl-nonyl)-2-acetamido-benzamide hydrochloride: $R_f$(W)=0.45. HPLC $R_t$=10.0 min. MS(FAB) m/e 473 [(M$^+$+1)-H$_2$O].

h) From 62 mg of (2S,4S,5S,7S)-N-[4-(tert-butoxycarbonyl)amino-7-butylcarbamoyl-5-hydroxy-2-isopropyl-8-methyl-nonyl]-2-[2-(acetamido)-ethoxy]-benzamide, (2S,4S,5S,7S)-N-(4-amino-7-butylcarbamoyl-5-hydroxy-2-isopropyl-8-methyl-nonyl)-2-[2-(acetamido)-ethoxy]-benzamide hydrochloride: $R_f$ (W)=0.25. HPLC $R_t$=10.4 min. MS(FAB) m/e 535 (M$^+$+1).

i) From 54 mg of (2S,4S,5S,7S)-N-[4-(tert-butoxycarbonyl)amino-7-butylcarbamoyl-5-hydroxy-2-isopropyl-8-methyl-nonyl]-2-(4-methoxybut-2-enoxy)-benzamide, (2S,4S,5S,7S)-N-(4-amino-7-butylcarbamoyl-5-hydroxy-2-isopropyl-8-methyl-nonyl)-2-(4-methoxybut-2-enoxy)-benzamide hydrochloride: $R_f$ (W)=0.38. HPLC $R_t$=12.6 min. MS(FAB) m/e 534 (M$^+$+1).

j) From 59 mg of (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-methyl-benzamide, (2S,4S,5S,7S)-N-(4-amino-7-butylcarbamoyl-5-hydroxy-2-isopropyl-8-methyl-nonyl)-2-(4-methoxybutoxy)-4-methyl-benzamide hydrochloride: $R_f$ (W)=0.33. HPLC $R_t$=14.2 min. MS(FAB) m/e 550 (M$^+$+1).

k) From 54 mg of (2S,4S,5S,7S)-N-[4-(tert-butoxycarbonyl)amino-7-butylcarbamoyl-5-hydroxy-2-isopropyl-8-methyl-nonyl]-2-(3-methoxypropoxy)- nicotinamide, with subsequent purification of the crude product by FC (eluant gradient from V to U), (2S,4S,5S,7S)-N-[4-amino-7-butylcarbamoyl-5-hydroxy-2-isopropyl-8-methyl-nonyl]-2-(3-methoxypropoxy)-nicotinamide hydrochloride: $R_f$ (W)=0.50. HPLC $R_t$=12.4 min. MS(FAB) m/e 523 (M$^+$+1).

l) From 45 mg of (2S,4S,5S,7S)-N-[4-(tert-butoxycarbonyl)amino-7-butylcarbamoyl-5-hydroxy-2-isopropyl-8-methyl-nonyl]-3-(4-methoxybutoxy)-pyridine-2-carboxylic acid amide, (2S,4S,5S,7S)-N-[4-amino-7-butylcarbamoyl-5-hydroxy-2-isopropyl-8-methyl-nonyl]-3-(4-methoxybutoxy)-pyridine-2-carboxylic acid amide hydrochloride: $R_f$(W)=0.33. HPLC $R_t$=10.2 min. MS(FAB) m/e 537 (M$^+$+1).

EXAMPLE 24

Trifluoroacetic acid (0.5 ml) is added at 0° C., with stirring, to a solution of (2S,4S,5S,7S)-N-[4-(tert-butoxycarbonyl)amino-7-butylcarbamoyl-5-hydroxy-2-isopropyl-8-methyl-nonyl]-2-(methoxymethoxy)-benzamide (46 mg) in dichloromethane (2 ml). When the reaction is complete (after approximately 30 minutes), toluene (2 ml) is added and the reaction mixture is concentrated. The crude product obtained after briefly drying under a high vacuum is purified by FC on 6 g of silica gel (eluant Q), and (2S,4S,5S,7S)-N-(4-amino-7-butylcarbamoyl-5-hydroxy-2-isopropyl-8-methyl-nonyl)-2-hydroxy-benzamide trifluoroacetate is obtained: $R_f$ (W)=0.34. HPLC $R_t$=12.1 min. MS(FAB) m/e 450 (M$^+$+1).

EXAMPLE 25

In a manner analogous to that described in Example 24), (2S,4S,5S,7S)-N-(4-amino-7-butylcarbamoyl-5-hydroxy-2-isopropyl-8-methyl-nonyl)-2-[2-(methoxymethoxy)-ethoxy]-benzamide trifluoroacetate, $R_f$ (W)=0.29; HPLC $R_t$=12.3 min; MS(FAB) m/e 538 (M$^+$+1), is obtained by de-Bocylation from 44 mg of (2S,4S,5S,7S)-N-[4-(tert-butoxycarbonyl)amino-7-butylcarbamoyl-5-hydroxy-2-isopropyl-8-methyl-nonyl]-2-[2-(methoxymethoxy)-ethoxy]-benzamide.

EXAMPLE 26

In a manner analogous to that described in Example 27), and with subsequent purification of the crude product by FC on 10 to 25 g of silica gel in each case (eluant system: dichloromethane-methanol-conc. ammonia), the following compounds are obtained by lactone opening with N-(2-aminoethyl)-morpholine (0.5 ml) at 80° C. overnight:

a) From 75 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-benzamide, (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(4-methoxybutoxy)-benzamide, $R_f$ (W)=0.35, in the form of a colourless oil.

b) From 68 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(2-methoxyethoxy)-benzamide, (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(2-methoxyethoxy)-benzamide, $R_f$ (W)=0.24, in the form of a yellowish oil.

c) From 60 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-methoxypropoxy)-nicotinamide, with purification of the crude product by FC on 25 g of silica gel (eluant gradient from P to O), (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(3-methoxypropoxy)-nicotinamide, $R_f$ (L)=0.35, in the form of a yellow oil.

d) From 65 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-3-(4-methoxybutoxy)-pyridine-2-carboxylic acid amide, with purification of the crude product by FC on 25 g of silica gel (eluant V), (2S,4S,5S,7S)-N-[4-(tert-butoxycarbonyl)amino-5-hydroxy-2-isopropyl-8-methyl-7-(2-morpholin-4-ylethylcarbamoyl)-nonyl]-3-(4-methoxybutoxy)-pyridine-2-carboxylic acid amide, $R_f$ (W)=0.38, in the form of a foamy solid.

e) From 45 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybut-2-enoxy)-benzamide, (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(4-methoxybut-2-enoxy)-benzamide, $R_f$(W)=0.50, in the form of an oil.

f) From 75 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-methyl-benzamide, with purification of the crude product on 25 g of silica gel (eluant gradient from Q to M), (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(4-methoxybutoxy)-4-methyl-benzamide, $R_f$ (L)=0.38, in the form of an oil.

g) From 90 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(5-methoxypentoxy)-benzamide (Example 17o), (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(5-methoxypentoxy)-benzamide, $R_f$ (L)=0.55, in the form of a colourless oil.

EXAMPLE 27

A mixture of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-benzamide (150 mg) and N-(3-aminopropyl)-morpholine (0.5 ml) is stirred overnight at 80° C. After cooling to room temperature, the reaction mixture is immediately chromatographed on 25 g of silica gel (eluant V). (2S,4S,5S,7S)-N-[4-(tert-butoxycarbonyl)amino-5-hydroxy-2-isopropyl-8-methyl-7-(3-morpholin-4-ylpropylcarbamoyl)-nonyl]-2-(4-methoxybutoxy)-benzamide, $R_f$(W)=0.43, is obtained in the form of an oil.

EXAMPLE 28

(2S,4S,5S,7S)-N-[4-(tert-Butoxycarbonyl)amino-5-hydroxy-2-isopropyl-8-methyl-7-(2-morpholin-4-ylethylcarbamoyl)-nonyl]-2-(3-methoxypropoxy)-benzamide (64 mg) is stirred in 2 ml of a 4N hydrochloric acid solution in dioxane at 0° C. for one hour, in a manner analogous to that described in Example 21). Removal of the solvent and drying under a high vacuum yield (2S,4S,5S,7S)-N-[4-amino-5-hydroxy-2-isopropyl-8-methyl-7-(2-morpholin-4-ylethylcarbamoyl)-nonyl]-2-(3- methoxypropoxy)-benzamide dihydrochloride: $R_f$ (W)= 0.13. HPLC $R_t$=9.59 min. MS(FAB) m/e 579 (M$^+$+1).

EXAMPLE 29

In a manner analogous to that described in Example 21), the following compounds are obtained by de-Bocylation:

a) From 80 mg of (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(4-methoxybutoxy)-benzamide, (2S,4S,5S,7S)-N-[4-amino-5-hydroxy-2-isopropyl-8-methyl-7-(2-morpholin-4-ylethylcarbamoyl)-nonyl]-2-(4-methoxybutoxy)-benzamide dihydrochloride: $R_f$(W)=0.26. HPLC $R_t$=9.9 min. MS(FAB) m/e 593 (M$^+$+1).

b) From 72 mg of (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(2-methoxyethoxy)-benzamide, (2S,4S,5S,7S)-N-[4-amino-5-hydroxy-2-isopropyl-8-methyl-7-(2-morpholin-4-ylethylcarbamoyl)-nonyl]-2-(2-methoxyethoxy)-benzamide dihydrochloride: $R_f$(W)=0.40. HPLC $R_t$=8.9 min. MS(FAB) m/e 565 (M$^+$+1).

c) From 63 mg of (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(3-methoxypropoxy)-nicotinamide, (2S,4S,5S,7S)-N-[4-amino-5-hydroxy-2-isopropyl-8-methyl-7-(2-morpholin-4-yl-ethylcarbamoyl)-nonyl]-2-(3-methoxypropoxy)-nicotinamide dihydrochloride: $R_f$ (W)=0.27. HPLC $R_t$=8.4 min. MS(FAB) m/e 580 (M$^+$+1).

d) From 46 mg of (2S,4S,5S,7S)-N-[4-(tert-butoxycarbonyl)amino-5-hydroxy-2-isopropyl-8-methyl-7-(2-morpholin-4-ylethylcarbamoyl)-nonyl]-3-(4-methoxybutoxy)-pyridine-2-carboxylic acid amide, (2S,4S,5S,7S)-N-[4-amino-5-hydroxy-2-isopropyl-8-methyl-7-(2-morpholin-4-ylethylcarbamoyl)-nonyl]-3-(4-methoxybutoxy)-pyridine-2-carboxylic acid amide dihydrochloride: $R_f$ (W)=0.16. MS(FAB) m/e 593 (M$^+$+1).

e) From 50 mg of (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(4-methoxybut-2-enoxy)-benzamide, (2S,4S,5S,7S)-N-[4-amino-5-hydroxy-2-isopropyl-8-methyl-7-(2-morpholin-4-ylethylcarbamoyl)-nonyl]-2-(4-methoxybut-2-enoxy)-benzamide dihydrochloride: $R_f$ (W)=0.17. HPLC $R_t$=9.15 min. MS(FAB) m/e 591 (M$^+$+1).

f) From 75 mg of (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(4-methoxybutoxy)-4-methyl-benzamide, (2S,4S,5S,7S)-N-[4-amino-5-hydroxy-2-isopropyl-8-methyl-7-(2-morpholin-4ylethylcarbamoyl)-nonyl]-2-(4-methoxybutoxy)-4-methyl-benzamide dihydrochloride: $R_f$ (W)=0.28. HPLC $R_t$=10.6 min. MS(FAB) m/e 607 (M$^+$+1).

g) From 75 mg of (2S,4S,5S,7S)-N-[4-(tert-butoxycarbonyl)amino-5-hydroxy-2-isopropyl-8-methyl-7-(2-morpholin-4-ylethylcarbamoyl)-nonyl]-2-(5-methoxypentoxy)-benzamide, (2S,4S,5S,7S)-N-[4-amino-5-hydroxy-2-isopropyl-8-methyl-7-(2-morpholin-4ylethylcarbamoyl)-methyl-nonyl]-2-(5-methoxypentoxy)-benzamide dihydrochloride: $R_f$ (W)=0.29. HPLC $R_t$=10.2 min. MS(FAB) m/e 607 (M$^+$+1).

h) From 96 mg of (2S,4S,5S,7S)-N-[4-(tert-butoxycarbonyl)amino-5-hydroxy-2-isopropyl-8-methyl-7-(3-morpholin-4-ylpropylcarbamoyl)-nonyl]-2-(4-methoxybutoxyl-benzamide, (2S,4S,5S,7S)-N-[4-amino-5-hydroxy-2-isopropyl-8-methyl-7-(3-morpholin-4ylpropylcarbamoyl)-nonyl]-2-(methoxybutoxy)-benzamide dihydrochloride: $R_f$ (W)=0.14. HPLC $R_t$=10.0 min. MS(FAB) m/e 607 (M$^+$+1).

EXAMPLE 30

In a manner analogous to that described in Example 1), the following compounds are prepared:

a) From 100 mg of (3S,5S,1'S,3'S)-5-[3'-aminomethyl-1'-(tert-butoxycarbonyl)amino-4'-methylpentyl]-3-isopropyl-dihydrofuran-2-one and 172 mg of 2-(4-methoxybutoxy)-4-(morpholin-4-ylmethyl)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(morpholin-4-ylmethyl)-benzamide, $R_f$ (W)=0.55, in the form of a yellow oil.

b) From 100 mg of (3S,5S,1'S,3'S)-5-[3'-aminomethyl-1'-(tert-butoxycarbonyl)amino-4'-methylpentyl]-3-isopropyl-dihydrofuran-2-one and 198 mg of 2-(4-methoxybutoxy)-4-(2-morpholin-4-ylethoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(2-morpholin-4-ylethoxy)-benzamide, $R_f$ (W)=0.65, in the form of a yellow oil.

c) From 50 mg of (3S,5S,1'S,3'S)-5-[3'-aminomethyl-1'-(tert-butoxycarbonyl)amino-4'-methylpentyl]-3-isopropyl-dihydrofuran-2-one and 91 mg of 4-[3-(dimethylamino)-propoxy]-2-(4-methoxybutoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-[3-(dimethylamino)propoxy]-2-(4-methoxybutoxy)-benzamide, $R_f$ (W)=0.44, in the form of an oil.

d) From 50 mg of (3S,5S,1'S,3'S)-5-[3'-aminomethyl-1'-(tert-butoxycarbonyl)amino-4'-methylpentyl]-3-isopropyl-dihydrofuran-2-one and 90 mg of 2-(4-methoxybutoxy)-4-(piperidin-1-yl)methyl-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(piperidin-1-yl)methyl-benzamide, $R_f$ (W)=0.60, in the form of an oil.

e) From 50 mg of (3S,5S,1'S,3'S)-5-[3'-aminomethyl-1'-(tert-butoxycarbonyl)amino-4'-methylpentyl]-3-isopropyl-dihydrofuran-2-one and 86 mg of 2-(4-methoxybutoxy)-4-(pyrrolidin-1-yl)methyl-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(pyrrolidin-1-yl)methyl-benzamide, $R_f$ (W)=0.56, in the form of an oil.

f) From 125 mg of (3S,5S,1'S,3'S)-5-[3'-aminomethyl-1'-(tert-butoxycarbonyl)amino-4'-methylpentyl]-3-isopropyl-dihydrofuran-2-one and 246 mg of 2-(4-methoxybutoxy)-4-(2-piperidin-1-ylethoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(2-piperidin-1-ylethoxy)-benzamide, $R_f$ (W)=0.58, in the form of an oil.

g) From 80 mg of (3S,5S,1'S,3'S)-5-[3'-aminomethyl-1'-(tert-butoxycarbonyl)amino-4'-methylpentyl]-3-isopropyl-dihydrofuran-2-one and 252 mg of 4-dimethylaminomethyl-2-(4-methoxybutoxy)-benzoic acid, with subsequent purification by FC (eluant N), (2S,2'S,2"S,4"S)-N-{2-[2'-(tert-butoxycarbonyl)amino-2'-(4"-isopropyl-5"-oxo-tetrahydrofuran-2'-yl)-ethyl]-3-methylbutyl}-4-dimethylaminomethyl-2-(4-methoxybutoxy)-benzamide, $R_f$ (L)=0.41, in the form of an oil.

h) From 80 mg of (3S,5S,1'S,3'S)-5-[3'-aminomethyl-1'-(tert-butoxycarbonyl)amino-4'-methylpentyl]-3-isopropyl-dihydrofuran-2-one and 274 mg of 2-(4-methoxybutoxy)-4-(4-methylpiperazin-1-yl)methyl-benzoic acid, with subsequent purification by FC (eluant gradient from P to N), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(4-methylpiperazin-1-yl)methyl-benzamide, $R_f$ (W)=0.28, in the form of a yellowish solid.

i) From 80 mg of (3S,5S,1'S,3'S)-5-[3'-aminomethyl-1'-(tert-butoxycarbonyl)amino-4'-methylpentyl]-3-isopropyl-dihydrofuran-2-one and 255 mg of 4-(4-acetylpiperazin-1-yl)methyl-2-(4-methoxybutoxy)-benzoic acid, with subsequent purification by FC (eluant O), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-(4-acetylpiperazin-1-yl)-methyl-2-(4-methoxybutoxy)benzamide, $R_f$ (W)=0.55, in the form of a yellowish solid.

The benzoic acids used as starting materials are prepared as described below:

A) 2-(4-Methoxybutoxy)-4-(morpholin-4-ylmethyl)-benzoic acid: Hydrolysis of 2-(4-methoxybutoxy)-4-(morpholin-4-ylmethyl)-benzoic acid methyl ester (1.08 g) with 1N sodium hydroxide solution (4.75 ml) in a 2:1 mixture of ethanol and water (15 ml) at 50° C. and customary working-up yield the title compound in the form of a yellow oil: $R_f$ (L)=0.36.

The 2-(4-methoxybutoxy)-4-(morpholin-4-ylmethyl)-benzoic acid methyl ester that is used is prepared as follows: A mixture of 2-(4-methoxybutoxy)-4-methyl-benzoic acid methyl ester (1.0 g), N-bromosuccinimide (0.70 g), 2',2"-azoisobutyronitrile (23 mg) and dibenzoyl peroxide (34 mg) in carbon tetrachloride (10 ml) is stirred under reflux for 5 hours. After cooling to room temperature, the precipitate is filtered off, morpholine (1.03 ml) is added to the filtrate, and stirring is carried out for a further 2 hours at room temperature. The crude product obtained after filtration and concentration is purified by FC on silica gel (40 g, eluant gradient from C to F). The title compound, $R_f$ (F)=0.14, is obtained in the form of a yellowish oil.

B) 2-(4-Methoxybutoxy)-4-(2-morpholin-4-ylethoxy)-benzoic acid: A mixture of 2-(4-methoxybutoxy)-4-(2-morpholin-4-ylethoxy)-benzoic acid methyl ester (2.95 g) and 1N sodium hydroxide solution (8.83 ml) in ethanol (10 ml) and water (5 ml) is stirred overnight at 50° C. After customary working-up, the title compound (2.50 g), $R_f$ (L)=0.51, is obtained in the form of a yellowish oil.

The 2-(4-methoxybutoxy)-4-(2-morpholin-4-ylethoxy)-benzoic acid methyl ester used as starting material is prepared as follows:

a) A suspension of 4-hydroxy-2-(4-methoxybutoxy)-benzoic acid methyl ester (2.0 g), 2-chloroethylmorpholine (11.8 g) and caesium carbonate (12.8 g) in acetone (30 ml) is stirred under reflux for 2 hours. Filtration and purification by FC (80 g of silica gel, eluant F and ethyl acetate-conc. ammonia 10:0.1) yield 2-(4-methoxy butoxy)-4-(2-morpholin-4-ylethoxy)-benzoic acid methyl ester (2.96 g), $R_f$ (N)=0.73, in the form of a pale-yellow oil.

b) 4-Hydroxy-2-(4-methoxybutoxy)-benzoic acid methyl ester: A solution of 4-benzyloxy-2-(4-methoxybutoxy)-benzoic acid methyl ester (13.8 g) in ethyl acetate (130 ml) is hydrogenated for 2 hours at room temperature in the presence of 10% Pd/C (1.37 g). The title compound (10.1 g), $R_f$ (C)=0.09; m.p. 62°–63° C., is obtained in the form of a white solid.

C) 2-(4-Methoxybutoxy)-4-(3-dimethylaminopropoxy)-benzoic acid: 2-(4-Metholoxybutoxy)-4-(3-dimethylaminopropoxy)-benzoic acid methyl ester (2.12 g), dissolved in a mixture of ethanol (10 ml) and water (5 ml), is hydrolysed in the presence of 1N sodium hydroxide solution (6.87 ml). When the reaction is complete, dichloro methane (100 ml) is added and the aqueous phase is adjusted to pH 6 by the addition of 1M potassium hydrogen sulfate solution. The aqueous phase is again extracted with dichloromethane, and the combined organic phases are washed with brine (20 ml), dried over magnesium sulfate and concentrated. The title compound is obtained in admixture with inorganic salts in the form of a yellowish oil, which is reacted further without additional purification.

The 2-(4-methoxybutoxy)-4-(3-dimethylaminopropoxy)-benzoic acid methyl ester used as starting material is obtained in the form of an oil in a manner analogous to that described in Example 30Aa) from 2-(4-methoxybutoxy)-4-methyl-benzoic acid methyl ester (2.0 g) and dimethylaminopropyl chloride (2.4 g), with subsequent purification by FC on 40 g of silica gel (eluant F and ethyl acetate-conc. ammonia 99:1).

D) 2-(4-Methoxybutoxy)-4-(piperidin-1-ylmethyl)-benzoic acid: 1N sodium hydroxide solution (4.8 ml) is added to 2-(4-methoxybutoxy)-4-(piperidin-1-ylmethyl)-benzoic acid methyl ester (1.35 g), dissolved in ethanol (20 ml) and water (10 ml), and the mixture is stirred overnight at room temperature. The reaction mixture is adjusted to pH 6 by the addition of 1M potassium hydrogen sulfate solution and is largely concentrated. The residue is taken up in dioxane (30 ml) and the solution is frozen in a dry-ice-bath and lyophilised under a high vacuum. The title compound is obtained in admixture with inorganic salts in the form of a light-brown solid (1.60 g), which is reacted without being purified further: $R_f$ (L)=0.05.

The 2-(4-methoxybutoxy)-4-(piperidin-1-ylmethyl)-benzoic acid methyl ester that is used is prepared in a manner analogous to that described in Example 30 An) from 2-(4-methoxybutoxy)-4-methyl-benzoic acid methyl ester and piperidine, with subsequent purification of the crude product by FC (eluants C and M): brown oil, $R_f$ (N)=0.34.

E) 2-(4-Methoxybutoxy)-4-(pyrrolidin-1-ylmethyl)-benzoic acid: The title compound is obtained in admixture with inorganic salts in a manner analogous to that described in Example 30D) from 2-(4-methoxybutoxy)-4-(pyrrolidin-1-ylmethyl)-benzoic acid methyl ester.

The 2-(4-methoxybutoxy)-4-(pyrrolidin-1-ylmethyl)-benzoic acid methyl ester that is used is prepared in a manner analogous to that described in Example 30Aa) from 2-(4-methoxybutoxy)-4-methyl-benzoic acid methyl ester and pyrrolidine, with subsequent purification of the crude product by FC (eluants C and M): brown-black oil, $R_f$ (N)=0.22.

F) 2-(4-Methoxybutoxy)-4-(piperidin-1-ylethoxy)-benzoic acid: Alkaline hydrolysis of 2-(4-methoxybutoxy)-4-(piperidin-1-ylethoxy)-benzoic acid methyl ester, in a manner analogous to that described in Example 30D), and subsequent purification by FC (eluant gradient from N to dichloromethane-methanol 8:2) yield the title compound in the form of a yellowish oil, which slowly crystallises out when left to stand: $R_f$ (dichloromethane-methanol 8:2)= 0.50; m.p. 91°–94° C.

The 2-(4-methoxybutoxy)-4-(piperidin-1-ylethoxy)-benzoic acid methyl ester used as starting material is prepared as follows:

a) A solution of 2-(4-methoxybutoxy)-4-(piperidin-1-ylcarbamoylmethoxy)-benzoic acid methyl ester (2.29 g) in tetrahydrofuran (10 ml) is added dropwise at 0°–5° C. over a period of 15 minutes to a 1M borane THF complex solution in tetrahydrofuran (10.0 ml). The mixture is then heated to reflux temperature and stirred for 4 hours. A further 2.0 ml of a 1M borane THF complex solution are added. After one hour under reflux, the mixture is allowed to cool, the solvent is removed, and anhydrous methanol (0.97 ml) and 3.75N hydrochloric acid solution in diethyl ether (1.61 ml) are added to the residue. After stirring overnight at room temperature, the mixture is concentrated and the crude product is purified by FC (eluant gradient from P to N). 2-(4-Methoxybutoxy)-4-(piperidin-1-ylethoxy)-benzoic acid methyl ester, $R_f$(L)=0.38, is obtained in the form of a brown oil (1.39 g).

b) 2-(4-Methoxybutoxy)-4-(piperidin-1-ylcarbamoylmethoxy)-benzoic acid methyl ester: Cyanophosphonic acid diethyl ester (0.88 ml), piperidine (0.57 ml) and triethylamine (0.73 ml) are added at 0° C. to a suspension of 4-carboxymethoxy-2-(4-methoxybutoxy)-benzoic acid methyl ester (1.64 g) in anhydrous dichloromethane (20 ml). The reaction mixture is stirred for 4 hours at 0° C. and for one hour at room temperature. Further cyanophosphonic acid diethyl ester (0.40 ml) and piperidine (0.25 ml) are added, and the mixture is stirred for a further 45 minutes at room temperature and is then diluted with dichloromethane (50 ml). The organic phase is washed with a 1M potassium hydrogen sulfate solution, saturated sodium hydrogen carbonate solution and saturated sodium chloride solution, dried over magnesium sulfate and concentrated. Purification by FC (eluant gradient from E to hexane-ethyl acetate 1:3) yields the title compound (1.95 g) in the form of a pale-yellow solid: $R_f$(E)=0.13; MS(EI) m/e 365 ($M^+$).

c) 4-Carboxymethoxy-2-(4-methoxybutoxy)-benzoic acid methyl ester: 4-tert-Butoxycarbonylmethoxy-2-(4-methoxybutoxy)-benzoic acid methyl ester (3.0 g), which is obtained in the form of a pale-yellow oil ($R_f$(C)=0.13) in a manner analogous to that described in Example 30Ba) from 4-hydroxy-2-(4-methoxybutoxy)-benzoic acid methyl ester and tert-butyl bromoacetate, is dissolved in 4N hydrochloric acid solution in dioxane (25 ml) and the mixture is stirred overnight at room temperature. The solvent is then removed under a high vacuum and the solid residue is dissolved in hot ethyl acetate (10 ml). Hexane (approximately 20 ml) is added until the mixture begins to turn cloudy. After cooling to room temperature, the white precipitate is filtered off, washed with hexane and dried. The title compound (1.64 g) is obtained in the form of a white solid: $R_f$ (hexane-ethyl acetate-glacial acetic acid 50:50:1)=0.12.

G) 2-(4-Methoxybutoxy)-4-[(4-methyl-piperazin-1-yl)methyl]-benzoic acid methyl ester: The title compound is prepared in a manner analogous to that described in Example 30Aa) from 2-(4-methoxybutoxy)-4-methyl-benzoic acid methyl ester and N-methylpiperidine, with subsequent purification of the crude product by FC (eluant T): yellow oil, $R_f$(V)=0.37.

H) 4-[(4-Acetyl-piperazin-1-yl)methyl]-2-(4-methoxybutoxy)-benzoic acid methyl ester: The title compound is prepared in a manner analogous to that described in Example 30Aa) from 2-(4-methoxybutoxy)-4-methyl-benzoic acid methyl ester and N-acetylpiperazine, with subsequent purification by FC (eluant T): yellow oil, $R_f$(V)=0.30.

EXAMPLE 31

In a manner analogous to that described in Example 18), with subsequent purification of the crude product by FC on 25 to 50 g of silica gel in each case (eluant system: dichloromethane-methanol-conc. ammonia), the following compounds are prepared by lactone opening:

a) From 202 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(morpholin-4-ylmethyl)-benzamide, (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(morpholin-4-ylmethyl)-benzamide, $R_f$(W)=0.60, in the form of a foamy solid.

b) From 185 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-[2-(morpholin-4-yl)ethoxy]-benzamide, (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-[2-(morpholin-4-yl)-ethoxy]-benzamide, $R_f$(W)=0.54, in the form of an oil.

c) From 70 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-[3-(dimethylamino)-propoxy]-2-(4-methoxybutoxy)-benzamide, (2S,4S,5S,7S)-N-[4-(tert-butoxycarbonyl)amino-7-butylcarbamoyl-5-hydroxy-2-isopropyl-8-methyl-nonyl]-4-[3-(dimethylamino)-propoxy]-2-(4-methoxybutoxy)-benzamide, $R_f$(W)=0.29, in the form of an oil.

d) From 84 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(piperidin-1-yl)-methyl-benzamide, (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(piperidin-1-yl)methyl-benzamide, $R_f$(W)=0.66; MS(FAB) m/e 733 ($M^+$+1), in the form of an oil.

e) From 60 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(pyrrolidin-1-yl)-methyl-benzamide, (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(pyrrolidin-1-yl)methyl-benzamide, $R_f$(W)=0.54; MS(FAB) m/e 719 ($M^+$+1), in the form of an oil.

f) From 68 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(2-piperidin-1-ylethoxy)-benzamide, (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(2-piperidin-1-ylethoxy)-benzamide, $R_f$(W)=0.54, in the form of a colourless solid.

g) From 100 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-dimethylaminomethyl-2-(4-methoxybutoxy)-benzamide, (2S,4S,5S,7S)-N-[4-(tert-butoxycarbonyl)amino-7-butylcarbamoyl-5-hydroxy-2-isopropyl-8-methyl-nonyl]-4-dimethylaminomethyl-2-(4-methoxybutoxy)-benzamide, $R_f$(W)=0.48, in the form of a yellowish solid.

h) From 151 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(4-methylpiperazin-1-yl)methyl-benzamide, with purification by FC (25 g of silica gel, eluant V), (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(4-methylpiperazin-1-yl)methyl-benzamide, $R_f$(W)=0.37; HPLC $R_t$=13.8 min, in the form of an oil.

i) From 130 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-(4-acetylpiperazin-1-yl)methyl-2-(4-methoxybutoxy)-benzamide, with purification by FC (eluant T), (2S,4S,5S,7S)-N-[4-(tert-butoxycarbonyl)amino-7-butylcarbamoyl-5-hydroxy-2-isopropyl-8-methyl-nonyl]-4-(4-acetylpiperazin-1-yl)methyl-2-(4-methoxybutoxy)-benzamide, $R_f$ (W)= 0.46; HPLC $R_t$=17.9 min, in the form of a yellowish solid.

EXAMPLE 32

In a manner analogous to that described in Example 21), the following compounds are prepared by de-Bocylation:

a) From 144 mg of (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(morpholin-4-ylmethyl)-benzamide, (2S,4S,5S,7S)-N-(4-amino-7-butylcarbamoyl-5-hydroxy-2-isopropyl-8-methylnonyl)-2-(4-methoxybutoxy)-4-(morpholin-4-ylmethyl)-benzamide dihydrochloride: $R_f$ (W)=0.25. HPLC $R_t$=9.6 min. MS(FAB) m/e 635 (M$^+$+1).

b) From 155 mg of (2S,4S,5S,7S)-N-[4-(tert-butoxycarbonyl)amino-7-butylcarbamoyl-5-hydroxy-2-isopropyl-8-methyl-nonyl]-2-(4-methoxybutoxyl-4-[2-(morpholin-4-yl)-ethoxy]-benzamide, (2S,4S,5S,7S)-N-(4-amino-7-butylcarbamoyl-5-hydroxy-2-isopropyl-8-methylnonyl)-2-(4-methoxybutoxy)-4-[2-(morpholin-4-yl)-ethoxy]-benzamide dihydrochloride, $R_f$ (W)=0.18. HPLC $R_t$=10.0 min. MS(FAB) m/e 665 (M$^+$+1).

c) From 36 mg of (2S,4S,5S,7S)-N-[4-(tert-butoxycarbonyl)amino-7-butylcarbamoyl-5-hydroxy-2-isopropyl-8-methyl-nonyl]-4-[3-(dimethylamino)-propoxy]-2-(4-methoxybutoxy)-benzamide, (2S,4S,5S,7S)-N-(4-amino-7-butylcarbamoyl-5-hydroxy-2-isopropyl-8-methylnonyl)-4-[3-(dimethylamino)-propoxy]-2-(4-methoxybutoxy)-benzamide dihydrochloride: $R_f$ (W)=0.11. HPLC $R_t$=9.3 min. MS(FAB) m/e 637 (M$^+$+1).

d) From 50 mg of (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(piperidin-1-yl)methyl-benzamide, (2S,4S,5S,7S)-N-(4-amino-7-butylcarbamoyl-5-hydroxy-2-isopropyl-8-methylnonyl)-2-(4-methoxybutoxy)-4-(piperidin-1-yl)methyl-benzamide dihydrochloride: $R_f$ (W)=0.41. HPLC $R_t$=10.5 min. MS(FAB) m/e 633 (M$^+$+1).

e) From 48 mg of (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(pyrrolidin-1-yl)methyl-benzamide, (2S,4S,5S,7S)-N-(4-amino-7-butylcarbamoyl-5-hydroxy-2-isopropyl-8-methylnonyl)-2-(4-methoxybutoxy)-4-(pyrrolidin-1-yl)methyl-benzamide dihydrochloride: $R_f$ (W)=0.32. HPLC $R_t$=10.2 min. MS(FAB) m/e 619 (M$^+$+1).

f) From 53 mg of (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(2-piperidin-1-yletoxy)-benzamide, (2S,4S,5S,7S)-N-(4-amino-7-butylcarbamoyl-5-hydroxy-2-isopropyl-8-methylnonyl)-2-(4-methoxybutoxy)-4-(2-piperidin-1-yletoxy)-benzamide dihydrochloride: $R_f$ (W)=0.16. HPLC $R_t$=9.98 min. MS(FAB) m/e 663 (M$^+$+1).

g) From 79 mg of (2S,4S,5S,7S)-N-[4-(tert-butoxycarbonyl)amino-7-butylcarbamoyl-5-hydroxy-2-isopropyl-8-methyl-nonyl]-4-dimethylaminomethyl-2-(4-methoxybutoxy)-benzamide, (2S,4S,5S,7S)-N-(4-amino-7-butylcarbamoyl-5-hydroxy-2-isopropyl-8-methyl-nonyl)-4-dimethylaminomethyl-2-(4-methoxybutoxy)-benzamide dihydrochloride: $R_f$ (W)=0.21. HPLC $R_t$=9.57 min. MS(FAB) m/e 593 (M$^+$+1).

h) From 124 mg of (2S,4S,5S,7S)-N-[4-(tert-butoxycarbonyl)amino-7-butyl carbamoyl-5-hydroxy-2-isopropyl-8-methyl-nonyl]-2-(4-methoxybutoxy)-4-(4-methylpiperazin-1-yl)methylbenzamide, (2S,4S,5S,7S)-N-(4-amino-7-butylcarbamoyl-5-hydroxy-2-isopropyl-8-methylnonyl)-2-(4-methoxybutoxy)-4-(4-methylpiperazin-1-yl)methyl-benzamide trihydrochloride: $R_f$ (W)=0.21. HPLC $R_t$=10.2 min. MS(FAB) m/e 648 (M$^+$+1).

i) From 83 mg of (2S,4S,5S,7S)-N-[4-(tert-butoxycarbonyl)amino-7-butylcarbamoyl-5-hydroxy-2-isopropyl-8-methyl-nonyl]-4-(4-acetylpiperazin-1-yl)methyl-2-(4-methoxybutoxy)-benzamide, (2S,4S,5S,7S)-N-(4-amino-7-butylcarbamoyl-5-hydroxy-2-isopropyl-8-methylnonyl)-4-(4-acetylpiperazin-1-yl)methyl-2-(4-methoxybutoxy)-benzamide dihydrochloride: $R_f$ (W)=0.29. HPLC $R_t$=10.6 min. HRMS(FAB) m/e 676.5017 (M$^+$+1).

EXAMPLE 33

In a manner analogous to that described in Example 1), the following compounds are prepared:

a) From 100 mg of (3S,5S,1'S,3'S)-5-[3'-aminomethyl-1'-(tert-butoxycarbonyl)amino-4'-methylpentyl]-3-isopropyl-dihydrofuran-2-one and 124 mg of 2-(3-azidopropoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-azidopropoxy)-benzamide, $R_f$ (hexane-diethyl ether 1:4)= 0.46; HPLC $R_t$=19.2 min.

b) From 100 mg of (3S,5S,1'S,3'S)-5-[3'-aminomethyl-1'-(tert-butoxycarbonyl)amino-4'-methylpentyl]-3-isopropyl-dihydrofuran-2-one and 116 mg of 2-(2-azidoethoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(2-azidoethoxy)-benzamide, $R_f$ (hexane-diethyl ether 1:4)= 0.41; HPLC $R_t$=18.6 min.

c) From 150 mg of (3S,5S,1'S,3'S)-5-[3'-aminomethyl-1'-(tert-butoxycarbonyl)amino-4'-methylpentyl]-3-isopropyl-dihydrofuran-2-one and 246 mg of 2-[2-(4-acetylpiperazin-1-yl)-ethoxy]-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(4-acetylpiperazin-1-yl)-ethoxy]-benzamide, $R_f$ (J)=0.45; HPLC $R_t$=13.6 min.

d) From 100 mg of (3S,5S,1'S,3'S)-5-[3'-aminomethyl-1'-(tert-butoxycarbonyl)amino-4'-methylpentyl]-3-isopropyl-dihydrofuran-2-one and 132 mg of 2-[2-(morpholin-4-yl)-ethyl]-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(morpholin-4-yl)-ethyl]-benzamide, $R_f$ (L)=0.50; HPLC $R_t$=15.8 min.

e) From 100 mg of (3S,5S,1'S,3'S)-5-[3'-aminomethyl-1'-(tert-butoxycarbonyl)amino-4'-methylpentyl]-3-isopropyl-dihydrofuran-2-one and 125 mg of 2-(3-dimethylaminopropoxy)-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-dimethylaminopropoxy)-benzamide, $R_f$ (J)=0.70; HPLC $R_t$=14.6 min.

f) From 50 mg of (3S,5S,1'S,3'S)-5-[3'-aminomethyl-1'-(tert-butoxycarbonyl)amino-4'-methylpentyl]-3-isopropyl-dihydrofuran-2-one and 72 mg of 2-[3-(morpholin-4-yl)-propoxy]-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[3-(morpholin-4-yl)-propoxy]-benzamide, $R_f$ (H)=0.25; HPLC $R_t$=14.4 min.

g) From 50 mg of (3S,5S,1'S,3'S)-5-[3'-aminomethyl-1'-(tert-butoxycarbonyl)amino-4'-methylpentyl]-3-isopropyl-dihydrofuran-2-one and 70 mg of 2-[2-(morpholin-4-yl)-ethoxy]-benzoic acid, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(morpholin-4-yl)-ethoxy]-benzamide, $R_f$ (H)=0.43; HPLC $R_t$=14.2 min.

The benzoic acid derivatives used as starting materials are prepared in accordance with customary methods from the literature, unless otherwise described in greater detail below:

A) 2-(3-Azidopropoxy)-benzoic acid: 1N sodium hydroxide solution (3 ml) is added to a solution of 2-(3-azidopropoxy)-benzoic acid methyl ester (0.5 g) in methanol (7 ml), and the reaction mixture is stirred at reflux for 15 minutes. The mixture is concentrated by evaporation, water (25 ml) is added and the pH is adjusted to 6 at 0° C. with 1N hydrochloric acid. The aqueous solution is extracted with dichloromethane (2×100 ml), and the organic phase is dried over sodium sulfate and concentrated by evaporation. The title compound, $R_f$ (L)=0.62, is obtained.

a) 2-(3-Azidopropoxy)-benzoic acid methyl ester: Sodium azide (0.45 g) is added to a solution of 2-(3-bromopropoxy)-benzoic acid methyl ester (1.5 g; prepared in accordance with the procedure described by Smith et al. in J. Chem. Soc. Perkin Trans I (1988) 77) in N,N-dimethylformamide (10 ml), and the suspension is heated at 50° C. for 15 hours. The reaction mixture is concentrated by evaporation and partitioned between water (50 ml) and dichloromethane (100 ml). The organic phase is washed with water (2×50 ml), dried over sodium sulfate and concentrated by evaporation. The evaporation residue is purified by FC (200 g of silica gel, eluant A). The title compound, $R_f$ (B)=0.25, is obtained.

B) 2-(2-Azidoethoxy)-benzoic acid: In a manner analogous to that described in Example 33A), from 1.3 g of 2-(2-azidoethoxy)-benzoic acid methyl ester, in the form of an oil, $R_f$ (L)=0.59.

a) 2-(2-Azidoethoxy)-benzoic acid methyl ester: Sodium azide (0.6 g) is added to a solution of 2-(3-bromoethoxy)-benzoic acid methyl ester (2.0 g; prepared in accordance with the procedure described by W. A. Jacobs and M. Heidelberger in J. Biol. Chem. (1915) 21, 448) in 1,3-dimethyl-3,4,5,6-tetrahydro-2(1H)-pyrimidinone (20 ml), and the suspension is heated at 50° C. for 5 hours. The reaction mixture is concentrated by evaporation and partitioned between water (100 ml) and diethyl ether (200 ml). The organic phase is washed with water (50 ml), dried over sodium sulfate and concentrated by evaporation. The evaporation residue is purified by FC (360 g of silica gel, eluant E). The title compound, $R_f$ (E)=0.43, is obtained.

C) 2-[2-(4-Acetylpiperazin-1-yl)-ethoxy]-benzoic acid: In an analogous manner from 2-[2-(4-acetylpiperazin-1-yl)-ethoxy]-benzoic acid methyl ester (2.5 g), in the form of an oil: $R_f$ (dichloromethane-methanol 4:1)=0.20.

a) 2-[2-(4-Acetylpiperazin-1-yl)-ethoxy]-benzoic acid methyl ester: N-Acetylpiperazine (3.0 g) is added to a solution of 2-(2-bromopropoxy)-benzoic acid methyl ester (2.0 g) in acetonitrile (50 ml), and the reaction mixture is heated at 50° C. When the reaction is complete, the mixture is concentrated by evaporation and the crude product is purified by FC (150 g of silica gel, dichloromethane-methanol 4:1). The title compound, $R_f$ (dichloromethane-methanol 4:1)=0.76, is obtained.

D) 2-[2-(Morpholin-4-yl)-ethyl]-benzoic acid: In an analogous manner from 2-[2-(morpholin-4-yl)-ethyl]-benzoic acid ethyl ester (1.0 g), in the form of an oil: $R_f$ (ethyl acetate-methanol 9:1)=0.05.

a) 2-[2-(Morpholin-4-yl)-ethyl]-benzoic acid ethyl ester: The title compound is obtained from 2-(2-bromoethyl)-benzoic acid ethyl ester (1.0 g) in a manner analogous to that described in Example 33Ca): $R_f$ (ethyl acetate-methanol 9:1)=0.55.

b) 2-(2-Bromoethyl)-benzoic acid ethyl ester: Phosphorus tribromide (5.58 ml) and bromine (3.33 ml) are added at 15° C. to a solution of 1-oxo-isochroman (8.0 g) in carbon tetrachloride (80 ml). The mixture is stirred at room temperature overnight and then at 60° C. for 3 hours. Ethanol (16 ml) is added at room temperature, and the mixture is stirred for one hour. Finally, the reaction mixture is partitioned between dichloromethane (500 ml) and water (50 ml) and the organic phase is washed with water (50 ml), dried over sodium sulfate and concentrated by evaporation. The residue is purified by FC (eluant E). The title compound, $R_f$ (E)=0.70, is obtained.

E) In a manner analogous to that described in Examples 33A–D), the following compounds are obtained:

a) From 2-[3-(morpholin-4-yl)-propoxy]-benzoic acid methyl ester, 2-[3-(morpholin-4-yl)-propoxy]-benzoic acid, $R_f$ (dichloromethane-methanol 7:3)=0.46, in the form of an oil.

b) From 2-[2-(morpholin-4-yl)-ethoxy]-benzoic acid methyl ester, 2-[2-(morpholin-4-yl)-ethoxy]-benzoic acid, $R_f$ (dichloromethane-methanol 7:3)=0.47, in the form of an oil.

c) From 2-[2-(4-methoxypiperidin-1-yl)-ethyl]-benzoic acid ethyl ester ($R_f$ (ethyl acetate-methanol 9:1)=0.22), 2-[2-(4-methoxypiperidin-1-yl)-ethyl]-benzoic acid, $R_f$ (dichloromethane-methanol 7:3)=0.60, in the form of an oil.

d) From 2-[2-(4-acetylpiperazin-1-yl)-ethyl]-benzoic acid ethyl ester ($R_f$ (acetic acid-methanol 9:1)=0.22), 2-[2-(4-acetylpiperazin-1-yl)-ethyl]-benzoic acid, $R_f$ (dichloromethane-methanol 7:3)=0.60, in the form of an oil.

EXAMPLE 34

A mixture of (3S,5S,1'S,3'S)-5-[3'-aminomethyl-1'-(tert-butoxycarbonyl)amino-4l'-methylpentyl]-3-isopropyl-dihydrofuran-2-one (100 mg), 2-[2-(4-methoxypiperidin-1-yl)-ethyl]-benzoic acid (89 mg), o-benzotriazol-1-yl-N,N,N',N'-tetramethyl-uronium hexafluorophosphate (128 mg) and triethylamine (59 ml ) in acetonitrile (5 ml) is stirred at room temperature for 24 hours. The mixture is concentrated by evaporation and the residue is partitioned between dichloromethane and water. The organic phase is dried over sodium sulfate and concentrated by evaporation. FC on silica gel (50 g, eluant I) yields (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(4-metholoxypiperidin-1-yl)-ethyl]-benzamide, $R_f$ (L)=0.44; HPLC $R_t$=16.1 min.

EXAMPLE 35

In a manner analogous to that described in Example 34), (2S,2'S,2"S,4"S)-N-{2-[2'-(tert-butoxycarbonyl)amino-2'-

(4"-isopropyl-5"-oxo-tetrahydrofuran-2"-yl)-ethyl]-3-methylbutyl}-2-[2-(4-acetylpiperazin-1-yl)-ethyl]-benzamide, $R_f$ (ethyl acetate-methanol 9:1)=0.26; HPLC $R_t$=14.4 min, is obtained from (3S,5S,1'S,3'S)-5-[3'-aminomethyl-1'-tert-butoxycarbonyl)amino-4'-methylpentyl]-3-isopropyl-dihydrofuran-2-one (100 mg), 2-[2-(4-acetylpiperazin-1-yl)-ethyl]-benzoic acid (93 mg), o-benzotriazol-1-yl-N,N,N',N'-tetramethyl-uronium hexafluorophosphate (128 mg) and triethylamine (59 ml) in acetonitrile (5 ml), with purification of the crude product by FC (50 g of silica gel, ethyl acetate-methanol 9:1).

EXAMPLE 36

In a manner analogous to that described in Example 31), the following compounds are prepared by lactone opening with n-butylamine:

a) From 110 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-azidopropoxy)-benzamide, (2S,4S,5S,7S)-N-[4-(tert-butoxycarbonyl)amino-7-butylcarbamoyl-5-hydroxy-2-isopropyl-8-methyl-nonyl]-2-(3-azidopropoxy)-benzamide, $R_f$ (E)=0.14; HPLC $R_t$=18.8 min.

b) From 100 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(2-azidoethoxy)-benzamide, (2S,4S,5S,7S)-N-[4-(tert-butoxycarbonyl)amino-7-butylcarbamoyl-5-hydroxy-2-isopropyl-8-methyl-nonyl]-2-(2-azidoethoxy)-benzamide, $R_f$ (ethyl acetate)=0.11; HPLC $R_t$=18.0 min.

c) From 200 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(4-acetylpiperazin-1-yl)-ethoxy]-benzamide, (2S,4S,5S,7S)-N-[4-(tert-butoxycarbonyl)amino-7-butylcarbamoyl-5-hydroxy-2-isopropyl-8-methyl-nonyl]-2-[2-(4-acetylpiperazin-1-yl)-ethoxy]-benzamide, $R_f$ (dichloromethane-methanol 4:1)=0.70; HPLC $R_t$=13.4 min.

d) From 54 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(morpholin-4-yl)-ethyl]-benzamide, (2S,4S,5S,7S)-N-[4-(tert-butoxycarbonyl)amino-7-butylcarbamoyl-5-hydroxy-2-isopropyl-8-methyl-nonyl]-2-[2-(morpholin-4-yl)-ethyl]-benzamide, $R_f$ (L)=0.38; HPLC $R_t$=15.7 min.

e) From 60 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(3-dimethylaminopropoxy)-benzamide, (2S,4S,5S,7S)-N-[4-(tert-butoxycarbonyl)amino-7-butylcarbamoyl-5-hydroxy-2-isopropyl-8-methyl-nonyl]-2-(3-dimethylaminopropoxy)-benzamide, $R_f$ (J)=0.65; HPLC $R_t$=14.3 min.

f) From 49 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[3-(morpholin-4-yl)-propoxy]-benzamide, (2S,4S,5S,7S)-N-[4-(tert-butoxycarbonyl)amino-7-butylcarbamoyl-5-hydroxy-2-isopropyl-8-methyl-nonyl]-2-[3-(morpholin-4-yl)-propoxy]-benzamide, $R_f$(W)=0.70; HPLC $R_t$=14.2 min.

g) From 65 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl)}-2-[2-(morpholin-4-yl)-ethoxy]-benzamide, (2S,4S,5S,7S)-N-[4-(tert-butoxycarbonyl)amino-7-butylcarbamoyl-5-hydroxy-2-isopropyl-8-methyl-nonyl]-2-[2-(morpholin-4-yl)-ethoxy]-benzamide, $R_f$ (H)=0.16; HPLC $R_t$=14.0 min.

h) From 135 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(4-methoxypiperidin-1-yl)-ethyl]-benzamide, (2S,4S,5S,7S)-N-[4-(tert-butoxycarbonyl)amino-7-butylcarbamoyl-5-hydroxy-2-isopropyl-8-methyl-nonyl]-2-[2-(4-methoxypiperidin-1-yl)-ethyl]-benzamide, $R_f$(ethyl acetate-methanol-conc. ammonia 90:15:5)=0.72; HPLC $R_t$=15.3 min.

i) From 165 mg of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-[2-(4-acetylpiperazin-1-yl)-ethyl]-benzamide, (2S,4S,5S,7S)-N-[4-(tert-butoxycarbonyl)amino-7-butyl carbamoyl-5-hydroxy-2-isopropyl-8-methyl-nonyl]-2-[2-(4-acetylpiperazin-1-yl)-ethyl]-benzamide, $R_f$(L)=0.45; HPLC $R_t$=13.9 min.

EXAMPLE 37

In a manner analogous to that described in Example 1a), the following compounds are prepared:

a) From 75 mg of (2S,4S,5S,7S)-N-[4-(tert-butoxycarbonyl)amino-7-butylcarbamoyl-5-hydroxy-2-isopropyl-8-methyl-nonyl]-2-(3-azidopropoxy)-benzamide, (2S,4S,5S,7S)-N-[4-(tert-butoxycarbonyl)amino-7-butylcarbamoyl-5-hydroxy-2-isopropyl-8-methyl-nonyl]-2-(3-aminopropoxy)-benzamide, $R_f$ (J)=0.18; HPLC $R_t$=13.8 min.

b) From 47 mg of (2S,4S,5S,7S)-N-[4-(tert-butoxycarbonyl)amino-7-butylcarbamoyl-5-hydroxy-2-isopropyl-8-methyl-nonyl]-2-(2-azidoethoxy)-benzamide, (2S,4S,5S,7S)-N-[4-(tert-butoxycarbonyl)amino-7-butylcarbamoyl-5-hydroxy-2-isopropyl-8-methyl-nonyl]-2-(2-aminoethoxy)-benzamide, $R_f$ (J)=0.25; HPLC $R_t$=13.4 min.

EXAMPLE 38

In a manner analogous to that described in Example 21), the following compounds are prepared by de-Bocylation:

a) From 58 mg of (2S,4S,5S,7S)-N-[4-(tert-butoxycarbonyl)amino-7-butylcarbamoyl-5-hydroxy-2-isopropyl-8-methyl-nonyl]-2-(3-aminopropoxy)-benzamide, (2S,4S,5S,7S)-N-(4-amino-7-butylcarbamoyl-5-hydroxy-2-isopropyl-8-methyl-nonyl)-2-(3-aminopropoxy)-benzamide dihydrochloride: $R_f$ (ethyl acetate-methanol-conc. ammonia 50:45:5)=0.15. HPLC $R_t$=8.8 min. MS(FAB) m/e 507 (M$^+$+1).

b) From 22 mg of (2S,4S,5S,7S)-N-[4-(tert-butoxycarbonyl)amino-7-butylcarbamoyl-5-hydroxy-2-isopropyl-8-methyl-nonyl]-2-(2-aminoethoxy)-benzamide, (2S,4S,5S,7S)-N-(4-amino-7-butylcarbamoyl-5-hydroxy-2-isopropyl-8-methyl-nonyl)-2-(2-aminoethoxy)-benzamide dihydrochloride: $R_f$(ethyl acetate-methanol-conc. ammonia 50:45:5)=0.14. HPLC $R_t$=8.4 min. MS(FAB) m/e 493 (M$^+$+1).

c) From 185 mg of (2S,4S,5S,7S)-N-[4-(tert-butoxycarbonyl)amino-7-butylcarbamoyl-5-hydroxy-2-isopropyl-8-methyl-nonyl]-2-[2-(4-acetylpiperazin-1-yl)-ethoxy]-benzamide, (2S,4S,5S,7S)-N-(4-amino-7-butylcarbamoyl-5-hydroxy-2-isopropyl-8-methyl-nonyl)-2-[2-(4-acetylpiperazin-1-yl)-ethoxy]-benzamide dihydrochloride: $R_f$(J)=0.35. HPLC $R_t$=10.0 min. MS(FAB) m/e 604 (M$^+$+1).

d) From 48 mg of (2S,4S,5S,7S)-N-[4-(tert-butoxycarbonyl)amino-7-butylcarbamoyl-5-hydroxy-2- isopropyl-8-methyl-nonyl]-2-[2-(morpholin-4-yl)-ethyl]-benzamide, (2S,4S,5S,7S)-N-(4-amino-7-butylcarbamoyl-5-hydroxy-2-isopropyl-8-methyl-nonyl)-2-[2-(morpholin-4-yl)-ethyl]-benzamide dihydrochloride: $R_f$ (J)=0.54. HPLC $R_f$=10.7 min. MS(FAB) m/e 547 (M$^+$+1).

e) From 32 mg of (2S,4S,5S,7S)-N-[4-(tert-butoxycarbonyl)amino-7-butylcarbamoyl-5-hydroxy-2-isopropyl-8-methyl-nonyl]-2-(3-dimethylaminopropoxy)-benzamide, (2S,4S,5S,7S)-N-(4-amino-7-butylcarbamoyl-5-hydroxy-2-isopropyl-8-methyl-nonyl)-2-(3-dimethylaminopropoxy)-benzamide dihydrochloride: $R_f$ (J)=0.31. HPLC $R_f$=9.2 min. MS(FAB) m/e 535 (M$^+$+1).

f) From 40 mg of (2S,4S,5S,7S)-N-[4-(tert-butoxycarbonyl)amino-7-butylcarbamoyl-5-hydroxy-2-isopropyl-8-methyl-nonyl]-2-[3-(morpholin-4-yl)-propoxy]-benzamide, (2S,4S,5S,7S)-N-(4-amino-7-butylcarbamoyl-5-hydroxy-2-isopropyl-8-methyl-nonyl)-2-[3-(morpholin-4-yl)-propoxy]-benzamide dihydrochloride: $R_f$ (W)=0.20. HPLC $R_f$=9.4 min. MS(FAB) m/e 577 (M$^+$+1).

g) From 53 mg of (2S,4S,5S,7S)-N-[4-(tert-butoxycarbonyl)amino-7-butylcarbamoyl-5-hydroxy-2-isopropyl-8-methyl-nonyl]-2-[2-(morpholin-4-yl)-ethoxy]-benzamide, (2S,4S,5S,7S)-N-(4-amino-7-butylcarbamoyl-5-hydroxy-2-isopropyl-8-methyl-nonyl)-2-[2-(morpholin-4-yl)-ethoxy]-benzamide dihydrochloride: $R_f$ (J)=0.54. HPLC $R_f$=9.3 min. MS(FAB) m/e 563 (M$^+$+1).

h) From 32 mg of (2S,4S,5S,7S)-N-[4-(tert-butoxycarbonyl)amino-7-butylcarbamoyl-5-hydroxy-2-isopropyl-8-methyl-nonyl]-2-[2-(4-methoxypiperidin-1-yl)-ethyl]-benzamide, (2S,4S,5S,7S)-N-(4-amino-7-butylcarbamoyl-5-hydroxy-2-isopropy-8-methyl-nonyl)-2-[2-methoxypiperidin-1-yl)-ethyl]-benzamide dihydrochloride: $R_f$ (ethyl acetate-methanol-conc. ammonia 90:15:5)=0.29. HPLC $R_f$=10.4 min. MS(FAB) m/e 575 (M$^+$+1).

i) From 137 mg of (2S,4S,5S,7S)-N-[4-(tert-butoxycarbonyl)amino-7-butyl carbamoyl-5-hydroxy-2-isopropyl-8-methyl-nonyl]-2-[2-(4-acetylpiperazin-1-yl)-ethyl]-benzamide, (2S,4S,5S,7S)-N-(4-amino-7-butylcarbamoyl-5-hydroxy-2-isopropyl-8-methyl-nonyl)-2-[2-(4-acetylpiperazin-1-yl)-ethyl]-benzamide dihydrochloride: $R_f$ (ethyl acetate-methanol-conc. ammonia 90:15:5)=0.19. HPLC $R_f$=9.5 min. MS(FAB) m/e 588 (M$^+$+1).

EXAMPLE 39

Triethylamine (117 μl) and cyanophosphonic acid diethyl ester (137 μl) are added dropwise in succession at 0° C., with stirring, to a solution of (2S,2'S,2"S,4"S)-2-[2-azido-2'-(4"-isopropyl-5"-oxo-tetrahydrofuran-2"-yl)-ethyl]-3-methylbutyric acid (208 mg) (Case 4-19919/P1) in dichloromethane (17 ml). The reaction mixture is stirred for a further 10 minutes at 0° C. and then a solution of 2-(3-methoxypropoxy)-benzylamine (164 mg) in dichloromethane (2 ml) is added dropwise. The mixture is stirred for a further 16 hours at room temperature and is then diluted with dichloromethane (100 ml), and the organic phase is washed with 10% citric acid solution (50 ml), saturated sodium hydrogen carbonate solution (50 ml) and saturated sodium chloride solution (50 ml). The aqueous phases are each back-extracted with dichloromethane (2×50 ml). The combined organic phases are dried over magnesium sulfate and concentrated by evaporation and the residue is purified by FC (18 g of silica gel, eluant E), yielding (2S,2'S,2"S,4"S)-2-[2'-azido-2'-(4"-isopropyl-5"-oxo-tetrahydrofuran-2"-yl)-ethyl]-N-[2-(3-methoxypropoxy)-benzyl]-3-methylbutyric acid amide, $R_f$(E)=0.32; HPLC $R_f$=18.0 min; MS(FAB) m/e 475 (M$^+$+1), in the form of a light-yellow oil.

EXAMPLE 40

In a manner analogous to that described in Example 39), the following compounds are prepared:

a) From 208 mg of (2S,2'S,2"S,4"S)-2-[2'-azido-2'-(4"-isopropyl-5"-oxo-tetrahydrofuran-2"-yl)-ethyl]-3-methylbutyric acid and 164 mg of 3-(3-methoxypropoxy)-benzylamine, (2S,2"S,2"S,4"S)-2-[2'-azido-2'-(4"-isopropyl-5"-oxo-tetrahydrofuran-2"-yl)-ethyl]-N-[3-(3-methoxypropoxy)-benzyl]-3-methylbutyric acid amide, $R_f$ (hexane-ethyl acetate-glacial acetic acid 66:33:1)=0.17; MS(FAB) m/e 475 (M$^+$+1), in the form of a yellow oil.

b) From 210 mg of (2S,2'S,2"S,4"S)-2-[2'-azido-2'-(4"-isopropyl-5"-oxo-tetrahydrofuran-2"-yl)-ethyl]-3-methylbutyric acid and 177 mg of 2-(4-methoxybutoxy)-benzylamine, (2S,2'S,2"S,4"S)-2-[2'-azido-2'-(4"-isopropyl-5"-oxo-tetrahydrofuran-2"-yl)-ethyl-N-[2-(4-methoxybutoxy)-benzyl]-3-methylbutyric acid amide, $R_f$ (hexane-ethyl acetate-glacial acetic acid 66:33:1)=0.2; HPLC $R_f$=18.3 min; MS(FAB) m/e 489 (M$^+$+1), in the form of a light-yellow oil.

c) From 194 mg of (2S,2'S,2"S,4"S)-2-[2'-azido-2'-(4"-isopropyl-5"-oxo-tetrahydrofuran-2"-yl)-ethyl]-3-methylbutyric acid and 175 mg of 2-(5-methoxypentoxy)-benzylamine, (2S,2'S,2"S,4"S)-2-[2'-azido-2'-(4"-isopropyl-5"-oxo-tetrahydrofuran-2"-yl)-ethyl]-N-[2-(5-methoxypentoxy)-benzyl]-3-methylbutyric acid amide, $R_f$ (hexane-ethyl acetate-glacial acetic acid 66:33:1)=0.38; HPLC $R_f$=19.1 min; MS(FAB) m/e 503 (M$^+$+1), in the form of a colourless oil.

EXAMPLE 41

A solution of (2S,2'S,2"S,4"S)-2-[2'-azido-2'-(4"-isopropyl-5"-oxo-tetrahydrofuran-2"-yl)-ethyl]-N-[2-(3-methoxypropoxy)-benzyl]-3-methylbutyric acid amide (100 mg) in n-butylamine (0.5 ml) is stirred at 50°–55° C. for 16 hours and is then concentrated to dryness by evaporation. Purification of the residue by FC (5.5 g of silica gel, eluant F) yields (2S,4S,5S,7S)-N-[4-azido-5-hydroxy-2,7-diisopropyl-octanedioic acid 8-butylamide 1-[2-(3-methoxypropoxy)-benzyl]amide, $R_f$ (F)=0.14; MS(FAB) m/e 548 (M$^+$+1), in the form of a colourless oil.

EXAMPLE 42

In a manner analogous to that described in Example 41), the following compounds are prepared:

a) From 150 mg of (2S,2'S,2"S,4S)-2-[2'-azido-2'-(4"-isopropyl-5"-oxo-tetrahydrofuran-2"-yl)-ethyl]-N-[3-(3-methoxypropoxy)-benzyl]-3-methylbutyric acid amide, (2S,4S,5S,7S)-N-[4-azido-5-hydroxy-2,7-diisopropyl-octanedioic acid 8-butylamide 1-[3-(3-methoxypropoxy)-benzyl]amide, $R_f$ (F)=0.28; MS(FAB) m/e 548 (M$^+$+1), in the form of a yellow oil.

b) From 282 mg of (2S,2'S,2"S,4S)-2-[2'-azido-2'-(4"-isopropyl-5"-oxo-tetrahydrofuran-2"-yl)-ethyl]-N-[2-(4-methoxybutoxy)-benzyl]-3-methylbutyric acid amide, (2S,4S,5S,7S)-N-[4-azido-5-hydroxy-2,7-diisopropyl-octanedioic acid 1-[2-(4-methoxybutoxy)-benzyl]amide, $R_f$ (F)=0.21; HPLC $R_f$=17.6 min; MS(FAB) m/e 562 (M$^+$+1), in the form of a light-yellow foam.

c) From 274 mg of (2S,2'S,2"S,4S)-2-[2'-azido-2'-(4"-isopropyl-5"-oxo-tetrahydrofuran-2"-yl)-ethyl]-N-[2-(5-methoxypentyloxy)-benzyl]-3-methylbutyric acid amide, (2S,4S,5S,7S)-N-[4-azido-5-hydroxy-2,7-diisopropyl-octanedioic acid 8-butylamide 1-[2-(5-methoxypentyloxy)-benzyl]amide, $R_f$ (F)=0.5; HPLC $R_t$=18.3 min; MS(FAB) m/e 576 (M$^+$+1), in the form of a light-yellow oil.

EXAMPLE 43

A solution of (2S,4S,5S,7S)-N-[4-azido-5-hydroxy-2,7-diisopropyl-octanedioic acid 8-butylamide 1-[2-(3-methoxypropoxy)-benzyl]amide (38 mg) in methanol (8 ml) is hydrogenated for 4 hours at room temperature and under normal pressure in the presence of 10% Pd/C (20 mg), the pH being kept at a constant value of 6 by the addition of 0.1N methanolic hydrochloric acid solution. The reaction mixture is then filtered over kieselguhr and concentrated by evaporation. The residue is dissolved twice in a small amount of toluene and is again concentrated by evaporation; one drop of 4N hydrochloric acid solution in dioxane is then added and concentration by evaporation is carried out again under a high vacuum. Purification of the crude product by FC (1.4 g of silica gel, eluant L) yields (2S,4S,5S,7S)-4-amino-5-hydroxy-2,7-diisopropyl-octanedioic acid 8-butylamide 1-[2-(3-methoxypropoxy)-benzyl]amide hydrochloride in the form of a yellowish amorphous powder: $R_f$ (dichloromethane-methanol 8:2)=0.37; HPLC $R_t$=12.8 min; MS(FAB) m/e 522 (M$^+$+1).

EXAMPLE 44

In a manner analogous to that described in Example 43), the following compounds are prepared:

a) From 135 mg of (2S,4S,5S,7S)-N-[4-azido-5-hydroxy-2,7-diisopropyl-octane dioic acid 8-butyliamide 1-[3-(3-methoxypropoxy)-benzyl]amide, (2S,4S,5S,7S)-4-amino-5-hydroxy-2,7-diisopropyl-octanedioic acid 8-butylamide 1-[3-(3-methoxy propoxy)-benzyl]amide hydrochloride in the form of a yellowish amorphous solid: $R_f$ (dichloromethane-methanol 8:2)=0.62; HPLC $R_t$=12.4 min; MS(FAB) m/e 522 (M$^+$+1).

b) From 234 mg of (2S,4S,5S,7S)-N-[4-azido-5-hydroxy-2,7-diisopropyl-octanedioic acid 8-butylamide 1-[2-(4-methoxybutoxy)-benzyl]amide, (2S,4S,5S,7S)-4-amino-5-hydroxy-2,7-diisopropyl-octanedioic acid 8-butylamide 1-[2-(4-methoxy butoxy)-benzyl]amide hydrochloride in the form of a colourless amorphous powder: $R_f$(L)=0.27; HPLC $R_t$=13.2 min; MS(FAB) m/e 536 (M$^+$+1).

c) From 228 mg of (2S,4S,5S,7S)-N-[4-azido-5-hydroxy-2,7-diisopropyl-octanedioic acid 8-butylamide 1-[2-(5-methoxypentyloxy)-benzyl]amide, (2S,4S,5S,7S)-4-amino-5-hydroxy-2,7-diisopropyl-octanedioic acid 8-butylamide 1-[2-(5-methoxypentyloxy)-benzyl]amide hydrochloride in the form of a yellowish amorphous powder: $R_f$ (L)=0.33; HPLC $R_t$=13.2 min; MS(FAB) m/e 550 (M$^+$+1).

EXAMPLE 45

Reaction of (3S,5S,1'S,3'S)-5-[3'-aminomethyl-1l'-(tert-butoxycarbonyl)amino-4'-methylpentyl]-3-isopropyl-dihydrofuran-2-one (100 mg) with 3-(4-methoxybutoxy)-terephthalic acid N-(methyl)amide (119 mg) in a manner analogous to that described in Example 1) yields (2S,2'S,2"S,4"S)-N1-{2-[2'-(tert-butoxycarbonyl)amino-2'-(4"-isopropyl-5"-oxo-tetrahydrofuran-2"-yl)-ethyl]-3-methylbutyl}-N4-methyl-2-(4-methoxybutoxy)-terephthalamide, $R_f$(L)=0.59; MS(FAB) m/e 620 (M$^+$+1), in the form of an amorphous white powder.

EXAMPLE 46

In a manner analogous to that described in Example 45), the following compounds are prepared:

a) From 400 mg of (3S,5S,1'S,3'S)-5-[3'-aminomethyl-1'-(tert-butoxycarbonyl)amino-4'-methylpentyl]-3-isopropyl-dihydrofuran-2-one and 546 mg of 3-(4-methoxybutoxy)-terephthalic acid (tert-butyl) ester, (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-3-(4-methoxybutoxy)-terephthalamic acid (tert-butyl) ester, $R_f$ (E)=0.48; MS(FAB) m/e 664 (M$^+$+1), in the form of a slightly yellowish oil.

b) From 100 mg of (3S,5S,1'S,3'S)-5-[3'-aminomethyl-1'-(tert-butoxycarbonyl)amino-4'-methylpentyl]-3-isopropyl-dihydrofuran-2-one and 160 mg of 3-(4-methoxybutoxy)-terephthalic acid N-[2-morpholin-4-yl)-ethyl]amide, (2S,2'S,2"S,4"S)-N1-{2-[2'-(tert-butoxycarbonyl)amino-2'-(4"-isopropyl-5"-oxo-tetrahydrofuran-2"-yl)-ethyl]-3-methylbutyl}-N4-[2-morpholin-4-yl)-ethyl]-2-(4-methoxybutoxy)-terephthaldiamide, $R_f$ (L)=0.63; MS(FAB) m/e 719 (M$^+$+1), in the form of a yellowish oil.

c) From 120 mg of (3S,5S, 1'S,3'S)-5-[3'-aminomethyl-1'-(tert-butoxycarbonyl)amino-4'-methylpentyl]-3-isopropyl-dihydrofuran-2-one and 135 mg of 3-(4-methoxybutoxy)-terephthalic acid monoamide, (2S,2'S,2"S,4"S)-N1-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-terephthaldiamide, $R_f$ (L)=0.58; MS(FAB) m/e 606 (M$^+$+1), in the form of a yellow amorphous powder.

The terephthalic acid derivatives used as starting materials are prepared in accordance with customary methods from the literature, unless described otherwise in greater detail below:

A) 2-(4-Methoxybutoxy)-N-methyl-terephthalamic acid: Alkaline hydrolysis of 300 mg of 2-(4-methoxybutoxy)-N-methyl-terephthalamic acid methyl ester in the manner described in Example 30) yields the title compound, $R_f$ (L)=0.15, in the form of a white powder.

a) 2-(4-Methoxybutoxy)-N-methyl-terephthalamic acid methyl ester: 2-(4-Methoxybutoxy)-terephthalic acid 1-methyl ester (564 mg) and thionyl chloride (3 ml) are stirred under reflux for one hour. The acid chloride obtained after concentration by evaporation is dissolved in tetrahydrofuran (5 ml) and added in metered amounts at −10° C. to a 40% aqueous methylamine solution (5 ml). When the addition is complete, the solvent is concentrated by evaporation and the residue is partitioned between ethyl acetate and a 2N aqueous hydrochloric acid solution. The organic phase is separated off, washed with water, dried over magnesium sulfate and concentrated by evaporation. Purification by FC (eluant Q) yields the title compound, $R_f$(N)=0.55, in the form of a yellowish amorphous powder.

b) 2-(4-Methoxybutoxy)-terephthalic acid 1-methyl ester: Alkaline hydrolysis of 2-(4-methoxybutoxy)-terephthalic acid dimethyl ester (5 g) in the manner described in Example 16a) yields the title compound, $R_f$(L)=0.32, in the form of a white powder.

c) 2-(4-Methoxybutoxy)-terephthalic acid dimethyl ester: Alkylation of 2-hydroxy-terephthalic acid dimethyl ester (10 g) with 4-methoxybutyl bromide in anhydrous acetone in the presence of dried potassium carbonate and potassium iodide in a manner analogous to that described in Example 16a) yields the title compound, $R_f$ (B)=0.20, in the form of a slightly yellowish oil.

B) 2-(4-Methoxybutoxy)-terephthalic acid 4-tert-butyl ester 1-methyl ester: 1,1'-Carbonyldiimidazole (1.65 g) is added to a solution of 2-(4-methoxybutoxy)-terephthalic acid 1-methyl ester (2.8 g) in N,N-dimethylformamide (10 ml), and the mixture is stirred at 40° C. for one hour. After the addition of tert-butanol (1.48 g) and 1,8-diazabicyclo[5.4.0]undec-7-ene (1.52 g), stirring is continued at 40° C. for 24 hours and the reaction mixture is then concentrated by evaporation. The residue is partitioned between ethyl acetate and water and the organic phase is separated off, dried over magnesium sulfate and concentrated by evaporation. Purification by FC (eluant B) yields the title compound, $R_f$ (B)=0.3, in the form of a yellowish oil.

C) 2-(4-Methoxybutoxy)-N-(2-morpholin-4-ylethyl)-terephthalamic acid: Alkaline hydrolysis of 300 mg of 2-(4-methoxybutoxy)-N-(2-morpholin-4-ylethyl)-terephthalamic acid methyl ester in the manner described in Example 16a) yields the title compound, $R_f$(L)=0.33, in the form of a white powder.

a) 2-(4-Methoxybutoxy)-N-(2-morpholin-4-ylethyl)-terephthalamic acid methyl ester: Reaction of 500 mg of 2-(4-methoxybutoxy)-terephthalic acid 1-methyl ester with thionyl chloride and then reaction with a solution of 4-(2-aminoethyl)-morpholine and triethylamine in dichlormethane, in a manner analogous to that described in Example 46Aa), yield the title compound, $R_f$(L)=0.6, in the form of a white amorphous powder.

D) 2-(4-Methoxybutoxy)-terephthalamic acid: Alkaline hydrolysis of 2-(4-methoxybutoxy)-terephthalamic acid methyl ester (300 mg) in the manner described in Example 16a) yields the title compound, $R_f$ (dichloromethane-methanol-acetic acid-water 90:10:0.5:1)=0.33, in the form of a white powder.

a) 2-(4-Methoxybutoxy)-terephthalamic acid methyl ester: Reaction of 2-(4-methoxy butoxy)-terephthalic acid 1-methyl ester (500 mg) with thionyl chloride and then reaction with 25% aqueous ammonia, in a manner analogous to that described in Example 46Aa), yield the title compound, $R_f$(N)=0.38, in the form of a white amorphous powder.

EXAMPLE 47

In a manner analogous to that described in Example 18), the following compounds are prepared by lactone opening:

a) From 100 mg of (2S,2'S,2"S,4"S)-N1-{2-[2'-(tert-butoxycarbonyl)amino-2'-(4"-isopropyl-5"-oxo-tetrahydrofuran-2"-yl)-ethyl]-3-methylbutyl}-N4-methyl-2-(4-methoxybutoxy)-terephthaldiamide, (2S,4S,5S,7S)-N1-(4-(tert-butoxycarbonyl)amino-7-butylcarbamoyl-5-hydroxy-2-isopropyl-8-methyl-nonyl]-N4-methyl-2-(4-methoxybutoxy)-terephthaldiamide, $R_f$(L)=0.34; MS(FAB) m/e 693 (M⁺+1), in the form of a white amorphous powder.

b) From 200 mg of (2S,2'S,2"S,4"S)-N1-{2-[2'-(tert-butoxycarbonyl)amino-2'-(4"-isopropyl-5"-oxo-tetrahydrofuran-2"-yl)-ethyl]-3-methylbutyl}-3-(4-methoxybutoxy)-terephthalamic acid (tert-butyl) ester, (2S,4S,5S,7S)-N1-(4-(tert-butoxycarbonyl) amino-7-butylcarbamoyl-5-hydroxy-2-isopropyl-8-methyl-nonyl]-3-(4-methoxybutoxy)-terephthalamic acid (tert-butyl) ester, $R_f$ (E)=0.20; MS(FAB) m/e 737 (M⁺+1), in the form of a yellow oil.

c) From 170 mg of (2S,2'S,2"S,4"S)-N1-{2-[2'-(tert-butoxycarbonyl)amino-2'-(4"-isopropyl-5"-oxo-tetrahydrofuran-2"-yl)-ethyl]-3-methylbutyl}-N4-[(2-morpholin-4-yl)-ethyl]-2-(4-methoxybutoxy)-terephthaldiamide, (2S,4S,5S,7S)-N-(4-(tert-butoxycarbonyl)amino-7-butylcarbamoyl-5-hydroxy-2-isopropyl-8-methyl-nonyl]-N4-[2-morpholin-4-yl)-ethyl]-2-(4-methoxybutoxy)-terephthaldiamide, $R_f$ (L)=0.43; MS(FAB) m/e 792 (M⁺+1), in the form of a yellow amorphous powder.

d) From 200 mg of (2S,2'S,2"S,4"S)-N1-{2-[2'-(tert-butoxycarbonyl)amino-2'-(4"isopropyl-5"-oxo-tetrahydrofuran-2"-yl)-ethyl]-3-methylbutyl}-2-(4-methoxybutoxy)-terephthaldiamide, (2S,4S,5S,7S)-N1-[4-(tert-butoxycarbonyl)amino-7-butylcarbamoyl-5-hydroxy-2-isopropyl-8-methyl-nonyl]-2-(4-methoxybutoxy)-terephthaldiamide, $R_f$(L)=0.38; MS(FAB) m/e 679 (M⁺+1).

EXAMPLE 48

In a manner analogous to that described in Example 21), the following compounds are obtained by de-Bocylation:

a) From 100 mg of (2S,4S,5S,7S)-N1-[4-(tert-butoxycarbonyl)amino-7-butylcarbamoyl-5-hydroxy-2-isopropyl-8-methyl-nonyl]-N4-methyl-2-(4-methoxybutoxy)-terephthaldiamide, (2S,4S,5S,7S)-N1-(4-amino-7-butylcarbamoyl-5-hydroxy-2-isopropyl-8-methyl-nonyl)-N4-methyl-2-(4-methoxybutoxy)-terephthaldiamide hydrochloride: $R_f$ (L)=0.13. HPLC $R_t$=11.6 min. MS(FAB) m/e 593 (M⁺+1).

b) From 170 mg of (2S,4S,5S,7S)-N1-(4-(tert-butoxycarbonyl)amino-7-butylcarbamoyl-5-hydroxy-2-isopropyl-8-methyl-nonyl]-N4-[(2-morpholin-4-yl)-ethyl]-2-(4-methoxybutoxy)-terephthaldiamide, (2S,4S,5S,7S)-N1-(4-amino-7-butylcarbamoyl-5-hydroxy-2-isopropyl-8-methyl-nonyl)-N4-[2-morpholin-4-yl)-ethyl]-2-(4-methoxybutoxy)-terephthaldiamide dihydrochloride: HPLC $R_t$=9.73 min. MS(FAB) m/e 692 (M⁺+1).

c) From 175 mg of (2S,4S,5S,7S)-N1-(4-(tert-butoxycarbonyl)amino-7-butylcarbamoyl-5-hydroxy-2-isopropyl-8-methyl-nonyl]-2-(4-methoxybutoxy)-terephthalic acid diamide, (2S,4S,5S,7S)-N1-(4-amino-7-butylcarbamoyl-5-hydroxy-2-isopropyl-8-methyl-nonyl)-2-(4-methoxybutoxy)-terephthalic acid diamide hydrochloride: $R_f$ (L)=0.1. HPLC $R_t$=11.0 min. MS(FAB) m/e 579 (M⁺+1).

EXAMPLE 49

Reaction of (2S,4S,5S,7S)-N1-[4-(tert-butoxycarbonyl)amino-7-butylcarbamoyl-5-hydroxy-2-isopropy-8-methylnonyl]-3-(4-methoxybutoxy)-terephthalamic acid (tert-butyl) ester (205 mg) in 3 ml of a 1:1 mixture of dichloromethane and trifluoroacetic acid at 0° C. yields (2S,4S,5S,7S)-N4-(4-amino-7-butylcarbamoyl-5-hydroxy-2-isopropyl-8-methyl-nonyl)-3-(4-methoxybutoxy)-terephthalamic acid trifluoroacetate: HPLC $R_t$=11.9 min MS(FAB) m/e 580 (M⁺+1).

EXAMPLE 50

In a manner analogous to that described in Example 21), reaction of (2S,4S,5S,7S)-N-[4-(tert-butoxycarbonyl)amino-7-butylcarbamoyl-5-hydroxy-2-isopropyl-8-methyl-nonyl]-4-butylcarbamoylmethoxy-2-(4-methoxybutoxy)-benzamide (80 mg) in 4N hydrochloric acid solution in dioxane at 0° C. for one hour, rapid concentration of the solvent under a high vacuum and lyophilisation yield (2S,4S,5S,7S)-N-(4-amino-7-butylcarbamoyl-5-hydroxy-2-isopropyl-8-methyl-nonyl)-4-butylcarbamoylmethoxy-2-(4-methoxybutoxy)-benzamide hydrochloride: $R_f$ (W)=0.23. HPLC $R_t$=13.8 min. MS(FAB) m/e 665 (M⁺+1).

The (2S,4S,5S,7S)-N-[4-(tert-butoxycarbonyl)amino-7-butyl carbamoyl-5-hydroxy-2-isopropyl-8-methyl-nonyl]-4-butylcarbamoylmethoxy-2-(4-methoxybutoxy)-benzamide used as starting material is prepared as follows:

a) A solution of (2S,2'S,2"S,4"S)-4-{2-[2'-(tert-butoxycarbonyl)amino-2'-(4"-isopropyl-5"-oxotetrahydrofuran-2"-yl)-ethyl]-3-methylbutylcarbamoyl}-3-(4-methoxybutoxy)-phenoxy)-acetic acid (tert-butyl) ester (239 mg) in n-butylamine (3 ml) is stirred at 50° C. for 18 hours. The reaction mixture is concentrated and the residue is chromatographed (FC on 50 g of silica gel, eluant T). There are obtained (2S,4S,5S,7S)-N-[4-(tert-butoxycarbonyl)amino-7-butylcarbamoyl-5-hydroxy-2-isopropyl-8-methyl-nonyl]-4-butylcarbamoylmethoxy-2-(4-methoxybutoxy)-benzamide (83 mg; $R_f$ (W)=0.46; HPLC $R_t$=18.7 min) and 94 mg of (2S,4S,5S,7S)-{4-[4-(tert-butoxycarbonyl)amino-7-butylcarbamoyl-5-hydroxy-2-isopropyl-8-methyl-nonylcarbamoyl]-3-(4-methoxybutoxy)-phenoxy}-acetic acid (tert-butyl) ester ($R_f$ (W)=0.50; HPLC $R_t$=20.1 min), as well as 26 mg of a mixed fraction of the two products.

b) (2S,2'S,2"S,4"S)-4-{2-[2'-(tert-Butoxycarbonyl) amino-2'-(4"-isopropyl-5"-oxo-tetrahydrofuran-2"-yl)-ethyl]-3-methylbutylcarbamoyl}-3-(4-methoxybutoxy)-phenoxy)-acetic acid (tert-butyl) ester: tert-Butyl bromoacetate (76 µl) and caesium carbonate (169 mg) are added at room temperature to a solution of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-hydroxy-2-(4-methoxybutoxy)-benzamide (200 mg) in acetone (10 ml). The white suspension is stirred under reflux for 2 hours, cooled and then filtered, and the filtrate is concentrated. Drying under a high vacuum yields the title compound in the form of a yellow oil (255 mg). $R_f$(L)=0.73. HPLC $R_t$=19.9 min.

c) (2S,2'S,2"S,4"S)-N-{2-[2'-(tert-Butoxycarbonyl) amino-2'-(4"-isopropyl-5"-oxo-tetrahydrofuran-2"-yl)-ethyl]-3-methylbutyl}-4-hydroxy-2-(4-methoxybutoxy)-benzamide: (2S,2'S,2"S,4"S)-N-{2-[2'-(tert-Butoxycarbonyl)amino-2'-(4"-isopropyl-5"-oxo-tetrahydrofuran-2"-yl)-ethyl]-3-methylbutyl}-4-benzyloxy-2-(4-methoxybutoxy)-benzamide (2.46 g), dissolved in ethyl acetate (60 ml), is hydrogenated for 15 hours at room temperature in the presence of 5% Pd/C (Degussa) (250 mg). Filtration over Celite 545 and concentration of the filtrate yield the title compound (2.05 g). $R_f$ (L)=0.47. HPLC $R_t$=16.0 min.

d) (2S,2'S,2"S,4"S)-N-{2-[2'-(tert-Butoxycarbonyl) amino-2'-(4"-isopropyl-5"-oxo-tetrahydrofuran-2"-yl)-ethyl]-3-methylbutyl}-4-benzyloxy-2-(4-methoxybutoxy)-benzamide: Reaction of (3S,5S,1'S,3'S)-5-[3'-aminomethyl-1'-(tert-butoxycarbonyl)amino-4'-methylpentyl]-3isopropyldihydrofuran-2-one (3.33 g) with 4-benzyloxy-2-(4-methoxybutoxy)-benzoic acid (3.70 g) in a manner analogous to that described in Example 1) and then purification by FC (eluant Q) yield the title compound, $R_f$ (L)=0.79, in the form of an oil.

The 4-benzyloxy-2-(4-methoxybutoxy)-benzoic acid used as starting material is prepared as follows:

a) 4-Benzyloxy-2-(4-methoxybutoxy)-benzoic acid: The title compound is obtained in the form of a pale-yellow oil, $R_f$ (G)=0.38, by alkaline hydrolysis of 4-benzyloxy-2-(4-methoxybutoxy)-benzoic acid methyl ester.

b) 4-Benzyloxy-2-(4-methoxybutoxy)-benzoic acid methyl ester: A 30% methanolic sodium methoxide solution (21 ml) is added dropwise under reflux over a period of 30 minutes to a solution of 4-benzyloxy-2-(4-bromobutoxy)-benzoic acid methyl ester (29.6 g) in anhydrous methanol (250 ml), and the mixture is stirred overnight. After cooling, the mixture is concentrated to half its volume, water (50 ml) is added, and the pH is adjusted to 2 by the addition of 1M potassium hydrogen sulfate solution. Extraction with dichloromethane and purification of the crude product by FC (2 kg of silica gel, hexane-ethyl acetate 7:1) yield the title compound in the form of a solid (18.8 g): $R_f$ (C)=0.24. M.p. 72°–74° C.

c) 4-Benzyloxy-2-(4-bromobutoxy)-benzoic acid methyl ester: 4-Benzyloxy-2-hydroxybenzoic acid methyl ester (20.0 g) (prepared in accordance with the procedure described in J. Med. Chem. (1985), 28, 717–727) and 1,4-dibromobutane (91.2 ml), dissolved in acetone (200 ml), are stirred under reflux for 30 hours in the presence of anhydrous powdered potassium carbonate (16.0 g). After filtration and concentration, the crude product is purified by FC (400 g of silica gel, eluant A). The title compound is obtained in the form of a yellowish solid (29.7 g): $R_f$ (C)=0.35.

EXAMPLE 51

After reaction of (2S,4S,5S,7S)-{4-[4-(tert-butoxycarbonyl)amino-7-butylcarbamoyl-5-hydroxy-2-isopropyl-8-methyl-nonylcarbamoyl]-3-(4-methoxybutoxy)-phenoxy}-acetic acid (tert-butyl) ester (93 mg) in a 4N hydrochloric acid solution in dioxane (2 ml) at 0° C. for 45 minutes and then at room temperature for 13 hours, the solvent is rapidly concentrated under a high vacuum with vigorous stirring until frozen and is subsequently removed by lyophilisation. (2S,4S,5S,7S)-[4-(4-Amino-7-butylcarbamoyl-5-hydroxy-2-isopropyl-8-methyl-nonylcarbamoyl)-3-(4-methoxybutoxy)-phenoxy]-acetic acid is obtained: HPLC $R_t$=11.7 min. MS(FAB) m/e 610 (M$^+$+1).

EXAMPLE 52

In a manner analogous to that described in Example 21), 85 mg of (2S,4S,5S,7S)-N-{4-(tert-butoxycarbonyl)amino-7-[2-(morpholin-4-yl)-ethylcarbamoyl]-5-hydroxy-2-isopropyl-8-methyl-nonyl}-2-(4-methoxybutoxy)-4-[2-(morpholin-4-yl)-ethylcarbamoylmethoxy]-benzamide yield (2S,4S,5S,7S)-N-{4-amino-5-hydroxy-2-isopropyl-8-methyl-7-[2-(morpholin-4-yl)-ethylcarbamoyl]-nonyl}-2-(4-methoxybutoxy)-4-[2-(morpholin-4-yl)-ethylcarbamoylmethoxy]-benzamide trihydrochloride: $R_f$ (W)=0.07. HPLC $R_t$=7.69 min. HRMS(FAB) m/e 779.5264.

The (2S,4S,5S,7S)-N-{4-(tert-butoxycarbonyl)amino-7-[2-(morpholin-4-yl)-ethylcarbamoyl]-5-hydroxy-2-isopropyl-8-methyl-nonyl}-2-(4-methoxybutoxy)-4-[2-(morpholin-4-yl)-ethylcarbamoylmethoxy]-benzamide used as starting material is prepared as follows:

a) A solution of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-carbamoylmethoxylbenzamide (98 mg) in N-(2-aminoethyl)morpholine (0.5 ml) is stirred overnight at 80° C. The reaction mixture is then immediately chromatographed on 25 g of silica gel (eluant gradient from P to L). The title compound, $R_f$ (W)=0.41; HPLC $R_t$=9.85 min; MS(FAB) m/e 880 (M$^+$+1), is obtained in the form of a yellowish foam.

b) (2S,2'S,2"S, 4"S )-N-{2-[2'-(tert-Butoxycarbonyl) amino-2'-(4"-isopropyl-5"-oxo-tetrahydrofuran-2"-yl)-ethyl]-3-methylbutyl}-2-(4-methoxybutoxy)-4-carbamoylmethoxylbenzamide: A mixture of (2S,2'S,2"S, 4"S)-N-{2-[2'-(tert-butoxycarbonyl)amino-2'-(4"-isopropyl-5"-oxo-tetrahydrofuran-2"-yl)-ethyl]-3-methylbutyl}-4-hydroxy-2-(4-methoxybutoxy)-benzamide (200 mg), 2-bromoacetamide (72 mg) and caesium carbonate (169 mg) in anhydrous acetone (10 ml) is stirred under reflux for 2 hours. After cooling, filtration is carried out, the filtrate is concentrated and the residue is dried under a high vacuum. 169 mg of the title compound, $R_f$(L)=0.59; MS(FAB) m/e 636 (M$^+$+1), are obtained in the form of a white solid.

EXAMPLE 53

In a manner analogous to that described in Example 21), reaction of (2S,4S,5S,7S)-N-[4-(tert-butoxycarbonyl) amino-7-butylcarbamoyl-5-hydroxy-2-isopropyl-8-methyl-nonyl]-2-(4-methoxybutoxy)-4-(1H-tetrazol-5-ylmethoxy)-benzamide (88 mg) in a 4N hydrochloric acid solution in dioxane at 0° C. for 6 hours, rapid concentration of the solvent under a high vacuum and lyophilisation yield (2S,4S,5S,7S)-N-(4-amino-7-butylcarbamoyl-5-hydroxy-2-isopropyl-8-methyl-nonyl)-2-(4-methoxybutoxy)-4-(1H-tetrazol-5-ylmethoxy)-benzamide hydrochloride: $R_f$ (W)=0.06. HPLC $R_t$=11.5 min. MS(FAB) m/e 634 (M$^+$+1).

The (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(1H-tetrazol-5-ylmethoxy)-benzamide used as starting material is prepared as follows:

a) From (2S,2'S,2"S,4"S)-N-{2-[2'-(tert-butoxycarbonyl) amino-2'-(4"-isopropyl-5"-oxo-tetrahydrofuran-2"-yl)-ethyl]-3-methylbutyl}-2-(4-methoxybutoxy)-4-(1H-tetrazol-5-ylmethoxy)-benzamide (104 mg) in a manner analogous to that described in Example 18), by reaction in n-butylamine at 50° C. for 20 hours. The reaction mixture is concentrated and the residue is taken up in dichloromethane (50 ml). The organic phase is washed with ice-water (pH 4), and the aqueous phase is back-extracted twice with dichloromethane. The combined organic phases are washed with saturated sodium chloride solution and dried over magnesium sulfate and the solvent is removed in vacuo. Drying under a high vacuum yields (2S,4S,5S,7S)-N-[4-(tert-butoxycarbonyl)amino-7-butylcarbamoyl-5-hydroxy-2-isopropyl-8-methyl-nonyl]-2-(4-methoxybutoxy)-4-(1H-tetrazol-5-ylmethoxy)-benzamide, $R_f$ (dichloromethane-methanol-glacial acetic acid 9:1:0.1)=0.31, in the form of a yellowish solid.

b) (2S,2'S,2"S,4"S)-N-{2-[2'-(tert-Butoxycarbonyl) amino-2'-(4"-isopropyl-5"-oxo-tetrahydrofuran-2"-yl)-ethyl]-3-methylbutyl}-2-(4-methoxybutoxy)-4-(1H-tetrazol-5-ylmethoxy)-benzamide: The title compound, $R_f$ (W)=0.32, is obtained in the form of a solid from (3S,5S,1'S,3'S)-5-[3'-aminomethyl-1'-(tert-butoxycarbonyl)amino-4'-methylpentyl]-3-isopropyl-dihydrofuran-2-one (80 mg) and 2-(4-methoxybutoxy)-4-(1H-tetrazol-5-ylmethoxy)-benzoic acid (145 mg) after purification of the crude product by FC on 25 g of silica gel (eluant: dichloromethane-methanol-glacial acetic acid 95:5:1; mixed fractions are chromatographed repeatedly under the same conditions or with dichloromethane-methanol-conc. ammonia 95:5:1).

The 2-(4-methoxybutoxy)-4-(1H-tetrazol-5-ylmethoxy)-benzoic acid used as starting material is prepared as follows:

a) 2-(4-Methoxybutoxy)-4-(1H-tetrazol-5-ylmethoxy)-benzoic acid methyl ester (1.0 g) is hydrolysed with 1N sodium hydroxide solution (3.6 ml) in methanol (10 ml) and water (5 ml). The reaction mixture is diluted with dichloromethane (50 ml) and the aqueous phase is adjusted to pH 2 with a 1M potassium hydrogen sulfate solution. Extraction is carried out repeatedly with dichloromethane, the combined organic phases are washed with saturated sodium chloride solution and dried over magnesium sulfate, and the solvent is removed. The title compound (780 g), $R_f$ (dichloromethane-methanol-glacial acetic acid 40:10:1)= 0.61, is obtained in the form of a white powder.

b) 2-(4-Methoxybutoxy)-4-(1H-tetrazol-5-ylmethoxy)-benzoic acid methyl ester: A mixture of 2-(4-methoxybutoxy)-4-(cyanomethoxy)-benzoic acid methyl ester (1.0 g), sodium azide (1.02 g) and ammonium chloride (0.84 g) in absolute N,N-dimethylformamide (30 ml) is stirred overnight at 135° C. The brown suspension is concentrated and the residue is purified by FC (80 g of silica gel, eluant: dichloromethane-methanol-conc. ammonia 40:10:1). The title compound, $R_f$ (dichloromethane-methanol-glacial acetic acid 40:10:1)=0.71; $R_f$ (dichloromethane-methanol-conc. ammonia 40:10:1)=0.29, is obtained in the form of a brown oil.

c) 2-(4-Methoxybutoxy)-4-(cyanomethoxy)-benzoic acid methyl ester: The title compound is obtained in the form of an oil, $R_f$ (E)=0.38, from 4-hydroxy-2-(4-methoxybutoxy)-benzoic acid methyl ester (3.0 g), chloroacetonitrile (1.9 ml) and caesium carbonate (5.8 g) in a manner analogous to that described in Example 30Ba).

EXAMPLE 54

Cyanophosphonic acid diethyl ester (26 µl) and 2-aminopropionic acid N,N-(dimethyl)amide (26 mg) are added at 0° C., with stirring, to a solution of (2S,4S,5S,7S)-5-(tert-butoxycarbonyl)amino-4-(tert-butyl) dimethylsilyloxy-2-isopropyl-7-{[2-(4-methoxybutoxy)-benzoylamino]-methyl}-8-methyl-nonanoic acid (100 mg) and triethylamine (48 µl) in N,N-dimethylformamide (4 ml). After 30 minutes, the mixture is allowed to warm to room temperature and stirring is continued overnight. The mixture is concentrated and the residue is taken up in ethyl acetate. After washing the organic phase with 10% citric acid solution, saturated sodium hydrogen carbonate solution and saturated sodium chloride solution, drying over magnesium sulfate and concentration are carried out. Purification by FC (25 g of silica gel, eluant V) yields (2S,4S,5S,7S)-N-(4-(tert-butoxycarbonyl)amino-5-(tert-butyl)-dimethylsilyloxy-7-[2-(dimethylaminocarbamoyl)-ethylcarbamoyl]-2-isopropyl-8-methyl-nonyl)-2-(4-methoxybutoxy)-benzamide, $R_f$ (dichloromethane-methanol-conc. ammonia 95:5:1)=0.21; MS(FAB) m/e 794 (M$^+$+1), in the form of a yellow oil.

The (2S,4S,5S,7S)-5-(tert-butoxycarbonyl)amino-4-(tert-butyl)dimethylsilyloxy-2-isopropyl-7-{[2-(4-methoxybutoxy)-benzoylamino]-methyl}-8-methyl-nonanoic acid used as starting material is prepared as follows:

a) (2S,4S,5S,7S)-5-(tert-Butoxycarbonyl)amino-4-(tert-butyl)dimethylsilyloxy-2-isopropyl-7-{[2-(4-methoxybutoxy)-benzoylamino]-methyl}-8-methyl-nonanoic acid: A solution of (2S,4S,5S,7S)-5-(tert-butoxycarbonyl)amino-4-hydroxy-2-isopropyl-7-{[2-(4-methoxybutoxy)-benzoylamino]-methyl}-8-methyl-nonanoic acid (2.96 g), tert-butyldimethylsilyl chloride (1.69 g) and imidazole (1.46 g) in N,N-dimethylformamide (30 ml) is stirred at room temperature for 3 days. Then the reaction mixture is concentrated and the residue is partitioned between ice-water and ethyl acetate. After extraction of the aqueous phase with ethyl acetate, the ice-cold organic phase is washed with 10% citric acid solution, saturated sodium hydrogen carbonate solution and water, dried over magnestrated. The crude concentrated. The crude silyl ester (3.81 g, yellow oil) is stirred overnight at room temperature in a mixture of tetrahydrofuran (15 ml), water (6 ml) and glacial acetic acid (15 ml). Concentration of the reaction mixture and customary working-up by extraction with ethyl acetate yield a yellow oil, from which the title compound (2.01 g) is obtained in the form of a foamy solid, R_f (E)=0.32; MS(FAB) m/e 695 (M⁺+1), after FC (400 g of silica gel, elution first with eluant gradient from D to F, then complete elution of the product with eluant L).

b) (2S,4S,5S,7S)-5-(tert-Butoxycarbonyl)amino-4-hydroxy-2-isopropyl-7-{[2-(4-methoxybutoxy)-benzoylamino]-methyl}-8-methyl-nonanoic acid: 21.6 ml of a 1M lithium hydroxide solution are added to a solution of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-benzamide (3.04 g) in a 2:1 mixture of 1,2-dimethoxyethane-water (150 ml), and the reaction mixture is stirred at room temperature for one hour. After removal of the ether in a rotary evaporator (bath temperature 85° C.), the mixture is acidified with ice-cold 10% citric acid solution (45 ml) and extraction is carried out with dichloromethane. The organic phase is dried over magnesium sulfate and concentrated in vacuo at room temperature. 2.96 g of the title compound, R_f (L)=0.26, are obtained in the form of a pale-yellow foamy solid.

EXAMPLE 55

In a manner analogous to that described in Example 54), the following compounds are prepared:

a) From 100 mg of (2S,4S,5S,7S)-5-(tert-butoxycarbonyl) amino-4-(tert-butyl)dimethylsilyloxy-2-isopropyl-7-{[2-(4-methoxybutoxy)-benzoylamino]-methyl}-8-methyl-nonanoic acid and 24 mg of 3-aminobutyric acid amide, with subsequent purification by FC (eluant gradient from U to dichloromethane-methanol-conc. ammonia 95:5:1), (2S,4S,5S,7S)-N-(4-(tert-butoxycarbonyl)amino-5-(tert-butyl) dimethylsiyloxy-7-(3-carbamoylpropylcarbamoyl)-2-isopropyl-8-methyl-nonyl)-2-(4-methoxybutoxy)-benzamide, R_f (W)=0.48, in the form of a yellow oil.

b) From 100 mg of (2S,4S,5S,7S)-5-(tert-butoxycarbonyl)amino-4-(tert-butyl)dimethylsilyloxy-2-isopropyl-7-{[2-(4-methoxybutoxy)-benzoylamino]-methyl}-8-methyl-nonanoic acid and 26.3 mg of 3-amino-2,2-dimethylpropionic acid amide, (2S,4S,5S,7S)-N-(4-(tert-butoxycarbonyl)amino-5-(tert-butyl)dimethylsilyloxy-7-(2-carbamoyl-2-methylpropylcarbamoyl)-2-isopropyl-8-methyl-nonyl)-2-(4-methoxybutoxy)-benzamide, R_f (W)= 0.59, in the form of a colourless oil.

c) From 100 mg of (2S,4S,5S,7S)-5-(tert-butoxycarbonyl) amino-4-(tert-butyl)dimethylsilyloxy-2-isopropyl-7-{[2-(4-methoxybutoxy)-benzoylamino]-methyl}-8-methyl-nonanoic acid and 48 mg of 3-aminopropionic acid N-(morpholine)amide hydrochloride, (2S,4S,5S,7S)-N-{4-(tert-butoxycarbonyl)amino-5-(tert-butyl)dimethylsilyloxy-2-isopropyl-8-methyl-7-[3-(morpholin-4-yl)-3-oxo-propylcarbamoyl]-nonyl}-2-(4-methoxybutoxy)-benzamide, R_f (W)=0.62, in the form of a colourless oil.

d) From 100 mg of (2S,4S,5S,7S)-5-(tert-butoxycarbonyl)amino-4-(tert-butyl)dimethylsilyloxy-2-isopropyl-7-{[2-(4-methoxybutoxy)-benzoyliamino]-methyl}-8-methyl-nonanoic acid and 41 mg of 1-[4-(2-aminoethyl)-piperidin-1-yl]-ethanone, (2S,4S,5S,7S)-N-{7-[2-(4-acetylpiperidin-1-yl)-ethylcarbamoyl]-4-(tert-butoxycarbonyl)amino-5-(tert-butyl)dimethylsilyloxy-2-isopropyl-8-methyl-nonyl}-2-(4-methoxybutoxy)-benzamide, R_f (W)=0.58, in the form of an oil.

e) From 100 mg of (2S,4S,5S,7S)-5-(tert-butoxycarbonyl) amino-4-(tert-butyl)dimethylsilyloxy-2-isopropyl-7-{[2-(4-methoxybutoxy)-benzoylamino]-methyl}-8-methyl-nonanoic acid and 31 mg of 2-aminoethyl-thiomorpholine, with purification by FC (25 g of silica gel, eluant T), (2S,4S,5S,7S)-N-[7-(2-thiomorpholin-4-ylethylcarbamoyl)-4-(tert-butoxycarbonyl)amino-5-(tert-butyl) dimethylsilyloxy-2-isopropyl-8-methyl-nonyl]-2-(4-methoxybutoxyl-benzamide, R_f (dichloromethane-methanol-conc. ammonia 95:5:1)=0.36, in the form of an oil.

EXAMPLE 56

In a manner analogous to that described in Example 54), (2S,4S,5S,7S)-5-(tert-butoxycarbonyl)amino-4-(tert-butyl) dimethylsilyloxy-2-isopropyl-7-{[2-(4-methoxybutoxy)-4-[2-(morpholin-4-yl)-ethoxy)-benzoylamino]-methyl}-8-methyl-nonanoic acid (258 mg), cyanophosphonic acid diethyl ester (0.138 ml), 3-amino-2,2-dimethylpropionic acid amide hydrochloride (139 mg) and triethylamine (0.20 ml) in anhydrous N,N-dimethylformamide (10 ml) are reacted. Purification by FC (eluant V) yields (2S,4S,5S,7S) -N-(4-(tert-butoxycarbonyl)amino-5-(tert-butyl) dimethylsilyloxy-7-(2-carbamoyl-2-methylpropylcarbamoyl)-2-isopropyl-8-methyl-nonyl)-2-(4-methoxybutoxy)-4-(2-morpholin-4-ylethoxy)-benzamide, R_f (W)=0.50, in the form of a white solid.

The (2S,4S,5S,7S)-5-(tert-butoxycarbonyl)amino-4-(tert-butyl)dimethylsilyloxy-2-isopropyl-7-{[2-(4-methoxybutoxy)-4-(2-morpholin-4-ylethoxy)-benzoylamino]-methyl}-8-methyl-nonanoic acid used as starting material is prepared as follows:

a) (2S,4S,5S,7S)-5-(tert-Butoxycarbonyl)amino-4-(tert-butyl)dimethylsilyloxy-2-isopropyl-7-{[2-(4-methoxybutoxyl-4-(2-morpholin-4-ylethoxy)-benzoylamino]-methyl}-8-methyl-nonanoic acid: In a manner analogous to that described in Example 54a), (2S,4S,5S,7S)-5-(tert-butoxycarbonyl)amino-4-hydroxy-2-isopropyl-7-{[2-(4-methoxybutoxy)-4-(2-morpholin-4-ylethoxy)-benzoylamino]-methyl}-8-methyl-nonanoic acid (629 mg), tert-butyldimethylsilyl chloride (294 mg) and imidazole (253 mg) in anhydrous N,N-dimethylformamide (5 ml) are stirred at room temperature for 5 days. Working-up yields 611 mg of a yellowish oil, which is dissolved in a 2:1 mixture of tetrahydrofuran-water (4 ml) and glacial acetic acid (3 ml) and is stirred overnight at room temperature. Concentration of the reaction mixture and working-up by extraction with ethyl acetate yield 920 mg of the title compound, R_f (W)=0.26, in the form of a yellow oil.

b) (2S,4S,5S,7S)-5-(tert-Butoxycarbonyl)amino-4-hydroxy-2-isopropyl-7-{[2-(4-methoxybutoxy)-4-(2-morpholin-4-ylethoxy)-benzoylamino]-methyl}-8-methyl-nonanoic acid: In a manner analogous to that described in Example 54b), (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-4-(2-morpholin-4-ylethoxy)-benzamide (622 mg) (Example 30b), dissolved in 30 ml of a 2:1 mixture of 1,2-dimethoxyethane-water, is reacted with a 1M lithium hydroxide solution (3.6 ml). Working-up yields the title compound (630 mg) in the form of a pale-yellow foamy solid, R_f (L)=0.29, which is immediately reacted further.

EXAMPLE 57

Reaction of (2S,4S,5S,7S)-5-(tert-butoxycarbonyl) amino-7-aminomethyl-4-(tert-butyl)dimethylsilyloxy-2-isopropyl-8-methyl-nonanoic acid N-(2-carbamoyl-2-methylpropyl)amide (100 mg) and 2-(4-methoxybutoxy)-4-(morpholin-4-ylmethyl)-benzoic acid (116 mg) in a manner analogous to that described in Example 15) and purification by FC (30 g of silica gel, eluant T) yield (2S,4S,5S,7S)-N-(4-(tert-butoxycarbonyl)amino-5-(tert-butyl)

dimethylsilyloxy-7-(2-carbamoyl-2-methylpropylcarbamoyl)-2-isopropyl-8-methyl-nonyl)-2-(4-methoxybutoxy)-4-(morpholin-4-ylmethyl)-benzamide, $R_f$ (W)=0.57, in the form of a white solid.

The (2S,4S,5S,7S)-5-(tert-butoxycarbonyl)amino-7-aminomethyl-4-(tert-butyl)dimethylsilyloxy-2-isopropyl-8-methyl-nonanoic acid N-(2-carbamoyl-2-methylpropyl) amide used as starting material is prepared as follows:

a) After hydrogenation of (2S,4S,5S,7S)-5-(tert-butoxycarbonyl)amino-7-azidomethyl-4-(tert-butyl) dimethylsilyloxy-2-isopropyl-8-methyl-nonanoic acid N-(2-carbamoyl-2-methylpropyl)amide (534 mg), dissolved in ethyl acetate (30 ml), for 5 hours at room temperature in the presence of 10% Pd/C (106 mg), filtration is carried out over Celite 545, the filtrate is concentrated and the crude product so obtained is hydrogenated again for 24 hours in the presence of fresh catalyst (106 mg of 10% Pd/C). Purification by FC (25 g of silica gel, eluant gradient dichloromethane-methanol-conc. ammonia from 94:6:1 to T) yields (2S,4S,5S,7S)-5-(tert-butoxycarbonyl)amino-7-aminomethyl-4-(tert-butyl)dimethylsilyloxy-2-isopropyl-8-methyl-nonanoic acid N-(2-carbamoyl-2-methylpropyl) amide, $R_f$ (W)=0.28, in the form of a white solid.

b) (2S,4S,5S,7S)-5-(tert-Butoxycarbonyl)amino-7-azidomethyl-4-(tert-butyl)dimethylsilyloxy-2-isopropyl-8-methyl-nonanoic acid N-(2-carbamoyl-2-methylpropyl) amide: Reaction of (2S,4S,5S,7S)-5-(tert-butoxycarbonyl) amino-7-azidomethyl-4-(tert-butyl)dimethylsilyloxy-2-isopropyl-8-methyl-nonanoic acid (490 mg) with 3-amino-2,2-dimethylpropionic acid amide hydrochloride (290 mg) in a manner analogous to that described in Example 56) and purification by FC (50 g of silica gel, eluant T) yield the title compound, $R_f$ (W)=0.67; MS(FAB) m/e 613 (M$^+$+1), in the form of a white solid.

c) (2S,4S,5S,7S)-5-(tert-Butoxycarbonyl)amino-7-azidomethyl-4-(tert-butyl)dimethylsilyloxy-2-isopropyl-8-methyl-nonanoic acid is obtained in a manner analogous to that described in Examples 54a) and 54b) from 500 mg of (3S,5S,1'S,3'S)-5-[3'-azidomethyl-1'-(tert-butoxycarbonyl) amino-4'-methylpentyl]-3-isopropyl-dihydrofuran-2-one (Example 15b) via (2S,4S,5S,7S)-5-(tert-butoxycarbonyl) amino-7-azidomethyl-4-hydroxy-2-isopropyl-8-methyl-nonanoic acid ($R_f$(L)=0.43) after purification by FC (50 g of silica gel, eluant Q), in the form of a white solid (which contains a small amount of starting material on account of re-lactonisation): $R_f$ (L)=0.64.

EXAMPLE 58

Reaction of (2S,4S,5S,7S)-5-(tert-butoxycarbonyl) amino-7-aminomethyl-4-(tert-butyl)dimethylsilyloxy-2-isopropyl-8-methyl-nonanoic acid N-(2-carbamoyl-2-methylpropyl)amide (100 mg) and 2-(2-morpholin-4-ylethoxy)-benzoic acid (89 mg) in a manner analogous to that described in Example 54) and purification by FC yield (2S,4S,5S,7S)-N-[4-(tert-butoxycarbonyl)amino-5-(tert-butyl)dimethylsilyloxy-7-(2-carbamoyl-2-methylpropylcarbamoyl)-2-isopropyl-8-methyl-nonyl]-2-(2-morpholin-4-ylethoxy)-benzamide in the form of an oil: $R_f$(L)=0.40; HPLC $R_t$=17.3 min.

EXAMPLE 59

Tetrabutylammonium fluoride trihydrate (31 mg) is added to a solution of (2S,4S,5S,7S)-N-(4-(tert-butoxycarbonyl) amino-5-(tert-butyl)dimethylsilyloxy-7-[2-(dimethylaminocarbamoyl)-ethylcarbamoyl]-2-isopropyl-8-methyl-nonyl)-2-(4-methoxybutoxy)-benzamide (71 mg) in anhydrous N,N-dimethylformamide (5 ml), and the mixture is stirred overnight at room temperature. The reaction mixture is concentrated and the residue is partitioned between saturated sodium hydrogen carbonate solution (20 ml) and ethyl acetate (30 ml). The aqueous phase is separated off and extracted with ethyl acetate, and the combined organic phases are washed with saturated sodium chloride solution, dried over magnesium sulfate and concentrated. FC (25 g of silica gel, eluant 0) yields (2S,4S,5S,7S)-N-[4-(tert-butoxycarbonyl)amino-7-[2-(dimethylaminocarbamoyl)-ethylcarbamoyl]-5-hydroxy-2-isopropyl-8-methyl-nonyl)-2-(4-methoxybutoxy)-benzamide, $R_f$ (N)=0.32, in the form of a yellowish oil.

EXAMPLE 60

In a manner analogous to that described in Example 59), the following compounds are prepared by removal of the silyloxy-protecting group:

a) From 76 mg of (2S,4S,5S,7S)-N-(4-(tert-butoxycarbonyl)amino-5-(tert-butyl)dimethylsilyloxy-7-(3-carbamoylpropylcarbamoyl)-2-isopropyl-8-methyl-nonyl)-2-(4-methoxybutoxy)-benzamide, with purification by FC (25 g of silica gel, eluant gradient from N to L), (2S,4S,5S,7S)-N-[4-(tert-butoxycarbonyl)amino-7-(3-carbamoylpropylcarbamoyl)-5-hydroxy-2-isopropyl-8-methyl-nonyl)-2-(4-methoxybutoxy)-benzamide, $R_f$ (L)= 0.45, in the form of an oil.

b) From 66 mg of (2S,4S,5S,7S)-N-(4-(tert-butoxycarbonyl)amino-5-(tert-butyl)dimethylsilyloxy-7-(2-carbamoyl-2-methylpropylcarbamoyl)-2-isopropyl-8-methyl-nonyl)-2-(4-methoxybutoxy)-benzamide, (2S,4S,5S,7S)-N-[4-(tert-butoxycarbonyl)amino-7-(2-carbamoyl-2-methylpropylcarbamoyl)-5-hydroxy-2-isopropyl-8-methyl-nonyl)-2-(4-methoxybutoxy)-benzamide, $R_f$ (L)= 0.48, in the form of an oil.

c) From 101 mg of (2S,4S,5S,7S)-N-{4-(tert-butoxycarbonyl)amino-5-(tert-butyl)dimethylsilyloxy-2-isopropyl-8-methyl-7-[3-(morphoin-4-yl)-3-oxo-propylcarbamoyl]-nonyl}-2-(4-methoxybutoxy)-benzamide, (2S,4S,5S,7S)-N-{4-(tert-butoxycarbonyl) amino-5-hydroxy-2-isopropyl-8-methyl-7-[3-(morpholin-4-yl)-3-oxo-propylcarbamoyl]-nonyl}-2-(4-methoxybutoxy)-benzamide, $R_f$(W)=0.54; HPLC $R_t$=15.7 min, in the form of an oil.

d) From 134 mg of (2S,4S,5S,7S)-N-{7-[2-(4-acetylpiperidin-1-yl)-ethylcarbamoyl]-4-tert-butoxycarbonyl)amino-5-(tert-butyl)dimethylsilyloxy-2-isopropyl-8-methyl-nonyl}-2-(4-methoxybutoxy)-benzamide, (2S,4S,5S,7S)-N-{7-[2-(4-acetylpiperidin-1-yl)-ethylcarbamoyl]-4-(tert-butoxycarbonyl)amino-5-hydroxy-2-isopropyl-8-methyl-nonyl}-2-(4-methoxybutoxy)-benzamide, $R_f$(W)=0.46; HPLC $R_t$=17.1 min, in the form of a white solid.

e) From 76 mg of (2S,4S,5S,7S)-N-[4-(tert-butoxycarbonyl)amino-5-(tert-butyl)dimethylsilyloxy-2-isopropyl-8-methyl-7-(2-thiomorpholin-4-ylethylcarbamoyl)-nonyl]-2-(4-methoxybutoxy)-benzamide, (2S,4S,5S,7S)-N-[4-(tert-butoxycarbonyl) amino-5-hydroxy-2-isopropyl-8-methyl-7-(2-thiomorpholin-4-ylethylcarbamoyl)-nonyl]-2-(4-methoxybutoxy)-benzamide, $R_f$ (N)=0.28; HPLC $R_t$=14.7 min, in the form of an oil.

f) From 150 mg of (2S,4S,5S,7S)-N-(4-(tert-butoxycarbonyl)amino-5-(tert-butyl)dimethylsilyloxy-7-(2-carbamoyl-2-methylpropylcarbamoyl)-2-isopropyl-8-methyl-nonyl)-2-(4-methoxybutoxy)-4-(2-morpholin-4- ylethoxy)-benzamide, (2S,4S,5S,7S)-N-[4-(tert-butoxycarbonyl)amino-7-(2-carbamoyl-2-methylpropylcarbamoyl)-5-hydroxy-2-isopropyl-8-methyl-nonyl)-2-(4-methoxybutoxy)-4-(2-morpholin-4-ylethoxy)-benzamide, R$_f$(W)=0.40, in the form of an oil.

g) From 116 mg of (2S,4S,5S,7S)-N-(4-(tert-butoxycarbonyl)amino-5-(tert-butyl)dimethylsilyloxy-7-(2-carbamoyl-2-methylpropylcarbamoyl)-2-isopropyl-8-methyl-nonyl)-2-(4-methoxybutoxy)-4-(morpholin-4-ylmethyl)-benzamide, (2S,4S,5S,7S)-N-[4-(tert-butoxycarbonyl)amino-7-(2-carbamoyl-2-methylpropylcarbamoyl)-5-hydroxy-2-isopropyl-8-methyl-nonyl)-2-(4-methoxybutoxy)-4-(morpholin-4-ylmethyl)-benzamide, R$_f$(W)=0.33; HPLC R$_t$=11.5 min, in the form of an oil.

h) From 96 mg of (2S,4S,5S,7S)-N-[4-(tert-butoxycarbonyl)amino-5-(tert-butyl)dimethylsilyloxy-7-(2-carbamoyl-2-methylpropylcarbamoyl)-2-isopropyl-8-methyl-nonyl]-2-(4-methoxybutoxy)-4-(2-morpholin-4-ylethoxy)-benzamide, (2S,4S,5S,7S)-N-[4-(tert-butoxycarbonyl)-amino-7-(2-carbamoyl-2-methylpropylcarbamoyl)-5-hydroxy-2-isopropyl-8-methyl-nonyl]-2-(2-morpholin-4-ylethoxy)-benzamide, R$_f$ (L)= 0.35; HPLC R$_t$=11.6 min, in the form of an oil.

EXAMPLE 61

In a manner analogous to that described in Example 21), 71 mg of (2S,4S,5S,7S,2'R)-N-[4-(tert-butoxycarbonyl) amino-7-(2'-methylcarbamoyl-propylcarbamoyl)-5-hydroxy-2-isopropyl-8-methyl-nonyl]-2-(4-methoxybutoxy)-benzamide yield (2S,4S,5S,7S,2'R)-N-[4-amino-7-(2'-methylcarbamoyl-propylcarbamoyl)-5-hydroxy-2-isopropyl-8-methyl-nonyl]-2-(4-methoxybutoxy)-benzamide hydrochloride: R$_f$ (W)=0.33. HPLC R$_t$=12.7 min. MS(FAB) m/e 579 (M$^+$+1).

The (2S,4S,5S,7S,2'R)-N-[4-(tert-butoxycarbonyl)amino-7-(2'-methylcarbamoyl-propylcarbamoyl)-5-hydroxy-2-isopropyl-8-methyl-nonyl]-2-(4-methoxybutoxy)-benzamide used as starting material is prepared as follows:

a) In a manner analogous to that described in Example 59), (2S,4S,5S,7S,2'R)-N-[4-(tert-butoxycarbonyl)amino-(tert-butyl)dimethylsilyloxy-7-(2'-methylcarbamoyl-propylcarbamoyl)-2-isopropyl-8-methyl-nonyl]-2-(4-methoxybutoxy)-benzamide (132 mg) and tetrabutyl-ammonium fluoride trihydrate (52 mg) in N,N-dimethylformamide (5 ml) are stirred at room temperature for 20 hours. Aqueous working-up and purification by FC (25 g of silica gel, eluant V) yield (2S,4S,5S,7S,2'R)-N-[4-(tert-butoxycarbonyl)amino-7-(2'-methylcarbamoylpropylcarbamoyl)-5-hydroxy-2-isopropyl-8-methyl-nonyl]-2-(4-methoxybutoxy)-benzamide, R$_f$(W)= 0.51; HPLC R$_t$=17.6 min, in the form of a colourless foam.

b) (2S,4S,5S,7S,2'R)-N-[4-(tert-Butoxycarbonyl)amino-(tert-butyl)dimethylsilyloxy-7-(2'-methylcarbamoyl-propylcarbamoyl)-2-isopropyl-8-methyl-nonyl]-2-(4-methoxybutoxy)-benzamide: A solution of (2R,2'S,4'S,5"S, 7"S)-3-{5'-(tert-butoxycarbonyl)amino-4'-(tert-butyl)-dimethylsilyloxy-2'-isopropyl-7'-[2-(4-methoxybutoxy)-benzylcarbamoyl]-8-methyl-nonanoyl-amino}-2-methylpropionic acid methyl ester (150 mg) in a 33% ethanolic methylamine solution (6 ml) is stirred at 40° C. for 40 hours. After concentration of the reaction mixture, the residue is purified by FC (eluant W). The title compound, R$_f$ (W)=0.54, is obtained in the form of a yellow oil.

c) (2R,2'S,4'S,5'S,7'S)-3-{5'-(tert-Butoxycarbonyl) amino-4'-(tert-butyl)dimethylsilyloxy-2'-isopropyl-7'-[2-(4-methoxybutoxy)-benzylcarbamoyl]-8-methyl-nonanoylamino}-2-methylpropionic acid methyl ester: In a manner analogous to that described in Example 54), (2S, 4S,5S,7S)-5-(tert-butoxycarbonyl)amino-4-(tert-butyl) dimethylsilyloxy-2-isopropyl-7-{[2-(4-methoxybutoxy)-benzoylamino]-methyl}-8-methyl-nonanoic acid (800 mg), (2R)-3-amino-2-methyl-propionic acid methyl ester hydrochloride (112 mg), cyanophosphonic acid diethyl ester (110 µl) and triethylamine (204 µl) in N,N-dimethylformamide (10 ml) are reacted. The reaction mixture is concentrated and the residue is taken up in ethyl acetate. The organic phase is washed with 1M citric acid solution, saturated sodium hydrogen carbonate solution and saturated sodium chloride solution, dried over magnesium sulfate and concentrated. Purification of the crude product by FC (80 g of silica gel, eluant S) yields the title compound, R$_f$(W)=0.82, in the form of an oil.

EXAMPLE 62

In a manner analogous to that described in Example 21), the following compounds are prepared by de-Bocylation:

a) From 35 mg of (2S,4S,5S,7S)-N-[4-(tert-butoxycarbonyl)amino-7-[2-(dimethylaminocarbamoyl)-ethylcarbamoyl]-5-hydroxy-2-isopropyl-8-methyl-nonyl)-2-(4-methoxybutoxy)-benzamide, (2S,4S,5S,7S)-N-(4-amino-7-[2-(dimethylaminocarbamoyl)-ethylcarbamoyl]-5-hydroxy-2-isopropyl-8-methyl-nonyl)-2-(4-methoxybutoxy)-benzamide hydrochloride: R$_f$ (W)=0.26. HPLC R$_t$=11.5 min. MS(FAB) m/e 579 (M$^+$+1).

b) From 45 mg of (2S,4S,5S,7S)-N-[4-(tert-butoxycarbonyl)amino-7-(3-carbamoylpropylcarbamoyl)-5-hydroxy-2-isopropyl-8-methyl-nonyl]-2-(4-methoxybutoxy)-benzamide, (2S,4S,5S,7S)-N-[4-amino-7-(3-carbamoylpropylcarbamoyl)-5-hydroxy-2-isopropyl-8-methyl-nonyl]-2-(4-methoxybutoxy)-benzamide hydrochloride: R$_f$(W)=0.21. HPLC R$_t$=10.3 min. MS(FAB) m/e 565 (M$^+$+1).

c) From 46 mg of (2S,4S,5S,7S)-N-[4-(tert-butoxycarbonyl)amino-7-(2-carbamoyl-2-methylpropylcarbamoyl)-5-hydroxy-2-isopropyl-8-methyl-nonyl)-2-(4-methoxybutoxy)-benzamide, (2S,4S,5S,7S)-N-[4-amino-7-(2-carbamoyl-2-methylpropylcarbamoyl)-5-hydroxy-2-isopropyl-8-methyl-nonyl]-2-(4-methoxybutoxy)-benzamide hydrochloride: R$_f$ (W)=0.27. HPLC R$_t$=11.1 min. MS(FAB) m/e 579 (M$^+$+1).

d) From 65 mg of (2S,4S,5S,7S)-N-{4-(ted-butoxycarbonyl)amino-5-hydroxy-2-isopropyl-8-methyl-7-[3-(morpholin-4-yl)-3-oxo-propylcarbamoyl]-nonyl}-2-(4-methoxybutoxy)-benzamide, (2S,4S,5S,7S)-N-{4-amino-5-hydroxy-2-isopropyl-8-methyl-7-[3-(morpholin-4-yl)-3-oxo-propylcarbamoyl]-nonyl}-2-(4-methoxybutoxy)-benzamide hydrochloride: R$_f$(W)=0.25. HPLC R$_t$=11.3 min. MS(FAB) m/e 621 (M$^+$+1).

e) From 71 mg of (2S,4S,5S,7S)-N-{7-[2-(4-acetylpiperidin-1-yl)-ethylcarbamoyl]-4-(tert-butoxycarbonyl)amino-5-hydroxy-2-isopropyl-8-methyl-nonyl}-2-(4-methoxy butoxy)-benzamide, (2S,4S,5S,7S)-N-{7-[2-(4-acetylpiperidin-1-yl)-ethylcarbamoyl]-4-amino-5-hydroxy-2-isopropyl-8-methyl-nonyl}-2-(4-methoxybutoxy)-benzamide hydrochloride: R$_f$ (W)=0.29. HPLC R$_t$=12.7 min. MS(FAB) m/e 633 (M$^+$+1).

f) From 40 mg of (2S,4S,5S,7S)-N-[4-(tert-butoxycarbonyl)amino-5-hydroxy-2-isopropyl-8-methyl-7-(2-thiomorpholin-4-ylethylcarbamoyl)-nonyl]-2-(4-methoxybutoxy)-benzamide, (2S,4S,5S,7S)-N-[4-amino-5-hydroxy-2-isopropyl-8-methyl-7-(2-thiomorpholin-4- ylethylcarbamoyl)-methyl-nonyl]-2-(4-methoxybutoxy)-benzamide dihydrochloride: $R_f$ (W)=0.43. HPLC $R_t$=10.7 min. MS(FAB) m/e 609 (M$^+$+1).

g) From 102 mg of (2S,4S,5S,7S)-N-[4-(tert-butoxycarbonyl)amino-7-(2-carbamoyl-2-methylpropylcarbamoyl)-5-hydroxy-2-isopropyl-8-methyl-nonyl)-2-(4-methoxybutoxy)-4-(2-morpholin-4-ylethoxy)-benzamide, (2S,4S,5S,7S)-N-(4-amino-7-(2-carbamoyl-2-methylpropylcarbamoyl)-5-hydroxy-2-isopropyl-8-methyl-nonyl)-2-(4-methoxybutoxy)-4-(2-morpholin-4-ylethoxy-benzamide dihydrochloride: $R_f$ (W)=0.18. HPLC $R_t$=8.48 min. MS(FAB) m/e 708 (M$^+$+1).

h) From 78 mg of (2S,4S,5S,7S)-N-[4-(tert-butoxycarbonyl)amino-7-(2-carbamoyl-2-2-methylpropylcarbamoyl)-5-hydroxy-2-isopropy-8-methyl-nonyl)-2-(4-methoxybutoxy)-4-(morpholin-4-ylmethyl)-benzamide, (2S,4S,5S,7S)-N-(4-amino-7-(2-carbamoyl-2-methylpropylcarbamoyl)-5-hydroxy-2-isopropyl-8-methyl-nonyl)-2-(4-methoxybutoxy)-4-(morpholin-4-ylmethyl)-benzamide dihydrochloride: $R_f$ (W)=0.17. HPLC $R_t$=7.83 min. MS(FAB) m/e 678 (M$^+$+1).

i) From 62 mg of (2S,4S,5S,7S)-N-[4-(tert-butoxycarbonyl)amino-7-(2-carbamoyl-2-methylpropylcarbamoyl)-5-hydroxy-2-isopropyl-8-methyl-nonyl]-2-(2-morpholin-4-ylethoxy)-benzamide, (2S,4S,5S,7S)-N-[4-amino-7-(2-carbamoyl-2-methylpropylcarbamoyl)-5-hydroxy-2-isopropyl-8-methyl-nonyl]-2-(2-morpholin-4-ylethoxy)-benzamide dihydrochloride: $R_f$ (J)=0.20. HPLC $R_t$=7.0 min. MS(FAB) m/e 606 (M$^+$+1).

j) From 490 mg of (2S,4S,5S,7S)-N-{4-(tert-butoxycarbonyl)amino-5-hydroxy-2-isopropyl-7-[2-(4-methoxycarbonylpiperidin-1-yl)-ethylcarbamoyl]-8-methyl-nonyl}-2-(4-methoxybutoxy)-benzamide (Example 66), (2S,4S,5S,7S)-N-{4-amino-5-hydroxy-2-isopropyl-7-[2-(4-methoxycarbonylpiperidin-1-yl)-ethylcarbamoyl]-8-methyl-nonyl}-2-(4-methoxybutoxy)-benzamide hydrochloride: $R_f$ (W)=0.30. HPLC $R_t$=11.8 min. MS(FAB) m/e 649 (M$^+$+1).

EXAMPLE 63

A solution of (2S,4S,5S,7R)-N-{4-(tert-butoxycarbonyl)amino-5-hydroxy-2-isopropyl-7-[(2-morpholin-4-ylethyl)-carbamoyl]-octyl}-2-(3-methoxypropoxy)-benzamide (105 mg) in 4N hydrochloric acid solution in dioxane (4 ml) is stirred at 0° C. for one hour. The reaction mixture is then lyophilised. (2S,4S,5S,7R)-N-[4-Amino-5-hydroxy-2-methyl-7-[(2-morpholin-4-ylethyl)-carbamoyl]-octyl}-2-(3-methoxypropoxy)-benzamide dihydrochloride is obtained in the form of a beige powder: $R_f$ (dichloromethane-methanol 8:2)=0.28. HPLC $R_t$=7.73 min. MS(FAB) m/e 551 (M$^+$+1).

The (2S,4S,5S,7R)-N-{4-(tert-butoxycarbonyl)amino-5-hydroxy-2-isopropyl-7-[(2-morpholin-4-ylethyl)-carbamoyl]-octyl}-2-(3-methoxypropoxy)-benzamide used as starting material is prepared as follows:

a) (2S,4S,5S,7R)-N-{4-(tert-Butoxycarbonyl)amino-5-hydroxy-2-isopropyl-7-[(2-morpholin-4-ylethyl)-carbamoyl]-octyl}-2-(3-methoxypropoxy)-benzamide: A mixture of (2S,2S',2"S,4"R)-N-{2-[2'-(tert-butoxycarbonyl)amino-2'-(4"-isopropyl-5"-oxo-tetrahydrofuran-2"-yl)-ethyl]-3-methylbutyl}-2-(3-methoxypropoxy)-benzamide (104 mg) and 4-(2-aminoethyl)-morpholine (2 ml) is stirred at 80° C. for 2 hours. The excess 4-(2-aminoethyl)-morpholine is then distilled off and the evaporation residue is purified by FC (100 g of silica gel, eluant L). The title compound (110 mg) is obtained in the form of a white foam: $R_f$ (L)=0.36; HPLC $R_t$=12.1 min.

b) (2S,2'S,2"S,4"R)-N-{2-[2'-(tert-Butoxycarbonyl)amino-2'-(4"-isopropyl-5"-oxo-tetrahydrofuran-2"-yl)-ethyl]-3-methylbutyl}-2-(3-methoxypropoxy)-benzamide: p-Toluenesulfonic acid monohydrate (134 mg) is added at 0° C. to a solution of (2S,4S,5S,7R)-N-[4-(tert-butoxycarbonyl)amino-7-butylcarbamoyl-5-hydroxy-2-isopropyl-octyl]-2-(3-methoxypropoxy)-benzamide (380 mg) in chloroform (20 ml). The mixture is stirred at room temperature for 20 hours. The solvent is evaporated off and the residue is purified by FC (60 g of silica gel, eluant E). The title compound is obtained in the form of a colourless oil: $R_f$ (F)=0.36; HPLC $R_t$=17.1 min; MS(FAB) m/e 521 (M$^+$+1).

EXAMPLE 64

In a manner analogous to that described in Example 21), (2S,4S,5S,7S)-N-{4-amino-5-hydroxy-2-isopropyl-8-methyl-7-[2-(morpholin-4-yl)-ethylcarbamoyl]-nonyl}-4-carbamoylmethoxy-2-(4-methoxybutoxy)-benzamide dihydrochloride, $R_f$ (W)=0.23; HPLC $R_t$=9.81 min; MS(FAB) m/e 666 (M$^+$+1), is prepared from (2S,4S,5S,7S)-N-{4-(tert-butoxycarbonyl)amino-5-hydroxy-2-isopropyl-8-methyl-7-[2-(morpholin-4-yl)-ethylcarbamoyl]-nonyl}-4-carbamoylmethoxy-2-(4-methoxybutoxy)-benzamide (103 mg).

The (2S,4S,5S,7S)-N-{4-(tert-butoxycarbonyl)amino-5-hydroxy-2-isopropyl-8-methyl-7-[2-(morpholin-4-yl)-ethylcarbamoyl]-nonyl}-4-carbamoylmethoxy-2-(4-methoxybutoxy)-benzamide used as starting material is prepared as follows:

a) A mixture of (2S,4S,5S,7S)-N-{4-(tert-butoxycarbonyl)amino-5-hydroxy-2-isopropyl-8-methyl-7-[2-(morpholin-4-yl)-ethylcarbamoyl]-nonyl}-4-hydroxy-2-(4-methoxybutoxy)-benzamide (100 mg), 2-bromoacetamide (24 mg) and caesium carbonate (69 mg) in anhydrous acetone (5 ml) is stirred under reflux for 2 hours. The crude product obtained after filtration and concentration of the solvent is purified by FC on 25 g of silica gel (eluant gradient from V to dichloromethane-methanol-conc. ammonia 95:5:1). The title compound, $R_f$ (dichloromethane-methanol-conc. ammonia 95:5:1; double track)=0.24; HPLC $R_t$=13.7 min; MS(FAB) m/e 766 (M$^+$+1), is obtained in the form of a white solid.

b) (2S,4S,5S,7S)-N-{4-(tert-Butoxycarbonyl)amino-5-hydroxy-2-isopropyl-8-methyl-7-[2-(morpholin-4-yl)-ethylcarbamoyl]-nonyl}-4-hydroxy-2-(4-methoxybutoxy)-benzamide: A solution of (2S,4S,5S,7S)-N-{4-(tert-butoxycarbonyl)amino-5-hydroxy-2-isopropyl-8-methyl-7-[2-(morphoin-4-yl)-ethylcarbamoyl]-nonyl}-4-benzyloxy-2-(4-methoxybutoxy)-benzamide (0.86 g) in ethyl acetate (30 ml) is hydrogenated for 6 hours at room temperature in the presence of 5% Pd/C (Degussa) (170 mg). The crude product is purified by FC (eluant gradient from dichloromethane-methanol-conc. ammonia 96:4:1 to W), yielding the title compound (0.76 g) in the form of a white foamy solid: $R_f$ (L)=0.27.

c) (2S,4S,5S,7S)-N-{4-(tert-Butoxycarbonyl)amino-5-hydroxy-2-isopropyl-8-methyl-7-[2-(morpholin-4-yl)-ethylcarbamoyl]-nonyl}-4-benzyloxy-2-(4-methoxybutoxy)-benzamide: In a manner analogous to that described in Example 52a), the title compound, $R_f$(W)=0.50, is prepared by reaction of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-4-benzyloxy-2-(4-methoxybutoxy)-benzamide (0.79 g) in N-(2-aminoethyl)-morpholine (5 ml) and then purification by FC (eluant V).

EXAMPLE 65

A mixture of (2S,2'S,2"S,4"S)-N-{2-[2'-(tert-butoxycarbonyl)amino-2'-(4"-isopropyl-5"-oxo-tetrahydrofuran-2"-yl)-ethyl]-3-methylbutyl}-2-(4-methoxybutoxy)-benzamide (1.0 g), 1-[4-(2-aminoethyl)-piperidin-1-yl]-ethanone (0.91 g) and 2-hydroxypyridine (169 mg) in triethylamine (7.5 ml) is stirred at 80° C. for 16 hours (two phases). The upper phase is concentrated to approximately 25% of its volume, and the reaction mixture is stirred at 80° C. for a further 3 hours. After cooling, the mixture is diluted with dichloromethane and the organic phase is washed with saturated sodium hydrogen carbonate solution, dried over magnesium sulfate and concentrated. The crude product is purified by FC on silica gel (eluant V). (2S,4S,5S,7S)-N-{7-[2-(4-Acetylpiperidin-1-yl)-ethylcarbamoyl]-4-(tert-butoxycarbonyl)amino-5-hydroxy-2-isopropyl-8-methyl-nonyl}-2-(4-methoxybutoxy)-benzamide is obtained after lyophilisation from a solution in dioxane, in the form of a white powder: $R_f$ (W)=0.46.

EXAMPLE 66

In a manner analogous to that described in Example 65), the following compound is prepared:

a) From (2S,2'S,2"S,4"S)-N-{2-[2'-(tert-butoxycarbonyl) amino-2'-(4"-isopropyl-5"-oxo-tetrahydrofuran-2"-yl)-ethyl]-3-methylbutyl}-2-(4-methoxybutoxy)-benzamide (400 mg), 4-aminoethyl-1-methoxycarboxypiperidine (397 mg) and 2-hydroxypyridine (68 mg) in triethylamine (5 ml), (2S,4S,5S,7S)-N-{4-(tert-butoxycarbonyl)amino-5-hydroxy-2-isopropyl-7-[2-(4-methoxycarbonylpiperidin-1-yl)-ethylcarbamoyl]-8-methyl-nonyl}-2-(4-methoxybutoxy) -benzamide in the form of an oil: $R_f$ (L)=0.50; HPLC $R_t$=18.0 min.

EXAMPLE 66

In accordance with the processes described in Examples 1 to 65, the following compounds are prepared analogously:

a) (2R,4S,5S,7R)-1-(2-methoxypropyl)-1H-indole-3-carboxylic acid N-(4-amino-7-butylcarbamoyl-5-hydroxy-2-isopropyl-octyl)-amide hydrochloride b) (2R,4S,5S,7R)-1-(2-ethoxypropyl)-1H-indole-3-carboxylic acid N-(4-amino-7-butylcarbamoyl-5-hydroxy-2-isopropyl-octyl)-amide hydrochloride c) (2R,4S,5S,7R)-N-(4-amino-7-butylcarbamoyl-5-hydroxy-2-isopropyl-8-methyl-nonyl)-2-benzyloxy-benzamide hydrochloride d) (2S,4S,5S,7S)-N-(4-amino-7-butylcarbamoyl-5-hydroxy-2-isopropyl-8-methyl-nonyl)-2-[2-methoxyethoxy)-ethyl]-benzamide e) (2S,4S,5S,7S)-N-(4-amino-7-butylcarbamoyl-5-hydroxy-2-isopropyl-8-methyl-nonyl)-2-[2-ethoxyethyl)-benzamide hydrochloride f) (2R,4S,5S,7R,2'S)-N-{4-amino-5-hydroxy-2-isopropyl-8-methyl-7-[(5'-oxo-pyrrolidin-2'-ylmethyl)-carbamoyl]-nonyl}-2-(4-methoxybutoxy)-benzamide hydrochloride g) (2R,4S,5S,7R,2'R)-N-{4-amino-5-hydroxy-2-isopropyl-8-methyl-7-[(5'-oxo-pyrrolidin-2'-ylmethyl)-carbamoyl]-nonyl}-2-(4-methoxybutoxy)-benzamide hydrochloride h) (2R,4S,5S,7R)-N-{4-amino-5-hydroxy-2-isopropyl-8-methyl-7-[2-methyl-2-(morpholin-4-yl)-propylcarbamoyl]-nonyl}-2-(4-methoxybutoxy)-benzamide dihydrochloride i) (2R,4S,5S,7R,1'R)-N-[4-amino-5-hydroxy-2-isopropyl-8-methyl-7-(1'-methyl-2-methylcarbamoyl-ethylcarbamoyl)-nonyl]-2-(4-methoxybutoxy)-benzamide hydrochloride j) (2R,4S,5S,7R,1'S)-N-[4-amino-5-hydroxy-2-isopropyl-8-methyl-7-(1'-methyl-2-methylcarbamoyl-ethylcarbamoyl)-nonyl]-2-(4-methoxybutoxy)-benzamide hydrochloride k) (2R,4S,5S,7R,2'S)-N-[4-amino-5-hydroxy-2-isopropyl-7-(2'-carbamoyl-propylcarbamoyl)-8-methyl-nonyl]-2-(4-methoxybutoxy)-benzamide hydrochloride l) (2R,4S,5S,7R,2'R)-N-[4-amino-5-hydroxy-2-isopropyl-7-(2'-carbamoyl-propylcarbamoyl)-8-methyl-nonyl]-2-(4-methoxybutoxy)-benzamide hydrochloride m) (2R,4S,5S,7R)-N-[4-amino-5-hydroxy-2-isopropyl-7-(dimethylcarbamoylmethylcarbamoyl)-8-methyl-nonyl]-2-(4-methoxybutoxy)-benzamide hydrochloride n) (2S,4S,5S,7S,1'S)-N-{4-amino-7-[1-methyl-2'-(morpholin-4-yl)-2'-oxo-ethylcarbamoyl]-5-hydroxy-2-isopropyl-8-methyl-nonyl}-2-(4-methoxybutoxy)-benzamide hydrochloride o) (2S,4S,5S,7S,2R')-N-[4-amino-7-(2'-methyl-2'-methylcarbamoyl-propylcarbamoyl)-5-hydroxy-2-isopropyl-8-methyl-nonyl]-2-(4-methoxybutoxy)-benzamide hydrochloride p) (2S,4S,5S,7S)-3-{5-amino-4-hydroxy-7-[2-(4-methoxybutoxy)-benzoylamino)-methyl]-2-isopropyl-8-methyl-nonanoylamino}-2,2-dimethyl-propionic acid q) (2S,4S,5S,7S)-N-[4-amino-7-(3-methoxypropylcarbamoyl)-5-hydroxy-2-isopropyl-8-methyl-nonyl]-2-(4-methoxybutoxy)-benzamide hydrochloride r) (2S,4S,5S,7S,1'S,2'S)-N-[4-amino-7-(1'-carbamoyl-2'-methyl-butylcarbamoyl)-5-hydroxy-2-isopropyl-8-methyl-nonyl]-2-(4-methoxybutoxy)-benzamide hydrochloride s) (2S,4S,5S,7S)-N-[4-amino-7-(3-methylcarbamoyl-propylcarbamoyl)-5-hydroxy-2-isopropyl-8-methyl-nonyl]-2-(4-methoxybutoxy)-benzamide hydrochloride t) (2R,4S,5S,7R,1'R)-N-[4-amino-5-hydroxy-2-isopropyl-8-methyl-7-(1'-methyl-2'-carbamoylethylcarbamoyl)-nonyl]-2-(4-methoxybutoxy)-benzamide hydrochloride u) (2R,4S,5S,7R,1'S)-N-[4-amino-5-hydroxy-2-isopropyl-8-methyl-7-(1'-methyl-2'-carbamoyl-ethylcarbamoyl)-nonyl]-2-(4-methoxybutoxy)-benzamide hydrochloride v) (2S,4S,5S,7S,1'R)-N-[4-amino-7-(1'-isopropyl-2'-carbamoyl-ethylcarbamoyl)-5-hydroxy-2-isopropyl-8-methyl-nonyl]-2-(4-methoxybutoxy)-benzamide hydrochloride w) (2S,4S,5S,7S)-N-[4-amino-7-(3-dimethylcarbamoyl-propylcarbamoyl)-5-hydroxy-2-isopropyl-8-methyl-nonyl]-2-(4-methoxybutoxy)-benzamide hydrochloride x) (2S,4S,5S,7S,2S,)-N-[4-amino-7-(2'-methylcarbamoyl-propylcarbamoyl)-5-hydroxy-2-isopropyl-8-methyl-nonyl]-2-(4-methoxybutoxy)-benzamide hydrochloride.

EXAMPLE 67

Gelatin solution:

A sterile-filtered aqueous solution, comprising 20% cyclodextrins as solubiliser, of one of the compounds of formula I mentioned in the above Examples as active ingredient is mixed under aseptic conditions, with heating, with a sterile gelatin solution, which comprises phenol as preservative, in such a manner that 1.0 ml of the solution has the following composition:

| | |
|---|---|
| active ingredient | 3 mg |
| gelatin | 150.0 mg |
| phenol | 4.7 mg |
| distilled water comprising 20% cyclodextrins as solubiliser | 1.0 ml |

EXAMPLE 68

Sterile dry substance for injection:

5 mg of one of the compounds of formula I mentioned in the above Examples as active ingredient are dissolved in 1 ml of an aqueous solution comprising 20 mg of mannitol and 20% cyclodextrins as solubiliser. The solution is sterile-filtered, introduced under aseptic conditions into a 2 ml ampoule, deep-frozen and lyophilised. Prior to use, the lyophilisate is dissolved in 1 ml of distilled water or 1 ml of physiological saline. The solution is administered intramuscularly or intravenously. This formulation can also be introduced into double-chamber injection ampoules.

EXAMPLE 69

Nasal spray:

500 mg of finely ground (<5.0 μm) powder of one of the compounds of formula I mentioned in the above Examples as active ingredient am suspended in a mixture of 3.5 ml of "Myglyol 812®" and 0.08 g of benzyl alcohol. The suspension is introduced into a container having a metering valve. 5.0 g of "Freon 12®" are introduced under pressure into the container through the valve. The "Freon®" is dissolved in the Myglyol-®-benzyl alcohol mixture by shaking. The spray container contains approximately 100 single doses, which can be administered individually.

EXAMPLE 70

Film-coated tablets:

For the preparation of 10 000 tablets each comprising 100 mg of active ingredient, the following constituents are processed:

| | |
|---|---|
| active ingredient | 1000 g |
| corn starch | 680 g |
| colloidal silica | 200 g |
| magnesium stearate | 20 g |
| stearic acid | 50 g |
| sodium carboxymethyl starch | 250 g |
| water | quantum satis |

A mixture of one of the compounds of formula I mentioned in the above Examples as active ingredient, 50 g of corn starch and the colloidal silica is processed with a starch paste comprising 250 g of corn starch and 2.2 kg of demineralised water to form a moist mass. The mass is pressed through a sieve having a mesh size of 3 mm and is dried at 45° for 30 minutes in a fluidized bed dryer. The dried granules are pressed through a sieve having a mesh size of 1 mm, are mixed with a previously sieved mixture (1 mm sieve) of 330 g of corn starch, the magnesium stearate, the stearic acid and the sodium carboxymethyl starch, and the mixture is compressed to form slightly biconvex tablets.

What is claimed is:

1. A compound of formula I wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is an aliphatic or heterocycloaliphatic-aliphatic radical or free or aliphatically, araliphatically or heteroaraliphatically etherified hydroxy and the other is hydrogen, an aliphatic radical or free or esterified or amidated carboxy, $R_C$ is hydrogen, an aliphatic radical, free or aliphatically, araliphatically, heteroaraliphatically or heteroarylaliphatically etherified hydroxy or an unsubstituted or heteroaliphatically substituted amino group, and $R_D$ is an aliphatic, araliphatic or heteroaliphatic radical, one of the radicals $X_1$ and $X_2$ is carbonyl and the other is methylene, $R_2$ is an aliphatic radical, $R_3$ is unsubstituted or aliphatically substituted amino, $R_4$ is an aliphatic or araliphatic radical, and $R_5$ is an aliphatic or cycloaliphatic-aliphatic radical or an optionally hydrogenated and/or oxo-substituted heteroaryl radical or an optionally hydrogenated and/or oxo-substituted heteroaryl or heteroaliphatyl radical bonded via a carbon atom, or a salt thereof.

2. A compound according to claim 1 of formula I, wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is lower alkyl, hydroxy-lower alkyl, lower alkanoyloxy-lower alkyl, lower alkoxy-lower alkyl, lower alkoxy-lower alkoxy-lower alkyl; an amino-lower alkyl or amino-lower alkoxy radical that is unsubstituted or N-lower alkanoylated or N-mono- or N,N-di lower alkylated or N,N-disubstituted by lower alkylene, hydroxy-, lower alkoxy- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; hydroxy, lower alkoxy, hydroxy-lower alkoxy, lower alkanoyloxy-lower alkoxy, lower alkoxy-lower alkoxy, lower alkoxy-lower alkoxy-lower alkoxy, polyhalo-lower alkoxy, cyano-lower alkoxy, unsubstituted or substituted phenyl- or pyridyl-lower alkoxy, lower alkoxy-lower alkenyloxy, optionally S-oxidised lower alkylthio-lower alkoxy, or amino-lower alkoxy that is unsubstituted or N-lower alkanoylated or N-mono- or N,N-di-lower alkylated or N,N- disubstituted by lower alkylene, hydroxy-, lower alkoxy- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; and the other is hydrogen, lower alkyl, carbamoyl, hydroxy, lower alkoxy or polyhalo-lower alkoxy, $R_C$ is hydrogen, lower alkyl, hydroxy, lower alkoxy, hydroxy-lower alkoxy, lower alkoxy-lower alkoxy, morpholino-lower alkylcarbamoyl-lower alkoxy, lower alkoxy-lower alkoxy-lower alkyl; an amino, amino-lower alkyl or amino-lower alkoxy group that is unsubstituted or N-lower alkanoylated or N-mono- or N,N-di-lower alkylated or N,N-disubstituted by lower alkylene, hydroxy-, lower alkoxy-, lower alkoxycarbonyl- or lower alkoxy-lower alkoxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; or a free or amidated carboxy or carboxy-lower alkoxy group or tetrazolyl-lower alkoxy, and $R_D$ is lower alkyl, hydroxy-lower alkyl, lower alkoxy-lower alkyl, lower alkoxy-lower alkoxy-lower alkyl, hydroxy-lower alkoxy-lower alkyl, a free or amidated carboxy or carboxy-lower alkyl group or an unsubstituted or substituted phenyl- or pyridyl-lower alkyl group, one of the radicals $X_1$ and $X_2$ is carbonyl and the other is methylene, $R_2$ is lower alkyl, $R_3$ is unsubstituted or N-lower alkanoylated or N-mono- or N,N-di-lower alkylated amino, $R_4$ is lower alkyl or phenyl-lower alkyl, and $R_5$ is lower alkyl, cycloalkyl-lower alkyl, hydroxy-lower alkyl, lower alkoxy-lower alkyl, lower alkanoyloxy-lower alkyl; amino-lower alkyl that is unsubstituted or N-lower alkanoylated or N-mono- or N,N-di-lower alkylated or N,N-disubstituted by lower alkylene, hydroxy-, lower alkoxy-, lower alkoxy-lower alkyl- or lower alkanoyloxy-lower alkylene, by unsubstituted or N'-lower alkanoylated, lower alkoxycarbonyl- or lower alkoxy-lower alkyl-N'-substituted or N'-lower alkylated aza-lower alkylene, by oxa-lower alkylene or by optionally S-oxidised thia-lower alkylene; free or esterified or amidated carboxy-lower alkyl, cyano-lower alkyl, free or esterified or amidated dicarboxy-lower alkyl, free or esterified or amidated carboxy (hydroxy)-lower alkyl, free or esterified or amidated carboxycycloalkyl-lower alkyl, lower alkanesulfonyl-lower alkyl, unsubstituted or N-mono- or N,N-di-lower alkylated thio carbamoyl-lower alkyl, unsubstituted or N-mono- or N,N-di-lower alkylated sulfamoyl-lower alkyl or an optionally hydrogenated and/or oxo-substituted heteroaryl radical or lower alkyl substituted by an optionally hydrogenated and/or oxo-substituted heteroaryl radical that is bonded via a carbon atom, or a salt thereof.

3. A compound according to claim 1 of formula I, wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is lower alkyl, hydroxy-lower alkyl, lower alkanoyloxy-lower alkyl, lower alkoxy-lower alkyl, lower alkoxy-lower alkoxy-lower alkyl, amino-lower alkyl, lower alkanoylamino-lower alkyl, lower alkylamino-lower alkyl, di-lower alkylamino-lower alkyl; piperidino- or pyrrolidino-lower alkyl that is unsubstituted or substituted by hydroxy, lower alkoxy or by lower alkoxy-lower alkyl; piperazino-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholino-lower alkyl, optionally S-oxidised thiomorpholino-lower alkyl, amino-lower alkoxy, lower alkanoylamino-lower alkoxy, lower alkylamino-lower alkoxy, di-lower alkylamino-lower alkoxy; piperidino- or pyrrolidino-lower alkoxy that is unsubstituted or substituted by hydroxy, lower alkoxy or by lower alkoxy-lower alkyl; piperazino-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholino-lower alkoxy, optionally S-oxidised thiomorpholio-lower alkoxy, hydroxy, lower alkoxy, hydroxy-lower alkoxy, lower alkanoyloxy-lower alkoxy, lower alkoxy-lower alkoxy, lower alkoxy-lower alkoxy-lower alkoxy, polyhalo-lower alkoxy, cyano-lower alkoxy; phenyl- or pyridyl-lower alkoxy that is unsubstituted or substituted by lower alkyl, lower alkoxy, hydroxy, nitro, amino, lower alkylamino, di-lower alkylamino, halogen and/or by trifluoromethyl; lower alkoxy-lower alkenyloxy, lower alkylthio-lower alkoxy, lower alkanesulfinyl-lower alkoxy, lower alkanesulfonyl-lower alkoxy, amino-lower alkoxy, lower alkanoylamino-lower alkoxy, lower alkylamino-lower alkoxy, di-lower alkylamino-lower alkoxy; piperidino- or pyrrolidino-lower alkoxy that is unsubstituted or substituted by hydroxy, lower alkoxy or by lower alkoxy-lower alkyl; piperazino-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholino-lower alkoxy or optionally S-oxidised thiomorpholino-lower alkoxy, and the other is hydrogen, carbamoyl, hydroxy, lower alkoxy or polyhalo-lower alkoxy, $R_C$ is hydrogen, lower alkyl, lower alkoxy-lower alkoxy-lower alkyl, amino-lower alkyl, lower alkanoylamino-lower alkyl, lower alkylamino-lower alkyl, di-lower alkylamino-lower alkyl; piperidino- or pyrrolidino-lower alkyl that is unsubstituted or substituted by hydroxy, lower alkoxy or by lower alkoxy-lower alkyl; piperazino-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholino-lower alkyl, optionally S-oxidised thiomorpholino-lower alkyl, di-lower alkylamino; a piperidino or pyrrolidino group that is unsubstituted or substituted by hydroxy, lower alkoxy or by lower alkoxy-lower alkyl; piperazino that is unsubstituted or N'-lower alkylated, N'-lower alkanoylated or N'-substituted by lower alkoxycarbonyl or by lower alkoxy-lower alkyl; unsubstituted or lower alkylated morpholino, optionally S-oxidised thiomorpholino, hydroxy, lower alkoxy, hydroxy-lower alkoxy, lower alkoxy-lower alkoxy, morpholino-lower alkylcarbamoyl-lower alkoxy, amino-lower alkoxy, lower alkanoylamino-lower alkoxy, lower alkylamino-lower alkoxy, di-lower alkylamino-lower alkoxy; piperidino- or pyrrolidino-lower alkoxy that is unsubstituted or substituted by hydroxy, lower alkoxy or by lower alkoxy-lower alkyl; piperazino-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholino-lower alkoxy, optionally S-oxidised thiomorpholino-lower alkoxy, carboxy-lower alkoxy, carbamoyl-lower alkoxy, lower alkylcarbamoyl-lower alkoxy, di-lower alkylcarbamoyl-lower alkoxy; piperidino- or pyrrolidino-carbonyl-lower alkoxy that is unsubstituted or substituted by hydroxy, lower alkoxy or by lower alkoxy-lower alkyl; piperazinocarbonyl-lower alkoxy that is unsubstituted or N'-lower alkylated, N'-lower alkanoylated or N'-substituted by lower alkoxycarbonyl or by lower alkoxy-lower alkyl; unsubstituted or lower alkylated morpholinocarbonyl-lower alkoxy, optionally S-oxidised thiomorpholinocarbonyl-lower alkoxy, tetrazolyl-lower alkoxy, carboxy, carbamoyl, lower alkylcarbamoyl or di-lower alkylcarbamoyl, and $R_D$ is lower alkyl, hydroxy-lower alkyl, lower alkoxy-lower alkyl, lower alkoxy-lower alkoxy-lower alkyl, hydroxy-lower alkoxy-lower alkyl, carboxy, lower alkoxycarbonyl, carboxy-lower alkyl, lower alkoxycarbonyl-lower alkyl, carbamoyl-lower alkyl, lower alkylcarbamoyl-lower alkyl, di-lower alkylcarbamoyl-lower alkyl; piperidino- or pyrrolidino-carbonyl-lower alkyl that is unsubstituted or substituted by hydroxy, lower alkoxy or by lower alkoxy-lower alkyl; piperazinocarbonyl-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholinocarbonyl-lower alkyl, optionally S-oxidised thiomorpholinocarbonyl-carbonyl-lower alkyl, carboxy-lower alkyl, lower alkoxycarbonyl-lower alkyl or a phenyl- or pyridyl-lower alkyl group that is unsubstituted or substituted by lower alkyl, lower alkoxy, hydroxy, nitro, amino, lower alkylamino, di-lower alkylamino, halogen and/or by trifluoromethyl, one of the radicals $X_1$ and $X_2$ is carbonyl and the other is methylene, $R_2$ is lower alkyl, $R_3$ is amino, lower alkanoylamino, lower alkylamino or di-lower alkylamino, $R_4$ is lower alkyl or phenyl-lower alkyl and $R_5$ is lower alkyl, cycloalkyl-lower alkyl, hydroxy-lower alkyl, lower alkoxy-lower alkyl, lower alkanoyloxy-lower alkyl; piperidino- or pyrrolidino-carbonyl-lower alkyl that is unsubstituted or substituted by hydroxy, lower alkoxy or by lower alkoxy-lower alkyl; piperazinocarbonyl-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholinocarbonyl-lower alkyl, optionally S-oxidised thiomorpholinocarbonyl-lower alkyl, carboxy-lower alkyl, lower alkoxycarbonyl-lower alkyl, carbamoyl-lower alkyl, lower alkylcarbamoyl-lower alkyl, di-lower alkylcarbamoyl-lower alkyl; piperidino- or pyrrolidinocarbonyl-lower alkyl that is unsubstituted or substituted by hydroxy, lower alkoxy or by lower alkoxy-lower alkyl; piperazinocarbonyl-lower alkyl that is unsubstituted or N'-lower alkylated, N'-lower alkanoylated or N'-substituted by lower alkoxycarbonyl or by lower alkoxy-lower alkyl; unsubstituted or lower alkylated morpholinocarbonyl-lower alkyl, optionally S-oxidised thiomorpholinocarbonyl-lower alkyl, cyano-lower alkyl, dicarboxy-lower alkyl, lower alkoxycarbonyl(carbonyl)-lower alkyl, di-lower alkoxycarbonyl-lower alkyl, dicarbamoyl-lower alkyl, carbamoyl(carboxy)-lower alkyl, di-(lower alkylcarbamoyl)-lower alkyl, di-(di-lower alkylcarbamoyl)-lower alkyl, carboxy(hydroxy)-lower alkyl, lower alkoxycarbonyl(hydroxy)-lower alkyl, carbamoyl(hydroxy)-lower alkyl, lower alkylcarbamoyl(hydroxy)-lower alkyl or di-lower alkylcarbamoyl(hydroxy)-lower alkyl, carboxycycloalkyl-lower alkyl, lower alkoxycarbonylcycloalkyl-lower alkyl, carbamoylcycloalkyl-lower alkyl, lower alkylcarbamoylcycloalkyl-lower alkyl, di-lower alkylcarbamoylcycloalkyl-lower alkyl, lower alkanesulfonyl-lower alkyl, thiocarbamoyl-lower alkyl, N-lower alkylthiocarbamoyl-lower alkyl or N,N-di-lower alkylthiocarbamoyl-lower alkyl, sulfamoyl-lower alkyl, lower alkylsulfamoyl-lower alkyl or di-lower alkylsulfamoyl-lower alkyl, unsubstituted or oxo-substituted pyrrolidinyl, imidazolyl, benzimidazolyl, oxadiazolyl, pyridyl, oxopiperidinyl, dioxopiperidinyl, oxothiazolyl, oxo-oxazolinyl or quinolinyl, unsubstituted or oxo-substituted pyrrolidinyl-lower alkyl, imidazolyl-lower alkyl, benzimidazolyl-lower alkyl, oxadiazolyl-lower alkyl, pyridyl-lower alkyl, oxopiperidinyl-lower alkyl, dioxopiperidinyl-lower alkyl, oxothiazolyl-lower alkyl, oxo-oxazolinyl-lower alkyl or quinolinyl-lower alkyl, morpholinocarbonyl-lower alkyl or unsubstituted or N-lower alkanoylated piperidyl-lower alkyl or unsubstituted or N-lower alkanoylated piperidyl, or a salt thereof.

4. A compound according to claim 1 of formula I, wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is $C_1$–$C_4$alkyl, hydroxy-$C_1$–$C_4$alkyl, $C_1$–$C_4$alkanoyloxy-$C_1$–$C_4$alkyl, $C_1$–$C_4$alkoxy-$C_1$–$C_4$alkyl, $C_1$–$C_4$alkoxy-$C_1$–$C_4$alkoxy-$C_1$–$C_4$alkyl, amino-$C_1$–$C_4$alkyl, $C_1$–$C_4$alkanoylamino-$C_1$–$C_4$alkyl, $C_1$–$C_4$alkylamino-$C_1$–$C_4$alkyl, di-$C_1$–$C_4$alkylamino-$C_1$–$C_4$alkyl, piperidino-$C_1$–$C_4$-alkyl, hydroxypiperidino-$C_1$–$C_4$alkyl, $C_1$–$C_4$alkoxypiperidino-$C_1$–$C_4$alkyl, $C_1$–$C_4$alkoxy-$C_1$–$C_4$-alkoxypiperidino-$C_1$–$C_4$alkyl, $C_1$–$C_4$alkoxycarbonylpiperidino-$C_1$–$C_4$alkyl, pyrrolidino-$C_1$–$C_4$alkyl, hydroxypyrrolidino-$C_1$–$C_4$alkyl, $C_1$–$C_4$alkoxypyrrolidino-$C_1$–$C_4$alkyl, $C_1$–$C_4$alkoxy-$C_1$–$C_4$alkoxypyrrolidino-$C_1$–$C_4$alkyl, piperazino-$C_1$–$C_4$alkyl, N'-$C_1$–$C_4$alkylpiperazino-$C_1$–$C_4$alkyl, N'-$C_1$–$C_4$-alkanoylpiperazino-$C_1$–$C_4$alkyl, N'-$C_1$–$C_4$alkoxycarbonylpiperazino-$C_1$–$C_4$alkyl, N'-$C_1$–$C_4$alkoxy-$C_1$–$C_4$alkylpiperazino-$C_1$–$C_4$alkyl, morpholino-$C_1$–$C_4$alkyl, $C_1$–$C_4$alkylmorpholino-$C_1$–$C_4$alkyl, thiomorpholino-$C_1$–$C_4$alkyl, S-oxythiomorpholino-$C_1$–$C_4$alkyl, S,S-dioxythiomorpholino-$C_1$–$C_4$alkyl, $C_1$–$C_7$alkoxy, such as propyloxy, amino-$C_1$–$C_7$alkoxy, $C_1$–$C_4$alkanoylamino-$C_1$–$C_4$alkoxy, $C_1$–$C_4$alkylamino-$C_1$–$C_4$alkoxy, di-$C_1$–$C_4$alkylamino-$C_1$–$C_4$alkoxy, piperidino-$C_1$–$C_4$alkoxy, hydroxypiperidino-$C_1$-$C_4$alkoxy,
$C_1$-$C_4$alkoxypiperidino-$C_1$-$C_4$alkoxy, $C_1$-$C_4$alkoxy-$C_1$-$C_4$-alkoxypiperidino-$C_1$-$C_4$alkoxy, pyrrolidino-$C_1$-$C_4$alkoxy, hydroxypyrrolidino-$C_1$-$C_4$alkoxy, $C_1$-$C_4$-alkoxypyrrolidino-$C_1$-$C_4$alkoxy, $C_1$-$C_4$alkoxy-$C_1$-$C_4$alkoxypyrrolidino-$C_1$-$C_4$alkoxy, piperazino-$C_1$-$C_4$alkoxy, N'-$C_1$-$C_4$alkylpiperazino-$C_1$-$C_4$alkoxy, N'-$C_1$-$C_4$alkanoylpiperazino-$C_1$-$C_4$alkoxy, N'-$C_1$-$C_4$alkoxycarbonylpiperazino-$C_1$-$C_4$alkoxy, N'-$C_1$-$C_4$alkoxy-$C_1$-$C_4$alkylpiperazino-$C_1$-$C_4$alkoxy, morpholino-$C_1$-$C_4$alkoxy or $C_1$-$C_4$alkylmorpholino-$C_1$-$C_4$alkoxy, thiomorpholino-$C_1$-$C_4$alkoxy, S-oxythiomorpholino-$C_1$-$C_4$alkoxy, S,S-dioxythiomorpholino-$C_1$-$C_4$alkoxy, hydroxy, hydroxy-$C_1$-$C_4$alkoxy, $C_1$-$C_4$alkanoyloxy-$C_1$-$C_4$alkoxy, $C_1$-$C_4$alkoxy-$C_1$-$C_4$alkoxy, $C_1$-$C_4$alkoxy-$C_1$-$C_4$alkoxy-$C_1$-$C_4$alkoxy, polyhalo-$C_1$-$C_4$alkoxy, cyano-$C_1$-$C_4$alkoxy, carbamoyl-$C_1$-$C_4$alkoxy, such as 2-carbamoylethoxy; phenyl- or pyridyl-$C_1$-$C_4$alkoxy that is unsubstituted or substituted by $C_1$-$C_4$alkyl, $C_1$-$C_4$alkoxy, hydroxy, nitro, amino, $C_1$-$C_4$alkylamino, di-$C_1$-$C_4$alkylamino, halogen and/or by trifluoromethyl; $C_1$-$C_4$alkoxy-$C_1$-$C_4$alkenyloxy, $C_1$-$C_4$alkylthio-$C_1$-$C_4$alkoxy, $C_1$-$C_4$alkanesulfinyl-$C_1$-$C_4$alkoxy, $C_1$-$C_4$alkanesulfonyl-$C_1$-$C_4$alkoxy, amino-$C_1$-$C_7$alkoxy, $C_1$-$C_4$alkanoylamino-$C_1$-$C_4$alkoxy, $C_1$-$C_4$alkylamino-$C_1$-$C_4$alkoxy, di-$C_1$-$C_4$alkylamino-$C_1$-$C_4$alkoxy, piperidino-$C_1$-$C_4$alkoxy, hydroxypiperidino-$C_1$-$C_4$alkoxy, $C_1$-$C_4$alkoxypiperidino-$C_1$-$C_4$alkoxy, $C_1$-$C_4$alkoxy-$C_1$-$C_4$alkoxypiperidino-$C_1$-$C_4$alkoxy, pyrrolidino-$C_1$-$C_4$alkoxy, hydroxypyrrolidino-$C_1$-$C_4$alkoxy, $C_1$-$C_4$alkoxypyrrolidino-$C_1$-$C_4$alkoxy, $C_1$-$C_4$alkoxy-$C_1$-$C_4$alkoxypyrrolidino-$C_1$-$C_4$alkoxy, piperazino-$C_1$-$C_4$alkoxy, N'-$C_1$-$C_4$alkylpiperazino-$C_1$-$C_4$alkoxy, N'-$C_1$-$C_4$alkanoylpiperazino-$C_1$-$C_4$alkoxy, N'-$C_1$-$C_4$alkoxycarbonylpiperazino-$C_1$-$C_4$alkoxy, N'-$C_1$-$C_4$alkoxy-$C_1$-$C_4$alkylpiperazino-$C_1$-$C_4$alkoxy, morpholino-$C_1$-$C_4$alkoxy or $C_1$-$C_4$alkylmorpholino-$C_1$-$C_4$alkoxy or thiomorpholino-$C_1$-$C_4$alkoxy, and the other is hydrogen, carbamoyl, $C_1$-$C_4$alkyl, hydroxy, $C_1$-$C_4$alkoxy or trihalo-$C_1$-$C_4$alkoxy, $R_C$ is hydrogen, hydroxy, di-$C_1$-$C_4$alkylamino, piperidino, pyrrolidino, morpholino, thiomorpholino, S-oxythiomorpholino, S,S-dioxythiomorpholino, $C_1$-$C_4$alkoxy, hydroxy-$C_1$-$C_4$alkoxy, $C_1$-$C_4$alkoxy-$C_1$-$C_4$alkoxy, morpholino-$C_1$-$C_4$alkylcarbamoyl-$C_1$-$C_4$alkoxy, $C_1$-$C_4$alkoxy-$C_1$-$C_4$alkoxy-$C_1$-$C_4$alkyl, amino-$C_1$-$C_4$alkyl, $C_1$-$C_4$alkanoylamino-$C_1$-$C_4$alkyl, $C_1$-$C_4$alkylamino-$C_1$-$C_4$alkyl, di-$C_1$-$C_4$alkylamino-$C_1$-$C_4$alkyl; piperidino- or pyrrolidino-$C_1$-$C_4$alkyl that is unsubstituted or substituted by hydroxy, $C_1$-$C_4$alkoxy or by $C_1$-$C_4$alkoxy-$C_1$-$C_4$alkyl; amino-$C_1$-$C_4$alkyl, $C_1$-$C_4$alkanoylamino-$C_1$-$C_4$alkyl, $C_1$-$C_4$alkylamino-$C_1$-$C_4$alkyl, di-$C_1$-$C_4$alkylamino-$C_1$-$C_4$alkyl, piperidino-$C_1$-$C_4$alkyl, hydroxypiperidino-$C_1$-$C_4$alkyl, $C_1$-$C_4$alkoxypiperidino-$C_1$-$C_4$alkyl, $C_1$-$C_4$alkoxy-$C_1$-$C_4$alkoxypiperidino-$C_1$-$C_4$alkyl, $C_1$-$C_4$alkoxycarbonylpiperidino-$C_1$-$C_4$alkyl, pyrrolidino-$C_1$-$C_4$alkyl, hydroxypyrrolidino-$C_1$-$C_4$alkyl, $C_1$-$C_4$alkoxypyrrolidino-$C_1$-$C_4$alkyl, $C_1$-$C_4$alkoxy-$C_1$-$C_4$alkoxypyrolidino-$C_1$-$C_4$alkyl, piperazino-$C_1$-$C_4$alkyl, N'-$C_1$-$C_4$alkylpiperazino-$C_1$-$C_4$alkyl, N'-$C_1$-$C_4$alkanoylpiperazino-$C_1$-$C_4$alkyl, N'-$C_1$-$C_4$alkoxycarbonylpiperazino-$C_1$-$C_4$alkyl, N'-$C_1$-$C_4$alkoxy-$C_1$-$C_4$alkylpiperazino-$C_1$-$C_4$alkyl, morpholino-$C_1$-$C_4$alkyl, $C_1$-$C_4$alkylmorpholino-$C_1$-$C_4$alkyl, thiomorpholino-$C_1$-$C_4$alkyl, S-oxythiomorpholino-$C_1$-$C_4$alkyl, S,S-dioxythiomorpholino-$C_1$-$C_4$alkyl, amino-$C_1$-$C_7$alkoxy, $C_1$-$C_4$alkanoylamino-$C_1$-$C_4$alkoxy, $C_1$-$C_4$alkylamino-$C_1$-$C_4$alkoxy, di-$C_1$-$C_4$alkylamino-$C_1$-$C_4$alkoxy, piperidino-$C_1$-$C_4$alkoxy, hydroxypiperidino-$C_1$-$C_4$alkoxy, $C_1$-$C_4$alkoxypiperidino-$C_1$-$C_4$alkoxy, $C_1$-$C_4$alkoxy-$C_1$-$C_4$alkoxypiperidino-$C_1$-$C_4$alkoxy, pyrrolidino-$C_1$-$C_4$alkoxy, hydroxypyrrolidino-$C_1$-$C_4$alkoxy, $C_1$-$C_4$alkoxypyrrolidino-$C_1$-$C_4$alkoxy, $C_1$-$C_4$alkoxy-$C_1$-$C_4$alkoxypyrrolidino-$C_1$-$C_4$alkoxy, piperazino-$C_1$-$C_4$alkoxy, N'-$C_1$-$C_4$alkylpiperazino-$C_1$-$C_4$alkoxy, N'-$C_1$-$C_4$alkanoylpiperazino-$C_1$-$C_4$alkoxy, N'-$C_1$-$C_4$alkoxycarbonylpiperazino-$C_1$-$C_4$alkoxy, N'-$C_1$-$C_4$alkoxy-$C_1$-$C_4$alkylpiperazino-$C_1$-$C_4$alkoxy, morpholino-$C_1$-$C_4$alkoxy or $C_1$-$C_4$alkylmorpholino-$C_1$-$C_4$alkoxy, thiomorpholino-$C_1$-$C_4$alkoxy, S-oxythiomorpholino-$C_1$-$C_4$alkoxy, S,S-dioxythiomorpholino-$C_1$-$C_4$alkoxy, carboxy-$C_1$-$C_4$alkoxy, carbamoyl-$C_1$-$C_4$alkoxy, $C_1$-$C_4$alkylcarbamoyl-$C_1$-$C_4$alkoxy, di-$C_1$-$C_4$-alkylcarbamoyl-$C_1$-$C_4$alkoxy, di-$C_1$-$C_4$alkylamino-$C_1$-$C_4$alkoxy, such as 3-dimethylaminopropyloxy, piperidinocarbonyl-$C_1$-$C_4$alkoxy, hydroxypiperidinocarbonyl-$C_1$-$C_4$alkoxy, $C_1$-$C_4$alkoxypiperidinocarbonyl-$C_1$-$C_4$alkoxy, $C_1$-$C_4$alkoxy-$C_1$-$C_4$alkoxypiperidinocarbonyl-$C_1$-$C_4$alkoxy, pyrrolidinocarbonyl-$C_1$-$C_4$alkoxy, hydroxypiperidinocarbonyl-$C_1$-$C_4$alkoxy, $C_1$-$C_4$alkoxypyrrolidinocarbonyl-$C_1$-$C_4$alkoxy, $C_1$-$C_4$alkoxy-$C_1$-$C_4$alkoxypyrrolidinocarbonyl-$C_1$-$C_4$alkoxy, piperazinocarbonyl-$C_1$-$C_4$alkoxy, N'-$C_1$-$C_4$alkylpiperazinocarbonyl-$C_1$-$C_4$alkoxy, N'-$C_1$-$C_4$alkanoylpiperazinocarbonyl-$C_1$-$C_4$alkoxyl, N'-$C_1$-$C_4$alkoxycarbonylpiperazinocarbonyl or N'-$C_1$-$C_4$alkoxy-$C_1$-$C_4$alkylipiperazinocarbonyl-$C_1$-$C_4$alkoxy, morpholinocarbonyl-$C_1$-$C_4$alkoxy, $C_1$-$C_4$alkylmorpholinocarbonyl-$C_1$-$C_4$alkoxy, thiomorpholinocarbonyl-$C_1$-$C_4$alkoxy, S-oxythiomorpholinocarbonyl, S,S-dioxythiomorpholinocarbonyl-$C_1$-$C_4$alkoxy, tetrazolyl-$C_1$-$C_4$alkoxy, carboxy, carbamoyl or $C_1$-$C_4$alkylcarbamoyl, such as methylcarbamoyl, and $R_D$ is $C_1$-$C_4$alkyl, hydroxy-$C_1$-$C_4$alkyl, $C_1$-$C_4$alkoxy-$C_1$-$C_4$alkyl, $C_1$-$C_4$alkoxy-$C_1$-$C_4$alkoxy-$C_1$-$C_4$alkyl, hydroxy-$C_1$-$C_4$alkoxy-$C_1$-$C_4$alkyl, carboxy, $C_1$-$C_4$alkoxycarbonyl, carboxy-$C_1$-$C_4$alkyl, $C_1$-$C_4$alkoxycarbonyl-$C_1$-$C_4$alkyl, carbamoyl-$C_1$-$C_4$alkyl, $C_1$-$C_4$alkylcarbamoyl-$C_1$-$C_4$alkyl, di-$C_1$-$C_4$alkylcarbamoyl-$C_1$-$C_4$alkyl, piperidino-$C_1$-$C_4$alkyl, hydroxypiperidino-$C_1$-$C_4$alkyl, $C_1$-$C_4$alkoxypiperidino-$C_1$-$C_4$alkyl, $C_1$-$C_4$alkoxy-$C_1$-$C_4$alkoxypiperidino-$C_1$-$C_4$alkyl, $C_1$-$C_4$alkoxycarbonylpiperidino-$C_1$-$C_4$alkyl, pyrrolidino-$C_1$-$C_4$alkyl, hydroxypyrrolidino-$C_1$-$C_4$alkyl, $C_1$-$C_4$alkoxypyrrolidino-$C_1$-$C_4$alkyl, $C_1$-$C_4$alkoxy-$C_1$-$C_4$alkoxypyrrolidino-$C_1$-$C_4$alkyl, piperazino-$C_1$-$C_4$alkyl, N'-$C_1$-$C_4$alkylpiperazino-$C_1$-$C_4$alkyl, N'-$C_1$-$C_4$alkanoylpiperazino-$C_1$-$C_4$alkyl, N'-$C_1$-$C_4$alkoxycarbonylpiperazino-$C_1$-$C_4$alkyl, N'-$C_1$-$C_4$alkoxy-$C_1$-$C_4$alkylpiperazino-$C_1$-$C_4$alkyl, morpholino-$C_1$-$C_4$alkyl, $C_1$-$C_4$alkylmorpholino-$C_1$-$C_4$alkyl, thiomorpholino-$C_1$-$C_4$alkyl, S-oxythiomorpholino-$C_1$-$C_4$alkyl, S,S-dioxythiomorpholino-$C_1$-$C_4$alkyl, carboxy- $C_1$–$C_4$alkyl, $C_1$–$C_4$alkoxycarbonyl-$C_1$–$C_4$alkyl, or is phenyl-$C_1$–$C_4$alkyl or pyridyl-$C_1$–$C_4$alkyl that is unsubstituted or substituted by $C_1$–$C_4$alkyl, $C_1$–$C_4$alkoxy, hydroxy, nitro, amino, $C_1$–$C_4$alkylamino, di-$C_1$–$C_4$alkylamino, halogen and/ or by trifluoromethyl, one of the radicals $X_1$ and $X_2$ is carbonyl and the other is methylene, $R_2$ is $C_1$–$C_4$alkyl, $R_3$ is amino, $C_1$–$C_4$alkanoylamino, $C_1$–$C_4$alkylamino or di-$C_1$–$C_4$alkylamino, $R_4$ is $C_1$–$C_4$alkyl or phenyl-$C_1$–$C_4$alkyl, and $R_5$ is $C_1$–$C_4$alkyl, cycloalkyl-$C_1$–$C_4$alkyl, hydroxy-$C_1$–$C_4$alkyl, $C_1$–$C_4$alkoxyl-$C_1$–$C_4$alkyl, $C_1$–$C_4$alkanoyloxy-$C_1$–$C_4$alkyl, piperidino-$C_1$–$C_4$alkyl, hydroxypiperidino-$C_1$–$C_4$alkyl, $C_1$–$C_4$alkoxypiperidino-$C_1$–$C_4$alkyl, $C_1$–$C_4$alkoxy-$C_1$–$C_4$alkoxypiperidino-$C_1$–$C_4$alkyl, $C_1$–$C_4$alkoxycarbonylpiperidino-$C_1$–$C_4$alkyl, pyrrolidino-$C_1$–$C_4$alkyl, hydroxypyrrolidino-$C_1$–$C_4$alkyl, $C_1$–$C_4$alkoxypyrrolidino-$C_1$–$C_4$alkyl, $C_1$–$C_4$alkoxy-$C_1$–$C_4$alkoxypyrrolidino-$C_1$–$C_4$alkyl, piperazino-$C_1$–$C_4$alkyl, N'-$C_1$–$C_4$alkylpiperazino-$C_1$–$C_4$alkyl, N'-$C_1$–$C_4$alkanoylpiperazino-$C_1$–$C_4$alkyl, N'-$C_1$–$C_4$alkoxycarbonylpiperazino-$C_1$–$C_4$alkyl, N'-$C_1$–$C_4$alkoxy-$C_1$–$C_4$alkylpiperazino-$C_1$–$C_4$alkyl, morpholino-$C_1$–$C_4$alkyl, $C_1$–$C_4$alkylmorpholino-$C_1$–$C_4$alkyl, thiomorpholino-$C_1$–$C_4$alkyl, S-oxythiomorpholino-$C_1$–$C_4$alkyl, S,S-dioxythiomorpholino-$C_1$–$C_4$alkyl, carboxy-$C_1$–$C_4$alkyl, $C_1$–$C_4$alkoxycarbonyl-$C_1$–$C_4$alkyl, carbamoyl-$C_1$–$C_4$alkyl, $C_1$–$C_4$alkylcarbamoyl-$C_1$–$C_4$alkyl, di-$C_1$–$C_4$alkylcarbamoyl-$C_1$–$C_4$alkyl, piperidinocarbonyl-$C_1$–$C_4$alkyl, hydroxypiperidinocarbonyl-$C_1$–$C_4$alkyl, $C_1$–$C_4$alkoxypiperidinocarbonyl-$C_1$–$C_4$alkyl, $C_1$–$C_4$alkoxy-$C_1$–$C_4$alkoxypiperidinocarbonyl-$C_1$–$C_4$alkyl, pyrrolidinocarbonyl-$C_1$–$C_4$alkyl, hydroxypyrrolidinocarbonyl-$C_1$–$C_1$alkyl, $C_1$–$C_4$alkoxypyrrolidinocarbonyl-$C_1$–$C_4$alkyl, $C_1$–$C_4$alkoxy-$C_1$–$C_4$alkoxypyrrolidinocarbonyl-$C_1$–$C_4$alkyl, piperazinocarbonyl-$C_1$–$C_4$alkyl, N'-$C_1$–$C_4$alkylpiperazinocarbonyl-$C_1$–$C_4$alkyl, N'-$C_1$–$C_4$alkanoylpiperazinocarbonyl-$C_1$–$C_4$alkyl, N'-$C_1$–$C_4$alkoxycarbonylpiperazinocarbonyl, N'-$C_1$–$C_4$alkoxy-$C_1$–$C_4$alkylpiperazinocarbonyl-$C_1$–$C_4$alkyl, morpholinocarbonyl-$C_1$–$C_4$alkyl, $C_1$–$C_4$alkylmorpholinocarbonyl-$C_1$–$C_4$alkyl, thiomorpholinocarbonyl-$C_1$–$C_4$alkyl, S-oxythiomorpholinocarbonyl-$C_1$–$C_4$alkyl, S,S-dioxythiomorpholinocarbonyl-$C_1$–$C_4$alkyl, carbamoyl-$C_1$–$C_4$alkyl, $C_1$–$C_4$alkylcarbamoyl-$C_1$–$C_4$alkyl, di-$C_1$–$C_4$alkylcarbamoyl-$C_1$–$C_4$alkyl, cyano-$C_1$–$C_4$alkyl, dicarboxy-$C_1$–$C_4$alkyl, $C_1$–$C_4$alkoxycarbonyl(carboxy)-$C_1$–$C_4$alkyl, di-$C_1$–$C_4$alkoxycarbonyl-$C_1$–$C_4$alkyl, dicarbamoyl-$C_1$–$C_4$alkyl, carbamoyl(carboxy)-$C_1$–$C_4$alkyl, di-($C_1$–$C_4$alkylcarbamoyl)-$C_1$–$C_4$alkyl, di-(di-$C_1$–$C_4$alkylcarbamoyl)-$C_1$–$C_4$alkyl, carboxy(hydroxy)-$C_1$–$C_4$alkyl, $C_1$–$C_4$alkoxycarbonyl(hydroxy)-$C_1$–$C_4$alkyl, carbamoyl(hydroxy)-$C_1$–$C_4$alkyl, $C_1$–$C_4$alkylcarbamoyl(hydroxy)-$C_1$–$C_4$alkyl or di-$C_1$–$C_4$alkylcarbamoyl(hydroxy)-$C_1$–$C_4$alkyl, carboxycycloalkyl-$C_1$–$C_4$alkyl, $C_1$–$C_4$alkoxycarbonylcycloalkyl-$C_1$–$C_4$alkyl, carbamoylcycloalkyl-$C_1$–$C_4$alkyl, $C_1$–$C_4$alkylcarbamoylcycloalkyl-$C_1$–$C_4$alkyl, di-$C_1$–$C_4$alkylcarbamoylcycloalkyl-$C_1$–$C_4$alkyl, $C_1$–$C_4$alkanesulfonyl-$C_1$–$C_4$alkyl, thiocarbamoyl-$C_1$–$C_4$alkyl, N-$C_1$–$C_4$alkylthiocarbamoyl-$C_1$–$C_4$alkyl or N,N-di-$C_1$–$C_4$alkylthiocarbamoyl-$C_1$–$C_4$alkyl, sulfamoyl-$C_1$–$C_4$alkyl, $C_1$–$C_4$alkylsulfamoyl-$C_1$–$C_4$alkyl or di-$C_1$–$C_4$alkylsulfamoyl-$C_1$–$C_4$alkyl, unsubstituted or oxo-substituted pyrrolidinyl, imidazolyl, benzimidazolyl, oxadiazolyl, pyridyl, oxopiperidinyl, dioxopiperidinyl, oxothiazolyl, oxo-oxazolinyl or quinolinyl, unsubstituted or oxo-substituted pyrrolidinyl-$C_1$–$C_4$alkyl, imidazolyl-$C_1$–$C_4$alkyl, benzimidazolyl-$C_1$–$C_4$alkyl, oxadiazolyl-$C_1$–$C_4$alkyl, pyridyl-$C_1$–$C_4$alkyl, oxopiperidinyl-$C_1$–$C_4$alkyl, dioxopiperidinyl-$C_1$–$C_4$alkyl, oxothiazolyl-$C_1$–$C_4$alkyl, oxo-oxazolinyl-$C_1$–$C_4$alkyl or quinolinyl-$C_1$–$C_4$alkyl, morpholinocarbonyl-$C_1$–$C_4$alkyl or unsubstituted or N-$C_1$–$C_4$alkanoylated piperidyl-$C_1$–$C_4$alkyl or unsubstituted or N-$C_1$–$C_4$alkanoylated piperidyl, or a salt thereof.

5. A compound according to claim 1 of formula I, wherein $R_1$ is a 2-$R_A$-3-$R_B$-phenyl radical, a 2-$R_A$-4-$R_C$-phenyl radical, a 2-$R_A$-pyridin-3-yl radical, a 3-$R_A$-pyridin-2-yl radical or a 1-$R_D$-indol-3-yl radical, wherein one of the radicals $R_A$ and $R_B$ is $C_1$–$C_4$alkyl, $C_1$–$C_4$alkoxy-$C_1$–$C_4$alkyl, di-$C_1$–$C_4$alkylamino-$C_1$–$C_4$alkyl, piperidino-$C_1$–$C_4$alkyl, $C_1$–$C_4$alkanoylpiperidinyl-$C_1$–$C_4$alkyl, $C_1$–$C_4$alkoxycarbonylpiperidino-$C_1$–$C_4$alkyl, pyrrolidino-$C_1$–$C_4$alkyl, piperazino-$C_1$–$C_4$alkyl, N'-$C_1$–$C_4$alkylpiperazino-$C_1$–$C_4$alkyl, N'-$C_1$–$C_4$alkanoylpiperazino-$C_1$–$C_4$alkyl, morpholino-$C_1$–$C_4$alkyl, $C_1$–$C_4$alkylmorpholino-$C_1$–$C_4$alkyl, thiomorpholino-$C_1$–$C_4$alkyl, amino-$C_1$–$C_7$alkoxy, $C_1$–$C_4$alkanoylamino-$C_1$–$C_4$alkoxy, di-$C_1$–$C_4$alkylamino-$C_1$–$C_4$alkoxy, piperidino-$C_1$–$C_4$alkoxy, morpholino-$C_1$–$C_4$alkoxy, hydroxy, $C_1$–$C_7$alkoxy, $C_1$–$C_4$alkoxy-$C_1$–$C_4$alkoxy, $C_1$–$C_4$alkoxy-$C_1$–$C_4$alkoxy-$C_1$–$C_4$alkoxy, $C_1$–$C_4$alkoxy-$C_1$–$C_4$alkenyloxy, amino-$C_1$–$C_4$alkoxy, $C_1$–$C_4$alkanoylamino-$C_1$–$C_4$alkoxy, di-+$C_1$–$C_4$alkylamino-$C_1$–$C_4$alkoxy, piperidino-$C_1$–$C_4$alkoxy, morpholino-$C_1$–$C_4$alkoxy, carbamoyl or carbamoyl-$C_1$–$C_4$alkoxy, and the other is hydrogen, $C_1$–$C_4$alkyl, such as methyl, hydroxy or $C_1$–$C_4$alkoxy, $R_C$ is hydrogen, hydroxy, $C_1$–$C_4$alkoxy, $C_1$–$C_4$alkoxy-$C_1$–$C_4$alkoxy, morpholino-$C_1$–$C_4$alkylcarbamoyl-$C_1$–$C_4$alkoxy, di-$C_1$–$C_4$alkylamino-$C_1$–$C_4$alkyl, piperidino-$C_1$–$C_4$alkyl, $C_1$–$C_4$alkoxycarbonylpiperidino-$C_1$–$C_4$alkyl, pyrrolidino-$C_1$–$C_4$alkyl, piperazinocarbonyl-$C_1$–$C_4$alkyl, N'-$C_1$–$C_4$alkylpiperazinocarbonyl-$C_1$–$C_4$alkyl, N'-$C_1$–$C_4$alkanoylpiperazinocarbonyl-$C_1$–$C_4$alkyl, morpholino, morpholino-$C_1$–$C_4$alkyl, thiomorpholino-$C_1$–$C_4$alkyl, $C_1$–$C_4$alkoxy, amino-$C_1$–$C_1$–$C_4$alkoxy, $C_1$–$C_4$alkanoylamino-$C_1$–$C_4$alkoxy, di-$C_1$–$C_4$alkylamino-$C_1$–$C_4$alkoxy, piperidino-$C_1$–$C_4$alkoxy, morpholino-$C_1$–$C_4$alkoxy, morpholino-$C_1$–$C_4$alkylcarbamoyl-$C_1$–$C_4$alkoxy, carboxy, carbamoyl, $C_1$–$C_4$alkylcarbamoyl, carboxy-$C_1$–$C_4$alkoxy, carbamoyl-$C_1$–$C_4$alkoxy, $C_1$–$C_4$alkylcarbamoyl-$C_1$–$C_4$alkoxy, di-$C_1$–$C_4$alkylamino-$C_1$–$C_4$alkoxy or tetrazolyl-$C_1$–$C_4$alkoxy, and $R_D$ is $C_1$–$C_4$alkyl, $C_1$–$C_4$alkoxy-$C_1$–$C_4$alkyl, carbamoyl-$C_1$–$C_4$alkyl, $C_1$–$C_4$alkylcarbamoyl-$C_1$–$C_4$alkyl, di-$C_1$–$C_4$alkylcarbamoyl-$C_1$–$C_4$alkyl, piperidino-$C_1$–$C_4$alkyl, or $C_1$–$C_4$alkoxycarbonylpiperidino-$C_1$–$C_4$alkyl, one of the radicals $X_1$ and $X_2$ is carbonyl and the other is methylene, $R_2$ is $C_1$–$C_4$alkyl, $R_3$ is amino or $C_1$–$C_4$alkanoylamino, $R_4$ is $C_1$–$C_4$alkyl, and $R_5$ is $C_1$–$C_4$alkyl, $C_1$–$C_4$alkoxy-$C_1$–$C_4$alkyl, $C_1$–$C_4$alkoxycarbonylpiperidino-$C_1$–$C_4$alkyl, pyrrolidino-$C_1$–$C_4$alkyl, N'-$C_1$–$C_4$alkylpiperazino-$C_1$–$C_4$alkyl, N'-$C_1$–$C_4$alkoxycarbonylpiperazino-$C_1$–$C_4$alkyl or N'-$C_1$–$C_7$alkanoylpiperazino-$C_1$–$C_4$alkyl, morpholino-$C_1$–$C_4$alkyl, thiomorpholino-$C_1$–$C_4$alkyl, morpholinocarbonyl-$C_1$–$C_4$alkyl, carbamoyl-$C_1$–$C_4$alkyl, $C_1$–$C_4$alkylcarbamoyl-$C_1$–$C_4$alkyl, di-$C_1$–$C_4$alkylcarbamoyl-$C_1$–$C_4$alkyl, piperidinocarbonyl-$C_1$–$C_4$alkyl, piperazinocarbonyl-$C_1$–$C_4$alkyl, N'-$C_1$–$C_4$alkylpiperazinocarbonyl-$C_1$–$C_4$alkyl, N'-$C_1$–$C_4$alkanoylpiperazinocarbonyl-$C_1$–$C_4$alkyl, N'-$C_1$–$C_4$alkylpiperazinocarbonyl-$C_1$–$C_4$alkyl, or morpholinocarbonyl-$C_1$–$C_4$alkyl, or a salt thereof.

6. A compound according to claim 1 of formula Ia

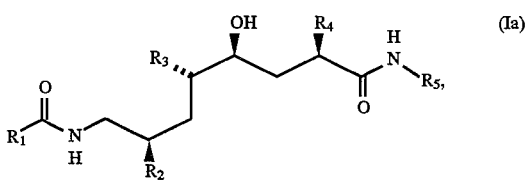

wherein $R_1$ is a 2-$R_A$-4-$R_C$-phenyl radical, a 2-$R_A$-pyridin-3-yl radical or a 3-$R_A$-pyridin-2-yl radical, wherein $R_A$ is $C_1$–$C_4$alkoxy-$C_1$–$C_4$alkyl, morpholino-$C_1$–$C_4$alkyl, $C_1$–$C_7$alkanoylpiperazino-$C_1$–$C_4$alkyl, $C_1$–$C_7$alkoxy, $C_1$–$C_4$alkoxy-$C_1$–$C_4$alkoxy, $C_1$–$C_4$alkoxy-$C_1$–$C_4$alkenyloxy, $C_1$–$C_4$alkoxy-$C_1$–$C_4$alkoxy-$C_1$–$C_4$alkoxy, amino-$C_1$–$C_4$alkoxy, di-$C_1$–$C_4$alkylamino-$C_1$–$C_4$alkoxy, carbamoyl-$C_1$–$C_4$alkoxy or carbamoyl, and $R_C$ is hydrogen, di-$C_1$–$C_4$alkylamino-$C_1$–$C_4$alkyl, piperidino-$C_1$–$C_4$alkyl, pyrrolidino-$C_1$–$C_4$alkyl, morpholino-$C_1$–$C_4$alkyl, $C_1$–$C_4$alkanoylpiperazino-$C_1$–$C_7$alkyl, or $C_1$–$C_4$alkylpiperazino-$C_1$–$C_4$alkyl, morpholino-$C_1$–$C_4$alkoxy, morpholino-$C_1$–$C_4$alkylcarbamoyl-$C_1$–$C_4$alkoxy, piperidino-$C_1$–$C_4$alkoxy, carboxy, carbamoyl, $C_1$–$C_4$alkylcarbamoyl, carboxy-$C_1$–$C_4$alkoxy, di-$C_1$–$C_4$alkylamino-$C_1$–$C_4$alkoxy, $C_1$–$C_4$alkylcarbamoyl-$C_1$–$C_4$alkoxy or tetrazolyl-$C_1$–$C_7$alkoxy, $X_1$ is carbonyl and $X_2$ is methylene, $R_2$ and $R_4$ are each independently of the other $C_1$–$C_4$alkyl, $R_3$ is amino and $R_5$ is $C_1$–$C_4$alkyl, morpholino-$C_1$–$C_4$alkyl, thiomorpholino-$C_1$–$C_4$alkyl, morpholinocarbonyl-$C_1$–$C_4$alkyl, carbamoyl-$C_1$–$C_4$alkyl, $C_1$–$C_4$alkylcarbamoyl-$C_1$–$C_4$alkyl, di-$C_1$–$C_4$alkylcarbamoyl-$C_1$–$C_4$alkyl, N'-$C_1$–$C_4$alkylpiperazino-$C_1$–$C_4$alkyl, N'-$C_1$–$C_4$alkoxycarbonylpiperazino-$C_1$–$C_4$alkyl or N'-$C_1$–$C_7$alkanoylpiperazino-$C_1$–$C_4$alkyl, or a salt thereof.

7. A compound according to claim 1 being (2S,4S,5S,7R)-N-(4-Amino-7-butylcarbamoyl-5-hydroxy-2-isopropyl-octyl)-2-(3-methoxypropoxy)-benzamide;

(2S,4S,5S,7R)-N-(4-Amino-7-butylcarbamoyl-5-hydroxy-2-isopropyl-octyl)-3-methoxy-2-(3-methoxypropoxy)-benzamide;

(2S,4S,5S,7R)-N-(4-Amino-7-butylcarbamoyl-5-hydroxy-2-isopropyl-octyl)-4-methoxy-2-(3-methoxypropoxy)-benzamide;

(2S,4S,5S,7R)-N-(4-Amino-7-butylcarbamoyl-5-hydroxy-2-isopropyl-octyl)-3-(3-methoxypropoxy)-benzamide;

(2S,4S,5S,7R)-N-(7-Butylcarbamoyl-4-formylamino-5-hydroxy-2-isopropyl-octyl)-3-methoxy-2-(3-methoxypropoxy)-benzamide;

(2R,4S,5S,7R)-1-Benzyl-1H-indole-3-carboxylic acid N-(4-amino-7-butylcarbamoyl-5-hydroxy-2-isopropyl-octyl)-amide;

(2R,4S,5S,7R)-1-(2-Methoxyethyl)-1H-indole-3-carboxylic acid N-(4-amino-7-butylcarbamoyl-5-hydroxy-2-isopropyl-octyl)-amide;

(2R,4S,5S,7R)-1-Pyridin-2-yl-1H-indole-3-carboxylic acid N-(4-amino-7-butylcarbamoyl-5-hydroxy-2-isopropyl-octyl)-amide;

(2R,4S,5S,7R)-1-(2-Methoxybenzyl)-1H-indole-3-carboxylic acid N-(4-amino-7-butylcarbamoyl-5-hydroxy-2-isopropyl-octyl)-amide;

(2R,4S,5S,7R)-N-(4-Amino-7-butylcarbamoyl-5-hydroxy-2-isopropyl-octyl)-2-(3-methoxypropoxy)-benzamide;

(2R,4S,5S,7R)-N-(4-Amino-7-butylcarbamoyl-5-hydroxy-2-methyl-octyl)-2-(3-methoxypropoxy)-benzamide;

(2R,4S,5S,7R)-N-(4-Amino-7-butylcarbamoyl-5-hydroxy-2-methyl-octyl)-2-(3-methoxypropoxy)-benzamide;

(2S,4S,5S,7S)-N-(4-Amino-7-butylcarbamoyl-5-hydroxy-2-isopropyl-8-methyl-nonyl)-2-(3-methoxypropoxy)-benzamide;

(2S,4S,5S,7S)-N-(4-Amino-7-butylcarbamoyl-5-hydroxy-2-isopropyl-8-methyl-nonyl)-2-(4-methoxybutoxy)-benzamide;

(2S,4S,5S,7S)-N-(4-Amino-7-butylcarbamoyl-5-hydroxy-2-isopropyl-8-methyl-nonyl)-2-propoxy-benzamide;

(2S,4S,5S,7S)-N-(4-amino-7-butylcarbamoyl-5-hydroxy-2-isopropyl-8-methyl-nonyl)-2-(2-methoxyethoxy)-benzamide;

(2S,4S,5S,7S)-N-(4-Amino-7-butylcarbamoyl-5-hydroxy-2-isopropyl-8-methyl-nonyl)-2-[2-(2-methoxyethoxy)-ethoxy]-benzamide;

(2S,4S,5S,7S)-N-(4-Amino-7-butylcarbamoyl-5-hydroxy-2-isopropyl-8-methyl-nonyl)-4-methoxy-2-(3-methoxypropoxy)-benzamide;

(2S,4S,5S,7S)-N-(4-Amino-7-butylcarbamoyl-5-hydroxy-2-isopropyl-8-methyl-nonyl)-4-methoxy-3-(3-methoxypropoxy)-benzamide;

4S,5S,7S)-N-(4-amino-7-butylcarbamoyl-5-hydroxy-2-isopropyl-8-methyl-nonyl)-2-(propoxymethyl)-benzamide;

4S,5S,7S)-N-(4-amino-7-butylcarbamoyl-5-hydroxy-2-isopropyl-8-methyl-nonyl)-2-acetamido-benzamide;

(2S,4S,5S,7S)-N-(4-Amino-7-butylcarbamoyl-5-hydroxy-2-isopropyl-8-methyl-nonyl)-2-[2-(acetamido)-ethoxy]-benzamide;

(2S,4S,5S,7S)-N-(4-Amino-7-butylcarbamoyl-5-hydroxy-2-isopropyl-8-methyl-nonyl)-2-(4-methoxybut-2-enoxy)-benzamide;

(2S,4S,5S,7S)-N-(4-Amino-7-butylcarbamoyl-5-hydroxy-2-isopropyl-8-methyl-nonyl)-2-(4-methoxybutoxy)-4-methyl-benzamide;

(2S,4S,5S,7S)-N-[4-Amino-7-butylcarbamoyl-5-hydroxy-2-isopropyl-8-methyl-nonyl]-2-(3-methoxypropoxy)-nicotinamide;

(2S,4S,5S,7S)-N-[4-Amino-7-butylcarbamoyl-5-hydroxy-2-isopropyl-8-methyl-nonyl]-3-(4-methoxybutoxy)-pyridine-2-carboxylic acid amide;

(2S,4S,5S,7S)-N-(4-Amino-7-butylcarbamoyl-5-hydroxy-2-isopropyl-8-methyl-nonyl)-2-hydroxy-benzamide;

(2S,4S,5S,7S)-N-(4-Amino-7-butylcarbamoyl-5-hydroxy-2-isopropyl-8-methyl-nonyl)-2-[2-(methoxymethoxy)-ethoxy]-benzamide;

(2S,4S,5S,7S)-N-[4-Amino-5-hydroxy-2-isopropyl-8-methyl-7-(2-morpholin-4-ylethylcarbamoyl)-nonyl]-2-(3-methoxypropoxy)-benzamide;

(2S,4S,5S,7S)-N-[4-Amino-5-hydroxy-2-isopropyl-8-methyl-7-(2-morpholin-4-ylethylcarbamoyl)-nonyl]-2-(4-methoxybutoxy)-benzamide;

(2S,4S,5S,7S)-N-[4-Amino-5-hydroxy-2-isopropyl-8-methyl-7-(2-morpholin-4-ylethylcarbamoyl)-nonyl]-2-(2-methoxyethoxy)-benzamide;

(2S,4S,5S,7S)-N-[4-Amino-5-hydroxy-2-isopropyl-8-methyl-7-(2-morpholin-4-ethylcarbamoyl)-nonyl]-2-(3-methoxypropoxy)-nicotinamide;

(2S,4S,5S,7S)-N-[4-Amino-5-hydroxy-2-isopropyl-8-methyl-7-(2-morpholin-4-ylethylcarbamoyl)-nonyl]-3-(4-methoxybutoxy)-pyridine-2-carboxylic acid amide;

(2S,4S,5S,7S)-N-[4-Amino-5-hydroxy-2-isopropyl-8-methyl-7-(2-morpholin-4-ylethylcarbamoyl)-nonyl]-2-(4-methoxybut-2-enoxy)-benzamide;

(2S,4S,5S,7S)-N-[4-Amino-5-hydroxy-2-isopropyl-8-methyl-7-(2-morpholin-4-ylethylcarbamoyl)-nonyl]-2-(4-methoxybutoxy)-4-methyl-benzamide;

(2S,4S,5S,7S)-N-[4-Amino-5-hydroxy-2-isopropyl-8-methyl-7-(2-morpholin-4-ylethylcarbamoyl)-methyl-nonyl]-2-(5-methoxypentyloxy)-benzamide;

(2S,4S,5S,7S)-N-[4-Amino-5-hydroxy-2-isopropyl-8-methyl-7-(3-morpholin-4-ylpropylcarbamoyl)-nonyl]-2-(4-methoxybutoxy)-benzamide;

(2S,4S,5S,7S)-N-(4-Amino-7-butylcarbamoyl-5-hydroxy-2-isopropyl-8-methyl-nonyl)-2-(4-methoxybutoxy)-4-(morpholin-4-ylmethyl)-benzamide;

(2S,4S,5S,7S)-N-(4-Amino-7-butylcarbamoyl-5-hydroxy-2-isopropyl-8-methyl-nonyl-2-(4-methoxybutoxy)-4-[2-(morpholin-4-yl)-ethoxy]-benzamide;

(2S,4S,5S,7S)-N-(4-Amino-7-butylcarbamoyl-5-hydroxy-2-isopropyl-8-methyl-nonyl)-4-[3-(dimethylamino)-propoxy]-2-(4-methoxybutoxy)-benzamide;

(2S,4S,5S,7S)-N-(4-Amino-7-butylcarbamoyl-5-hydroxy-2-isopropyl-8-methyl-nonyl)-2-(4-methoxybutoxy)-4-(piperidin-1-yl)methyl-benzamide;

(2S,4S,5S,7S)-N-(4-Amino-7-butylcarbamoyl-5-hydroxy-2-isopropyl-8-methyl-nonyl)-2-(4-methoxybutoxy)-4-(pyrrolidin-1-yl)methyl-benzamide;

(2S,4S,5S,7S)-N-(4-Amino-7-butylcarbamoyl-5-hydroxy-2-isopropyl-8-methyl-nonyl)-2-(4-methoxybutoxy)-4-(2-piperidin-1-ylethoxy)-benzamide;

(2S,4S,5S,7S)-N-(4-Amino-7-butylcarbamoyl-5-hydroxy-2-isopropyl-8-methyl-nonyl)-4-dimethylaminomethyl-2-(4-methoxybutoxy)-benzamide;

(2S,4S,5S,7S)-N-(4-Amino-7-butylcarbamoyl-5-hydroxy-2-isopropyl-8-methyl-nonyl)-2-(4-methoxybutoxy)-4-(4-methylpiperazin-1-yl)methyl-benzamide;

(2S,4S,5S,7S)-N-(4-Amino-7-butylcarbamoyl-5-hydroxy-2-isopropyl-8-methyl-nonyl)-4-(4-acetylpiperazin-1-yl)methyl-2-(4-methoxybutoxy)-benzamide;

(2S,4S,5S,7S)-N-(4-Amino-7-butylcarbamoyl-5-hydroxy-2-isopropyl-8-methyl-nonyl)-2-(3-aminopropoxy)-benzamide;

(2S,4S,5S,7S)-N-(4-Amino-7-butylcarbamoyl-5-hydroxy-2-isopropyl-8-methyl-nonyl)-2-(2-aminoethoxy)-benzamide;

(2S,4S,5S,7S)-N-(4-Amino-7-butylcarbamoyl-5-hydroxy-2-isopropyl-8-methyl-nonyl)-2-[2-(4-acetylpiperazin-1-yl)-ethoxy]-benzamide;

(2S,4S,5S,7S)-N-(4-Amino-7-butylcarbamoyl-5-hydroxy-2-isopropyl-8-methyl-nonyl)-2-[2-(morpholin-4-yl)-ethyl]-benzamide;

(2S,4S,5S,7S)-N-(4-Amino-7-butylcarbamoyl-5-hydroxy-2-isopropyl-8-methyl-nonyl)-2-(3-dimethylaminopropoxy)-benzamide;

(2S,4S,5S,7S)-N-(4-Amino-7-butylcarbamoyl-5-hydroxy-2-isopropyl-8-methyl-nonyl)-2-[3-(morpholin-4-yl)-propoxy]-benzamide;

(2S,4S,5S,7S)-N-(4-Amino-7-butylcarbamoyl-5-hydroxy-2-isopropyl-8-methyl-nonyl)-2-[2-(morpholin-4-yl)-ethoxy]-benzamide;

(2S,4S,5S,7S)-N-(4-Amino-7-butylcarbamoyl-5-hydroxy-2-isopropyl-8-methyl-nonyl)-2-[2(4-methoxypiperidin-1-yl)-ethyl]-benzamide;

(2S,4S,5S,7S)-N-(4-Amino-7-butylcarbamoyl-5-hydroxy-2-isopropyl-8-methyl-nonyl)-2-[2(4-acetylpiperazin-1-yl)-ethyl]-benzamide;

(2S,4S,5S,7S)-4-Amino-5-hydroxy-2,7-diisopropyl-octanedioic acid 8-butylamide 1-[2-(3-methoxypropoxy)-benzyl]amide;

(2S,4S,5S,7S)-4-Amino-5-hydroxy-2,7-diisopropyl-octanedioic acid 8-butylamide 1-[3-(3-methoxypropoxy)-benzyl]amide;

(2S,4S,5S,7S)-4-Amino-5-hydroxy-2,7-diisopropyl-octandioic acid 8-butylamide 1-[2-(4-methoxybutoxy)-benzyl]amide;

(2S,4S,5S,7S)-4-Amino-5-hydroxy-2,7-diisopropyl-octandioic acid 8-butylamide 1-[2-(5-methoxypentyloxy)-benzyl]amide;

(2S,4S,5S,7S)-N1-(4-Amino-7-butylcarbamoyl-5-hydroxy-2-isopropyl-8-methyl-nonyl)-N4-methyl-2-(4-methoxybutoxy)-terephthaldiamide;

(2S,4S,5S,7S)-N1-(4-Amino-7-butylcarbamoyl-5-hydroxy-2-isopropyl-8-methyl-nonyl)-N4-[(2-morpholin-4-yl)-ethyl]-2-(4-methoxybutoxy)-terephthaldiamide;

(2S,4S,5S,7S)-N1-(4-Amino-7-butylcarbamoyl-5-hydroxy-2-isopropyl-8-methyl-nonyl)-2-(4-methoxybutoxy)-terephthaldiamide;

(2S,4S,5S,7S)-N4-(4-Amino-7-butylcarbamoyl-5-hydroxy-2-isopropyl-8-methyl-nonyl)-3-(4-methoxybutoxy)-terephthalmic acid;

(2S,4S,5S,7S)-N-(4-Amino-7-butylcarbamoyl-5-hydroxy-2-isopropyl-8-methyl-nonyl)-4-butylcarbamoylmethoxy-2-(4-methoxybutoxy)-benzamide;

(2S,4S,5S,7S)-[4-(4-Amino-7-butylcarbamoyl-5-hydroxy-2-isopropyl-8-methyl-nonylcarbamoyl)-3-(4-methoxybutoxy)-phenoxy]-acetic acid;

(2S,4S,5S,7S)-N-{4-Amino-5-hydroxy-2-isopropyl-8-methyl-7-[2-(morpholin-4-yl)-ethylcarbamoyl]-nonyl}-2-(4-methoxybutoxy)-4-[2-(morpholin-4-yl)-ethylcarbamoylmethoxy]-benzamide;

(2S,4S,5S,7S)-N-(4-Amino-7-butylcarbamoyl-5-hydroxy-2-isopropyl-8-methyl-nonyl)-2-(4-methoxybutoxy)-4-(1H-tetrazol-5-ylmethoxy)-benzamide;

(2S,4S,5S,7S,2R')-N-[4-Amino-7-(2'-methylcarbamoyl-propylcarbamoyl)-5-hydroxy-2-isopropyl-8-methyl-nonyl]-2-(4-methoxybutoxy)-benzamide;

(2S,4S,5S,7S)-N-(4-Amino-7-[2-(dimethylaminocarbamoyl)-ethylcarbamoyl]-5-hydroxy-2-isopropyl-8-methyl-nonyl)-2-(4-methoxybutoxy)-benzamide;

(2S,4S,5S,7S)-N-[4-Amino-7-(3-carbamoylpropylcarbamoyl)-5-hydroxy-2-isopropyl-8-methyl-nonyl]-2-(4-methoxybutoxy)-benzamide;

(2S,4S,5S,7S)- N-[4-Amino-7-(2-carbamoyl-2-methylpropylcarbamoyl)-5-hydroxy-2-isopropyl-8-methyl-nonyl]-2-(4-methoxybutoxy)-benzamide;

(2S,4S,5S,7S)-N-{4-Amino-5-hydroxy-2-isopropyl-8-methyl-7-[3-(morpholin-4-yl)-3-oxopropylcarbamoyl]-nonyl}-2-(4-methoxybutoxy)-benzamide;

(2S,4S,5S,7S)-N-{7-[2-(4-Acetylpiperidin-1-yl)-ethylcarbamoyl]-4amino-5-hydroxy-2-isopropyl-8-methyl-nonyl}-2-(4-methoxybutoxy)-benzamide;

(2S,4S,5S,7S)-N-[4-Amino-5-hydroxy-2-isopropyl-8-methyl-7-(2-thiomorpholin-4-ylethylcarbamoyl)-methyl-nonyl]-2-(4-methoxybutoxy)-benzamide;

(2S,4S,5S,7S)-N-(4-Amino-7-(2-carbamoyl-2-methylpropylcarbamoyl)-5-hydroxy-2-isopropyl-8-methyl-nonyl)-2-(4-methoxybutoxy)-4-(2-morpholin-4-ylmethoxy)-benzamide;

(2S,4S,5S,7S)-N-(4-Amino-7-(2-carbamoyl-2-methylpropylcarbamoyl)-5-hydroxy-2-isopropyl-8-methy-nonyl)-2-(4-methoxybutoxy)-4-(morpholin-4-ylmethyl)-benzamide;

(2S,4S,5S,7S)-N-[4-Amino-7-(2-carbamoyl-2-methylpropylcarbamoyl)-5-hydroxy-2-isopropyl-8-methyl-nonyl]-2-(2-morpholin-4-ylethoxy)-benzamide;

(2S,4S,5S,7S)-N-{4-Amino-5-hydroxy-2-isopropyl-7-[2-(4-methoxycarbonylpiperidin-1-yl)-ethylcarbamoyl]-8-methyl-nonyl}-2-(4-methoxybutoxy)-benzamide;

(2S,4S,5S,7R)-N-[4-Amino-5-hydroxy-2-methyl-7-[(2-morpholin-4-ylethyl)-carbamoyl]-octyl}-2-(3-methoxypropoxy)-benzamide or (2S,4S,5S,7S)-N-{4-Amino-5-hydroxy-2-isopropyl-8-methyl-7-[2-(morpholin-4-yl)-ethyl-carbamoyl]-nonyl}-4-carbamoylmethoxy-2-(4-methoxybutoxy)-benzamide or, in each case, a salt thereof.

8. A pharmaceutical composition comprising as pharmaceutical active ingredient, together with customary pharmaceutical excipients, a compound according to claim 1 in free form or in pharmaceutically acceptable salt form.

9. A method for the treatment of high blood pressure, which comprises administering a compound according to claim 1 or a pharmaceutically acceptable salt to a warm-blooded organism in need of such treatment.

* * * * *